United States Patent
Cheng et al.

(10) Patent No.: US 12,428,430 B2
(45) Date of Patent: Sep. 30, 2025

(54) OXABICYCLO ACIDS AS LPA ANTAGONISTS

(71) Applicant: BRISTOL-MYERS SQUIBB COMPANY, Princeton, NJ (US)

(72) Inventors: Peter Tai Wah Cheng, Princeton, NJ (US); Jun Shi, Pennington, NJ (US); Shiwei Tao, Hillsborough, NJ (US); Hao Zhang, Belle Mead, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 1232 days.

(21) Appl. No.: 17/276,173

(22) PCT Filed: Sep. 16, 2019

(86) PCT No.: PCT/US2019/051272
§ 371 (c)(1),
(2) Date: Mar. 15, 2021

(87) PCT Pub. No.: WO2020/060914
PCT Pub. Date: Mar. 26, 2020

(65) Prior Publication Data
US 2021/0317131 A1    Oct. 14, 2021

Related U.S. Application Data

(60) Provisional application No. 62/732,588, filed on Sep. 18, 2018.

(51) Int. Cl.
*C07D 493/08* (2006.01)
*A61K 9/00* (2006.01)

(52) U.S. Cl.
CPC .......... *C07D 493/08* (2013.01); *A61K 9/0053* (2013.01)

(58) Field of Classification Search
CPC .................. C07D 493/08; A61K 9/0053
See application file for complete search history.

(56) References Cited

U.S. PATENT DOCUMENTS

| | | |
|---|---|---|
| 10,071,078 B2 | 9/2018 | Cheng et al. |
| 10,576,062 B2 | 3/2020 | Cheng et al. |
| 10,662,172 B2 | 5/2020 | Shi et al. |
| 2020/0138789 A1 | 5/2020 | Cheng et al. |
| 2020/0148665 A1 | 5/2020 | Shi et al. |
| 2020/0308148 A1 | 10/2020 | Cheng et al. |
| 2020/0308157 A1 | 10/2020 | Cheng et al. |
| 2020/0317655 A1 | 10/2020 | Cheng et al. |
| 2020/0317656 A1 | 10/2020 | Shi et al. |
| 2020/0317662 A1 | 10/2020 | Cheng et al. |
| 2021/0078982 A1 | 3/2021 | Shi et al. |
| 2021/0087173 A1 | 3/2021 | Shi et al. |

(Continued)

FOREIGN PATENT DOCUMENTS

| | | |
|---|---|---|
| WO | 2011017350 A2 | 2/2011 |
| WO | 2011041461 A2 | 4/2011 |
| WO | 2011041694 A2 | 4/2011 |

(Continued)

OTHER PUBLICATIONS

David Sek, European Pharmaceutical Review, Jul. 10, 2012, Breaking old habits: Moving away from commonly used buffers in pharmaceuticals.*

(Continued)

*Primary Examiner* — Rebecca L Anderson
(74) *Attorney, Agent, or Firm* — Jing G. Sun

(57) ABSTRACT

The present invention provides compounds of Formula (Ia) or (Ib) or a stereoisomer, tautomer, or pharmaceutically acceptable salt or solvate thereof, wherein all the variables are as defined herein. These compounds are selective LPA receptor inhibitors.

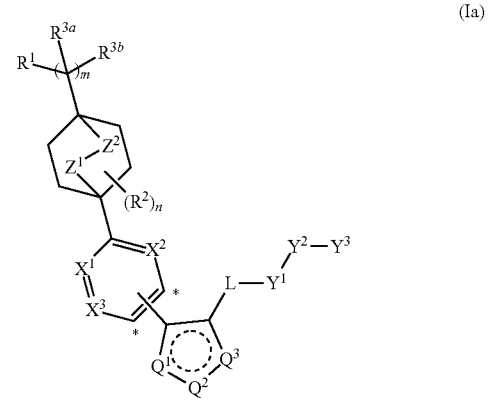

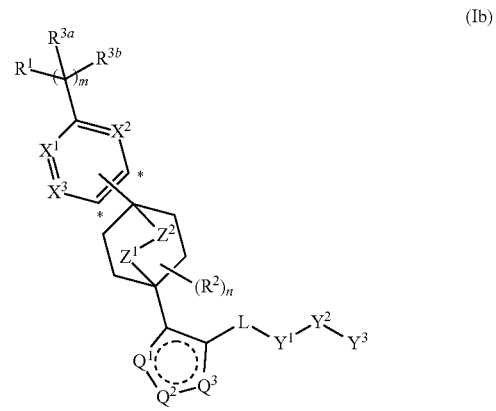

23 Claims, No Drawings

(56) References Cited

U.S. PATENT DOCUMENTS

2021/0087178 A1    3/2021    Shi et al.

FOREIGN PATENT DOCUMENTS

| WO | 2011071570 | A1 | 6/2011 |
|---|---|---|---|
| WO | 2012078593 | A2 | 6/2012 |
| WO | 2012078805 | A1 | 6/2012 |
| WO | 2012138648 | A1 | 10/2012 |
| WO | 2013070879 | A1 | 5/2013 |
| WO | 2013160873 | A1 | 10/2013 |
| WO | 2013189864 | A1 | 12/2013 |
| WO | 2013189865 | A1 | 12/2013 |
| WO | 2014113485 | A1 | 7/2014 |
| WO | 2014145873 | A2 | 9/2014 |
| WO | 2014151247 | A1 | 9/2014 |
| WO | 2017/223016 | A1 | 12/2017 |
| WO | 2019126085 | A1 | 6/2019 |
| WO | 2020060915 | A1 | 3/2020 |
| WO | 2020060916 | A1 | 3/2020 |

OTHER PUBLICATIONS

Registry No. 372-09-8, File Registry on STN, entered STN: Nov. 16, 1984.*
U.S. Appl. No. 17/221,859, filed Apr. 5, 2021, Cheng et al.
U.S. Appl. No. 17/224,161, filed Apr. 7, 2021, Shi et al.
U.S. Appl. No. 16/772,825, filed Jun. 15, 2020, Shi et al.
U.S. Appl. No. 16/772,842, filed Jun. 15, 2020, Shi et al.
U.S. Appl. No. 17/276,176, filed Mar. 15, 2021, Cheng et al.
U.S. Appl. No. 17/276,178, filed Mar. 15, 2021, Cheng et al.
Amishima, et al., "Expression of Epidermal Growth Factor and Epidermal Growth Factor Receptor Immunoreactivity in the Asthmatic Human Airway", Am. J. Respir. Critical Care Medicine, vol. 157, pp. 1907-1912 (1998 ).
Boucharaba, et al., "Platelet-derived lysophosphatidic acid supports the progression of osteolytic bone metastases in breast cancer", J. Clin. Invest., vol. 114(12), pp. 1714-1725 (2004).
Boucharaba, et al., "The type 1 lysophosphatidic acid receptor is a target for therapy in bone metastases", PNAS, vol. 103(25), pp. 9643-9648 (2006).
Chen, et al., "Specific receptor subtype mediation of LPA-induced dual effects incardiac fibroblasts", FEBS Letters, vol. 580(19), pp. 4737-4745 (2006).
Choi, et al., "Biological roles of lysophospholipid receptors revealedby genetic null mice: An update", Biochemica et Biophysica Acta, vol. 1781, pp. 531-539 (2008).
Contos, et al., "Lysophosphatidic Acid Receptors", Mol. Pharmacology, vol. 58(6), pp. 1188-1196 (2000).
Ediger, et al., "Transcription factor activation and mitogenic synergism in airway smooth muscle cells", Eur Respir Journal, vol. 21, pp. 759-769 (2003).
Gardell, et al., "Emerging medicinal roles for lysophospholipid signaling", Trends in Molecular Medicine, vol. 12(2), pp. 65-75 (2006).
Geoetzl, et al., "Lysophosphatidic Acid and Sphingosine 1-PhosphateProtection of T Cells from Apoptosis in Association with Suppression of Bax1", Journal of Immunology, vol. 162, pp. 2049-2056 (1999).
Guo, et al., "Mitogenic Signaling in Androgen Sensitive and Insensitive Prostate Cancer Cell Lines", Journal of Urology, vol. 163(3), pp. 1027-1032 (2000).
Hashimoto, et al., "Lysophosphatidic Acid (LPA) Induces Plasma Exudation and Histamine Release in Mice via LPA Receptors", J Pharmacol Science, vol. 100, pp. 82-87 (2006).
Holtsberg, et al., "Lysophosphatidic Acid Induces Necrosis and Apoptosis in Hippocampal Neurons", J. Neurochemistry, vol. 70, pp. 66-76 (1998).
Imamura, "Induction of In Vitro Tumor cell invasion of cellular monolayers by lysophosphatidic acid or phospholupase D", Biochem Biophys Res Commun., vol. 193(2), pp. 497-503 (1993).

Inoue, et al., "Initiation of neuropathic pain require lysophosphatidic acid receptor signaling" Nature Medicine, vol. 10, pp. 712-718 (2004).
Inoue, et al., "Lysophosphatidic acid and mesangial cells: implications for renal diseases", Clinical Science, vol. 96(4), pp. 431-436 (1999).
Ishii, et al., "Lysophospholipid Receptors:Signaling and Biology", Annu Rev Biochemistry, vol. 73, pp. 321-354 (2004).
Kantarci, et al., "Epithelial and connective tissue cell CTGF/CCN2 expression in gingival fibrosis", J Pathol., vol. 210, pp. 59-66 (2006).
Koh, et al., "Lysophosphatidic Acid Is a Major Serum Noncytokine Survival Factor for Murine Macrophages Which Acts via the Phosphatidylinositol 3-Kinase Signaling Pathway", J Clin Invest., vol. 102, pp. 716-727 (1998).
Kropp, et al., "Characterization of Cultured Bladder Smooth Muscle Cells: Assessment of In Vitro Contractility", Journal of Urology, vol. 162(5), pp. 1779-1784 (1999).
Kuroda, et al., "Phospholipid Concentration in Lung Lavage Fluid as Biomarker for Pulmonary Fibrosis", Inhalation Toxicology, vol. 18(5), pp. 389-393 (2006).
Lin, et al., "Lysophosphatidic acid regulates inflammation-related genes in human endothelial cells through LPA1 and LPA3", Biochem Biophys Res Communication, vol. 363(4), pp. 1001-1008, (2007).
Maguire, et al., "Regulation of vascular reactivity by established and emerging GPCRs", Trends in Pharmacological Sciences, vol. 26(9), pp. 448-454 (2005).
Mills, et al., "The Emerging Role of Lysophosphatidic Acid in Cancer", Nat Rev Cancer, vol. 3, pp. 582-591 (2003).
Moolenaar, "Lysophosphatidic acid signalling", Curr. Opin. Cell Biology, vol. 7, pp. 203-210 (1995).
Mototani, et al., "A functional SNP in EDG2 increases susceptibilityto knee osteoarthritis in Japanese", Hum. Mol. Genetics, vol. 17(12), pp. 1790-1797 (2008).
Munger, et al., "The Integrin avb6 Binds and Activates Latent TGFb1:A Mechanism for Regulating Pulmonary Inflammation and Fibrosis", Cell, vol. 96, pp. 319-328 (1999).
Murph, et al., "Sharpening the edges of understanding the structure/ function of the LPA1 receptor: Expression in cancer and mechanisms of regulation", Biochimica et Biophysica Acta, vol. 1781, pp. 547-557 (2008).
Nakagawa, et al. "Molecular Liver Cancer Prevention in Cirrhosis byOrgan Transcriptome Analysis and Lysophosphatidic Acid Pathway Inhibition" Cancer Cell, vol. 30, pp. 879-890 (2016).
Osborne, et al., "Lipid Receptors in Cardiovascular Development", Annual Rev. Physiol., vol. 65, pp. 23-43 (2003).
Palmer, et al. "Randomized, Double-Blind, Placebo Controlled, Phase 2 Trial of BMS-986020, a Lysophosphatidic Acid Receptor Antagonist for the Treatment of Idiopathic Pulmonary Fibrosis" Chest, vol. 154, pp. 1061-1069 (2018).
Pradere, et al "LPA1 Receptor Activation Promotes Renal Interstitial Fibrosis", J Am Soc Nephrol, vol. 18, pp. 3110-3118 (2007).
Pradere, et al., "Lysophosphatidic acid and renal fibrosis", Biochimica et Biophysica Acta, vol. 1781, pp. 582-587 (2008).
Rother, et al., "Subtype-Selective Antagonists of Lysophosphatidic Acid Receptors Inhibit Platelet Activation Triggered by the LipidCore of Atherosclerotic Plaques", Circulation, vol. 108, pp. 741-747 (2003).
Saunders, et al., "Identification of small-molecule inhibitors of autotaxin that inhibit melanoma cell migration and invasion", Mol Cancer Ther., vol. 7(10), pp. 3352-3362 (2008).
Siess, "Athero- and thrombogenic actions of lysophosphatidic acid and sphingosine-1-phosphate", Biochimica et Biophysica Acta, vol. 1582, pp. 204-215 (2002).
Simon, et al., "Lysophosphatidic Acid 1 Receptor-dependent Downregulation of Peroxisome Proliferator-activated Receptor γ 2" J.Biol. Chemistry, vol. 280(15) pp. 14656-14662 (2005).
Smalheiser, "Acute Neurite Retraction Elicited by Diverse Agents Is Prevented by Genistein, a Tyrosine Kinase Inhibitor", J. Neurochemistry, vol. 61(1), pp. 340-343 (1993).
Sutphen, et al., "Lysophospholipids Are Potential Biomarkers of Ovarian Cancer", Cancer Epidemiol. Biomarkers Prev. 13, pp. 1185-1191 (2004).

(56) References Cited

OTHER PUBLICATIONS

Tager, et al., The lysophosphatidic acid receptor LPA1 links pulmonaryfibrosis to lung injury by mediating fibroblast recruitmentand vascular leak, Nature Medicine, vol. 14, pp. 45-54 (2008).
Watanabe, et al., "Both Plasma Lysophosphatidic Acid and Serum Autotaxin Levels are Increased in Chronic Hepatitis C", J Clinical Gastroenterology, vol. 41, pp. 616-623 (2007).
Watanabe, et al., "Plasma lysophosphatidic acid level and serum autotaxin activity are increased in liver injury in rats in relation to its severity", Life Science, vol. 81, pp. 1009-1015 (2007).
Wiedmaier, et al., "Bacteria induce CTGF and CYR61 expression in epithelial cells ina lysophosphatidic acid receptor-dependent manner", Int J Med Microbiology, vol. 298(3-4), pp. 231-243 (2008).
Xu, et al., "Lysophosphatidic Acid Induces $\alpha v \beta 6$ Integrin-Mediated TGF-$\beta$ Activation via the LPA2 Receptor and the Small G Protein G$\alpha$q", Am J Pathology, vol. 174(4), pp. 1264-1279 (2009).
Yamada, et al., "Lysophosphatidic Acid (LPA) in Malignant Ascites Stimulates Motility of Human Pancreatic Cancer Cells through LPA1", J Biol Chemistry, vol. 279, pp. 6596-6605 (2004).
Yamada, et al., "Lysophosphatidic acid stimulates the proliferation and motility of malignant pleural mesothelioma cells through lysophosphatidic acid receptors, LPA1 and LPA2", Cancer Science, vol. 99(8), pp. 1603-1610 (2008).
Yasuda, et al., "Phospholipid Analysis of Alveolar Macrophagesand Bronchoalveolar Lavage Fluid Following Bleomycin Administration to Rabbits", Lung, vol. 172, pp. 91-102 (1994).
Zhao, et al., "Regulation of Lysophosphatidic Acid Receptor Expression and Function in Human Synoviocytes: Implications for Rheumatoid Arthritis" Mol. Pharmacology, vol. 73(2), pp. 587-600 (2008).

\* cited by examiner

OXABICYCLO ACIDS AS LPA ANTAGONISTS

CROSS-REFERENCE TO RELATED APPLICATIONS

This application is a 371 of International Application No. PCT/US2019/051272 filed on Sep. 16, 2019, which claims the priority benefit of U.S. Provisional Application No. 62/732,588, filed Sep. 18, 2018; the content of which is herein incorporated by reference in their entirety.

FIELD OF THE INVENTION

The present invention relates to novel substituted oxabicyclo acid compounds, compositions containing them, and methods of using them, for example, for the treatment of disorders associated with one or more of the lysophosphatidic acid (LPA) receptors.

BACKGROUND OF THE INVENTION

Lysophospholipids are membrane-derived bioactive lipid mediators, of which one of the most medically important is lysophosphatidic acid (LPA). LPA is not a single molecular entity but a collection of endogenous structural variants with fatty acids of varied lengths and degrees of saturation (Fujiwara et al., *J Biol. Chem.*, 2005, 280, 35038-35050). The structural backbone of the LPAs is derived from glycerol-based phospholipids such as phosphatidylcholine (PC) or phosphatidic acid (PA).

The LPAs are bioactive lipids (signaling lipids) that regulate various cellular signaling pathways by binding to the same class of 7-transmembrane domain G protein-coupled (GPCR) receptors (Chun, J., Hla, T., Spiegel, S., Moolenaar, W., Editors, *Lysophospholipid Receptors: Signaling and Biochemistry*, 2013, Wiley; ISBN. 978-0-470-56905-4 & Zhao, Y. et al, *Biochim. Biophys. Acta (BBA)—Mol. Cell Biol. Of Lipids*, 2013, 1831, 86-92). The currently known LPA receptors are designated as $LPA_1$, $LPA_2$, $LPA_3$, $LPA_4$, $LPA_5$ and $LPA_6$ (Choi, J. W., *Annu. Rev. Pharmacol. Toxicol.*, 2010, 50, 157-186; Kihara, Y., et al, *Br. J. Pharmacol.*, 2014, 171, 3575-3594).

The LPAs have long been known as precursors of phospholipid biosynthesis in both eukaryotic and prokaryotic cells, but the LPAs have emerged only recently as signaling molecules that are rapidly produced and released by activated cells, notably platelets, to influence target cells by acting on specific cell-surface receptors (see, e.g., Moolenaar et al., *BioEssays*, 2004, 26, 870-881, and van Leewen et al., *Biochem. Soc. Trans.*, 2003, 31, 1209-1212). Besides being synthesized and processed to more complex phospholipids in the endoplasmic reticulum, LPAs can be generated through the hydrolysis of pre-existing phospholipids following cell activation; for example, the sn-2 position is commonly missing a fatty acid residue due to deacylation, leaving only the sn-1 hydroxyl esterified to a fatty acid. Moreover, a key enzyme in the production of LPA, autotaxin (lysoPLD/NPP2), may be the product of an oncogene, as many tumor types up-regulate autotaxin (Brindley, D., *J. Cell Biochem.* 2004, 92, 900-12). The concentrations of LPAs in human plasma & serum as well as human bronchoalveolar lavage fluid (BALF) have been reported, including determinations made using sensitive and specific LC/MS & LC/MS/MS procedures (Baker et al. *Anal. Biochem.*, 2001, 292, 287-295; Onorato et al., *J. Lipid Res.*, 2014, 55, 1784-1796).

LPA influences a wide range of biological responses, ranging from induction of cell proliferation, stimulation of cell migration and neurite retraction, gap junction closure, and even slime mold chemotaxis (Goetzl, et al., *Scientific World J.*, 2002, 2, 324-338; Chun, J., Hla, T., Spiegel, S., Moolenaar, W., Editors, *Lysophospholipid Receptors: Signaling and Biochemistry*, 2013, Wiley; ISBN: 978-0-470-56905-4). The body of knowledge about the biology of LPA continues to grow as more and more cellular systems are tested for LPA responsiveness. For instance, it is now known that, in addition to stimulating cell growth and proliferation, LPAs promote cellular tension and cell-surface fibronectin binding, which are important events in wound repair and regeneration (Moolenaar et al., *BioEssays*, 2004, 26, 870-881). Recently, anti-apoptotic activity has also been ascribed to LPA, and it has recently been reported that PPARγ is a receptor/target for LPA (Simon et al., *J. Biol. Chem.*, 2005, 280, 14656-14662).

Fibrosis is the result of an uncontrolled tissue healing process leading to excessive accumulation and insufficient resorption of extracellular matrix (ECM) which ultimately results in end-organ failure (Rockey, D. C., et al., *New Engl. J. Med.*, 2015, 372, 1138-1149). Recently it was reported that the LPA1 receptor was over-expressed in idiopathic pulmonary fibrosis (IPF) patients. $LPA_1$ receptor knockout mice were also protected from bleomycin-induced lung fibrosis (Tager et al., *Nature Med.*, 2008, 14, 45-54). LPA pathway inhibitors (e.g. an $LPA_1$ antagonist) were recently shown to be chemopreventive anti-fibrotic agents in the treatment of hepatocellular carcinoma in a rat model (Nakagawa et al., Cancer Cell, 2016, 30, 879-890).

Thus, antagonizing the $LPA_1$ receptor may be useful for the treatment of fibrosis such as pulmonary fibrosis, hepatic fibrosis, renal fibrosis, arterial fibrosis and systemic sclerosis, and thus the diseases that result from fibrosis (pulmonary fibrosis-Idiopathic Pulmonary Fibrosis [IPF], hepatic fibrosis-Non-alcoholic Steatohepatitis [NASH], renal fibrosis-diabetic nephropathy, systemic sclerosis-scleroderma, etc.).

SUMMARY OF THE INVENTION

The present invention provides novel oxabicyclo acid compounds including stereoisomers, tautomers, pharmaceutically acceptable salts or solvates thereof, which are useful as antagonists against one or more of the lysophosphatidic acid (LPA) receptors, especially the LPA1 receptor.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts or solvates thereof.

The compounds of the invention may be used in the treatment of conditions in which LPA plays a role.

The compounds of the present invention may be used in therapy.

The compounds of the present invention may be used for the manufacture of a medicament for the treatment of a condition in which inhibition of the physiological activity of LPA is useful, such as diseases in which an LPA receptor participates, is involved in the etiology or pathology of the disease, or is otherwise associated with at least one symptom of the disease.

In another aspect, the present invention is directed to a method of treating fibrosis of organs (liver, kidney, lung, heart and the like as well as skin), liver diseases (acute hepatitis, chronic hepatitis, liver fibrosis, liver cirrhosis, portal hypertension, regenerative failure, non-alcoholic steatohepatitis (NASH), liver hypofunction, hepatic blood flow disorder, and the like), cell proliferative disease [cancer (solid tumor, solid tumor metastasis, vascular fibroma, myeloma, multiple myeloma, Kaposi's sarcoma, leukemia, chronic lymphocytic leukemia (CLL) and the like) and invasive metastasis of cancer cell, and the like], inflammatory disease (psoriasis, nephropathy, pneumonia and the like), gastrointestinal tract disease (irritable bowel syndrome (IBS), inflammatory bowel disease (IBD), abnormal pancreatic secretion, and the like), renal disease, urinary tract-associated disease (benign prostatic hyperplasia or symptoms associated with neuropathic bladder disease, spinal cord tumor, hernia of intervertebral disk, spinal canal stenosis, symptoms derived from diabetes, lower urinary tract disease (obstruction of lower urinary tract, and the like), inflammatory disease of lower urinary tract, dysuria, frequent urination, and the like), pancreas disease, abnormal angiogenesis-associated disease (arterial obstruction and the like), scleroderma, brain-associated disease (cerebral infarction, cerebral hemorrhage, and the like), neuropathic pain, peripheral neuropathy, and the like, ocular disease (age-related macular degeneration (AMD), diabetic retinopathy, proliferative vitreoretinopathy (PVR), cicatricial pemphigoid, glaucoma filtration surgery scarring, and the like).

In another aspect, the present invention is directed to a method of treating diseases, disorders, or conditions in which activation of at least one LPA receptor by LPA contributes to the symptomology or progression of the disease, disorder or condition. These diseases, disorders, or conditions may arise from one or more of a genetic, iatrogenic, immunological, infectious, metabolic, oncological, toxic, surgical, and/or traumatic etiology.

In another aspect, the present invention is directed to a method of treating renal fibrosis, pulmonary fibrosis, hepatic fibrosis, arterial fibrosis and systemic sclerosis comprising administering to a patient in need of such treatment a compound of the present invention as described above.

In one aspect, the present invention provides methods, compounds, pharmaceutical compositions, and medicaments described herein that comprise antagonists of LPA receptors, especially antagonists of LPA1.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF THE INVENTION

I. Compounds of the Invention

In a 1st aspect, the present invention provides, inter alia, a compound of Formula (Ia) or (Ib):

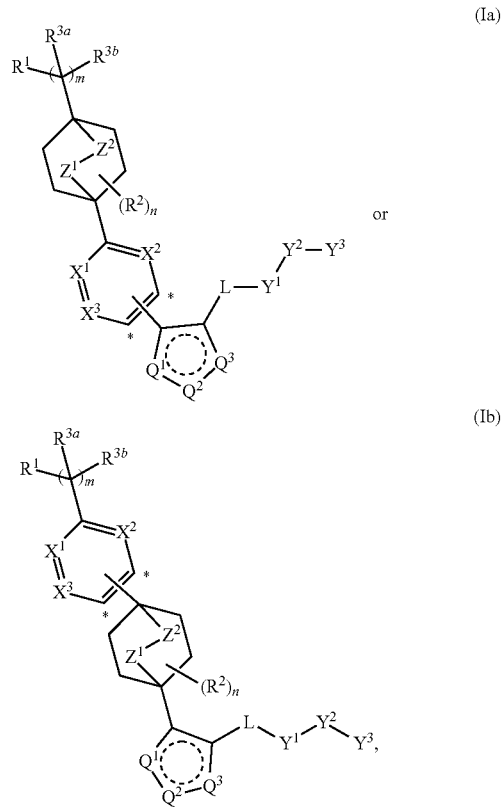

or a stereoisomer, tautomer, or pharmaceutically acceptable salt or solvate thereof, wherein:
one of $Z^1$ and $Z^2$ is O, and the other one is $CH_2$;
$X^1$, $X^2$, and $X^3$ are each independently $CR^6$ or N; provided that no more than two of $X^1$, $X^2$, or $X^3$ are N;
$Q^1$, $Q^2$, and $Q^3$ are independently N, O, $NR^{5a}$, or $CR^{5b}$, and the dashed circle denotes bonds forming an aromatic ring; provided that at least one of $Q^1$, $Q^2$, and $Q^3$ is not $CR^{5b}$;
the

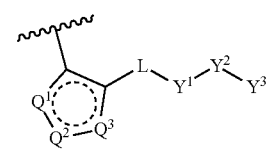

moiety is attached to one of the two asterisked (*) positions in Formula (Ia) or (Ib);
L is independently a covalent bond or $C_{1-4}$ alkylene substituted with 0 to 4 $R^9$;
$Y^1$ is independently O or $NR^7$;
$Y^2$ is independently or

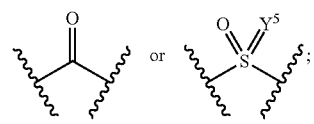

$Y^3$ is independently $OR^4$ or $NR^8R^4$, with the proviso that when $Y^1$ is O, then $Y^3$ is not $OR^4$;

$Y^5$ independently is O or NH;

$R^1$ is independently cyano, —C(O)OR$^{11}$, —C(O)NR$^{12}$R$^{12b}$,

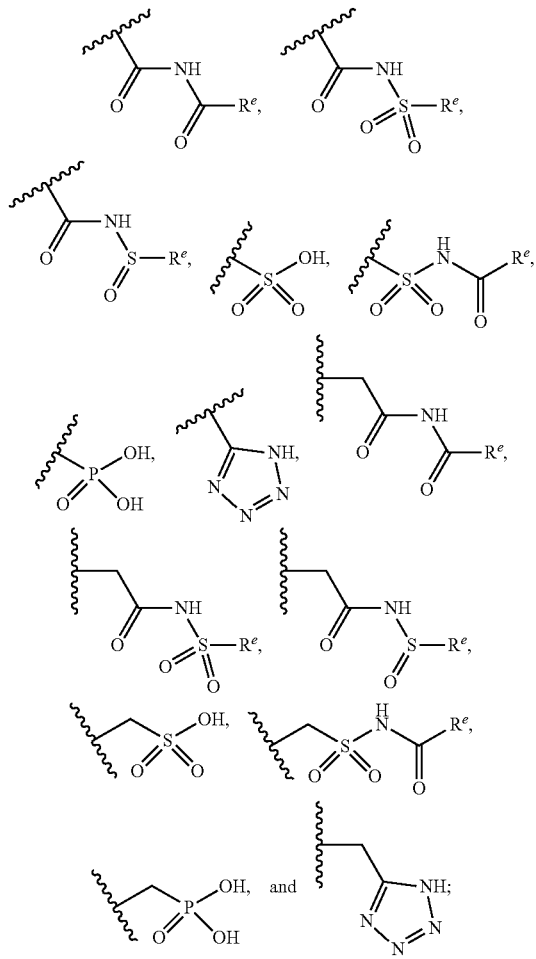

$R^2$ is each independently halo, cyano, hydroxyl, amino, $C_{1-4}$ alkoxy, $C_{1-4}$ haloalkyl, $C_{1-4}$ haloalkoxy, $C_{1-4}$ alkylamino, —(CH$_2$)$_{0-1}$—(C$_{3-6}$ cycloalkyl), —(CH$_2$)$_{0-1}$-phenyl, or $C_{1-6}$ alkyl substituted with 0 to 3 R$^c$;

$R^{3a}$ is independently hydrogen, halo, hydroxyl, or $C_{1-4}$ alkyl;

$R^{3b}$ is independently hydrogen, halo, cyano, hydroxyl, amino, $C_{1-4}$ alkyl, $C_{1-4}$ haloalkyl, $C_{1-4}$ alkoxy, $C_{1-4}$ haloalkoxy or $C_{1-6}$ alkyl substituted with 0 to 2 R$^a$;

or alternatively, $R^{3a}$ and $R^{3b}$ together, with the carbon atom they are attached to, form a $C_{3-4}$ carbocyclyl;

$R^4$ is -L$_1$-R$^{4a}$;

$L^1$ is independently a covalent bond or $C_{1-4}$ alkylene substituted with 0 to 4 R$^9$;

$R^{4a}$ is independently $C_{1-10}$ alkyl, $C_{1-10}$ haloalkyl, $C_{1-10}$ alkenyl, $C_{3-8}$ cycloalkyl, $C_{6-10}$ aryl, 3 to 8-membered heterocyclyl, 5 to 6-membered heteroaryl; wherein each of the alkyl, alkenyl, alkylene, cycloalkyl, aryl, heterocyclyl, and heteroaryl, by itself or as part of other moiety, is independently substituted with 0 to 3 R$^{10}$;

$R^{5a}$ is independently hydrogen, $C_{1-4}$ haloalkyl, —(CH$_2$)$_{0-1}$—(C$_{3-6}$ cycloalkyl), —(CH$_2$)$_{0-1}$-phenyl, or $C_{1-6}$ alkyl substituted with 0 to 3 R$^a$;

$R^{5b}$ is independently hydrogen, halo, cyano, hydroxyl, amino, $C_{1-4}$ alkoxy, $C_{1-4}$ haloalkyl, $C_{1-4}$ haloalkoxy, $C_{1-4}$ alkylamino, —(CH$_2$)$_{0-1}$—(C$_{3-6}$ cycloalkyl), —(CH$_2$)$_{0-1}$-phenyl, or $C_{1-6}$ alkyl substituted with 0 to 3 R$^b$;

$R^6$ is each independently hydrogen, halo, cyano, hydroxyl, amino, $C_{1-4}$ alkylamino, $C_{1-4}$ haloalkyl, $C_{1-4}$ alkoxy, $C_{1-4}$ haloalkoxy or $C_{1-6}$ alkyl substituted with 0 to 1 R$^b$;

$R^7$ and $R^8$ are each independently hydrogen, $C_{1-6}$ alkyl, $C_{1-4}$ haloalkyl, $C_{3-6}$ cycloalkyl or $C_{1-6}$ alkyl substituted with 0 to 1 R$^c$;

$R^9$ is each independently halo, oxo, cyano, hydroxyl, amino, $C_{1-4}$ haloalkyl, $C_{1-4}$ alkoxy, $C_{1-4}$ haloalkoxy, $C_{3-6}$ cycloalkyl, or $C_{1-6}$ alkyl substituted with 0 to 3 R$^a$;

$R^{10}$ is each independently halo, hydroxyl, amino, cyano, $C_{2-6}$ alkenyl, $C_{2-6}$ alkynyl, $C_{1-4}$ alkylamino, $C_{1-4}$ haloalkyl, $C_{1-4}$ alkoxy, $C_{1-4}$ haloalkoxy, phenyl, or 5 to 6 membered heteroaryl, $C_{1-6}$ alkyl substituted with 0 to 3 R$^b$;

$R^{11}$, $R^{12a}$ and $R^{12b}$ are each independently hydrogen, $C_{1-6}$ alkyl, $C_{3-6}$ cycloalkyl or benzyl;

$R^a$ is independently halo, cyano, hydroxyl, $C_{1-4}$ alkoxy, $C_{1-4}$ haloalkyl, or $C_{1-4}$ haloalkoxy;

$R^b$ is independently halo, cyano, hydroxyl, amino, $C_{1-4}$ alkoxy, $C_{1-4}$ haloalkyl, or $C_{1-4}$ haloalkoxy;

$R^c$ is independently $C_{1-4}$ haloalkyl, $C_{3-6}$ cycloalkyl, or $C_{1-6}$ alkyl substituted with 0 to 3 R$^a$;

m is an integer of 0, 1, or 2; and n is an integer of 0, 1, or 2.

In one embodiment of Formula (Ia) or (Ib), within the scope of the 1st aspect, wherein $X^1$, $X^2$, and $X^3$ are CR$^6$; where $R^6$ is hydrogen, halo or $C_{1-4}$ alkyl, e.g., methyl.

In a 2nd aspect, within the scope of the 1st aspect, wherein:
the

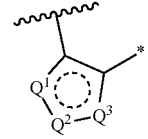

moiety is independently

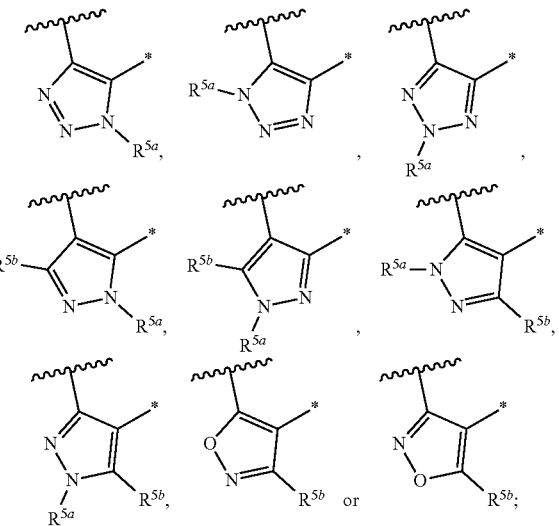

* denotes the attachment point to L; and $R^{5a}$ and $R^{5b}$ are the same as defined in Claim 1.

In a 3rd aspect, within the scope of the 1st or 2nd aspect, wherein:

the

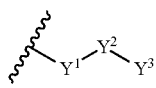

moiety is independently

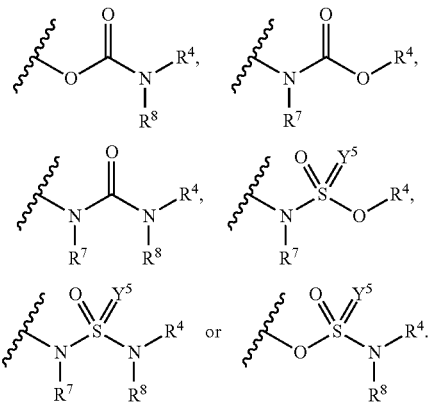

In a 4th aspect, within the scope of any of the 1st to 3rd aspects, wherein L is a covalent bond or $C_{1-2}$ alkylene.

In one embodiment of Formula (Ia) or (Ib), within the scope of any of the 1st to 3rd aspects, wherein L is a covalent bond or methylene.

In a 5th aspect, within the scope of any of the 1st to 4th aspects, wherein $X^1$, $X^2$, and $X^3$ are independently CH or $CR^{6a}$; or one of $X^1$, $X^2$, and $X^3$ is N, and the remaining ones are CH or $CR^{6a}$; and $R^{6a}$ is independently halo, hydroxyl, $C_{1-6}$ alkyl, $C_{1-4}$ haloalkyl, or $C_{1-4}$ alkoxy.

In a 6th aspect, within the scope of any of the 1st to 5th aspects, wherein $R^{3a}$ and $R^{3b}$ are independently hydrogen or $C_{1-4}$ alkyl.

In a 7th aspect, within the scope of any of the 1st to 6th aspects, wherein $R^1$ is $CO_2H$.

In an 8th aspect, within the scope of any of the 1st to 7th aspects, wherein:

the

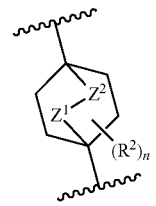

moiety is independently

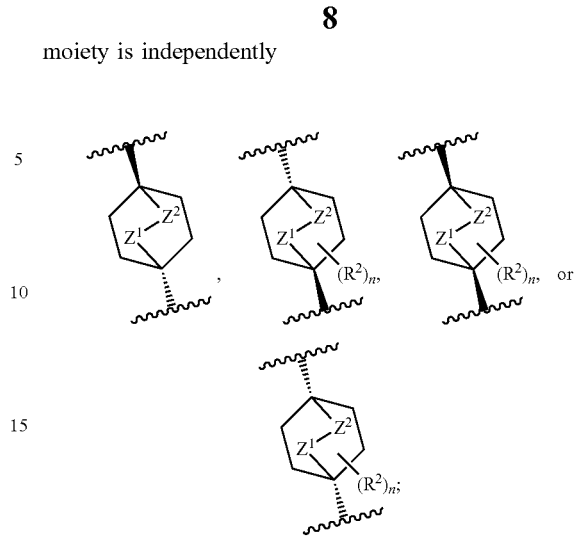

$-Z^1-Z^2-$ is $-O-CH_2-$ or $-CH_2-O-$; and n is 0.

In a 9th aspect, the present invention provides a compound of Formula (IIa) or (IIb):

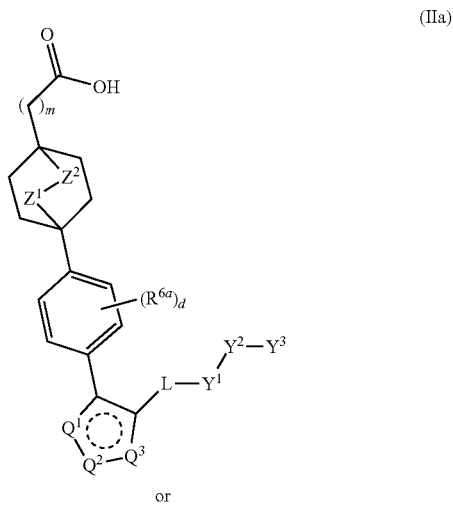

(IIa)

or

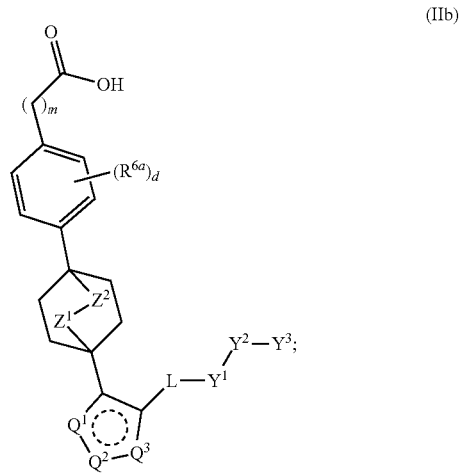

(IIb)

or a stereoisomer, tautomer, or pharmaceutically acceptable salt or solvate thereof, wherein:

$-Z^1-Z^2-$ is $-O-CH_2-$ or $-CH_2-O-$;

the

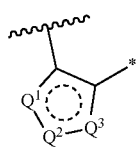

moiety is independently

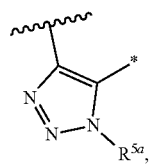 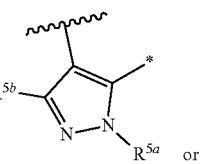 or 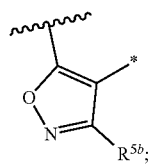;

m is an integer of 1 or 2;

* denotes the attachment point to L;

L is independently a covalent bond or $-CH_2-$;

the

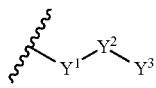

moiety is independently

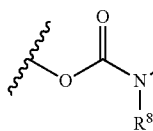 or 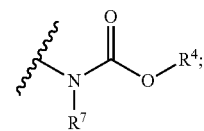;

$R^4$ is independently $C_{3-6}$ cycloalkyl, $-(CH_2)-C_{3-6}$ cycloalkyl, $-(CH(C_{1-2}$ alkyl))-$C_{3-6}$ cycloalkyl, $-(CH_2)$-phenyl or $-(CH(C_{1-2}$ alkyl))-phenyl, wherein each of said cycloalkyl and phenyl is independently substituted with 0 to 3 $R^{10}$;

$R^{5a}$ is independently $C_{1-6}$ alkyl, or $-CH_2-(C_{3-6}$ cycloalkyl);

$R^{5b}$ is independently hydrogen, halo, cyano, hydroxyl, $C_{1-4}$ alkyl, $C_{1-4}$ alkoxy, $C_{1-4}$ haloalkyl, or $C_{1-4}$ haloalkoxy;

$R^{6a}$ is each independently halo, hydroxyl, $C_{1-6}$ alkyl, $C_{1-4}$ haloalkyl, or $C_{1-4}$ alkoxy;

$R^7$ and $R^8$ are each independently hydrogen or $C_{1-2}$ alkyl;

$R^{10}$ is each independently halo, cyano, hydroxyl, $C_{1-6}$ alkyl, $C_{1-6}$ haloalkyl, $C_{1-6}$ alkoxy, or $C_{1-6}$ haloalkoxy; and d is independently 0, 1 or 2.

In a 10th aspect, within the scope of the 9th aspect, wherein:

the

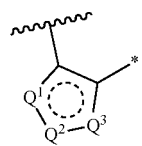

moiety is independently

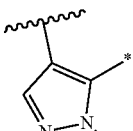 or 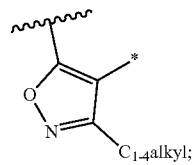;

m is an integer of 1; and $R^4$ is independently $-(CH_2)-C_{3-6}$ cycloalkyl, $-(CH(C_{1-2}$ alkyl))-$C_{3-6}$ cycloalkyl, $-(CH_2)$-phenyl or $-(CH(C_{1-2}$ alkyl))-phenyl, wherein each of said cycloalkyl and phenyl is independently substituted with 0 to 2 $R^{10}$.

In an 11th aspect, the present invention provides a compound of Formula (IIIa) or (IIIb):

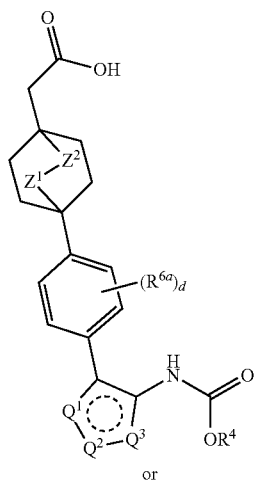

(IIIa)

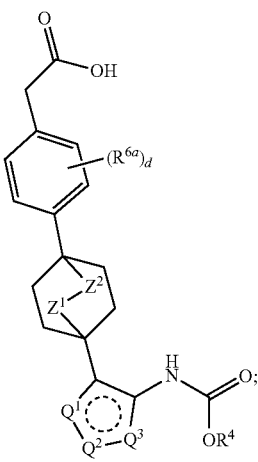

(IIIb)

wherein: —$Z^1$—$Z^2$— is —O—$CH_2$— or —$CH_2$—O—; the

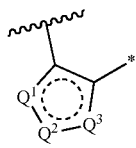

moiety is independently

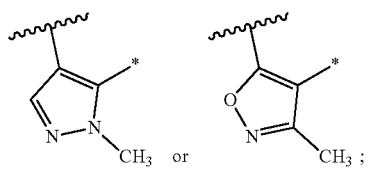

* denotes the attachment point to the nitrogen atom of —NH—C(O)—$OR^4$;
$R^4$ is independently —($CH_2$)-phenyl, or —(CH($CH_3$))-phenyl, wherein said phenyl is independently substituted with 0 to 2 $R^{10}$;
$R^{6a}$ is each independently halo or $C_{1-4}$ alkyl;
$R^{10}$ is each independently halo, cyano, hydroxyl, $C_{1-4}$ alkyl, $C_{1-4}$ haloalkyl, or $C_{1-4}$ alkoxy; and
d is independently 0 or 1.

In one embodiment of the present invention, the compound is selected from any one of the Examples as described in the specification, or a stereoisomer, a tautomer, or a pharmaceutically acceptable salt or solvate thereof.

In one embodiment, the compounds of the present invention have hLPA1 $EC_{50}$ values ≤5000 nM, using the LPA1 functional antagonist assay; in another embodiment, the compounds of the present invention have hLPA1 $EC_{50}$ values ≥1000 nM; in another embodiment, the compounds of the present invention have hLPA1 $EC_{50}$ values ≥500 nM; in another embodiment, the compounds of the present invention have hLPA1 $EC_{50}$ values ≤200 nM; in another embodiment, the compounds of the present invention have hLPA1 $EC_{50}$ values ≤100 nM; in another embodiment, the compounds of the present invention have hLPA1 $EC_{50}$ values ≤50 nM.

II. Other Embodiments of the Invention

In some embodiments, the compound of the present invention, or a pharmaceutically acceptable salt thereof, is an antagonist of at least one LPA receptor. In some embodiments, the compound of the present invention, or a pharmaceutically acceptable salt thereof, is an antagonist of $LPA_1$. In some embodiments, the compound of the present invention, or a pharmaceutically acceptable salt thereof, is an antagonist of $LPA_2$. In some embodiments, the compound of the present invention, or a pharmaceutically acceptable salt thereof, is an antagonist of $LPA_3$.

In some embodiments, presented herein are compounds selected from active metabolites, tautomers, pharmaceutically acceptable salts or solvates of a compound of the present invention.

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s).

In another embodiment, the present invention provides a method for the treatment of a condition associated with LPA receptor mediated fibrosis, comprising administering to a patient in need of such treatment a therapeutically effective amount of at least one of the compounds of the present invention or a stereoisomer, a tautomer, a pharmaceutically acceptable salt, or a solvate thereof. As used herein, the term "patient" encompasses all mammalian species.

In another embodiment, the present invention provides a method of treating a disease, disorder, or condition associated with dysregulation of lysophosphatidic acid receptor 1 (LPA1) in a patient in need thereof, comprising administering a therapeutically effective amount of a compound of the present invention, or a stereoisomer, a tautomer, or a pharmaceutically acceptable salt or solvate thereof, to the patient. In one embodiment of the method, the disease, disorder, or condition is related to pathological fibrosis, transplant rejection, cancer, osteoporosis, or inflammatory disorders. In one embodiment of the method, the pathological fibrosis is pulmonary, liver, renal, cardiac, dermal, ocular, or pancreatic fibrosis. In one embodiment of the method, the disease, disorder, or condition is idiopathic pulmonary fibrosis (IPF), non-alcoholic steatohepatitis (NASH), non-alcoholic fatty liver disease (NAFLD), chronic kidney disease, diabetic kidney disease, and systemic sclerosis. In one embodiment of the method, the cancer is of the bladder, blood, bone, brain, breast, central nervous system, cervix, colon, endometrium, esophagus, gall bladder, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid.

In another embodiment, the present invention provides a method of treating fibrosis in a mammal comprising administering a therapeutically effective amount of a compound of the present invention, or a stereoisomer, a tautomer, or a pharmaceutically acceptable salt or solvate thereof, to the mammal in need thereof. In one embodiment of the method, the fibrosis is idiopathic pulmonary fibrosis (IPF), nonalcoholic steatohepatitis (NASH), chronic kidney disease, diabetic kidney disease, and systemic sclerosis.

In another embodiment, the present invention provides a method of treating lung fibrosis (idiopathic pulmonary fibrosis), asthma, chronic obstructive pulmonary disease (COPD), renal fibrosis, acute kidney injury, chronic kidney disease, liver fibrosis (non-alcoholic steatohepatitis), skin fibrosis, fibrosis of the gut, breast cancer, pancreatic cancer, ovarian cancer, prostate cancer, glioblastoma, bone cancer, colon cancer, bowel cancer, head and neck cancer, melanoma, multiple myeloma, chronic lymphocytic leukemia, cancer pain, tumor metastasis, transplant organ rejection, scleroderma, ocular fibrosis, age related macular degeneration (AMD), diabetic retinopathy, collagen vascular disease, atherosclerosis, Raynaud's phenomenon, or neuropathic pain in a mammal comprising administering a therapeutically effective amount of a compound of the present invention, or a stereoisomer, a tautomer, or a pharmaceutically acceptable salt or solvate thereof, to the mammal in need thereof.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state. As used herein, "treating" or "treatment" also include the protective treatment of a disease state to reduce and/or minimize the risk and/or reduction in the risk of recurrence of a disease state by administering to a patient a therapeutically effective amount of at least one of the compounds of the present invention or a or a stereoisomer, a tautomer, a pharmaceutically acceptable salt, or a solvate thereof. Patients may be selected for such protective therapy based on factors that are known to increase risk of suffering a clinical disease state compared to the general population. For protective treatment, conditions of the clinical disease state may or may not be presented yet. The protective treatment can be divided into (a) primary prophylaxis and (b) secondary prophylaxis. Primary prophylaxis is defined as treatment to reduce or minimize the risk of a disease state in a patient that has not yet presented with a clinical disease state, whereas secondary prophylaxis is defined as minimizing or reducing the risk of a recurrence or second occurrence of the same or similar clinical disease state.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, *Pure and Applied Chemistry*, 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. While "alkyl" denotes a monovalent saturated aliphatic radical (such as ethyl), "alkylene" denotes a bivalent saturated aliphatic radical (such as ethylene). For example, "$C_1$ to $C_{10}$ alkyl" or "$C_{1-10}$ alkyl" is intended to include $C_1$, $C_2$, $C_3$, $C_4$, $C_5$, $C_6$, $C_7$, $C_8$, $C_9$, and $C_{10}$ alkyl groups. "$C_1$ to $C_{10}$ alkylene" or "$C_{1-10}$ alkylene", is intended to include $C_1$, $C_2$, $C_3$, $C_4$, $C_5$, $C_6$, $C_7$, $C_8$, $C_9$, and $C_{10}$ alkylene groups. Additionally, for example, "$C_1$ to $C_6$ alkyl" or "$C_{1-6}$ alkyl" denotes alkyl having 1 to 6 carbon atoms; and "$C_1$ to $C_6$ alkylene" or "$C_{1-6}$ alkylene" denotes alkylene having 1 to 6 carbon atoms; and "$C_1$ to $C_4$ alkyl" or "$C_{1-4}$ alkyl" denotes alkyl having 1 to 4 carbon atoms; and "$C_1$ to $C_4$ alkylene" or "$C_{1-4}$ alkylene" denotes alkylene having 1 to 4 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond. Furthermore, the term "alkyl", by itself or as part of another group, such as alkylamino, haloalkyl, hydroxyalkyl, aminoalkyl, alkoxy, alkoxyalkyl, haloalkoxy-alkyl, and haloalkoxy, can be an alkyl having 1 to 4 carbon atoms, or 1 to 6 carbon atoms, or 1 to 10 carbon atoms.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —$OCH_3$, etc.), an alkylamino (e.g., —$NHCH_3$, —$N(CH_3)_2$, etc.), or a thioalkyl group (e.g., —$SCH_3$). If a non-terminal carbon atom of the alkyl group which is not attached to the parent molecule is replaced with a heteroatom (e.g., O, N, or S) and the resulting heteroalkyl groups are, respectively, an alkyl ether (e.g., —$CH_2CH_2$—O—$CH_3$, etc.), an alkylaminoalkyl (e.g., —$CH_2NHCH_3$, —$CH_2N(CH_3)_2$, etc.), or a thioalkyl ether (e.g., —$CH_2$—S—$CH_3$). If a terminal carbon atom of the alkyl group is replaced with a heteroatom (e.g., O, N, or S), the resulting heteroalkyl groups are, respectively, a hydroxyalkyl group (e.g., —$CH_2CH_2$—OH), an aminoalkyl group (e.g., —$CH_2NH_2$), or an alkyl thiol group (e.g., —$CH_2CH_2$—SH). A heteroalkyl group can have, for example, 1 to 20 carbon atoms, 1 to 10 carbon atoms, or 1 to 6 carbon atoms. A $C_1$-$C_6$ heteroalkyl group means a heteroalkyl group having 1 to 6 carbon atoms.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

As used herein, "arylalkyl" (a.k.a. aralkyl), "heteroarylalkyl" "carbocyclylalkyl" or "heterocyclylalkyl" refers to an acyclic alkyl radical in which one of the hydrogen atoms bonded to a carbon atom, typically a terminal or $sp^3$ carbon atom, is replaced with an aryl, heteroaryl, carbocyclyl, or heterocyclyl radical, respectively. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl, heteroarylalkyl, carbocyclylalkyl, or heterocyclylalkyl group can comprise 4 to 20 carbon atoms and 0 to 5 heteroatoms, e.g., the alkyl moiety may contain 1 to 6 carbon atoms.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$. "Benzyl" can also be represented by formula "Bn".

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example, methyl-S— and ethyl-S—.

The term "alkanoyl" or "alkylcarbonyl" as used herein alone or as part of another group refers to alkyl linked to a carbonyl group. For example, alkylcarbonyl may be represented by alkyl-C(O)—. "$C_1$ to $C_6$ alkylcarbonyl" (or alkylcarbonyl), is intended to include $C_1$, $C_2$, $C_3$, $C_4$, $C_5$, and $C_6$ alkyl-C(O)— groups.

The term "alkylsulfonyl" or "sulfonamide" as used herein alone or as part of another group refers to alkyl or amino linked to a sulfonyl group. For example, alkylsulfonyl may be represented by —S(O)$_2$R', while sulfonamide may be represented by —S(O)$_2$NR$^c$R$^d$. R' is $C_1$ to $C_6$ alkyl; and R$^c$ and R$^d$ are the same as defined below for "amino".

The term "carbamate" as used herein alone or as part of another group refers to oxygen linked to an amido group. For example, carbamate may be represented by N(R$^c$R$^d$)—C(O)—O—, and R$^c$ and R$^d$ are the same as defined below for "amino".

The term "amido" as used herein alone or as part of another group refers to amino linked to a carbonyl group. For example, amido may be represented by N(R$^c$R$^d$)—C(O)—, and R$^c$ and R$^d$ are the same as defined below for "amino".

The term "amino" is defined as —NR$^{c1}$R$^{c2}$, wherein R$^{c1}$ and R$^{c2}$ are independently H or $C_{1-6}$ alkyl; or alternatively, R$^{c1}$ and R$^{c2}$, taken together with the atoms to which they are attached, form a 3- to 8-membered heterocyclic ring which is optionally substituted with one or more group selected from halo, cyano, hydroxyl, amino, oxo, $C_{1-6}$ alkyl, alkoxy, and aminoalkyl. When R$^{c1}$ or R$^{c2}$ (or both of them) is $C_{1-6}$ alkyl, the amino group can also be referred to as alkylamino. Examples of alkylamino group include, without limitation, methylamino, ethylamino, propylamino, isopropylamino and the like. In one embodiment, amino is —$NH_2$.

The term "aminoalkyl" refers to an alkyl group on which one of the hydrogen atoms is replaced by an amino group. For example, aminoalkyl may be represented by N(R$^{c1}$R$^2$)-alkylene-. "$C_1$ to $C_6$" or "$C_{1-6}$ aminoalkyl" (or aminoalkyl), is intended to include $C_1$, $C_2$, $C_3$, $C_4$, $C_5$, and $C_6$ aminoalkyl groups.

The term "halogen" or "halo" as used herein alone or as part of another group refers to chlorine, bromine, fluorine, and iodine, with chlorine or fluorine being preferred.

"Haloalkyl" is intended to include both branched and straight-chain saturated aliphatic hydrocarbon groups having the specified number of carbon atoms, substituted with one or more halogens. "$C_1$ to $C_6$ haloalkyl" or "$C_{1-6}$ haloalkyl" (or haloalkyl), is intended to include $C_1$, $C_2$, $C_3$, $C_4$, $C_5$, and $C_6$ haloalkyl groups. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms. The term "polyhaloalkyl" as used herein refers to an "alkyl" group as defined above which includes from 2 to 9, preferably from 2 to 5, halo substituents, such as F or Cl, preferably F, such as polyfluoroalkyl, for example, $CF_3CH_2$, $CF_3$ or $CF_3CF_2CH_2$.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—. The term "polyhaloalkyloxy" as used herein refers to an "alkoxy" or "alkyloxy" group as defined above which includes from 2 to 9, preferably from 2 to 5, halo substituents, such as F or Cl, preferably F, such as polyfluoroalkoxy, for example, $CF_3CH_2O$, $CF_3O$ or $CF_3CF_2CH_2O$.

"Hydroxyalkyl" is intended to include both branched and straight-chain saturated aliphatic hydrocarbon groups having the specified number of carbon atoms, substituted with 1 or more hydroxyl (OH). "$C_1$ to $C_6$ hydroxyalkyl" (or hydroxyalkyl), is intended to include $C_1$, $C_2$, $C_3$, $C_4$, $C_5$, and $C_6$ hydroxyalkyl groups.

The term "cycloalkyl" refers to cyclized alkyl groups, including mono-, bi- or poly-cyclic ring systems. "$C_3$ to $C_8$ cycloalkyl" or "$C_{3-8}$ cycloalkyl" is intended to include $C_3$, $C_4$, $C_5$, $C_6$, $C_7$, and $C_8$ cycloalkyl groups, including monocyclic, bicyclic, and polycyclic rings. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl and spiro and bridged cycloalkyl groups are included in the definition of "cycloalkyl".

The term "cycloheteroalkyl" refers to cyclized heteroalkyl groups, including mono-, bi- or poly-cyclic ring systems. "$C_3$ to $C_7$ cycloheteroalkyl" or "$C_{3-7}$ cycloheteroalkyl" is intended to include $C_3$, $C_4$, $C_5$, $C_6$, and $C_7$ cycloheteroalkyl groups. Example cycloheteroalkyl groups include, but are not limited to, oxetanyl, tetrahydrofuranyl, tetrahydropyranyl, azetidinyl, pyrrolidinyl, piperidinyl, morpholinyl, and piperazinyl. Branched cycloheteroalkyl groups, such as piperidinylmethyl, piperazinylmethyl, morpholinylmethyl, pyridinylmethyl, pyridizylmethyl, pyrimidylmethyl, and pyrazinylmethyl, are included in the definition of "cycloheteroalkyl".

As used herein, "carbocycle", "carbocyclyl" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocyclyl" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

Furthermore, the term "carbocyclyl", including "cycloalkyl" and "cycloalkenyl", as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons or 3 to 6 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

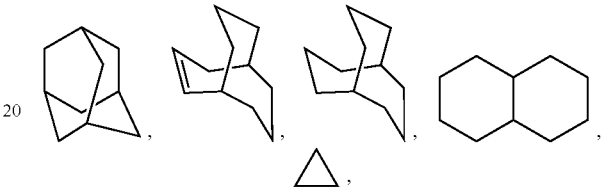

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, nitro, cyano, thiol and/or alkylthio and/or any of the alkyl substituents.

As used herein, the term "bicyclic carbocyclyl" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

As used herein, the term "aryl", as employed herein alone or as part of another group, refers to monocyclic or polycyclic (including bicyclic and tricyclic) aromatic hydrocarbons, including, for example, phenyl, naphthyl, anthracenyl, and phenanthranyl. Aryl moieties are well known and described, for example, in Lewis, R. J., ed., *Hawley's Condensed Chemical Dictionary,* 13th Edition, John Wiley & Sons, Inc., New York (1997). In one embodiment, the term "aryl" denotes monocyclic and bicyclic aromatic groups containing 6 to 10 carbons in the ring portion (such as phenyl or naphthyl including 1-naphthyl and 2-naphthyl). For example, "$C_6$ or $C_{10}$ aryl" or "$C_{6-10}$ aryl" refers to phenyl and naphthyl. Unless otherwise specified, "aryl", "$C_6$ or $C_{10}$ aryl", "$C_{6-10}$ aryl", or "aromatic residue" may be unsubstituted or substituted with 1 to 5 groups, preferably 1 to 3 groups, selected from OH, $OCH_3$, Cl, F, Br, I, CN, $NO_2$, $NH_2$, $N(CH_2)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, CF$_3$, OCF$_3$, C(=O)CH$_3$, SCH$_3$, S(=O)CH$_3$, S(=O)$_2$CH$_3$, CH$_3$, CH$_2$CH$_3$, CO$_2$H, and CO$_2$CH$_3$.

As used herein, the term "heterocycle", "heterocyclyl", or "heterocyclic group" is intended to mean a stable 3-, 4-, 5-, 6-, or 7-membered monocyclic or 5-, 6-, 7-, 8-, 9-, 10-, 11-, 12-, 13-, or 14-membered polycyclic (including bicyclic and tricyclic) heterocyclic ring that is saturated, or partially unsaturated, and that contains carbon atoms and 1, 2, 3 or 4 heteroatoms independently selected from N, O and S; and including any polycyclic group in which any of the above-defined heterocyclic rings is fused to a carbocyclic or an aryl (e.g., benzene) ring. That is, the term "heterocycle", "heterocyclyl", or "heterocyclic group" includes non-aromatic ring systems, such as heterocycloalkyl and heterocycloalkenyl. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. Examples of heterocyclyl include, without limitation, azetidinyl, piperazinyl, piperidinyl, piperidonyl, piperonyl, pyranyl, morpholinyl, tetrahydrofuranyl, tetrahydroisoquinolinyl, tetrahydroquinolinyl, morpholinyl, dihydrofuro[2,3-b]tetrahydrofuran.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1. Examples of a bicyclic heterocyclic group are, but not limited to, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

As used herein, the term "heteroaryl" is intended to mean stable monocyclic and polycyclic (including bicyclic and tricyclic) aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2).

Examples of heteroaryl also include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathianyl, phenoxazinyl, phthalazinyl, pteridinyl, purinyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Examples of 5- to 10-membered heteroaryl include, but are not limited to, pyridinyl, furanyl, thienyl, pyrazolyl, imidazolyl, imidazolidinyl, indolyl, tetrazolyl, isoxazolyl, oxazolyl, oxadiazolyl, oxazolidinyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl. Examples of 5- to 6-membered heteroaryl include, but are not limited to, pyridinyl, furanyl, thienyl, pyrrolyl, pyrazolyl, pyrazinyl, imidazolyl, imidazolidinyl, indolyl, tetrazolyl, isoxazolyl, oxazolyl, oxadiazolyl, oxazolidinyl, thiadiazinyl, thiadiazolyl, thiazolyl, triazinyl, and triazolyl. In some embodiments, the heteroaryl are selected from benzthiazolyl, imidazolpyridinyl, pyrrolopyridinyl, quinolinyl, and indolyl.

Unless otherwise indicated, "carbocyclyl" or "heterocyclyl" includes one to three additional rings fused to the carbocyclic ring or the heterocyclic ring (such as aryl, cycloalkyl, heteroaryl or cycloheteroalkyl rings), for example,

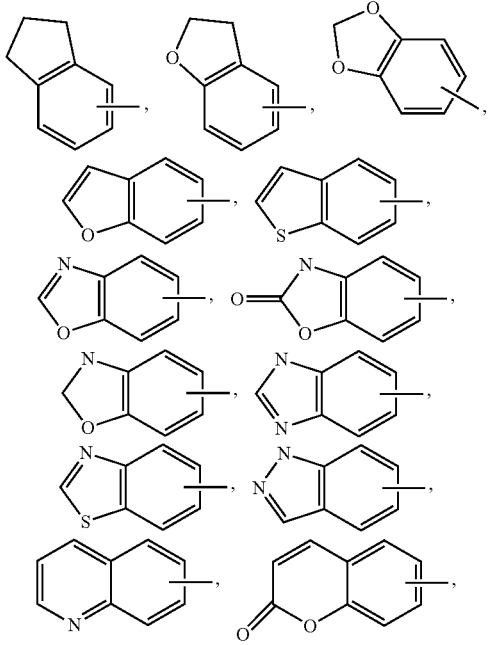

and may be optionally substituted through available carbon or nitrogen atoms (as applicable) with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino and arylsulfonaminocarbonyl and/or any of the alkyl substituents set out herein.

When any of the terms alkyl, alkenyl, alkynyl, cycloalkyl, carbocyclyl, heterocyclyl, aryl, and heteroaryl are used as part of another group, the number of carbon atoms and ring members are the same as those defined in the terms by themselves. For example, alkoxy, haloalkoxy, alkylamino, haloalkyl, hydroxyalkyl, aminoalkyl, haloalkoxy, alkoxyalkoxy, haloalkylamino, alkoxyalkylamino, haloalkoxyalkylamino, alkylthio, and the like each independently contains the number of carbon atoms which are the same as defined for the term "alkyl", such as 1 to 4 carbon atoms, 1 to 6 carbon atoms, 1 to 10 carbon atoms, etc. Similarly, cycloalkoxy, heterocyclyloxy, cycloalkylamino, heterocyclylamino, aralkylamino, arylamino, aryloxy, aralkyloxy, heteroaryloxy, heteroarylalkyloxy, and the like each independently contains ring members which are the same as defined for the terms "cycloalkyl", "heterocyclyl", "aryl", and "heteroaryl", such as 3 to 6-membered, 4 to 7-membered, 6 to 10-membered, 5 to 10-membered, 5 or 6-membered, etc.

In accordance with a convention used in the art, a bond pointing to a bold line, such as

as used in structural formulas herein, depicts the bond that is the point of attachment of the moiety or substituent to the core or backbone structure.

In accordance with a convention used in the art, a wavy or squiggly bond in a structural formula, such as

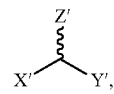

is used to depict a stereogenic center of the carbon atom to which X', Y', and Z' are attached and is intended to represent both enantiomers in a single figure. That is, a structural formula with such as wavy bond denotes each of the enantiomers individually, such as

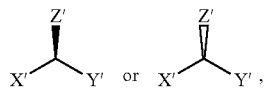

as well as a racemic mixture thereof. When a wavy or squiggly bond is attached to a double bond (such as C═C or C═N) moiety, it include cis- or trans- (or E- and Z-) geometric isomers or a mixture thereof.

It is understood herein that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3- or 4-pyridyl, the term "thienyl" means 2- or 3-thienyl, and so forth.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

One skilled in the art will recognize that substituents and other moieties of the compounds of the present invention should be selected in order to provide a compound which is sufficiently stable to provide a pharmaceutically useful compound which can be formulated into an acceptably stable pharmaceutical composition. Compounds of the present invention which have such stability are contemplated as falling within the scope of the present invention.

The term "counter ion" is used to represent a negatively charged species such as chloride, bromide, hydroxide, acetate, and sulfate. The term "metal ion" refers to alkali metal ions such as sodium, potassium or lithium and alkaline earth metal ions such as magnesium and calcium, as well as zinc and aluminum.

As referred to herein, the term "substituted" means that at least one hydrogen atom (attached to carbon atom or heteroatom) is replaced with a non-hydrogen group, provided that normal valencies are maintained and that the substitution results in a stable compound. When a substituent is oxo (i.e., =O), then 2 hydrogens on the atom are replaced. Oxo substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N). The term "substituted" in reference to alkyl, cycloalkyl, heteroalkyl, cycloheteroalkyl, alkylene, aryl, arylalkyl, heteroaryl, heteroarylalkyl, carbocyclyl, and heterocyclyl, means alkyl, cycloalkyl, heteroalkyl, cycloheteroalkyl, alkylene, aryl, arylalkyl, heteroaryl, heteroarylalkyl, carbocyclyl, and heterocyclyl, respectively, in which one or more hydrogen atoms, which are attached to either carbon or heteroatom, are each independently replaced with one or more non-hydrogen substituent(s).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0, 1, 2, or 3 R groups, then said group be unsubstituted when it is substituted with 0 R group, or be substituted with up to three R groups, and at each occurrence R is selected independently from the definition of R.

Also, combinations of substituents and/or variables are permissible only if such combinations result in stable compounds.

As used herein, the term "tautomer" refers to each of two or more isomers of a compound that exist together in equilibrium, and are readily interchanged by migration of an atom or group within the molecule For example, one skilled in the art would readily understand that a 1,2,3-triazole exists in two tautomeric forms as defined above:

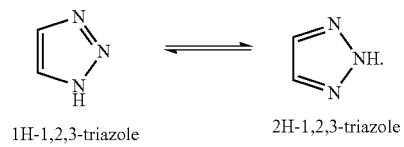

1H-1,2,3-triazole    2H-1,2,3-triazole

Thus, this disclosure is intended to cover all possible tautomers even when a structure depicts only one of them.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

The compounds of the present invention can be present as salts, which are also within the scope of this invention. Pharmaceutically acceptable salts are preferred. As used herein, "pharmaceutically acceptable salts" refer to derivatives of the disclosed compounds wherein the parent compound is modified by making acid or base salts thereof. The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, PA (1990), the disclosure of which is hereby incorporated by reference.

If the compounds of the present invention have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms, for example acetic acid, which are unsubstituted or substituted, for example, by halogen as chloroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of the present invention having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of the present invention, or their pharmaceutically acceptable salts, are also included.

Preferred salts of the compounds of the present invention which contain a basic group include monohydrochloride, hydrogensulfate, methanesulfonate, phosphate, nitrate or acetate.

Preferred salts of the compounds of the present invention which contain an acid group include sodium, potassium and magnesium salts and pharmaceutically acceptable organic amines.

In addition, compounds of the present invention may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:
 a) Bundgaard, H., ed., *Design of Prodrugs*, Elsevier (1985), and Widder, K. et al., eds., *Methods in Enzymology*, 112:309-396, Academic Press (1985);
 b) Bundgaard, H., Chapter 5, "Design and Application of Prodrugs", *A Textbook of Drug Design and Development*, pp. 113-191, Krosgaard-Larsen, P. et al., eds., Harwood Academic Publishers (1991);
 c) Bundgaard, H., *Adv. Drug Deliv. Rev.*, 8:1-38 (1992);
 d) Bundgaard, H. et al., *J. Pharm. Sci.*, 77:285 (1988); and
 e) Kakeya, N. et al., *Chem. Pharm. Bull.*, 32:692 (1984).

The compounds of the present invention contain a carboxy group which can form physiologically hydrolyzable esters that serve as prodrugs, i.e., "prodrug esters", by being hydrolyzed in the body to yield the compounds of the present invention per se. Examples of physiologically hydrolyzable esters of compounds of the present invention include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art. The "prodrug esters" can be formed by reacting the carboxylic acid moiety of the compounds of the present invention with either alkyl or aryl alcohol, halide, or sulfonate employing procedures known to those skilled in the art. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, CA (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Deuterium has one proton and one neutron in its nucleus and that has twice the mass of ordinary hydrogen. Deuterium can be represented by symbols such as "$^2H$" or "D". The term "deuterated" herein, by itself or used to modify a compound or group, refers to replacement of one or more hydrogen atom(s), which is attached to carbon(s), with a deuterium atom. Isotopes of carbon include $^{13}C$ and $^{14}C$.

Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example, when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "RBF" for round bottom flask, "atm" for atmosphere, "psi" for pounds per square inch, "conc." for concentrate, "RCM" for ring-closing metathesis, "sat" or "sat'd" for saturated, "SFC" for supercritical fluid chromatography "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "γ", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Boc or BOC tert-butyloxycarbonyl
$Boc_2O$ di-tert-butyl dicarbonate
AcOH or HOAc acetic acid
$AlCl_3$ aluminum trichloride
AIBN Azobis-isobutyronitrile
$BBr_3$ boron tribromide
$BCl_3$ boron trichloride BEMP 2-tert-butylimino-2-diethylamino-1,3-dimethylperhydro-1,3,2-diazaphosphorine
BOP reagent benzotriazol-1-yloxytris(dimethylamino)phosphonium hexafluorophosphate
Burgess reagent 1-methoxy-N-triethylammoniosulfonyl-methanimidate
CBz carbobenzyloxy
DCM or $CH_2Cl_2$ dichloromethane
$CH_3CN$ or ACN acetonitrile
$CDCl_3$ deutero-chloroform
$CHCl_3$ chloroform
mCPBA or m-CPBA meta-chloroperbenzoic acid
$Cs_2CO_3$ cesium carbonate
$Cu(OAc)_2$ copper (II) acetate
$Cy_2NMe$ N-cyclohexyl-N-methylcyclohexanamine
DBU 1,8-diazabicyclo[5.4.0]undec-7-ene
DCE 1,2 dichloroethane
DEA Diethylamine
DEAD Diethyl azodicarboxylate
Dess-Martin 1,1,1-tris(acetyloxy)-1,1-dihydro-1,2-benziodoxol-3-(1H)-one
DIAD Diisopropyl azodicarboxylate
DIBALH Diisobutyl aluminum hydride
DIC or DIPCDI diisopropylcarbodiimide
DIEA, DIPEA or diisopropylethylamine Hunig's base
DMAP 4-dimethylaminopyridine
DME 1,2-dimethoxyethane
DMF dimethyl formamide
DMSO dimethyl sulfoxide
cDNA complementary DNA
Dppp (R)-(+)-1,2-bis(diphenylphosphino)propane
DuPhos (+)-1,2-bis((2S,5S)-2,5-diethylphospholano)benzene
EDC N-(3-dimthylaminopropyl)-N'-ethylcarbodiimide
EDCI N-(3-dimthylaminopropyl)-N'-ethylcarbodiimide hydrochloride
EDTA ethylenediaminetetraacetic acid
(S,S)-EtDuPhosRh(I) (+)-1,2-bis((2S,5S)-2,5-diethylphospholano)benzene(1,5-cyclooctadiene)rhodium (I) trifluoromethanesulfonate
$Et_3N$ or TEA triethylamine
EtOAc ethyl acetate
$Et_2O$ diethyl ether
EtOH ethanol
GMF glass microfiber filter
Grubbs II (1,3-bis(2,4,6-trimethylphenyl)-2-imidazolidinylidene)dichloro (phenylmethylene)(tricyclohexylphosphine)ruthenium
HCl hydrochloric acid
HATU 0-(7-azabenzotriazol-1-yl)-N,N,N',N'-tetramethyluronium hexafluorophosphate
HEPES 4-(2-hydroxyethyl)piperaxine-1-ethanesulfonic acid
Hex hexane
HOBt or HOBT 1-hydroxybenzotriazole
$H_2O_2$ hydrogen peroxide
IBX 2-iodoxybenzoic acid
$H_2SO_4$ sulfuric acid
Jones reagent $CrO_3$ in aqueous $H_2SO_4$, 2 M solution
$K_2CO_3$ potassium carbonate
$K_2HPO_4$ potassium phosphate dibasic (potassium hydrogen phosphate)
KOAc potassium acetate
$K_3PO_4$ potassium phosphate tribasic
LAH lithium aluminum hydride
LG leaving group
LiOH lithium hydroxide
MeOH methanol
$MgSO_4$ magnesium sulfate
MsOH or MSA methylsulfonic acid/methanesulfonic acid
NaCl sodium chloride
NaH sodium hydride
$NaHCO_3$ sodium bicarbonate
$Na_2CO_3$ sodium carbonate
NaOH sodium hydroxide
$Na_2SO_3$ sodium sulfite
$Na_2SO_4$ sodium sulfate
NBS N-bromosuccinimide
NCS N-chlorosuccinimide
$NH_3$ ammonia
$NH_4Cl$ ammonium chloride
$NH_4OH$ ammonium hydroxide
$NH_4^+HCO_2^-$ ammonium formate
NMM N-methylmorpholine
OTf triflate or trifluoromethanesulfonate
$Pd_2(dba)_3$ tris(dibenzylideneacetone)dipalladium(O)
$Pd(OAc)_2$ palladium(II) acetate
Pd/C palladium on carbon
$Pd(dppf)Cl_2$ [1,1'-bis(diphenylphosphino)-ferrocene]dichloropalladium(II)
$Ph_3PCl_2$ triphenylphosphine dichloride
PG protecting group
$POCl_3$ phosphorus oxychloride
PPTS pyridinium p-toluenesulfonate
i-PrOH or IPA isopropanol
PS Polystyrene
RT or rt room temperature
SEM-Cl 2-(trimethylsilyl)ethoxymethyl chloride
$SiO_2$ silica oxide
$SnCl_2$ tin(II) chloride
TBAF tra-n-butylammonium fluoride
TBAI tetra-n-butylammonium iodide
TFA trifluoroacetic acid
THF tetrahydrofuran
THP tetrahydropyran
$TMSCHN_2$ Trimethylsilyldiazomethane
$TMSCH_2N_3$ Trimethylsilylmethyl azide
T3P propane phosphonic acid anhydride
TRIS tris (hydroxymethyl) aminomethane
pTsOH p-toluenesulfonic acid IV. Biology Lysophospholipids are membrane-derived bioactive lipid mediators. Lysophospholipids include, but are not limited to, lysophosphatidic acid (1-acyl-2-hydroxy-sn-glycero-3-phosphate; LPA), sphingosine 1-phosphate (SiP), lysophosphatidylcholine (LPC), and sphingosylphosphorylcholine (SPC). Lysophospholipids affect fundamental cellular functions that include cellular proliferation, differentiation, survival, migration, adhesion, invasion, and morphogenesis. These functions influence many biological processes that include neurogenesis, angiogenesis, wound healing, immunity, and carcinogenesis.

LPA acts through sets of specific G protein-coupled receptors (GPCRs) in an autocrine and paracrine fashion. LPA binding to its cognate GPCRs ($LPA_1$, $LPA_2$, $LPA_3$, $LPA_4$, $LPA_5$, $LPA_6$) activates intracellular signaling pathways to produce a variety of biological responses.

Lysophospholipids, such as LPA, are quantitatively minor lipid species compared to their major phospholipid counterparts (e.g., phosphatidylcholine, phosphatidylethanolamine, and sphingomyelin). LPA has a role as a biological effector molecule, and has a diverse range of physiological actions such as, but not limited to, effects on blood pressure, platelet activation, and smooth muscle contraction, and a variety of cellular effects, which include cell growth, cell rounding, neurite retraction, and actin stress fiber formation and cell migration. The effects of LPA are predominantly receptor mediated.

Activation of the LPA receptors ($LPA_1$, $LPA_2$, $LPA_3$, $LPA_4$, $LPA_5$, $LPA_6$) with LPA mediates a range of downstream signaling cascades. These include, but are not limited to, mitogen-activated protein kinase (MAPK) activation, adenylyl cyclase (AC) inhibition/activation, phospholipase C (PLC) activation/$Ca^{2+}$ mobilization, arachidonic acid release, Akt/PKB activation, and the activation of small GTPases, Rho, ROCK, Rac, and Ras. Other pathways that are affected by LPA receptor activation include, but are not limited to, cyclic adenosine monophosphate (cAMP), cell division cycle 42/GTP-binding protein (Cdc42), proto-oncogene serine/threonine-protein kinase Raf (c-RAF), proto-oncogene tyrosine-protein kinase Src (c-src), extracellular signal-regulated kinase (ERK), focal adhesion kinase (FAK), guanine nucleotide exchange factor (GEF), glycogen synthase kinase 3b (GSK3b), c-jun amino-terminal kinase (JNK), MEK, myosin light chain II (MLC II), nuclear factor kB (NF-kB), N-methyl-D-aspartate (NMDA) receptor activation, phosphatidylinositol 3-kinase (PI3K), protein kinase A (PKA), protein kinase C (PKC), ras-related C3 botulinum toxin substrate 1 (RAC1). The actual pathway and realized end point are dependent on a range of variables that include receptor usage, cell type, expression level of a receptor or signaling protein, and LPA concentration. Nearly all mammalian cells, tissues and organs co-express several LPA-receptor subtypes, which indicates that LPA receptors signal in a cooperative manner. $LPA_1$, $LPA_2$, and $LPA_3$ share high amino acid sequence similarity.

LPA is produced from activated platelets, activated adipocytes, neuronal cells, and other cell types. Serum LPA is produced by multiple enzymatic pathways that involve monoacylglycerol kinase, phospholipase $A_1$, secretory phospholipase $A_2$, and lysophospholipase D (lysoPLD), including autotaxin. Several enzymes are involved in LPA degradation: lysophospholipase, lipid phosphate phosphatase, and LPA acyl transferase such as endophilin. LPA concentrations in human serum are estimated to be 1-5 μM. Serum LPA is bound to albumin, low-density lipoproteins, or other proteins, which possibly protect LPA from rapid degradation. LPA molecular species with different acyl chain lengths and saturation are naturally occurring, including 1-palmitoyl (16:0), 1-palmitoleoyl (16:1), 1-stearoyl (18:0), 1-oleoyl (18:1), 1-linoleoyl (18:2), and 1-arachidonoyl (20:4) LPA. Quantitatively minor alkyl LPA has biological activities similar to acyl LPA, and different LPA species activate LPA receptor subtypes with varied efficacies.

LPA Receptors $LPA_1$ (previously called VZG-1/EDG-2/mrec1.3) couples with three types of G proteins, $G_{i/o}$, $G_q$, and $G_{12/13}$. Through activation of these G proteins, LPA induces a range of cellular responses through $LPA_1$ including but not limited to: cell proliferation, serum-response element (SRE) activation, mitogen-activated protein kinase (MAPK) activation, adenylyl cyclase (AC) inhibition, phospholipase C (PLC) activation, $Ca^{2+}$ mobilization, Akt activation, and Rho activation.

Wide expression of $LPA_1$ is observed in adult mice, with clear presence in testis, brain, heart, lung, small intestine, stomach, spleen, thymus, and skeletal muscle. Similarly, human tissues also express $LPA_1$; it is present in brain, heart, lung, placenta, colon, small intestine, prostate, testis, ovary, pancreas, spleen, kidney, skeletal muscle, and thymus.

$LPA_2$ (EDG-4) also couples with three types of G proteins, $G_{i/o}$, $G_q$, and $G_{12/13}$, to mediate LPA-induced cellular signaling. Expression of $LPA_2$ is observed in the testis, kidney, lung, thymus, spleen, and stomach of adult mice and in the human testis, pancreas, prostate, thymus, spleen, and peripheral blood leukocytes. Expression of $LPA_2$ is upregulated in various cancer cell lines, and several human $LPA_2$ transcriptional variants with mutations in the 3-untranslated region have been observed. Targeted deletion of $LPA_2$ in mice has not shown any obvious phenotypic abnormalities, but has demonstrated a significant loss of normal LPA signaling (e.g., PLC activation, $Ca^{2+}$ mobilization, and stress fiber formation) in primary cultures of mouse embryonic fibroblasts (MEFs). Creation of lpa1 (−/−) lpa2 (−/−) double-null mice has revealed that many LPA-induced responses, which include cell proliferation, AC inhibition, PLC activation, $Ca^{2+}$ mobilization, JNK and Akt activation, and stress fiber formation, are absent or severely reduced in double-null MEFs. All these responses, except for AC inhibition (AC inhibition is nearly abolished in $LPA_1$ (−/−) MEFs), are only partially affected in either $LPA_1$ (−/−) or $LPA_2$ (−/−) MEFs. $LPA_2$ contributes to normal LPA-mediated signaling responses in at least some cell types (Choi et al, *Biochemica et Biophysica Acta* 2008, 1781, p531-539).

$LPA_3$ (EDG-7) is distinct from $LPA_1$ and $LPA_2$ in its ability to couple with Goo and $G_q$ but not $G_{12/13}$ and is much less responsive to LPA species with saturated acyl chains. $LPA_3$ can mediate pleiotropic LPA-induced signaling that includes PLC activation, $Ca^{2+}$ mobilization, AC inhibition/activation, and MAPK activation. Overexpression of $LPA_3$ in neuroblastoma cells leads to neurite elongation, whereas that of $LPA_1$ or $LPA_2$ results in neurite retraction and cell rounding when stimulated with LPA. Expression of $LPA_3$ is observed in adult mouse testis, kidney, lung, small intestine, heart, thymus, and brain. In humans, it is found in the heart, pancreas, prostate, testis, lung, ovary, and brain (frontal cortex, hippocampus, and amygdala).

$LPA_4$ ($p2y_9$/GPR23) is of divergent sequence compared to $LPA_1$, $LPA_2$, and $LPA_3$ with closer similarity to the platelet-activating factor (PAF) receptor. $LPA_4$ mediates LPA induced $Ca^{2+}$ mobilization and cAMP accumulation, and functional coupling to the G protein Gs for AC activation, as well as coupling to other G proteins. The $LPA_4$ gene is expressed in the ovary, pancreas, thymus, kidney and skeletal muscle.

$LPA_5$ (GPR92) is a member of the purinocluster of GPCRs and is structurally most closely related to $LPA_4$. $LPA_5$ is expressed in human heart, placenta, spleen, brain, lung and gut. $LPA_5$ also shows very high expression in the CD8+ lymphocyte compartment of the gastrointestinal tract.

$LPA_6$ (p2y5) is a member of the purinocluster of GPCRs and is structurally most closely related to $LPA_4$. $LPA_6$ is an LPA receptor coupled to the $G_{12/13}$-Rho signaling pathways and is expressed in the inner root sheaths of human hair follicles.

Illustrative Biological Activity

Wound Healing

Normal wound healing occurs by a highly coordinated sequence of events in which cellular, soluble factors and matrix components act in concert to repair the injury. The healing response can be described as taking place in four broad, overlapping phases—hemostasis, inflammation, proliferation, and remodeling. Many growth factors and cytokines are released into a wound site to initiate and perpetuate wound healing processes.

When wounded, damaged blood vessels activate platelets. The activated platelets play pivotal roles in subsequent repair processes by releasing bioactive mediators to induce cell proliferation, cell migration, blood coagulation, and angiogenesis. LPA is one such mediator that is released from activated platelets; this induces platelet aggregation along with mitogenic/migration effects on the surrounding cells, such as endothelial cells, smooth muscle cells, fibroblasts, and keratinocytes.

Topical application of LPA to cutaneous wounds in mice promotes repair processes (wound closure and increased neoepithelial thickness) by increasing cell proliferation/migration without affecting secondary inflammation.

Activation of dermal fibroblasts by growth factors and cytokines leads to their subsequent migration from the edges of the wound into the provisional matrix formed by the fibrin clot whereupon the fibroblasts proliferate and start to restore the dermis by secreting and organizing the characteristic dermal extracellular matrix (ECM). The increasing number of fibroblasts within the wound and continuous precipitation of ECM enhances matrix rigidity by applying small tractional forces to the newly formed granulation tissue. The increase in mechanical stress, in conjunction with transforming growth factor β (TGFβ), induces α-smooth muscle actin (α-SMA) expression and the subsequent transformation of fibroblasts into myofibroblasts. Myofibroblasts facilitate granulation tissue remodeling via myofibroblast contraction and through the production of ECM components.

LPA regulates many important functions of fibroblasts in wound healing, including proliferation, migration, differentiation and contraction. Fibroblast proliferation is required in wound healing in order to fill an open wound. In contrast, fibrosis is characterized by intense proliferation and accumulation of myofibroblasts that actively synthesize ECM and proinflammatory cytokines. LPA can either increase or suppress the proliferation of cell types important in wound healing, such as epithelial and endothelial cells (EC), macrophages, keratinocytes, and fibroblasts. A role for $LPA_1$ in LPA-induced proliferation was provided by the observation that LPA-stimulated proliferation of fibroblasts isolated from $LPA_1$ receptor null mice was attenuated (Mills et al, Nat Rev. Cancer 2003; 3: 582-591). LPA induces cytoskeletal changes that are integral to fibroblast adhesion, migration, differentiation and contraction.

Fibrosis

Tissue injury initiates a complex series of host wound-healing responses; if successful, these responses restore normal tissue structure and function. If not, these responses can lead to tissue fibrosis and loss of function.

For the majority of organs and tissues the development of fibrosis involves a multitude of events and factors. Molecules involved in the development of fibrosis include proteins or peptides (profibrotic cytokines, chemokines, metalloproteinases etc.) and phospholipids. Phospholipids involved in the development of fibrosis include platelet activating factor (PAF), phosphatidyl choline, sphingosine-1 phosphate (SiP) and lysophosphatidic acid (LPA).

A number of muscular dystrophies are characterized by a progressive weakness and wasting of musculature, and by extensive fibrosis. It has been shown that LPA treatment of cultured myoblasts induced significant expression of connective tissue growth factor (CTGF). CTGF subsequently induces collagen, fibronectin and integrin expression and induces dedifferentiation of these myoblasts. Treatment of a variety of cell types with LPA induces reproducible and high level induction of CTGF (J. P. Pradere, et al., $LPA_1$ receptor activation promotes renal interstitial fibrosis, J. Am. Soc. Nephrol. 18 (2007) 3110-3118; N. Wiedmaier, et al., Int J Med Microbiol; 298(3-4):231-43, 2008). CTGF is a profibrotic cytokine, signaling down-stream and in parallel with TGFβ.

CTGF expression by gingival epithelial cells, which are involved in the development of gingival fibromatosis, was found to be exacerbated by LPA treatment (A. Kantarci, et al., J. Pathol. 210 (2006) 59-66).

LPA is associated with the progression of liver fibrosis. In vitro, LPA induces stellate cell and hepatocyte proliferation. These activated cells are the main cell type responsible for the accumulation of ECM in the liver. Furthermore, LPA plasma levels rise during $CCl_4$-induced liver fibrosis in rodents, or in hepatitis C virus-induced liver fibrosis in humans (N. Watanabe, et al., Plasma lysophosphatidic acid level and serum autotaxin activity are increased in liver injury in rats in relation to its severity, Life Sci. 81 (2007) 1009-1015; N. Watanabe, et al., J. Clin. Gastroenterol. 41 (2007) 616-623).

An increase of phospholipid concentrations in the bronchoalveolar lavage fluid in rabbits and rodents injected with bleomycin has been reported (K. Kuroda, et al., Phospholipid concentration in lung lavage fluid as biomarker for pulmonary fibrosis, Inhal. Toxicol. 18 (2006) 389-393; K. Yasuda, et al., Lung 172 (1994) 91-102).

LPA is associated with heart disease and myocardial remodeling. Serum LPA levels are increased after myocardial infarction in patients and LPA stimulates rat cardiac fibroblast proliferation and collagen production (Chen et al. FEBS Lett. 2006 Aug. 21; 580(19):4737-45).

Pulmonary Fibrosis

In the lung, aberrant wound healing responses to injury contribute to the pathogenesis of fibrotic lung diseases. Fibrotic lung diseases, such as idiopathic pulmonary fibrosis (IPF), are associated with high morbidity and mortality.

LPA is an important mediator of fibroblast recruitment in pulmonary fibrosis. LPA and $LPA_1$ play key pathogenic roles in pulmonary fibrosis. Fibroblast chemoattractant activity plays an important role in the lungs in patients with pulmonary fibrosis. Profibrotic effects of $LPA_1$-receptor stimulation is explained by $LPA_1$-receptor-mediated vascular leakage and increased fibroblast recruitment, both profibrotic events. The LPA-$LPA_1$ pathway has a role in mediating fibroblast migration and vascular leakage in IPF. The end result is the aberrant healing process that characterizes this fibrotic condition.

The $LPA_1$ receptor is the LPA receptor most highly expressed on fibroblasts obtained from patients with IPF. Furthermore, BAL obtained from IPF patients induced chemotaxis of human foetal lung fibroblasts that was blocked by the dual $LPA_1$-$LPA_3$ receptor antagonist Ki16425. In an experimental bleomycin-induced lung injury mouse model, it was shown that LPA levels were high in bronchoalveolar lavage samples compared with unexposed controls. $LPA_1$ knockout mice are protected from fibrosis after bleomycin challenge with reduced fibroblast accumulation and vascular leakage. In human subjects with IPF, high LPA levels were observed in bronchoalveolar lavage samples compared with healthy controls. Increased fibroblast chemotactic activity in these samples was inhibited by the Ki16425 indicating that fibroblast migration is mediated by the LPA-LPA receptor(s) pathway (Tager et al. Nature Medicine, 2008, 14, 45-54).

The LPA-$LPA_1$ pathway is crucial in fibroblast recruitment and vascular leakage in pulmonary fibrosis.

Activation of latent TGF-β by the αvβ6 integrin plays a critical role in the development of lung injury and fibrosis (Munger et al. *Cell*, vol. 96, 319-328, 1999). LPA induces αvβ6-mediated TGF-β activation on human lung epithelial cells (Xu et al. *Am. J. Pathology*, 2009, 174, 1264-1279). The LPA-induced αvβ6-mediated TGF-β activation is mediated by the LPA2 receptor. Expression of the LPA2 receptor is increased in epithelial cells and mesenchymal cells in areas of lung fibrosis from IPF patients compared to normal human lung tissue. The LPA-LPA2 pathway contributes to the activation of the TGF-β pathway in pulmonary fibrosis. In some embodiments, compounds that inhibit LPA2 show efficacy in the treatment of lung fibrosis. In some embodiments, compounds that inhibit both LPA1 and LPA2 show improved efficacy in the treatment of lung fibrosis compared to compounds which inhibit only LPA1 or LPA2.

Renal Fibrosis

LPA and $LPA_1$ are involved in the etiology of kidney fibrosis. LPA has effects on both proliferation and contraction of glomerular mesangial cells and thus has been implicated in proliferative glomerulonephritis (C. N. Inoue, et al., *Clin. Sci.* (Colch.) 1999, 96, 431-436). In an animal model of renal fibrosis [unilateral ureteral obstruction (UUO)], it was found that renal LPA receptors are expressed under basal conditions with an expression order of $LPA_2 > LPA_3 = LPA_1 \gg LPA_4$. This model mimics in an accelerated manner the development of renal fibrosis including renal inflammation, fibroblast activation and accumulation of extracellular matrix in the tubulointerstitium. UUO significantly induced LPA1-receptor expression. This was paralleled by renal LPA production (3.3 fold increase) in conditioned media from kidney explants. Contra-lateral kidneys exhibited no significant changes in LPA release and LPA-receptors expression. This shows that a prerequisite for an action of LPA in fibrosis is met: production of a ligand (LPA) and induction of one of its receptors (the $LPA_1$ receptor) (J. P. Pradere et al., *Biochimica et Biophysica Acta*, 2008, 1781, 582-587).

In mice where the $LPA_1$ receptor was knocked out ($LPA_1$ (−/−), the development of renal fibrosis was significantly attenuated. UUO mice treated with the LPA receptor antagonist Ki16425 closely resembled the profile of $LPA_1$ (−/−) mice.

LPA can participate in intraperitoneal accumulation of monocyte/macrophages and LPA can induce expression of the profibrotic cytokine CTGF in primary cultures of human fibroblasts (J. S. Koh, et al., *J. Clin. Invest.*, 1998, 102, 716-727).

LPA treatment of a mouse epithelial renal cell line, MCT, induced a rapid increase in the expression of the profibrotic cytokine CTGF. CTGF plays a crucial role in UUO-induced tubulointerstitial fibrosis (TIF), and is involved in the profibrotic activity of TGFβ. This induction was almost completely suppressed by co-treatment with the LPA-receptor antagonist Ki16425. In one aspect, the profibrotic activity of LPA in kidney results from a direct action of LPA on kidney cells involving induction of CTGF.

Hepatic Fibrosis

LPA is implicated in liver disease and fibrosis. Plasma LPA levels and serum autotaxin (enzyme responsible for LPA production) are elevated in hepatitis patients and animal models of liver injury in correlation with increased fibrosis. LPA also regulates liver cell function. $LPA_1$ and $LPA_2$ receptors are expressed by mouse hepatic stellate cells and LPA stimulates migration of hepatic myofibroblasts.

Ocular Fibrosis

LPA is in involved in wound healing in the eye. $LPA_1$ and $LPA_3$ receptors are detectable in the normal rabbit corneal epithelial cells, keratocytes and endothelial cells and $LPA_1$ and $LPA_3$ expression are increased in corneal epithelial cells following injury.

LPA and its homologues are present in the aqueous humor and the lacrimal gland fluid of the rabbit eye and these levels are increased in a rabbit corneal injury model.

LPA induces actin stress fiber formation in rabbit corneal endothelial and epithelial cells and promotes contraction corneal fibroblasts. LPA also stimulates proliferation of human retinal pigmented epithelial cells Cardiac Fibrosis LPA is implicated in myocardial infarction and cardiac fibrosis. Serum LPA levels are increased in patients following myocardial infarction (MI) and LPA stimulates proliferation and collagen production (fibrosis) by rat cardiac fibroblasts. Both LPA1 and LPA3 receptors are highly expressed in human heart tissue.

Treatment of Fibrosis

In one aspect, a compound of the present invention, or a pharmaceutically acceptable salt thereof, is used to treat or prevent fibrosis in a mammal. In one aspect, a compound of Formulas (I), or a pharmaceutically acceptable salt thereof, is used to treat fibrosis of an organ or tissue in a mammal. In one aspect is a method for preventing a fibrosis condition in a mammal, the method comprising administering to the mammal at risk of developing one or more fibrosis conditions a therapeutically effective amount of a compound of Formulas (I), or a pharmaceutically acceptable salt thereof. In one aspect, the mammal has been exposed to one or more environmental conditions that are known to increase the risk of fibrosis of an organ or tissue. In one aspect, the mammal has been exposed to one or more environmental conditions that are known to increase the risk of lung, liver or kidney fibrosis. In one aspect, the mammal has a genetic predisposition of developing fibrosis of an organ or tissue. In one aspect, a compound of the present invention, or a pharmaceutically acceptable salt thereof, is administered to a mammal to prevent or minimize scarring following injury. In one aspect, injury includes surgery.

The terms "fibrosis" or "fibrosing disorder," as used herein, refers to conditions that are associated with the abnormal accumulation of cells and/or fibronectin and/or collagen and/or increased fibroblast recruitment and include but are not limited to fibrosis of individual organs or tissues such as the heart, kidney, liver, joints, lung, pleural tissue, peritoneal tissue, skin, cornea, retina, musculoskeletal and digestive tract.

Exemplary diseases, disorders, or conditions that involve fibrosis include, but are not limited to: Lung diseases associated with fibrosis, e.g., idiopathic pulmonary fibrosis, pulmonary fibrosis secondary to systemic inflammatory disease such as rheumatoid arthritis, scleroderma, lupus, cryptogenic fibrosing alveolitis, radiation induced fibrosis, chronic obstructive pulmonary disease (COPD), scleroderma, chronic asthma, silicosis, asbestos induced pulmonary or pleural fibrosis, acute lung injury and acute respiratory distress (including bacterial pneumonia induced, trauma induced, viral pneumonia induced, ventilator induced, non-pulmonary sepsis induced, and aspiration induced); Chronic nephropathies associated with injury/fibrosis (kidney fibrosis), e.g., glomerulonephritis secondary to systemic inflammatory diseases such as lupus and scleroderma, diabetes, glomerular nephritis, focal segmental glomerular sclerosis, IgA nephropathy, hypertension, allograft and Alport; Gut fibrosis, e.g., scleroderma, and radiation induced gut fibrosis; Liver fibrosis, e.g., cirrhosis, alcohol induced liver fibrosis, nonalcoholic steatohepatitis (NASH), biliary duct injury, primary biliary cirrhosis, infection or viral induced liver fibrosis (e.g., chronic HCV infection), and autoimmune hepatitis; Head and neck fibrosis, e.g., radiation induced; Corneal scarring, e.g., LASIK (laser-assisted in situ keratomileusis), corneal transplant, and trabeculectomy; Hypertrophic scarring and keloids, e.g., burn induced or surgical; and other fibrotic diseases, e.g., sarcoidosis, scleroderma, spinal cord injury/fibrosis, myelofibrosis, vascular restenosis, atherosclerosis, arteriosclerosis, Wegener's granulomatosis, mixed connective tissue disease, and Peyronie's disease.

In one aspect, a mammal suffering from one of the following non-limiting exemplary diseases, disorders, or conditions will benefit from therapy with a compound of the present invention, or a pharmaceutically acceptable salt thereof: atherosclerosis, thrombosis, heart disease, vasculitis, formation of scar tissue, restenosis, phlebitis, COPD (chronic obstructive pulmonary disease), pulmonary hypertension, pulmonary fibrosis, pulmonary inflammation, bowel adhesions, bladder fibrosis and cystitis, fibrosis of the nasal passages, sinusitis, inflammation mediated by neutrophils, and fibrosis mediated by fibroblasts.

In one aspect, a compound of the present invention, or a pharmaceutically acceptable salt thereof, is administered to a mammal with fibrosis of an organ or tissue or with a predisposition of developing fibrosis of an organ or tissue with one or more other agents that are used to treat fibrosis. In one aspect, the one or more agents include corticosteroids. In one aspect, the one or more agents include immunosuppressants. In one aspect, the one or more agents include B-cell antagonists. In one aspect, the one or more agents include uteroglobin.

In one aspect, a compound of the present invention, or a pharmaceutically acceptable salt thereof, is used to treat a dermatological disorders in a mammal. The term "dermatological disorder," as used herein refers to a skin disorder. Such dermatological disorders include, but are not limited to, proliferative or inflammatory disorders of the skin such as, atopic dermatitis, bullous disorders, collagenoses, psoriasis, scleroderma, psoriatic lesions, dermatitis, contact dermatitis, eczema, urticaria, rosacea, wound healing, scarring, hypertrophic scarring, keloids, Kawasaki Disease, rosacea, Sjogren-Larsso Syndrome, urticaria. In one aspect, a compound of the present invention, or a pharmaceutically acceptable salt thereof, is used to treat systemic sclerosis.

Pain

Since LPA is released following tissue injury, $LPA_1$ plays an important role in the initiation of neuropathic pain. $LPA_1$, unlike $LPA_2$ or $LPA_3$, is expressed in both dorsal root ganglion (DRG) and dorsal root neurons. Using the antisense oligodeoxynucleotide (AS-ODN) for $LPA_1$ and $LPA_1$-null mice, it was found that LPA-induced mechanical allodynia and hyperalgesia is mediated in an $LPA_1$-dependent manner. $LPA_1$ and downstream Rho-ROCK activation play a role in the initiation of neuropathic pain signaling. Pretreatment with *Clostridium botulinum* C3 exoenzyme (BoTXC3, Rho inhibitor) or Y-27632 (ROCK inhibitor) completely abolished the allodynia and hyperalgesia in nerve-injured mice. LPA also induced demyelination of the dorsal root, which was prevented by BoTXC3. The dorsal root demyelination by injury was not observed in $LPA_a$-null mice or AS-ODN injected wild-type mice. LPA signaling appears to induce important neuropathic pain markers such as protein kinase Cγ (PKCγ) and a voltage-gated calcium channel α2δ1 subunit (Caα2δ1) in an $LPA_1$ and Rho-dependent manner (M. Inoue, et al., Initiation of neuropathic pain requires lysophosphatidic acid receptor signaling, *Nat. Med.* 10 (2004) 712-718).

In one aspect, a compound of the present invention, or a pharmaceutically acceptable salt thereof, is used in the treatment of pain in a mammal. In one aspect, the pain is acute pain or chronic pain. In another aspect, the pain is neuropathic pain.

In one aspect, a compound of the present invention, or a pharmaceutically acceptable salt thereof, is used in the treatment of fibromyalgia. In one aspect, fibromyalgia stems from the formation of fibrous scar tissue in contractile (voluntary) muscles. Fibrosis binds the tissue and inhibits blood flow, resulting in pain.

Cancer

Lysophospholipid receptor signaling plays a role in the etiology of cancer. Lysophosphatidic acid (LPA) and its G protein-coupled receptors (GPCRs) $LPA_1$, $LPA_2$, and/or $LPA_3$ play a role in the development of several types of cancers. The initiation, progression and metastasis of cancer involve several concurrent and sequential processes including cell proliferation and growth, survival and anti-apoptosis, migration of cells, penetration of foreign cells into defined cellular layers and/or organs, and promotion of angiogenesis. The control of each of these processes by LPA signaling in physiological and pathophysiological conditions underscores the potential therapeutic usefulness of modulating LPA signaling pathways for the treatment of cancer, especially at the level of the LPA receptors or ATX/lysoPLD. Autotaxin (ATX) is a prometastatic enzyme initially isolated from the conditioned medium of human melanoma cells that stimulates a myriad of biological activities, including angiogenesis and the promotion of cell growth, migration, survival, and differentiation through the production of LPA (*Mol Cancer Ther* 2008; 7(10):3352-62).

LPA signals through its own GPCRs leading to activation of multiple downstream effector pathways. Such downstream effector pathways play a role in cancer. LPA and its GPCRs are linked to cancer through major oncogenic signaling pathways.

LPA contributes to tumorigenesis by increasing motility and invasiveness of cells. LPA has been implicated in the initiation or progression of ovarian cancer. LPA is present at significant concentrations (2-80 μM) in the ascitic fluid of ovarian cancer patients. Ovarian cancer cells constitutively produce increased amounts of LPA as compared to normal ovarian surface epithelial cells, the precursor of ovarian epithelial cancer. Elevated LPA levels are also detected in plasma from patients with early-stage ovarian cancers compared with controls. LPA receptors (LPA2 and LPA3) are also overexpressed in ovarian cancer cells as compared to normal ovarian surface epithelial cells. LPA stimulates Cox-2 expression through transcriptional activation and post-transcriptional enhancement of Cox-2 mRNA in ovarian cancer cells. Prostaglandins produced by Cox-2 have been implicated in a number of human cancers and pharmacological inhibition of Cox-2 activity reduces colon cancer development and decreases the size and number of adenomas in patients with familial adenomatous polyposis. LPA has also been implicated in the initiation or progression of prostate cancer, breast cancer, melanoma, head and neck cancer, bowel cancer (colorectal cancer), thyroid cancer and other cancers (Gardell et al, *Trends in Molecular Medicine*, vol. 12, no. 2, p 65-75, 2006; Ishii et al, *Annu. Rev. Biochem,* 73, 321-354, 2004; Mills et al., *Nat. Rev. Cancer,* 3, 582-591, 2003; Murph et al., *Biochimica et Biophysica Acta,* 1781, 547-557, 2008).

The cellular responses to LPA are mediated through the lysophosphatidic acid receptors. For example, LPA receptors mediate both migration of and invasion by pancreatic cancer cell lines: an antagonist of $LPA_1$ and $LPA_3$ (Ki16425) and $LPA_1$-specific siRNA effectively blocked in vitro migration in response to LPA and peritoneal fluid (ascites) from pancreatic cancer patients; in addition, Ki16425 blocked the LPA-induced and ascites-induced invasion activity of a highly peritoneal metastatic pancreatic cancer cell line (Yamada et al, *J. Biol. Chem.*, 279, 6595-6605, 2004).

Colorectal carcinoma cell lines show significant expression of $LPA_1$ mRNA and respond to LPA by cell migration and production of angiogenic factors. Overexpression of LPA receptors has a role in the pathogenesis of thyroid cancer. $LPA_3$ was originally cloned from prostate cancer cells, concordant with the ability of LPA to induce autocrine proliferation of prostate cancer cells.

LPA has stimulatory roles in cancer progression in many types of cancer. LPA is produced from and induces proliferation of prostate cancer cell lines. LPA induces human colon carcinoma DLD1 cell proliferation, migration, adhesion, and secretion of angiogenic factors through $LPA_1$ signaling. In other human colon carcinoma cells lines (HT29 and WiDR), LPA enhances cell proliferation and secretion of angiogenic factors. In other colon cancer cell lines, LPA2 and LPA3 receptor activation results in proliferation of the cells. The genetic or pharmacological manipulation of LPA metabolism, specific blockade of receptor signaling, and/or inhibition of downstream signal transduction pathways, represent approaches for cancer therapies.

It has been reported that LPA and other phospholipids stimulate expression of interleukin-8 (IL-8) in ovarian cancer cell lines. In some embodiments, high concentrations of IL-8 in ovarian cancer correlate with poor initial response to chemotherapy and with poor prognosis, respectively. In animal models, expression of IL-8 and other growth factors such as vascular endothelial growth factor (VEGF) is associated with increased tumorigenicity, ascites formation, angiogenesis, and invasiveness of ovarian cancer cells. In some aspects, IL-8 is an important modulator of cancer progression, drug resistance, and prognosis in ovarian cancer. In some embodiments, a compound of the present invention inhibits or reduces IL-8 expression in ovarian cancer cell lines.

In one aspect, a compound of the present invention, or a pharmaceutically acceptable salt thereof, is used in the treatment of cancer. In one aspect, a compound of the present invention, or a pharmaceutically acceptable salt thereof, is used in the treatment of malignant and benign proliferative disease. In one aspect, a compound of the present invention, or a pharmaceutically acceptable salt thereof, is used to prevent or reduce proliferation of tumor cells, invasion and metastasis of carcinomas, pleural mesothelioma (Yamada, *Cancer Sci.*, 2008, 99(8), 1603-1610) or peritoneal mesothelioma, cancer pain, bone metastases (Boucharaba et al, *J. Cin. Invest.*, 2004, 114(12), 1714-1725; Boucharaba et al, *Proc. Natl. acad. Sci.*, 2006, 103(25) 9643-9648). In one aspect is a method of treating cancer in a mammal, the method comprising administering to the mammal a compound of the present invention, or a pharmaceutically acceptable salt thereof, and a second therapeutic agent, wherein the second therapeutic agent is an anticancer agent.

The term "cancer," as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, lymphatic tissue (lymphoma), ovary, pancreas or other endocrine organ (thyroid), prostate, skin (melanoma or basal cell cancer) or hematological tumors (such as the leukemias) at any stage of the disease with or without metastases.

Additional non-limiting examples of cancers include, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, Hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, non-small cell lung cancer, small cell lung cancer, Burkitt lymphoma, cutaneous T-cell lymphoma, Hodgkin lymphoma, non-Hodgkin lymphoma, lymphoma, Waldenström macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sezary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenström macroglobulinemia, Wilms tumor.

The increased concentrations of LPA and vesicles in ascites from ovarian cancer patients and breast cancer effusions indicate that it could be an early diagnostic marker, a prognostic indicator or an indicator of response to therapy (Mills et al, *Nat. Rev. Cancer.*, 3, 582-591, 2003; Sutphen et al., *Cancer Epidemiol. Biomarkers Prev.* 13, 1185-1191, 2004). LPA concentrations are consistently higher in ascites samples than in matched plasma samples.

Respiratory and Allergic Disorders

In one aspect, LPA is a contributor to the pathogenesis of respiratory diseases. In one aspect the respiratory disease is asthma. Proinflammatory effects of LPA include degranulation of mast cells, contraction of smooth-muscle cells and release of cytokines from dendritic cells. Airway smooth muscle cells, epithelial cells and lung fibroblasts all show responses to LPA. LPA induces the secretion of IL-8 from human bronchial epithelial cells. IL-8 is found in increased concentrations in BAL fluids from patients with asthma, chronic obstructive lung disease, pulmonary sarcoidosis and acute respiratory distress syndrome and Il-8 has been shown to exacerbate airway inflammation and airway remodeling of asthmatics. LPA1, LPA2 and LPA3 receptors have all been shown to contribute to the LPA-induced IL-8 production. Studies cloning multiple GPCRs that are activated by LPA allowed the demonstration of the presence of mRNA for the $LPA_1$, $LPA_2$ and $LPA_3$ in the lung (J. J. A. Contos, et al., *Mol. Pharmacol.* 58, 1188-1196, 2000).

The release of LPA from platelets activated at a site of injury and its ability to promote fibroblast proliferation and contraction are features of LPA as a mediator of wound repair. In the context of airway disease, asthma is an inflammatory disease where inappropriate airway "repair" processes lead to structural "remodeling" of the airway. In asthma, the cells of the airway are subject to ongoing injury due to a variety of insults, including allergens, pollutants, other inhaled environmental agents, bacteria and viruses, leading to the chronic inflammation that characterizes asthma.

In one aspect, in the asthmatic individual, the release of normal repair mediators, including LPA, is exaggerated or the actions of the repair mediators are inappropriately prolonged leading to inappropriate airway remodeling. Major structural features of the remodeled airway observed in asthma include a thickened lamina reticularis (the basement membrane-like structure just beneath the airway epithelial cells), increased numbers and activation of myofibroblasts, thickening of the smooth muscle layer, increased numbers of mucus glands and mucus secretions, and alterations in the connective tissue and capillary bed throughout the airway wall. In one aspect, LPA contributes to these structural changes in the airway. In one aspect, LPA is involved in acute airway hyperresponsiveness in asthma. The lumen of the remodeled asthmatic airway is narrower due to the thickening of the airway wall, thus decreasing airflow. In one aspect, LPA contributes to the long-term structural remodeling and the acute hyperresponsiveness of the asthmatic airway. In one aspect, LPA contributes to the hyper-responsiveness that is a primary feature of acute exacerbations of asthma.

In addition to the cellular responses mediated by LPA, several of the LPA signaling pathway components leading to these responses are relevant to asthma. EGF receptor upregulation is induced by LPA and is also seen in asthmatic airways (M. Amishima, et al., *Am. J. Respir. Crit. Care Med.* 157, 1907-1912, 1998). Chronic inflammation is a contributor to asthma, and several of the transcription factors that are activated by LPA are known to be involved in inflammation (Ediger et al., *Eur Respir J* 21:759-769, 2003).

In one aspect, the fibroblast proliferation and contraction and extracellular matrix secretion stimulated by LPA contributes to the fibroproliferative features of other airway diseases, such as the peribronchiolar fibrosis present in chronic bronchitis, emphysema, and interstitial lung disease. Emphysema is also associated with a mild fibrosis of the alveolar wall, a feature which is believed to represent an attempt to repair alveolar damage. In another aspect, LPA plays a role in the fibrotic interstitial lung diseases and obliterative bronchiolitis, where both collagen and myofibroblasts are increased. In another aspect, LPA is involved in several of the various syndromes that constitute chronic obstructive pulmonary disease.

Administration of LPA in vivo induces airway hyperresponsiveness, itch-scratch responses, infiltration and activation of eosinophils and neutrophils, vascular remodeling, and nociceptive flexor responses. LPA also induces histamine release from mouse and rat mast cells. In an acute allergic reaction, histamine induces various responses, such as contraction of smooth muscle, plasma exudation, and mucus production. Plasma exudation is important in the airway, because the leakage and subsequent airway-wall edema contribute to the development of airway hyperresponsiveness. Plasma exudation progresses to conjunctival swelling in ocular allergic disorder and nasal blockage in allergic rhinitis (Hashimoto et al., *J Pharmacol Sci* 100, 82-87, 2006). In one aspect, plasma exudation induced by LPA is mediated by histamine release from mast cells via one or more LPA receptors. In one aspect, the LPA receptor(s) include $LPA_1$ and/or $LPA_3$. In one aspect, a compound of the present invention, or a pharmaceutically acceptable salt thereof, is used in the treatment of various allergic disorders in a mammal. In one aspect, a compound of the present invention, or a pharmaceutically acceptable salt thereof, is used in the treatment of respiratory diseases, disorders or conditions in a mammal. In one aspect, a compound of the present invention, or a pharmaceutically acceptable salt thereof, is used in the treatment of asthma in a mammal. In one aspect, a compound of the present invention, or a pharmaceutically acceptable salt thereof, is used in the treatment of chronic asthma in a mammal.

The term "respiratory disease," as used herein, refers to diseases affecting the organs that are involved in breathing, such as the nose, throat, larynx, eustachian tubes, trachea, bronchi, lungs, related muscles (e.g., diaphram and intercostals), and nerves. Respiratory diseases include, but are not limited to, asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

The term "asthma" as used herein refers to any disorder of the lungs characterized by variations in pulmonary gas flow associated with airway constriction of whatever cause (intrinsic, extrinsic, or both; allergic or non-allergic). The term asthma may be used with one or more adjectives to indicate cause.

In one aspect, presented herein is the use of a compound of the present invention, or a pharmaceutically acceptable salt thereof, in the treatment or prevention of chronic obstructive pulmonary disease in a mammal comprising administering to the mammal at least once an effective amount of at least one compound of the present invention, or a pharmaceutically acceptable salt thereof. In addition, chronic obstructive pulmonary disease includes, but is not limited to, chronic bronchitis or emphysema, pulmonary hypertension, interstitial lung fibrosis and/or airway inflammation, and cystic fibrosis.

Nervous System

The nervous system is a major locus for $LPA_1$ expression; there it is spatially and temporally regulated throughout brain development. Oligodendrocytes, the myelinating cells in the central nervous system (CNS), express $LPA_1$ in mammals. In addition, Schwann cells, the myelinating cells of the peripheral nervous system, also express $LPA_1$, which is involved in regulating Schwann cell survival and morphology. These observations identify important functions for receptor-mediated LPA signaling in neurogenesis, cell survival, and myelination.

Exposure of peripheral nervous system cell lines to LPA produces a rapid retraction of their processes resulting in cell rounding, which was, in part, mediated by polymerization of the actin cytoskeleton. In one aspect, LPA causes neuronal degeneration under pathological conditions when the blood-brain barrier is damaged and serum components leak into the brain (Moolenaar, Curr. Opin. Cell Biol. 7:203-10, 1995). Immortalized CNS neuroblast cell lines from the cerebral cortex also display retraction responses to LPA exposure through Rho activation and actomyosin interactions. In one aspect, LPA is associated with post-ischemic neural damage (J. Neurochem. 61, 340, 1993; J. Neurochem., 70:66, 1998).

In one aspect, provided is a compound of the present invention, or a pharmaceutically acceptable salt thereof, for use in the treatment or prevention of a nervous system disorder in a mammal. The term "nervous system disorder," as used herein, refers to conditions that alter the structure or function of the brain, spinal cord or peripheral nervous system, including but not limited to Alzheimer's Disease, cerebral edema, cerebral ischemia, stroke, multiple sclerosis, neuropathies, Parkinson's Disease, those found after blunt or surgical trauma (including post-surgical cognitive dysfunction and spinal cord or brain stem injury), as well as the neurological aspects of disorders such as degenerative disk disease and sciatica.

In one aspect, provided is a compound of the present invention, or a pharmaceutically acceptable salt thereof, for use in the treatment or prevention of a CNS disorder in a mammal. CNS disorders include, but are not limited to, multiple sclerosis, Parkinson's disease, Alzheimer's disease, stroke, cerebral ischemia, retinal ischemia, post-surgical cognitive dysfunction, migraine, peripheral neuropathy/neuropathic pain, spinal cord injury, cerebral edema and head injury.

Cardiovascular Disorders

Cardiovascular phenotypes observed after targeted deletion of lysophospholipid receptors reveal important roles for lysophospholipid signaling in the development and maturation of blood vessels, formation of atherosclerotic plaques and maintenance of heart rate (Ishii, I. et al. Annu. Rev. Biochem. 73, 321-354, 2004). Angiogenesis, the formation of new capillary networks from pre-existing vasculature, is normally invoked in wound healing, tissue growth and myocardial angiogenesis after ischemic injury. Peptide growth factors (e.g. vascular endothelial growth factor (VEGF)) and lysophospholipids control coordinated proliferation, migration, adhesion, differentiation and assembly of vascular endothelial cells (VECs) and surrounding vascular smooth-muscle cells (VSMCs). In one aspect, dysregulation of the processes mediating angiogenesis leads to atherosclerosis, hypertension, tumor growth, rheumatoid arthritis and diabetic retinopathy (Osborne, N. and Stainier, D. Y. Annu. Rev. Physiol. 65, 23-43, 2003).

Downstream signaling pathways evoked by lysophospholipid receptors include Rac-dependent lamellipodia formation (e.g. $LPA_1$) and Rho-dependent stress-fiber formation (e.g. $LPA_1$), which is important in cell migration and adhesion. Dysfunction of the vascular endothelium can shift the balance from vasodilatation to vasoconstriction and lead to hypertension and vascular remodeling, which are risk factors for atherosclerosis (Maguire, J. J. et al., Trends Pharmacol. Sci. 26, 448-454, 2005).

LPA contributes to both the early phase (barrier dysfunction and monocyte adhesion of the endothelium) and the late phase (platelet activation and intra-arterial thrombus formation) of atherosclerosis, in addition to its overall progression. In the early phase, LPA from numerous sources accumulates in lesions and activates its cognate GPCRs ($LPA_1$ and $LPA_3$) expressed on platelets (Siess, W. Biochim. Biophys. Acta 1582, 204-215, 2002; Rother, E. et al. Circulation 108, 741-747, 2003). This triggers platelet shape change and aggregation, leading to intra-arterial thrombus formation and, potentially, myocardial infarction and stroke. In support of its atherogenic activity, LPA can also be a mitogen and motogen to VSMCs and an activator of endothelial cells and macrophages. In one aspect, mammals with cardiovascular disease benefit from LPA receptor antagonists that prevent thrombus and neointima plaque formation.

In one aspect, a compound of the present invention, or a pharmaceutically acceptable salt thereof, is used to treat or prevent cardiovascular disease in mammal.

The term "cardiovascular disease," as used herein refers to diseases affecting the heart or blood vessels or both, including but not limited to: arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart or other organ or tissue; endotoxic, surgical, or traumatic shock; hypertension, valvular heart disease, heart failure, abnormal blood pressure; shock; vasoconstriction (including that associated with migraines); vascular abnormality, inflammation, insufficiency limited to a single organ or tissue.

In one aspect, provided herein are methods for preventing or treating vasoconstriction, atherosclerosis and its sequelae myocardial ischemia, myocardial infarction, aortic aneurysm, vasculitis and stroke comprising administering at least once to the mammal an effective amount of at least one compound of the present invention, or a pharmaceutically acceptable salt thereof, or pharmaceutical composition or medicament which includes a compound of the present invention, or a pharmaceutically acceptable salt thereof.

In one aspect, provided herein are methods for reducing cardiac reperfusion injury following myocardial ischemia and/or endotoxic shock comprising administering at least once to the mammal an effective amount of at least one compound of the present invention, or a pharmaceutically acceptable salt thereof.

In one aspect, provided herein are methods for reducing the constriction of blood vessels in a mammal comprising administering at least once to the mammal an effective amount of at least one compound of the present invention, or a pharmaceutically acceptable salt thereof.

In one aspect, provided herein are methods for lowering or preventing an increase in blood pressure of a mammal comprising administering at least once to the mammal an effective amount of at least one compound of the present invention, or a pharmaceutically acceptable salt thereof.

Inflammation

LPA has been shown to regulate immunological responses by modulating activities/functions of immune cells such as T-/B-lymphocytes and macrophages. In activated T cells, LPA activates IL-2 production/cell proliferation through LPA$_1$ (Gardell et al, *TRENDS in Molecular Medicine* Vol. 12 No. 2 Feb. 2006). Expression of LPA-induced inflammatory response genes is mediated by LPA$_1$ and LPA$_3$ (*Biochem Biophys Res Commun.* 363(4):1001-8, 2007). In addition, LPA modulates the chemotaxis of inflammatory cells (*Biochem Biophys Res Commun.*, 1993, 15; 193(2), 497). The proliferation and cytokine-secreting activity in response to LPA of immune cells (*J. Imuunol.* 1999, 162, 2049), platelet aggregation activity in response to LPA, acceleration of migration activity in monocytes, activation of NF-κB in fibroblast, enhancement of fibronectin-binding to the cell surface, and the like are known. Thus, LPA is associated with various inflammatory/immune diseases.

In one aspect, a compound of the present invention, or a pharmaceutically acceptable salt thereof, is used to treat or prevent inflammation in a mammal. In one aspect, antagonists of LPA$_1$ and/or LPA$_3$ find use in the treatment or prevention of inflammatory/immune disorders in a mammal. In one aspect, the antagonist of LPA$_1$ is a compound of the present invention, or a pharmaceutically acceptable salt thereof.

Examples of inflammatory/immune disorders include psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis (e.g., Hashimoto's and autoimmune thyroiditis), myasthenia gravis, autoimmune hemolytic anemia, multiple sclerosis, cystic fibrosis, chronic relapsing hepatitis, primary biliary cirrhosis, allergic conjunctivitis and atopic dermatitis.

Other Diseases, Disorders or Conditions

In accordance with one aspect, are methods for treating, preventing, reversing, halting or slowing the progression of LPA-dependent or LPA-mediated diseases or conditions once it becomes clinically evident, or treating the symptoms associated with or related to LPA-dependent or LPA-mediated diseases or conditions, by administering to the mammal a compound of the present invention, or a pharmaceutically acceptable salt thereof. In certain embodiments, the subject already has a LPA-dependent or LPA-mediated disease or condition at the time of administration, or is at risk of developing a LPA-dependent or LPA-mediated disease or condition.

In certain aspects, the activity of LPA$_1$ in a mammal is directly or indirectly modulated by the administration of (at least once) a therapeutically effective amount of at least one compound of the present invention, or a pharmaceutically acceptable salt thereof. Such modulation includes, but is not limited to, reducing and/or inhibiting the activity of LPA$_1$. In additional aspects, the activity of LPA in a mammal is directly or indirectly modulated, including reducing and/or inhibiting, by the administration of (at least once) a therapeutically effective amount of at least one compound of the present invention, or a pharmaceutically acceptable salt thereof. Such modulation includes, but is not limited to, reducing and/or inhibiting the amount and/or activity of a LPA receptor. In one aspect, the LPA receptor is LPA$_1$.

In one aspect, LPA has a contracting action on bladder smooth muscle cell isolated from bladder, and promotes growth of prostate-derived epithelial cell (*J. Urology*, 1999, 162, 1779-1784; *J. Urology*, 2000, 163, 1027-1032). In another aspect, LPA contracts the urinary tract and prostate in vitro and increases intraurethral pressure in vivo (WO 02/062389).

In certain aspects, are methods for preventing or treating eosinophil and/or basophil and/or dendritic cell and/or neutrophil and/or monocyte and/or T-cell recruitment comprising administering at least once to the mammal an effective amount of at least one compound of the present invention, or a pharmaceutically acceptable salt thereof.

In certain aspects, are methods for the treatment of cystitis, including, e.g., interstitial cystitis, comprising administering at least once to the mammal a therapeutically effective amount of at least one compound of the present invention, or a pharmaceutically acceptable salt thereof.

In accordance with one aspect, methods described herein include the diagnosis or determination of whether or not a patient is suffering from a LPA-dependent or LPA-mediated disease or condition by administering to the subject a therapeutically effective amount of a compound of the present invention, or a pharmaceutically acceptable salt thereof, and determining whether or not the patient responds to the treatment.

In one aspect provided herein are compounds of the present invention, pharmaceutically acceptable salts, pharmaceutically acceptable prodrugs, and pharmaceutically acceptable solvates thereof, which are antagonists of LPA$_1$, and are used to treat patients suffering from one or more LPA-dependent or LPA-mediated conditions or diseases, including, but not limited to, lung fibrosis, kidney fibrosis, liver fibrosis, scarring, asthma, rhinitis, chronic obstructive pulmonary disease, pulmonary hypertension, interstitial lung fibrosis, arthritis, allergy, psoriasis, inflammatory bowel disease, adult respiratory distress syndrome, myocardial infarction, aneurysm, stroke, cancer, pain, proliferative disorders and inflammatory conditions. In some embodiments, LPA-dependent conditions or diseases include those wherein an absolute or relative excess of LPA is present and/or observed.

In any of the aforementioned aspects the LPA-dependent or LPA-mediated diseases or conditions include, but are not limited to, organ fibrosis, asthma, allergic disorders, chronic obstructive pulmonary disease, pulmonary hypertension, lung or pleural fibrosis, peritoneal fibrosis, arthritis, allergy, cancer, cardiovascular disease, ult respiratory distress syndrome, myocardial infarction, aneurysm, stroke, and cancer.

In one aspect, a compound of the present invention, or a pharmaceutically acceptable salt thereof, is used to improve the corneal sensitivity decrease caused by corneal operations such as laser-assisted in situ keratomileusis (LASIK) or cataract operation, corneal sensitivity decrease caused by corneal degeneration, and dry eye symptom caused thereby.

In one aspect, presented herein is the use of a compound of the present invention, or a pharmaceutically acceptable salt thereof, in the treatment or prevention of ocular inflammation and allergic conjunctivitis, vernal keratoconjunctivitis, and papillary conjunctivitis in a mammal comprising administering at least once to the mammal an effective amount of at least one compound of the present invention, or a pharmaceutically acceptable salt thereof.

In one aspect, presented herein is the use of a compound of the present invention, or a pharmaceutically acceptable salt thereof, in the treatment or prevention of Sjogren disease or inflammatory disease with dry eyes in a mammal comprising administering at least once to the mammal an effective amount of at least one compound of the present invention, or a pharmaceutically acceptable salt thereof.

In one aspect, LPA and LPA receptors (e.g. $LPA_1$) are involved in the pathogenesis of osteoarthritis (Kotani et al, *Hum. Mol. Genet.*, 2008, 17, 1790-1797). In one aspect, presented herein is the use of a compound of the present invention, or a pharmaceutically acceptable salt thereof, in the treatment or prevention of osteoarthritis in a mammal comprising administering at least once to the mammal an effective amount of at least one compound of the present invention, or a pharmaceutically acceptable salt thereof.

In one aspect, LPA receptors (e.g. $LPA_1$, $LPA_3$) contribute to the pathogenesis of rheumatoid arthritis (Zhao et al, *Mol. Pharmacol.*, 2008, 73(2), 587-600). In one aspect, presented herein is the use of a compound of the present invention, or a pharmaceutically acceptable salt thereof, in the treatment or prevention of rheumatoid arthritis in a mammal comprising administering at least once to the mammal an effective amount of at least one compound of the present invention, or a pharmaceutically acceptable salt thereof.

In one aspect, LPA receptors (e.g. $LPA_1$) contribute to adipogenesis. (Simon et al, *J. Biol. Chem.*, 2005, vol. 280, no. 15, p.14656). In one aspect, presented herein is the use of a compound of the present invention, or a pharmaceutically acceptable salt thereof, in the promotion of adipose tissue formation in a mammal comprising administering at least once to the mammal an effective amount of at least one compound of the present invention, or a pharmaceutically acceptable salt thereof.

a. In Vitro Assays

The effectiveness of compounds of the present invention as LPA1 inhibitors can be determined in an LPA1 functional antagonist assay as follows:

Chinese hamster ovary cells overexpressing human LPA1 were plated overnight (15,000 cells/well) in poly-D-lysine coated 384-well microplates (Greiner bio-one, Cat #781946) in DMEM/F12 medium (Gibco, Cat #11039). Following overnight culture, cells were loaded with calcium indicator dye (AAT Bioquest Inc, Cat #34601) for 30 minutes at 37° C. The cells were then equilibrated to room temperature for 30 minutes before the assay. Test compounds solubilized in DMSO were transferred to 384 well non-binding surface plates (Corning, Cat #3575) using the Labcyte Echo acoustic dispense and diluted with assay buffer [1×HBSS with calcium/magnesium (Gibco Cat #14025-092), 20 mM HEPES (Gibco Cat #15630-080) and 0.1% fatty acid free BSA (Sigma Cat #A9205)] to a final concentration of 0.5% DMSO. Diluted compounds were added to the cells by FDSS6000 (Hamamatsu) at final concentrations ranging from 0.08 nM to 5 μM. and were then incubated for 20 min at room temperature at which time LPA (Avanti Polar Lipids Cat #857130C) was added at final concentrations of 10 nM to stimulate the cells. The compound $IC_{50}$ value was defined as the concentration of test compound which inhibited 50% of the calcium flux induced by LPA alone. $IC_{50}$ values were determined by fitting data to a 4-parameter logistic equation (GraphPad Prism, San Diego Calif.).

b. In Vivo Assays

LPA Challenge with Plasma Histamine Evaluation.

Compound is dosed orally p.o. 2 hours to CD-1 female mice prior to the LPA challenge. The mice are then dosed via tail vein (IV) with 0.15 mL of LPA in 0.1% BSA/PBS (2 μg/μL). Exactly 2 minutes following the LPA challenge, the mice are euthanized by decapitation and the trunk blood is collected. These samples are collectively centrifuged and individual 75 μL samples are frozen at −20° C. until the time of the histamine assay.

The plasma histamine analysis was run by standard EIA (Enzyme Immunoassay) methods. Plasma samples were thawed and diluted 1:30 in 0.1% BSA in PBS. The EIA protocol for histamine analysis as outlined by the manufacturer was followed (Histamine EIA, Oxford Biomedical Research, EA #31).

The LPA used in the assay is formulated as follows: LPA (1-oleoyl-2-hydroxy-sn-glycero-3-phosphate (sodium salt), 857130P, Avanti Polar Lipids) is prepared in 0.1% BSA/PBS for total concentration of 2 μg/μL. 13 mg of LPA is weighed and 6.5 mL 0.1% BSA added, vortexed and sonicated for ~1 hour until a clear solution is achieved.

V. Pharmaceutical Compositions, Formulations and Combinations

In some embodiments, provided is a pharmaceutical composition comprising a therapeutically effective amount of a compound of the present invention, or a pharmaceutically acceptable salt thereof. In some embodiments, the pharmaceutical composition also contains at least one pharmaceutically acceptable inactive ingredient.

In some embodiments, provided is a pharmaceutical composition comprising a therapeutically effective amount of a compound of the present invention, or a pharmaceutically acceptable salt thereof, and at least one pharmaceutically acceptable inactive ingredient. In one aspect, the pharmaceutical composition is formulated for intravenous injection, subcutaneous injection, oral administration, inhalation, nasal administration, topical administration, ophthalmic administration or otic administration. In some embodiments, the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

In some embodiments, the pharmaceutical composition further comprises one or more additional therapeutically active agents selected from: corticosteroids (e.g., dexamethasone or fluticasone), immunosuppressants (e.g., tacrolimus & pimecrolimus), analgesics, anti-cancer agent, anti-inflammatories, chemokine receptor antagonists, bronchodilators, leukotriene receptor antagonists (e.g., montelukast or zafirlukast), leukotriene formation inhibitors, monoacylglycerol kinase inhibitors, phospholipase $A_1$ inhibitors, phospholipase $A_2$ inhibitors, and lysophospholipase D (lysoPLD) inhibitors, autotaxin inhibitors, decongestants, antihistamines (e.g., loratidine), mucolytics, anticholinergics, antitussives, expectorants, anti-infectives (e.g., fusidic acid, particularly for treatment of atopic dermatitis), anti-fungals (e.g., clotriazole, particularly for atopic dermatitis), anti-IgE antibody therapies (e.g., omalizumab), β-2 adrenergic agonists (e.g., albuterol or salmeterol), other PGD2 antagonists acting at other receptors such as DP antagonists, PDE4 inhibitors (e.g., cilomilast), drugs that modulate cytokine production, e.g., TACE inhibitors, drugs that modulate activity of Th2 cytokines IL-4 & IL-5 (e.g., blocking monoclonal antibodies & soluble receptors), PPARγ agonists (e.g., rosiglitazone and pioglitazone), 5-lipoxygenase inhibitors (e.g., zileuton).

In some embodiments, the pharmaceutical composition further comprises one or more additional anti-fibrotic agents selected from pirfenidone, nintedanib, thalidomide, carlumab, FG-3019, fresolimumab, interferon alpha, lecithinized superoxide dismutase, simtuzumab, tanzisertib, tralokinumab, hu3G9, AM-152, IFN-gamma-1b, IW-001, PRM-151, PXS-25, pentoxifylline/N-acetyl-cysteine, pentoxifylline/vitamin E, salbutamol sulfate, [Sar9, Met(O2)11]-Substance P, pentoxifylline, mercaptamine bitartrate, obeticholic acid, aramchol, GFT-505, eicosapentaenoic acid ethyl ester, metformin, metreleptin, muromonab-CD3, oltipraz, IMM-124-E, MK-4074, PX-102, RO-5093151.

In some embodiments, provided is a method comprising administering a compound of the present invention, or a pharmaceutically acceptable salt thereof, to a human with a LPA-dependent or LPA-mediated disease or condition. In some embodiments, the human is already being administered one or more additional therapeutically active agents other than a compound of the present invention, or a pharmaceutically acceptable salt thereof. In some embodiments, the method further comprises administering one or more additional therapeutically active agents other than a compound of the present invention, or a pharmaceutically acceptable salt thereof.

In some embodiments, the one or more additional therapeutically active agents other than a compound of the present invention, or a pharmaceutically acceptable salt thereof, are selected from: corticosteroids (e.g., dexamethasone or fluticasone), immunosuppressants (e.g., tacrolimus & pimecrolimus), analgesics, anti-cancer agent, anti-inflammatories, chemokine receptor antagonists, bronchodilators, leukotriene receptor antagonists (e.g., montelukast or zafirlukast), leukotriene formation inhibitors, monoacylglycerol kinase inhibitors, phospholipase $A_1$ inhibitors, phospholipase $A_2$ inhibitors, and lysophospholipase D (lysoPLD) inhibitors, autotaxin inhibitors, decongestants, antihistamines (e.g., loratidine), mucolytics, anticholinergics, antitussives, expectorants, anti-infectives (e.g., fusidic acid, particularly for treatment of atopic dermatitis), anti-fungals (e.g., clotriazole, particularly for atopic dermatitis), anti-IgE antibody therapies (e.g., omalizumab), β-2 adrenergic agonists (e.g., albuterol or salmeterol), other PGD2 antagonists acting at other receptors such as DP antagonists, PDE4 inhibitors (e.g., cilomilast), drugs that modulate cytokine production, e.g. TACE inhibitors, drugs that modulate activity of Th2 cytokines IL-4 & IL-5 (e.g., blocking monoclonal antibodies & soluble receptors), PPARγ agonists (e.g., rosiglitazone and pioglitazone), 5-lipoxygenase inhibitors (e.g., zileuton).

In some embodiments, the one or more additional therapeutically active agents other than a compound of the present invention, or a pharmaceutically acceptable salt thereof, are other anti-fibrotic agents selected from pirfenidone, nintedanib, thalidomide, carlumab, FG-3019, fresolimumab, interferon alpha, lecithinized superoxide dismutase, simtuzumab, tanzisertib, tralokinumab, hu3G9, AM-152, IFN-gamma-1b, IW-001, PRM-151, PXS-25, pentoxifylline/N-acetyl-cysteine, pentoxifylline/vitamin E, salbutamol sulfate, [Sar9, Met(O2)11]-Substance P, pentoxifylline, mercaptamine bitartrate, obeticholic acid, aramchol, GFT-505, eicosapentyl ethyl ester, metformin, metreleptin, muromonab-CD3, oltipraz, IMM-124-E, MK-4074, PX-102, RO-5093151.

In some embodiments, the one or more additional therapeutically active agents other than a compound of the present invention, or a pharmaceutically acceptable salt thereof, are selected from ACE inhibitors, ramipril, AII antagonists, irbesartan, anti-arrythmics, dronedarone, PPARα activators, PPARγ activators, pioglitazone, rosiglitazone, prostanoids, endothelin receptor antagonists, elastase inhibitors, calcium antagonists, beta blockers, diuretics, aldosterone receptor antagonists, eplerenone, renin inhibitors, rho kinase inhibitors, soluble guanylate cyclase (sGC) activators, sGC sensitizers, PDE inhibitors, PDE5 inhibitors, NO donors, digitalis drugs, ACE/NEP inhibitors, statins, bile acid reuptake inhibitors, PDGF antagonists, vasopressin antagonists, aquaretics, NHE1 inhibitors, Factor Xa antagonists, Factor XIIIa antagonists, anticoagulants, anti-thrombotics, platelet inhibitors, profibroltics, thrombin-activatable fibrinolysis inhibitors (TAFI), PAI-1 inhibitors, coumarins, heparins, thromboxane antagonists, serotonin antagonists, COX inhibitors, aspirin, therapeutic antibodies, GPIIb/IIIa antagonists, ER antagonists, SERMs, tyrosine kinase inhibitors, RAF kinase inhibitors, p38 MAPK inhibitors, pirfenidone, multi-kinase inhibitors, nintedanib, sorafenib.

In some embodiments, the one or more additional therapeutically active agents other than a compound of the present invention, or a pharmaceutically acceptable salt thereof, are selected from Gremlin-1 mAb, PA1-1 mAb, Promedior (PRM-151; recombinant human Pentraxin-2); FGF21, TGFβ antagonists, αvβ6 & αvβ pan-antagonists; FAK inhibitors, TG2 inhibitors, LOXL2 inhibitors, NOX4 inhibitors, MGAT2 inhibitors, GPR120 agonists.

Pharmaceutical formulations described herein are administrable to a subject in a variety of ways by multiple administration routes, including but not limited to, oral, parenteral (e.g., intravenous, subcutaneous, intramuscular), intranasal, buccal, topical or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the compound of the present invention, or a pharmaceutically acceptable salt thereof, is administered orally.

In some embodiments, the compound of the present invention, or a pharmaceutically acceptable salt thereof, is administered topically. In such embodiments, the compound of the present invention, or a pharmaceutically acceptable salt thereof, is formulated into a variety of topically administrable compositions, such as solutions, suspensions, lotions, gels, pastes, shampoos, scrubs, rubs, smears, medicated sticks, medicated bandages, balms, creams or ointments. Such pharmaceutical compounds can contain solubilizers, stabilizers, tonicity enhancing agents, buffers and preservatives. In one aspect, the compound of the present invention, or a pharmaceutically acceptable salt thereof, is administered topically to the skin.

In another aspect, the compound of the present invention, or a pharmaceutically acceptable salt thereof, is administered by inhalation. In one embodiment, the compound of the present invention, or a pharmaceutically acceptable salt thereof, is administered by inhalation that directly targets the pulmonary system.

In another aspect, the compound of the present invention, or a pharmaceutically acceptable salt thereof, is formulated for intranasal administration. Such formulations include nasal sprays, nasal mists, and the like.

In another aspect, the compound of the present invention, or a pharmaceutically acceptable salt thereof, is formulated as eye drops.

In another aspect is the use of a compound of the present invention, or a pharmaceutically acceptable salt thereof, in the manufacture of a medicament for treating a disease, disorder or conditions in which the activity of at least one LPA receptor contributes to the pathology and/or symptoms of the disease or condition. In one embodiment of this aspect, the LPA is selected from $LPA_1$, $LPA_2$, $LPA_3$, $LPA_4$, $LPA_5$ and $LPA_6$. In one aspect, the LPA receptor is $LPA_1$. In one aspect, the disease or condition is any of the diseases or conditions specified herein.

In any of the aforementioned aspects are further embodiments in which: (a) the effective amount of the compound of the present invention, or a pharmaceutically acceptable salt thereof, is systemically administered to the mammal; and/or (b) the effective amount of the compound is administered orally to the mammal; and/or (c) the effective amount of the compound is intravenously administered to the mammal; and/or (d) the effective amount of the compound is administered by inhalation; and/or (e) the effective amount of the compound is administered by nasal administration; or and/or (f) the effective amount of the compound is administered by injection to the mammal; and/or (g) the effective amount of the compound is administered topically to the mammal; and/or (h) the effective amount of the compound is administered by ophthalmic administration; and/or (i) the effective amount of the compound is administered rectally to the mammal; and/or (j) the effective amount is administered non-systemically or locally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Also provided is a method of inhibiting the physiological activity of LPA in a mammal comprising administering a therapeutically effective amount of a compound of the present invention or a pharmaceutically acceptable salt thereof to the mammal in need thereof.

In one aspect, provided is a medicament for treating a LPA-dependent or LPA-mediated disease or condition in a mammal comprising a therapeutically effective amount of a compound of the present invention, or a pharmaceutically acceptable salt thereof.

In some cases disclosed herein is the use of a compound of the present invention, or a pharmaceutically acceptable salt thereof, in the manufacture of a medicament for the treatment of a LPA-dependent or LPA-mediated disease or condition.

In some cases disclosed herein is the use of a compound of the present invention, or a pharmaceutically acceptable salt thereof, in the treatment or prevention of a LPA-dependent or LPA-mediated disease or condition.

In one aspect, is a method for treating or preventing a LPA-dependent or LPA-mediated disease or condition in a mammal comprising administering a therapeutically effective amount of a compound of the present invention, or a pharmaceutically acceptable salt thereof.

In one aspect, LPA-dependent or LPA-mediated diseases or conditions include, but are not limited to, fibrosis of organs or tissues, scarring, liver diseases, dermatological conditions, cancer, cardiovascular disease, respiratory diseases or conditions, inflammatory disease, gastrointestinal tract disease, renal disease, urinary tract-associated disease, inflammatory disease of lower urinary tract, dysuria, frequent urination, pancreas disease, arterial obstruction, cerebral infarction, cerebral hemorrhage, pain, peripheral neuropathy, and fibromyalgia.

In one aspect, the LPA-dependent or LPA-mediated disease or condition is a respiratory disease or condition. In some embodiments, the respiratory disease or condition is asthma, chronic obstructive pulmonary disease (COPD), pulmonary fibrosis, pulmonary arterial hypertension or acute respiratory distress syndrome.

In some embodiments, the LPA-dependent or LPA-mediated disease or condition is selected from idiopathic pulmonary fibrosis; other diffuse parenchymal lung diseases of different etiologies including iatrogenic drug-induced fibrosis, occupational and/or environmental induced fibrosis, granulomatous diseases (sarcoidosis, hypersensitivity pneumonia), collagen vascular disease, alveolar proteinosis, langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease); radiation induced fibrosis; chronic obstructive pulmonary disease (COPD); scleroderma; bleomycin induced pulmonary fibrosis; chronic asthma; silicosis; asbestos induced pulmonary fibrosis; acute respiratory distress syndrome (ARDS); kidney fibrosis; tubulointerstitium fibrosis; glomerular nephritis; focal segmental glomerular sclerosis; IgA nephropathy; hypertension; Alport; gut fibrosis; liver fibrosis; cirrhosis; alcohol induced liver fibrosis; toxic/drug induced liver fibrosis; hemochromatosis; nonalcoholic steatohepatitis (NASH); biliary duct injury; primary biliary cirrhosis; infection induced liver fibrosis; viral induced liver fibrosis; and autoimmune hepatitis; corneal scarring; hypertrophic scarring; Duputren disease, keloids, cutaneous fibrosis; cutaneous scleroderma; spinal cord injury/fibrosis; myelofibrosis; vascular restenosis; atherosclerosis; arteriosclerosis; Wegener's granulomatosis; Peyronie's disease, chronic lymphocytic leukemia, tumor metastasis, transplant organ rejection, endometriosis, neonatal respiratory distress syndrome and neuropathic pain.

In one aspect, the LPA-dependent or LPA-mediated disease or condition is described herein.

In one aspect, provided is a method for the treatment or prevention of organ fibrosis in a mammal comprising administering a therapeutically effective amount of a compound of the present invention or a pharmaceutically acceptable salt thereof to a mammal in need thereof.

In one aspect, the organ fibrosis comprises lung fibrosis, renal fibrosis, or hepatic fibrosis.

In one aspect, provided is a method of improving lung function in a mammal comprising administering a therapeutically effective amount of a compound of the present invention, or a pharmaceutically acceptable salt thereof to the mammal in need thereof. In one aspect, the mammal has been diagnosed as having lung fibrosis.

In one aspect, compounds disclosed herein are used to treat idiopathic pulmonary fibrosis (usual interstitial pneumonia) in a mammal.

In some embodiments, compounds disclosed herein are used to treat diffuse parenchymal interstitial lung diseases in mammal: iatrogenic drug induced, occupational/environmental (Farmer lung), granulomatous diseases (sarcoidosis, hypersensitivity pneumonia), collagen vascular disease (scleroderma and others), alveolar proteinosis, langerhans cell granulonmatosis, lymphangioleiomyomatosis, Hermansky-Pudlak Syndrome, Tuberous sclerosis, neurofibromatosis, metabolic storage disorders, familial interstitial lung disease.

In some embodiments, compounds disclosed herein are used to treat post-transplant fibrosis associated with chronic rejection in a mammal: Bronchiolitis obliterans for lung transplant.

In some embodiments, compounds disclosed herein are used to treat cutaneous fibrosis in a mammal: cutaneous scleroderma, Dupuytren disease, keloids.

In one aspect, compounds disclosed herein are used to treat hepatic fibrosis with or without cirrhosis in a mammal: toxic/drug induced (hemochromatosis), alcoholic liver disease, viral hepatitis (hepatitis B virus, hepatitis C virus, HCV), nonalcoholic liver disease (NAFLD, NASH), metabolic and auto-immune disease.

In one aspect, compounds disclosed herein are used to treat renal fibrosis in a mammal: tubulointerstitium fibrosis, glomerular sclerosis.

In any of the aforementioned aspects involving the treatment of LPA dependent diseases or conditions are further embodiments comprising administering at least one additional agent in addition to the administration of a compound having the structure of the present invention, or a pharmaceutically acceptable salt thereof. In various embodiments, each agent is administered in any order, including simultaneously.

In any of the embodiments disclosed herein, the mammal is a human.

In some embodiments, compounds provided herein are administered to a human.

In some embodiments, compounds provided herein are orally administered.

In some embodiments, compounds provided herein are used as antagonists of at least one LPA receptor. In some embodiments, compounds provided herein are used for inhibiting the activity of at least one LPA receptor or for the treatment of a disease or condition that would benefit from inhibition of the activity of at least one LPA receptor. In one aspect, the LPA receptor is $LPA_1$.

In other embodiments, compounds provided herein are used for the formulation of a medicament for the inhibition of $LPA_1$ activity.

Articles of manufacture, which include packaging material, a compound of the present invention, or a pharmaceutically acceptable salt thereof, within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for inhibiting the activity of at least one LPA receptor, or for the treatment, prevention or amelioration of one or more symptoms of a disease or condition that would benefit from inhibition of the activity of at least one LPA receptor, are provided.

VI. General Synthesis Including Schemes

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al., (*Protective Groups in Organic Synthesis*, Fourth Edition, Wiley-Interscience (2006)).

The compounds of the present invention may be prepared by the exemplary processes described in the following schemes and working examples, as well as relevant published literature procedures that are used by one skilled in the art. Exemplary reagents and procedures for these reactions appear herein after and in the working examples. Protection and deprotection in the processes below may be carried out by procedures generally known in the art (see, for example, Wuts, P. G. M., Greene's *Protective Groups in Organic Synthesis*, 5th Edition, Wiley (2014)). General methods of organic synthesis and functional group transformations are found in: Trost, B. M. et al., Eds., *Comprehensive Organic Synthesis: Selectivity, Strategy & Efficiency in Modern Organic Chemistry*, Pergamon Press, New York, NY (1991); Smith, M. B. et al., *March's Advanced Organic Chemistry: Reactions, Mechanisms, and Structure.* 7th Edition, Wiley, New York, NY (2013); Katritzky, A. R. et al., Eds., *Comprehensive Organic Functional Group Transformations II*, 2nd Edition, Elsevier Science Inc., Tarrytown, NY (2004); Larock, R. C., *Comprehensive Organic Transformations*, $2^{nd}$ Edition, Wiley-VCH, New York, NY (1999), and references therein.

Scheme 1 describes the synthesis of pinacol boronate 9. A double Michael reaction of the anion of a 4-halo- (preferably 4-bromo-) phenyl acetic acid ester 1 with acrylate ester 2 (two equivalents) provides the β-keto cyclohexyl ester 3. Hydrolysis of diester 3 followed by decarboxylation of the β-keto cyclohexyl acid intermediate furnishes the cyclohexyl keto-acid 4. Horner-Emmons reaction with phosphonate-ester 5 provides the α,β-unsaturated ester-acid 6. Reduction of the acid moiety of ester-acid 6 furnishes the cyclohexyl alcohol 7, which undergoes a base-mediated intramolecular oxy-Michael reaction to provide the oxabicyclo[2.2.2] ester 8. Reaction of the haloarene 8 with bis(pinacolato)diboron in the presence of an appropriate transition metal catalyst (e.g. palladium, for instance Ishiyama, T. et al, *J. Org. Chem.* 1995, 60, 7508-7510) provides the corresponding pinacol boronate 9.

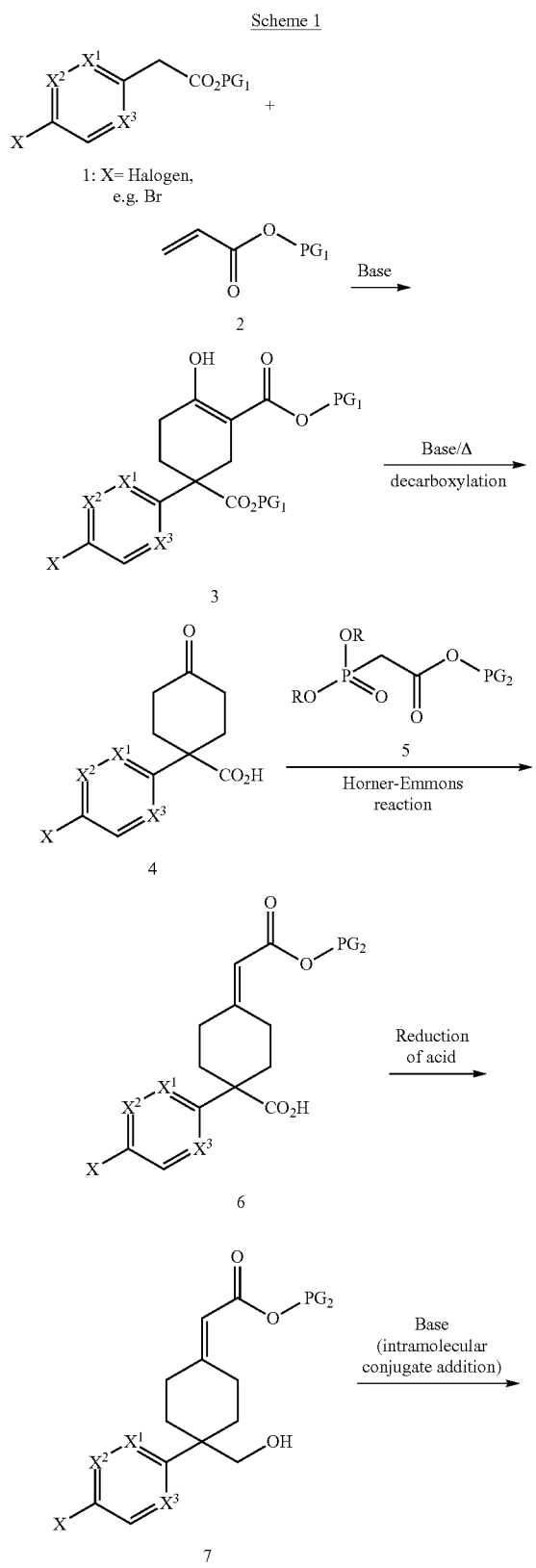

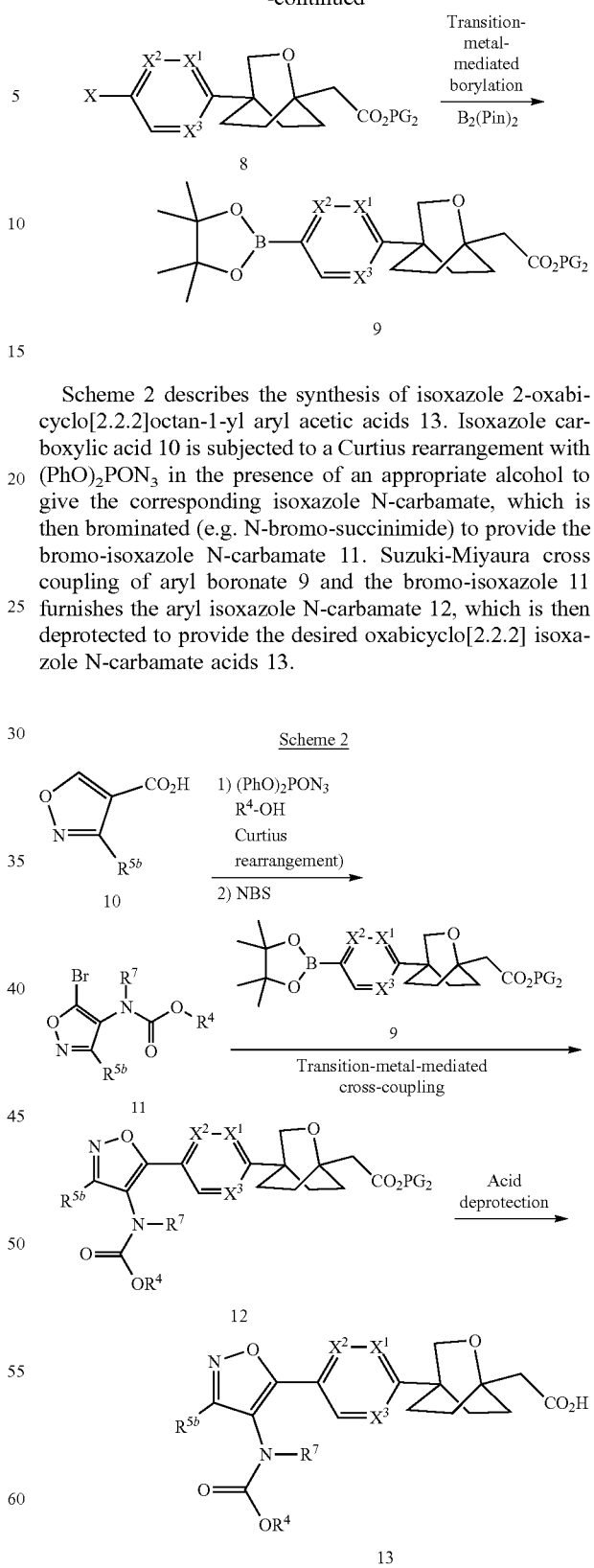

Scheme 2 describes the synthesis of isoxazole 2-oxabicyclo[2.2.2]octan-1-yl aryl acetic acids 13. Isoxazole carboxylic acid 10 is subjected to a Curtius rearrangement with $(PhO)_2PON_3$ in the presence of an appropriate alcohol to give the corresponding isoxazole N-carbamate, which is then brominated (e.g. N-bromo-succinimide) to provide the bromo-isoxazole N-carbamate 11. Suzuki-Miyaura cross coupling of aryl boronate 9 and the bromo-isoxazole 11 furnishes the aryl isoxazole N-carbamate 12, which is then deprotected to provide the desired oxabicyclo[2.2.2] isoxazole N-carbamate acids 13.

Scheme 3 describes the analogous synthesis of pyrazole 2-oxabicyclo[2.2.2]octan-1-yl acetic acids 17. 4-Bromopyrazole-5-carboxylic acid 14 is subjected to a Curtius rearrangement with (PhO)$_2$PON$_3$ in the presence of an appropriate alcohol to provide the corresponding bromo-pyrazole-N-carbamate 15. Suzuki-Miyaura cross coupling of aryl boronate 9 and the bromo-pyrazole 15 furnishes the aryl pyrazole N-carbamate 16, which is then deprotected to provide the desired oxabicyclo[2.2.2] pyrazole N-carbamate acids 17.

ester 26, to give the corresponding β-keto-imine ester 27. The β-keto-imine ester 27 is reacted with hydroxylamine to provide the phenyl isoxazole ester 28 (Ishiyama, T., et al., *J. Org. Chem.* 1995, 60, 7508). Deprotection of the isoxazole ester 28 provides the isoxazole acid 29, which is then subjected to a Curtius rearrangement and reaction with an appropriate alcohol to provide the corresponding isoxazole carbamate. Final deprotection of the isoxazole carbamate-oxabicyclic ester provides the desired isoxazole oxabicyclic [2.2.2] N-carbamate acetic acids 30.

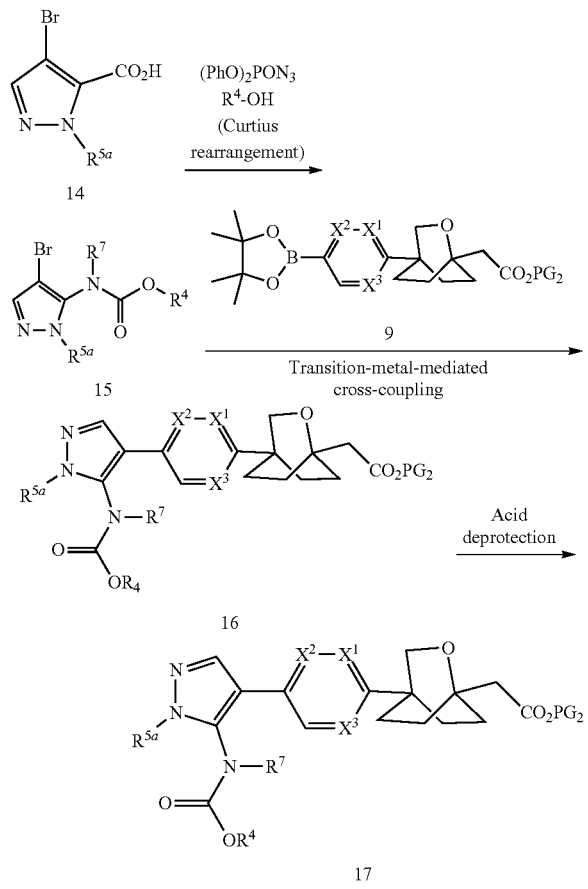

Scheme 3

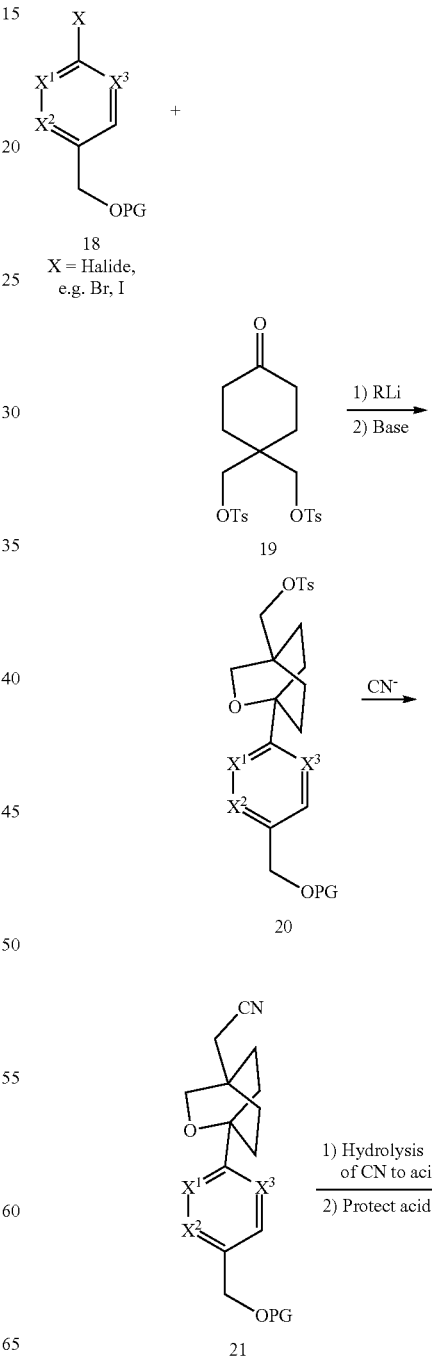

Scheme 4

Scheme 4 describes the synthesis of the regioisomeric isoxazole oxabicyclic[2.2.2] aryl acetic acids 30. An appropriately protected halo-benzyl alcohol 18 is lithiated (e.g. with n-BuLi) and reacted with the 4-oxocyclohexanone bis-tosylate 19 (synthesized from diethyl malonate and ethyl acrylate in 6 steps, as described in WO 2001034610) to furnish the corresponding aryl cyclohexanol bis-tosylate adduct, which is then subjected to base-mediated intramolecular displacement of a tosylate by the alcohol to provide the oxabicyclo[2.2.2]tosylate 20. Displacement of tosylate 20 by cyanide provides nitrile 21, which is subjected to hydrolysis to give the corresponding acid, which is then appropriately protected (with an orthogonal protecting group to the benzylic alcohol) as oxabicyclic ester 22. Selective deprotection of the benzylic alcohol (23) followed by oxidation (e.g., Swern oxidation or Dess-Martin periodinane followed by NaClO$_2$ oxidation to the acid, e.g. Lindgren, B. O., *Acta Chem. Scand.* 1973, 27, 888) provides the benzoic acid 24. Benzoic acid 24 is treated with Vilsmeier reagent 25 to give the acid chloride, which is then reacted with an appropriate (E)-3-(methyl-imino)butanoate

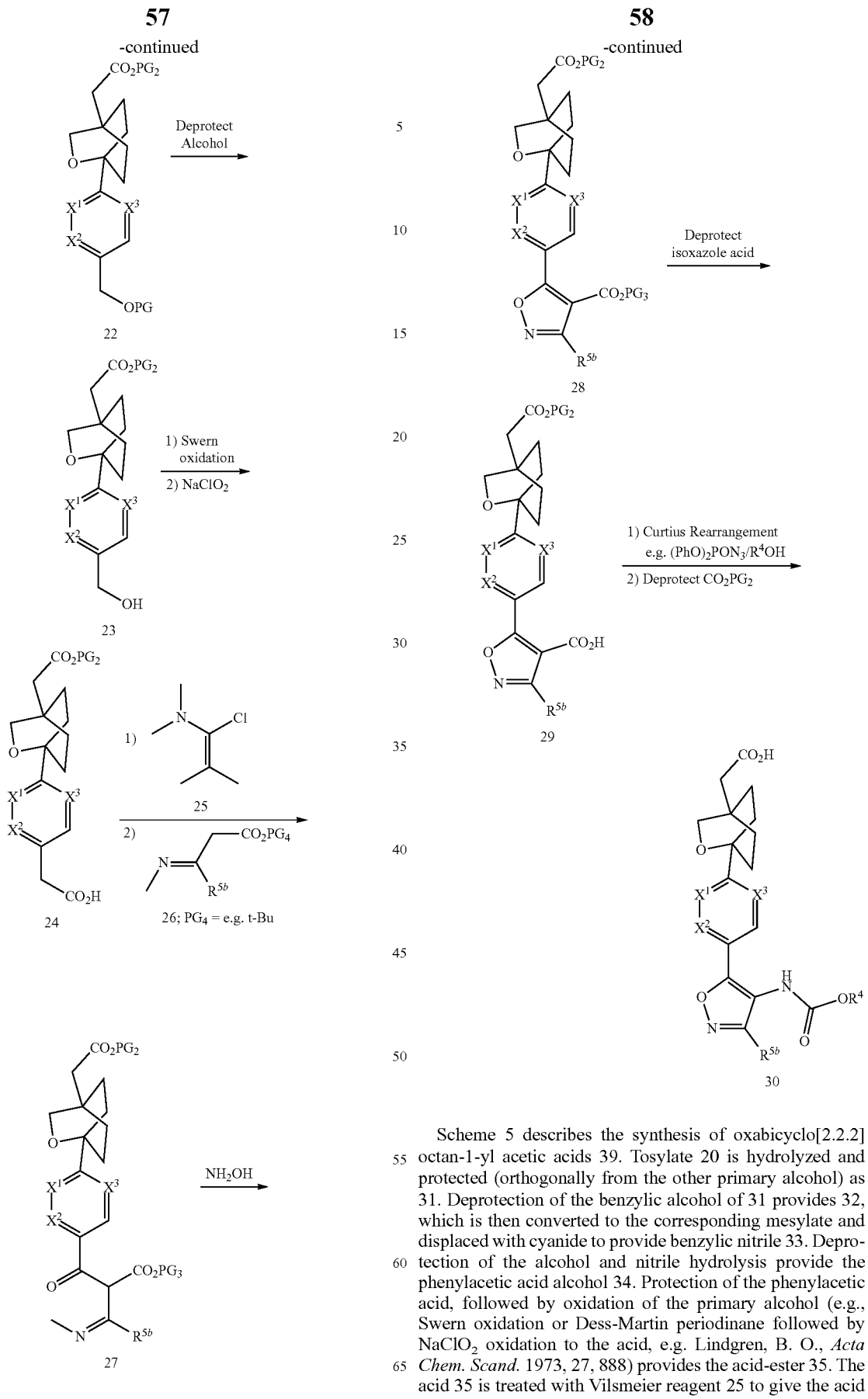

Scheme 5 describes the synthesis of oxabicyclo[2.2.2]octan-1-yl acetic acids 39. Tosylate 20 is hydrolyzed and protected (orthogonally from the other primary alcohol) as 31. Deprotection of the benzylic alcohol of 31 provides 32, which is then converted to the corresponding mesylate and displaced with cyanide to provide benzylic nitrile 33. Deprotection of the alcohol and nitrile hydrolysis provide the phenylacetic acid alcohol 34. Protection of the phenylacetic acid, followed by oxidation of the primary alcohol (e.g., Swern oxidation or Dess-Martin periodinane followed by $NaClO_2$ oxidation to the acid, e.g. Lindgren, B. O., *Acta Chem. Scand.* 1973, 27, 888) provides the acid-ester 35. The acid 35 is treated with Vilsmeier reagent 25 to give the acid chloride, which is then reacted with an appropriate (E)-3-

(methyl-imino) butanoate ester 26, to give the corresponding β-keto-imine ester 36. The β-keto-imine ester 36 is reacted with hydroxylamine to provide the isoxazole ester 37 (Ishiyama, T., et al., *J. Org. Chem.* 1995, 60, 7508). Deprotection of the isoxazole ester 37 provides the isoxazole acid 38, which is then subjected to a Curtius rearrangement and reaction with an appropriate alcohol to provide the corresponding isoxazole carbamate. Final deprotection of the isoxazole carbamate phenylacetic acid ester provides the desired oxabicyclo[2.2.2]octan-1-yl acetic acids 39.

Scheme 5

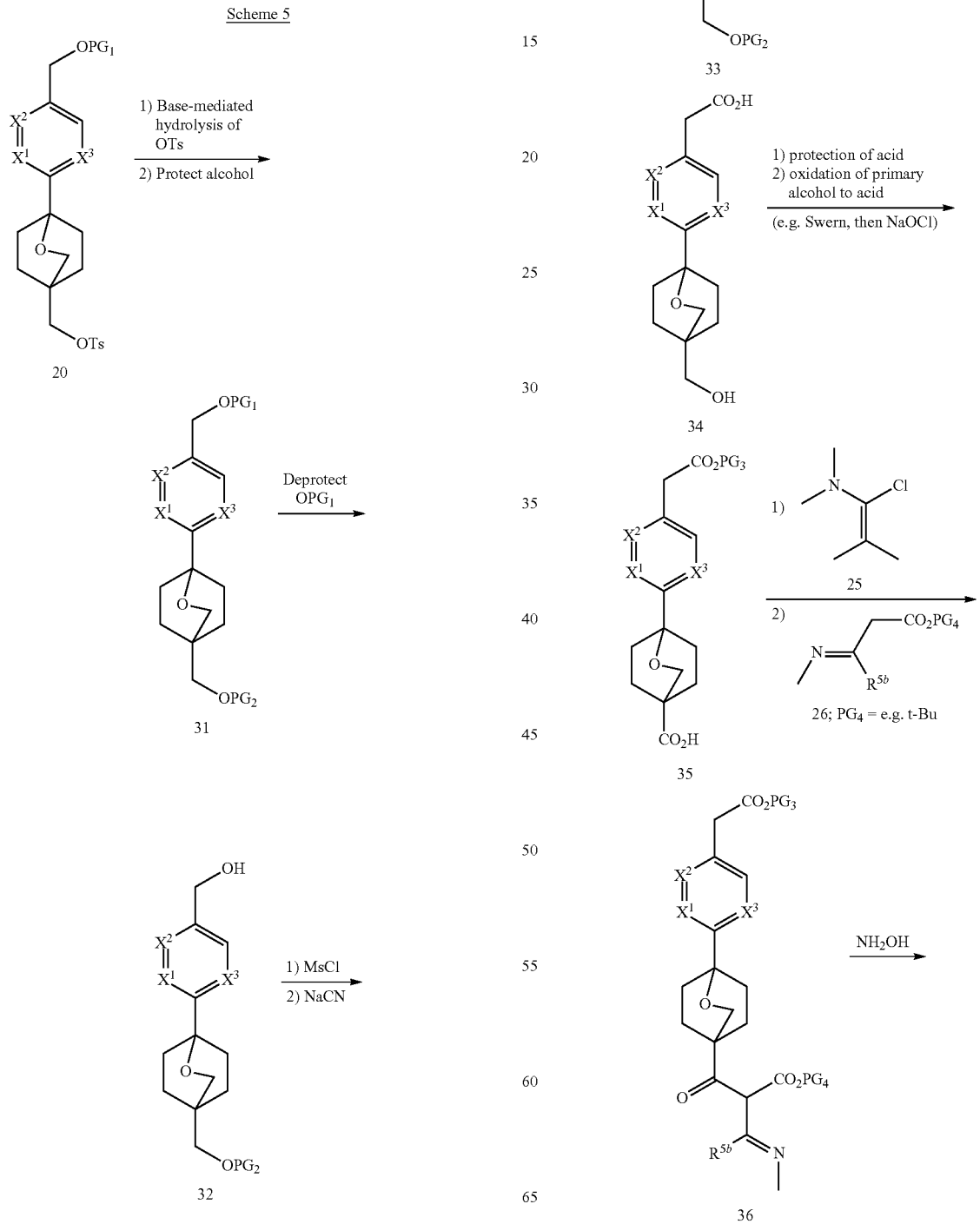

ester 44 provides the desired isoxazole O-carbamyl oxabicyclo [2.2.2]octan-1-yl acetic acids 45.

Scheme 6

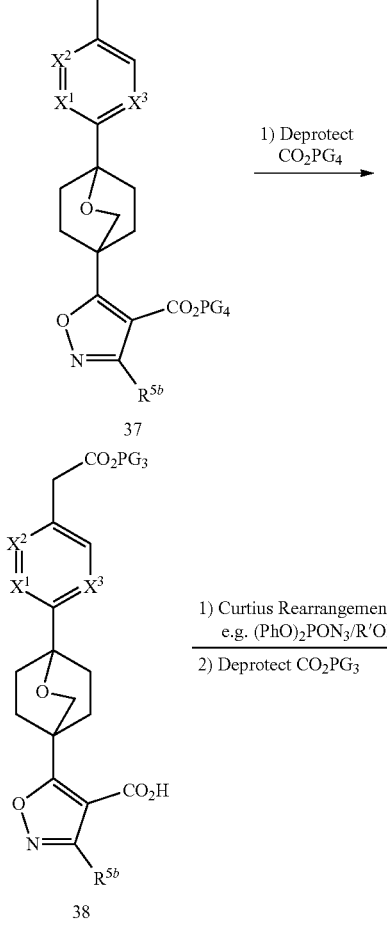

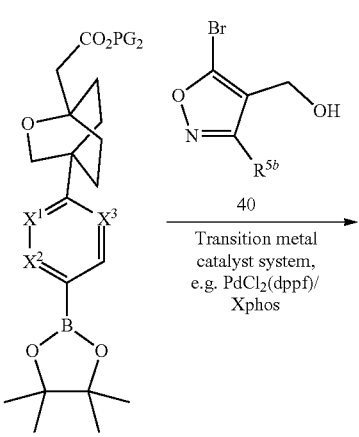

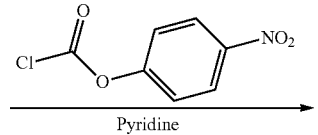

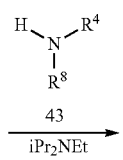

Scheme 6 describes the synthesis of isoxazole O-carbamyl oxabicyclo[2.2.2]octan-1-yl acetic acids 45. Cross-coupling (under standard transition metal-catalyzed conditions, e.g. PdCl$_2$(dppf)/Xphos) of the oxabicylo[2.2.2] acetic ester boronate 9 with 5-bromo-3-methyl-isoxazol-4-yl) methanol provides the aryl isoxazole alcohol 41. Reaction of isoxazole alcohol 41 with 4-nitrophenyl chloroformate provides the intermediate isoxazole 4-nitrophenyl carbonate 42, which is then reacted with amine 43 to provide the isoxazole O-carbamate 44. Hydrolysis of the oxabicyclo[2.2.2] acetic

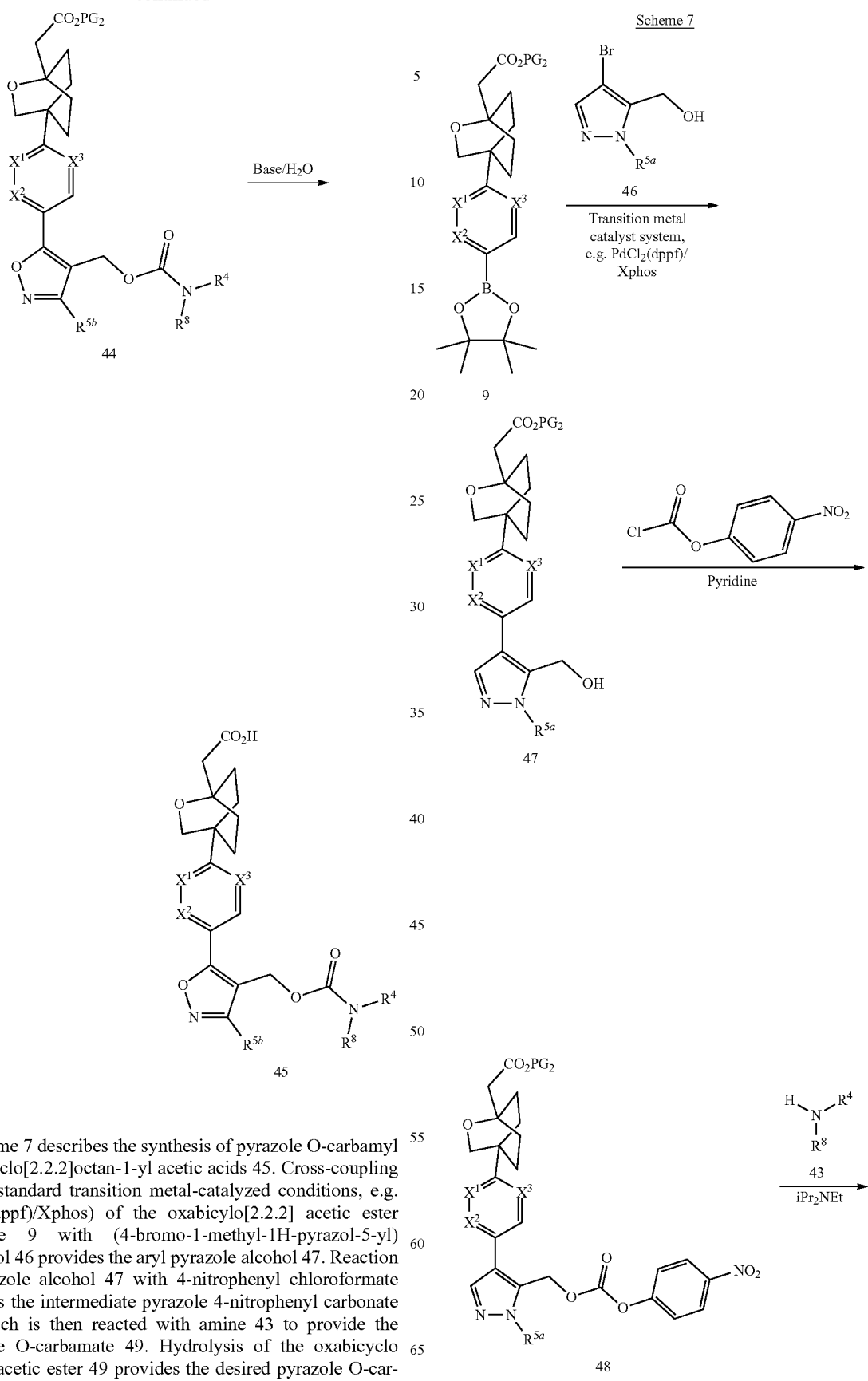

Scheme 7 describes the synthesis of pyrazole O-carbamyl oxabicyclo[2.2.2]octan-1-yl acetic acids 45. Cross-coupling (under standard transition metal-catalyzed conditions, e.g. PdCl₂(dppf)/Xphos) of the oxabicylo[2.2.2] acetic ester boronate 9 with (4-bromo-1-methyl-1H-pyrazol-5-yl) methanol 46 provides the aryl pyrazole alcohol 47. Reaction of pyrazole alcohol 47 with 4-nitrophenyl chloroformate provides the intermediate pyrazole 4-nitrophenyl carbonate 48, which is then reacted with amine 43 to provide the pyrazole O-carbamate 49. Hydrolysis of the oxabicyclo [2.2.2] acetic ester 49 provides the desired pyrazole O-carbamyl oxabicyclo[2.2.2] octan-1-yl acetic acids 50.

-continued

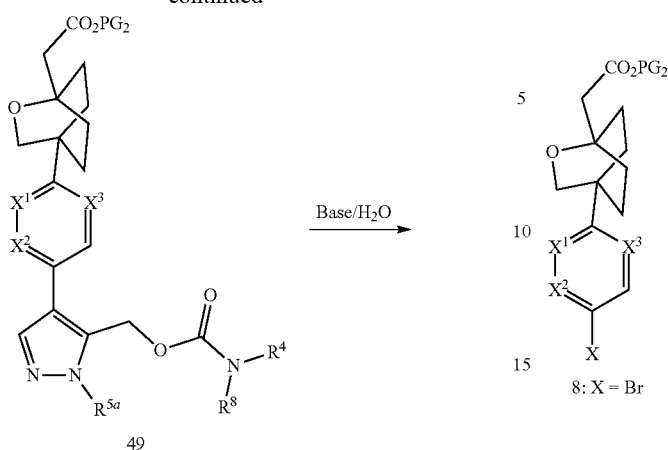

49

50

Scheme 8

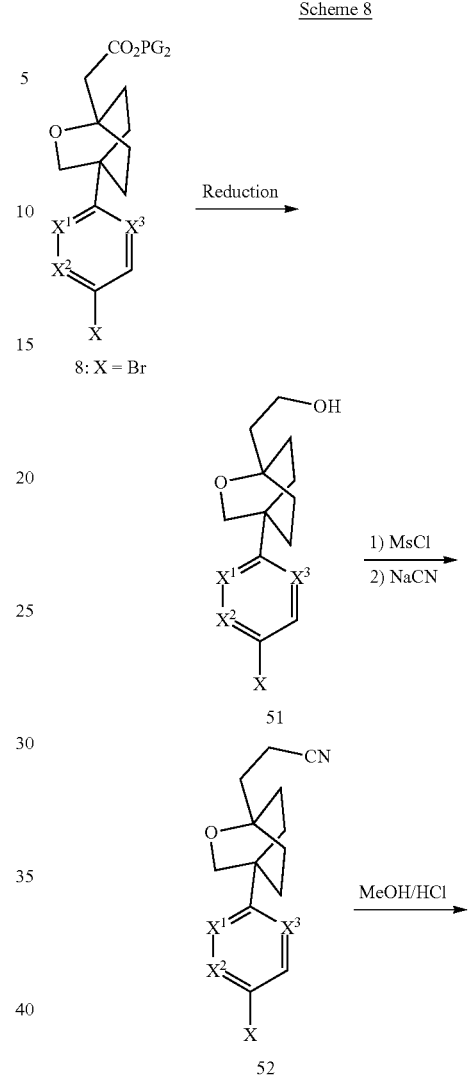

8: X = Br

51

52

Scheme 8 describes the synthesis of triazole O-carbamyl oxabicyclo[2.2.2]octan-1-yl propanoic acids 56. Reduction of oxabicyclo[2.2.2] acetic acid ester 8 (with e.g. DIBALH) provides the alcohol 51, which is converted (via the corresponding mesylate and displacement with NaCN) to the corresponding nitrile 52. Hydrolysis of the nitrile in the presence of methanol provides the corresponding methyl ester 53. Sonogashira coupling reaction (e.g. Alper, P. et al, WO 2008097428) of oxabicyclo[2.2.2] aryl halide 53 with propargyl alcohol furnishes the aryl propargyl alcohol 54. Reaction of propargyl alcohol 54 with trimethylsilyl methyl azide (Qian, Y. et al, *J. Med. Chem.*, 2012, 55, 7920-7939) under either thermal or transition-metal catalyzed conditions (Boren, B. C. et. al., *J. Am. Chem. Soc.*, 2008, 130, 8923-8930) provides the silylated 1,2,3 triazole; the trimethylsilyl group is subsequently removed under standard desilylation conditions (e.g. Bu$_4$NF, as in Qian, Y. et al, *J. Med. Chem.*, 2012, 55, 7920-7939) to give the triazole alcohol 55. Reaction of triazole alcohol 55 with 4-nitrophenyl chloroformate provides the intermediate triazole 4-nitrophenyl carbonate, which is then reacted with amine 43 followed by ester hydrolysis to provide the desired triazole O-carbamyl oxabicyclo[2.2.2]octan-1-yl propanoic acids 56.

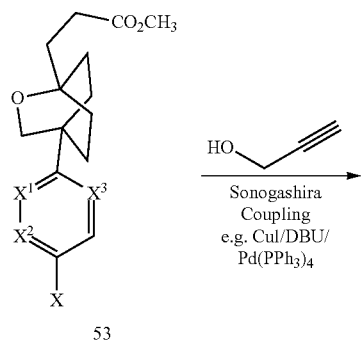

53

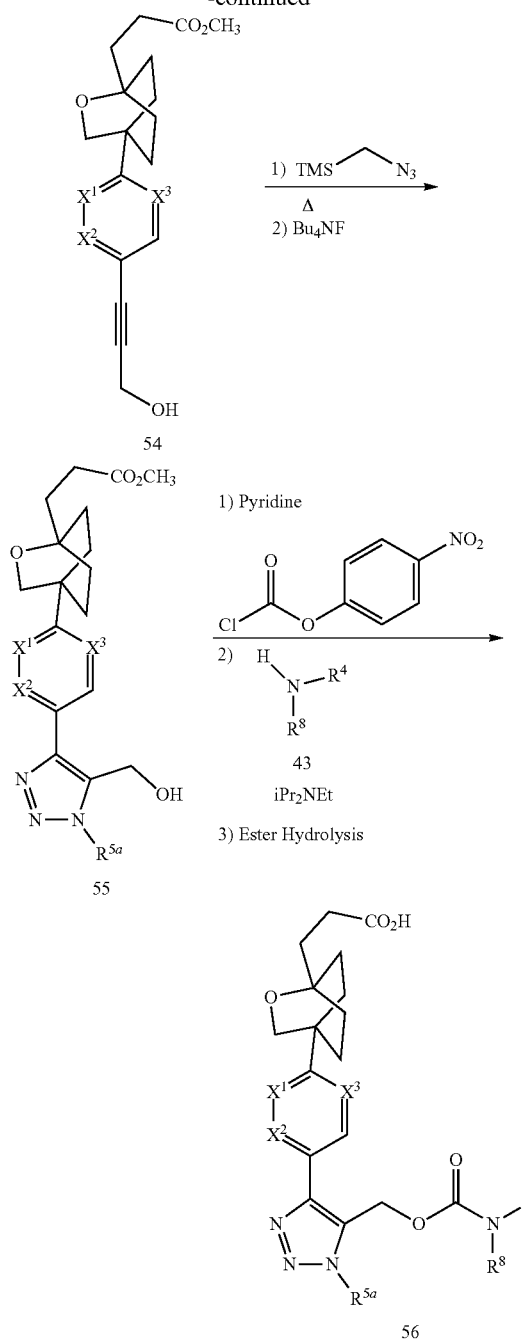
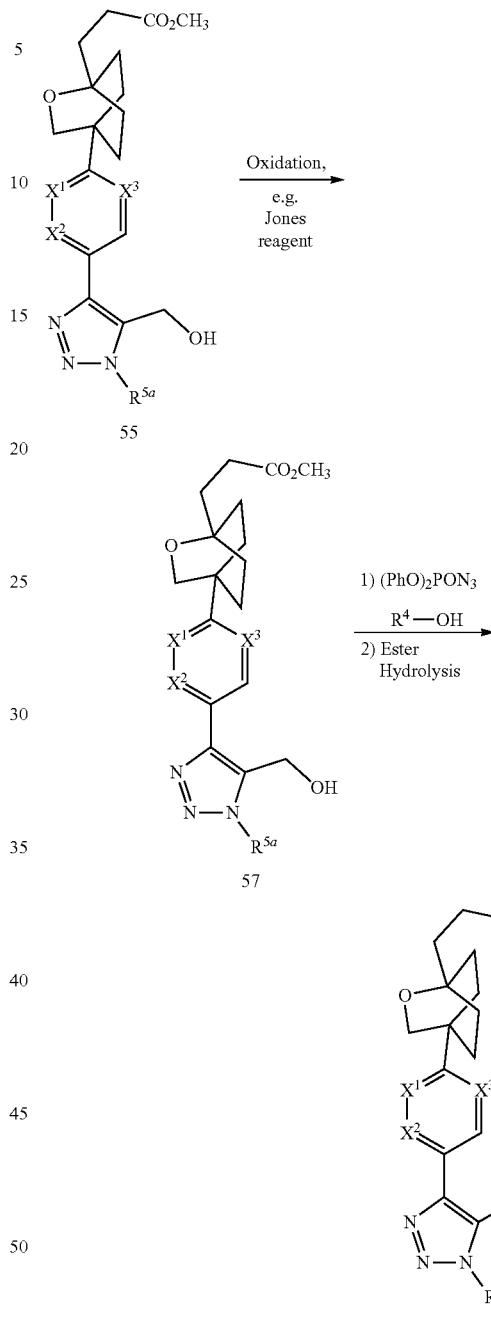

Scheme 9

Scheme 9 describes the synthesis of triazole N-carbamyl oxabicyclo[2.2.2]octan-1-yl propanoic acids 58. Oxidation of triazole alcohol 55 provides the triazole acid 57 (e.g. via direct oxidation to the acid with Jones reagent/pyridinium dichromate or via a 2-step procedure via the aldehyde [Swern oxidation or Dess-Martin periodinane followed by NaClO$_2$ oxidation to the acid, e.g. Lindgren, B. O., *Acta Chem. Scand.* 1973, 27, 888]). Curtius rearrangement of triazole acid 57 in the presence of an alcohol R$_1$—OH provides the triazole NH-carbamate, which is subjected to ester hydrolysis to provide the desired triazole N-carbamyl oxabicyclo[2.2.2]octan-1-yl propanoic acids 58.

Scheme 10 describes the synthesis of the intermediate haloaryl oxabicyclo[2.2.2]ester 61. The oxabicyclo[2.2.2] alcohol 51 is converted to the corresponding bromide (e.g. using a standard bromination protocol such as Ph$_3$P/CBr$_4$) 59. Elimination of bromide 59 provides the vinyl oxabicyclo[2.2.2]octane intermediate 60. Oxidative cleavage of the alkene 60 to the corresponding carboxylic acid, followed by acid protection, provides the desired haloaryl oxabicyclo[2.2.2]ester 61.

Scheme 10

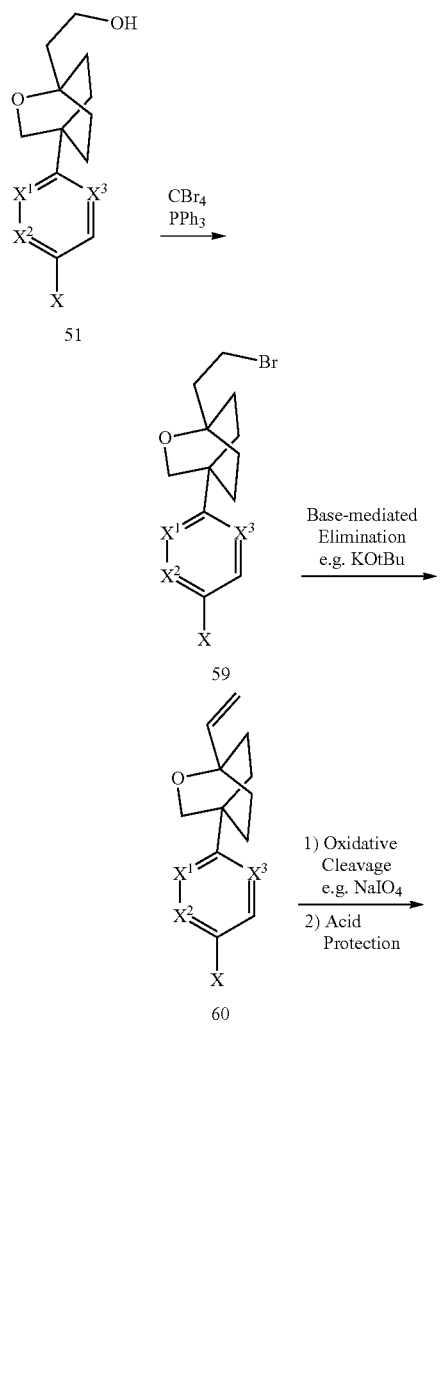

Scheme 11

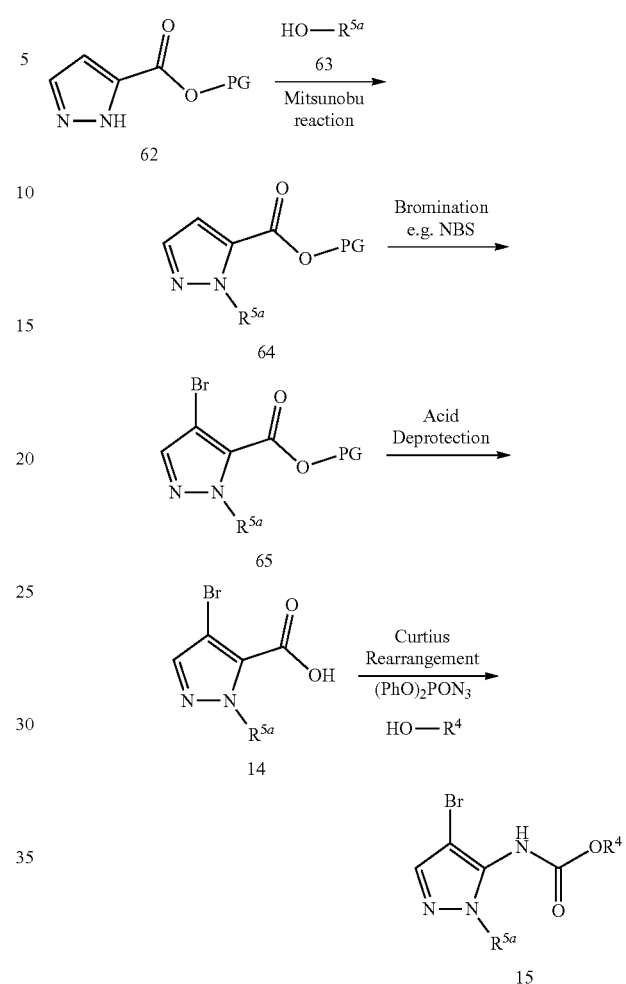

Scheme 11 describes the synthesis of 4-bromo-pyrazol-5-yl N-carbamates 15. Pyrazole 5-carboxylate ester 62 is subjected to a Mitsunobu reaction (Kumara Swamy, K. C., *Chem. Rev.*, 2009, 109, 2551-2651) with alcohol 63 to give N-alkylated pyrazole ester 64. Regioselective bromination (e.g. N-bromosuccinimide) of pyrazole ester 64 provides the 4-bromo-pyrazole ester 65. Deprotection of the ester provides the bromo-pyrazole carboxylic acid 14, which is subjected to a Curtius rearrangement in the presence of an alcohol 67 to provide the desired 4-bromo-pyrazol-5-yl N-carbamates 15.

Scheme 12 describes the synthesis of isoxazole 2-oxabicyclo[2.2.2]octan-1-yl aryl acetic acids 73 and pyrazole 2-oxabicyclo[2.2.2]octan-1-yl aryl acetic acids 74. A double Michael reaction of the anion of a 3-bromophenyl acetic acid ester 66 with acrylate ester 2 (2 equivalents) provides the β-keto cyclohexyl ester 67. Hydrolysis of diester 67 followed by decarboxylation of the intermediate β-keto-acid furnishes the cyclohexyl keto-acid 68. Horner-Emmons reaction with phosphonate-ester 5 provides the α,β-unsaturated ester-acid 69, which is reduced to the cyclohexyl alcohol 70. The cyclohexyl α,β-unsaturated ester-alcohol 70 is subjected to a base-mediated intramolecular oxy-Michael reaction to provide the oxabicylo[2.2.2] ester 71. Reaction of the 3-haloarene 71 with bis(pinacolato)diboron in the presence of an appropriate transition metal catalyst (e.g. palladium, for instance Ishiyama, T. et al, *J. Org. Chem.* 1995, 60, 7508-7510) provides the corresponding pinacol boronate 72, which is then converted to the desired oxabicyclo[2.2.2] isoxazole N-carbamate acids 73 using the procedures and general synthetic scheme described in Scheme 2. Similarly, the aryl pinacol boronate 72 is converted to the desired oxabicyclo[2.2.2] pyrazole N-carbamate acids 74 using the procedures and general synthetic scheme described in Scheme 3.

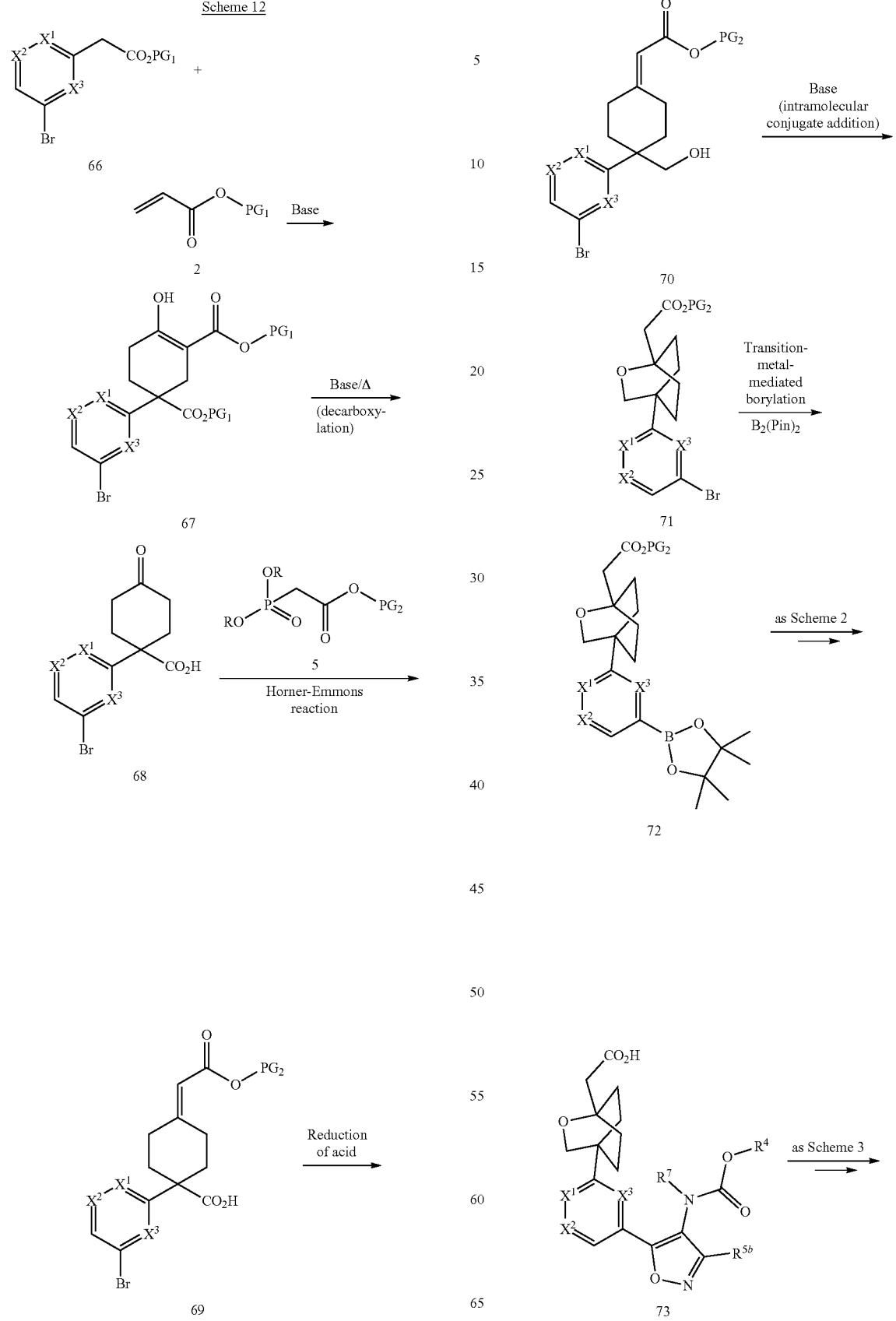

-continued

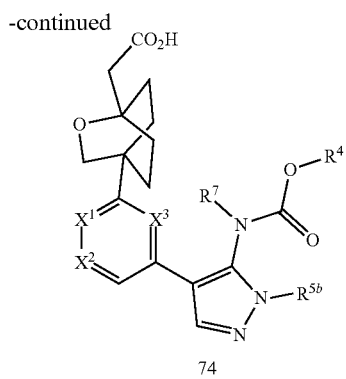

74

VII. Examples

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

As appropriate, reactions were conducted under an atmosphere of dry nitrogen (or argon). For anhydrous reactions, DRISOLV® solvents from EM were employed. For other reactions, reagent grade or HPLC grade solvents were utilized. Unless otherwise stated, all commercially obtained reagents were used as received.

Microwave reactions were carried out using a 400 W Biotage Initiator instrument in microwave reaction vessels under microwave (2.5 GHz) irradiation.

HPLC/MS and preparatory/analytical HPLC methods employed in characterization or purification of examples.

NMR (nuclear magnetic resonance) spectra were typically obtained on Bruker or JEOL 400 MHz and 500 MHz instruments in the indicated solvents. All chemical shifts are reported in ppm from tetramethylsilane with the solvent resonance as the internal standard. In the examples where $^1$H NMR spectra were collected in $d_6$-DMSO, a water-suppression sequence is often utilized. This sequence effectively suppresses the water signal and any proton peaks in the same region usually between 3.30-3.65 ppm which will affect the overall proton integration.

$^1$HNMR spectral data are typically reported as follows: chemical shift, multiplicity (s=singlet, br s=broad singlet, d=doublet, dd=doublet of doublets, t=triplet, q=quartet, sep=septet, m=multiplet, app=apparent), coupling constants (Hz), and integration.

The term HPLC refers to a Shimadzu high performance liquid chromatography instrument with one of following methods:

HPLC-1: Sunfire C18 column (4.6×150 mm) 3.5 μm, gradient from 10 to 100% B:A for 12 min, then 3 min hold at 100% B.
Mobile phase A: 0.05% TFA in water:CH$_3$CN (95:5)
Mobile phase B: 0.05% TFA in CH$_3$CN:water (95:5)
TFA Buffer pH=2.5; Flow rate: 1 mL/min; Wavelength: 254 nm, 220 nm.
HPLC-2: XBridge Phenyl (4.6×150 mm) 3.5 μm, gradient from 10 to 100% B:A for 12 min, then 3 min hold at 100% B.
Mobile phase A: 0.05% TFA in water:CH$_3$CN (95:5)
Mobile phase B: 0.05% TFA in CH$_3$CN:water (95:5)
TFA Buffer pH=2.5; Flow rate: 1 mL/min; Wavelength: 254 nm, 220 nm.
HPLC-3: Chiralpak AD-H, 4.6×250 mm, 5 μm.
Mobile Phase: 30% EtOH-heptane (1:1)/70% CO$_2$
Flow rate=40 mL/min, 100 Bar, 35° C.; Wavelength: 220 nm
HPLC-4: Waters Acquity UPLC BEH C18, 2.1×50 mm, 1.7-μm particles;
Mobile Phase A: 5:95 CH$_3$CN:water with 10 mM NH$_4$OAc;
Mobile Phase B: 95:5 CH$_3$CN:water with 10 mM NH$_4$OAc;
Temperature: 50° C.; Gradient: 0-100% B over 3 min, then a 0.75-min hold at 100% B;
Flow: 1.11 mL/min; Detection: UV at 220 nm.
HPLC-5: Waters Acquity UPLC BEH C18, 2.1×50 mm, 1.7-μm particles;
Mobile Phase A: 5:95 CH$_3$CN:water with 0.1% TFA;
Mobile Phase B: 95:5 CH$_3$CN:water with 0.1% TFA;
Temperature: 50° C.; Gradient: 0-100% B over 3 min, then a 0.75-min hold at 100% B;
Flow: 1.11 mL/min; Detection: UV at 220 nm.

Intermediate 1. methyl 2-(4-(4-(4,4,5,5-tetramethyl-1,3,2-dioxaborolan-2-yl)phenyl)-2-oxabicyclo[2.2.2]octan-1-yl)acetate

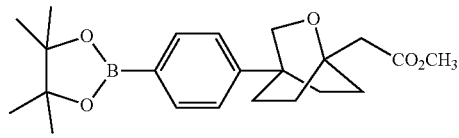 [SMILES: COC(=O)CC12CCC(c3ccc(B4OC(C)(C)C(C)(C)O4)cc3)(CC1)CO2]

A solution of methyl 2-(4-(4-bromophenyl)-2-oxabicyclo[2.2.2]octan-1-yl)acetate (340 mg, 1.00 mmol, prepared according to the procedures as described in U.S. Pat. No. 8,993,619), KOAc (295 mg, 3.01 mmol) and bis(pinacolato)diboron (305 mg, 1.20 mmol) in DMSO (4 mL) was degassed by bubbling with Ar for 5 min, after which PdCl$_2$(dppf) (73.3 mg, 0.100 mmol) was added. The reaction mixture was heated to 85° C. for 5 h under Ar, then was cooled to RT and partitioned between EtOAc (5 mL) and water (5 mL). The aqueous phase was extracted with EtOAc (2×8 mL). The combined organic extracts were washed with water (10 mL), brine (10 mL), dried (MgSO$_4$) and concentrated in vacuo. The crude product was chromatographed (SiO$_2$; continuous gradient from 0% to 100% EtOAc in hexanes over 20 min) to give the title compound as a white solid (310 mg, 0.80 mmol, 80% yield). $^1$H NMR (400 MHz, CDCl$_3$) δ 7.79 (d, J=8.4 Hz, 2H), 7.31 (d, J=8.4 Hz, 2H), 4.04 (s, 2H), 3.72 (s, 3H), 2.50 (s, 2H), 2.19-1.81 (m, 8H), 1.42-1.30 (m, 12H).

Intermediate 2. methyl 2-(4-(2-fluoro-4-(4,4,5,5-tetramethyl-1,3,2-dioxaborolan-2-yl)phenyl)-2-oxabicyclo [2.2.2]octan-1-yl)acetate

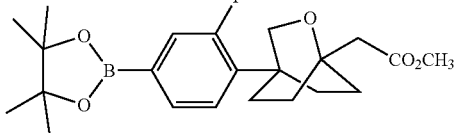

Intermediate 2 was prepared by the same synthetic sequence that was used to synthesize Intermediate 1. Methyl 2-(4-(4-bromo-2-fluorophenyl)-2-oxabicyclo[2.2.2]octan-1-yl)acetate was used as starting material instead of methyl 2-(4-(4-bromophenyl)-2-oxabicyclo[2.2.2]octan-1-yl)acetate. $^1$H NMR (400 MHz, CDCl$_3$) δ 7.51 (d, J=7.7 Hz, 1H), 7.42 (d, J=13.0 Hz, 1H), 7.12 (t, J=7.7 Hz, 1H), 4.14 (s, 2H), 3.69 (s, 3H), 2.47 (s, 2H), 2.22-1.99 (m, 6H), 1.96-1.85 (m, 2H), 1.32 (s, 12H).

Intermediate 3. methyl 2-(4-(3-fluoro-4-(4,4,5,5-tetramethyl-1,3,2-dioxaborolan-2-yl)phenyl)-2-oxabicyclo[2.2.2]octan-1-yl)acetate

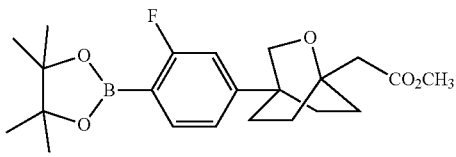 [SMILES: COC(=O)CC12CCC(c3ccc(B4OC(C)(C)C(C)(C)O4)c(F)c3)(CC1)CO2]

Intermediate 3 was prepared by the same synthetic sequence that was used to synthesize Intermediate 1. Methyl 2-(4-(4-bromo-3-fluorophenyl)-2-oxabicyclo[2.2.2]octan-1-yl)acetate was used as starting material instead of methyl 2-(4-(4-bromophenyl)-2-oxabicyclo[2.2.2]octan-1-yl)acetate. $^1$H NMR (400 MHz, CDCl$_3$) δ 7.70 (dd, J=7.8, 6.7 Hz, 1H), 7.07 (dd, J=7.8, 1.7 Hz, 1H), 6.95 (dd, J=11.2, 1.5 Hz, 1H), 4.01 (s, 2H), 3.72 (s, 3H), 2.50 (s, 2H), 2.22-2.03 (m, 4H), 2.00-1.85 (m, 4H), 1.37 (s, 10H).

Intermediate 4. (R)-1-phenylethyl (5-bromo-3-methylisoxazol-4-yl)carbamate

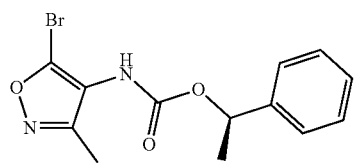 [SMILES: Cc1noc(Br)c1NC(=O)O[C@H](C)c1ccccc1]

Intermediate 4A. (R)-1-phenylethyl (3-methylisoxazol-4-yl)carbamate

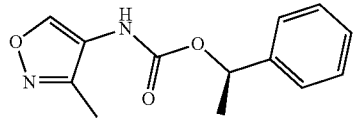 [SMILES: Cc1nocc1NC(=O)O[C@H](C)c1ccccc1]

A mixture of 3-methylisoxazole-4-carboxylic acid (2.0 g, 15.7 mmol), (PhO)$_2$PON$_3$ (4.24 mL, 18.9 mmol), (R)-1-phenylethanol (2.11 g, 17.3 mmol), Et$_3$N (2.85 mL, 20.5 mmol) in toluene (40 mL) was stirred at 80° C. for 4 h, then was cooled to RT and concentrated in vacuo. The crude product was chromatographed (SiO$_2$; continuous gradient from 0% to 100% EtOAc in hexanes over 25 min) to give the title compound as white solid (2.31 g, 9.38 mmol, 59.6% yield). LCMS [M+H]$^+$=247.0; $^1$H NMR (400 MHz, CDCl$_3$) δ 8.66 (br. S, 1H), 7.38 (d, J=4.4 Hz, 5H), 6.08 (br. S, 1H), 5.89 (q, J=6.6 Hz, 1H), 2.26 (s, 3H), 1.62 (d, J=6.6 Hz, 3H).

Intermediate 4

To a solution of intermediate 4A (248 mg, 1.01 mmol) in CH$_3$CN (10 mL) was slowly added NBS (233 mg, 1.31 mmol). The reaction mixture was stirred at RT overnight, then was concentrated in vacuo. The crude product was chromatographed (SiO$_2$; continuous gradient from 0% to 100% EtOAc in hexanes over 20 min) to give the title compound as a light yellow solid (241 mg, 0.73 mmol, 72.9% yield). LCMS [M+H]$^+$=327.0; $^1$H NMR (400 MHz, CDCl$_3$) δ 7.44-7.28 (m, 5H), 5.94-5.83 (m, 1H), 5.82-5.68 (m, 1H), 2.23 (s, 3H), 1.60 (d, J=6.8 Hz, 3H).

Intermediate 5. (R)-1-cyclopropylethyl (5-bromo-3-methylisoxazol-4-yl)carbamate

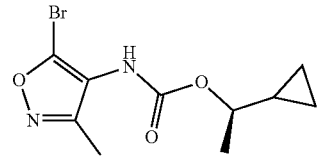 [SMILES: Cc1noc(Br)c1NC(=O)O[C@H](C)C1CC1]

Intermediate 5 was prepared by the same synthetic sequence that was used to synthesize Intermediate 4 from 3-methyl isoxazole-4-carboxylic acid, except that (R)-1-cyclopropylethanol was used as starting material instead of (R)-1-phenylethanol. $^1$H NMR (400 MHz, CDCl$_3$) δ 5.83 (br. s., 1H), 4.31 (dq, J=8.8, 6.3 Hz, 1H), 2.32 (s, 3H), 1.38 (d, J=5.1 Hz, 3H), 1.02 (br. s., 1H), 0.77-0.17 (m, 4H).

Intermediate 6. (R)-1-(2-chlorophenyl)ethyl (5-bromo-3-methylisoxazol-4-yl)carbamate

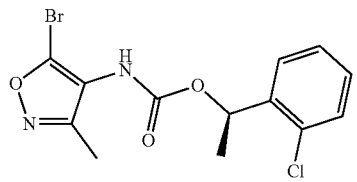 [SMILES: Cc1noc(Br)c1NC(=O)O[C@H](C)c1ccccc1Cl]

Intermediate 6 was prepared by the same synthetic sequence that was used to synthesize Intermediate 4 from 3-methyl isoxazole-4-carboxylic acid, except that (R)-1-(2-chlorophenyl) ethanol was used as starting material instead of (R)-1-phenylethanol. $^1$H NMR (400 MHz, CDCl$_3$) δ 7.38 (d, J=8.1 Hz, 3H), 7.25 (br. s., 1H), 6.22 (q, J=6.6 Hz, 1H), 5.91 (br. s., 1H), 2.26 (s, 3H), 1.66-1.58 (m, 3H).

Intermediate 7. (R)-1-(o-tolyl)ethyl (5-bromo-3-methylisoxazol-4-yl)carbamate

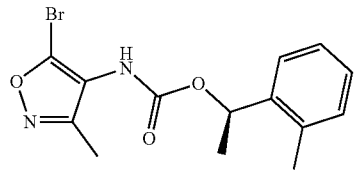 [SMILES: Cc1ccccc1[C@@H](C)OC(=O)Nc1c(C)noc1Br]

Intermediate 7 was prepared by the same synthetic sequence that was used to synthesize Intermediate 4 from 3-methyl isoxazole-4-carboxylic acid, except that (R)-1-(o-tolyl)ethan-1-ol was used as starting material instead of (R)-1-phenylethanol. $^1$H NMR (400 MHz, CDCl$_3$) δ 7.44 (br. s., 1H), 7.27-7.15 (m, 3H), 6.09 (q, J=6.6 Hz, 1H), 5.92 (br. s., 1H), 2.41 (s, 3H), 2.26 (s, 3H), 1.61 (d, 3H).

Intermediate 8. (±)-1-(4-chlorophenyl)ethyl (5-bromo-3-methylisoxazol-4-yl)carbamate

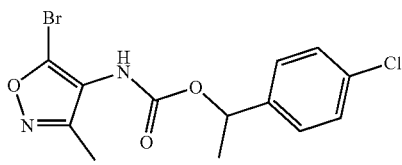 [SMILES: Cc1noc(Br)c1NC(=O)OC(C)c1ccc(Cl)cc1]

Intermediate 8 was prepared by the same synthetic sequence that was used to synthesize Intermediate 4 from 3-methyl isoxazole-4-carboxylic acid, except that (±)-1-(4-chlorophenyl) ethan-1-ol was used as starting material instead of (R)-1-phenylethanol. $^1$H NMR (400 MHz, CDCl$_3$) δ 7.33 (d, J=6.2 Hz, 4H), 5.96-5.87 (m, 1H), 5.83 (q, J=6.6 Hz, 1H), 2.24 (s, 3H), 1.59 (d, J=1.0 Hz, 3H).

Intermediate 9. (±)-1-(3-chlorophenyl)ethyl (5-bromo-3-methylisoxazol-4-yl)carbamate

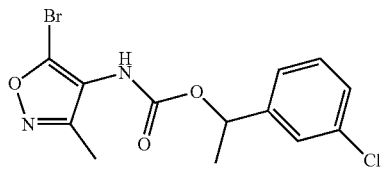 [SMILES: Cc1noc(Br)c1NC(=O)OC(C)c1cccc(Cl)c1]

Intermediate 9 was prepared by the same synthetic sequence that was used to synthesize Intermediate 4 from 3-methyl isoxazole-4-carboxylic acid, except that (±)-1-(3-chlorophenyl) ethan-1-ol was used as starting material instead of (R)-1-phenylethanol. $^1$H NMR (400 MHz, CDCl$_3$) δ 7.47 (s, 1H), 7.31 (br. s., 3H), 6.35-6.14 (m, 1H), 5.85 (q, J=6.6 Hz, 1H), 3.77 (s, 3H), 1.62 (bs, 3H; overlapping with water peak).

Intermediate 10. (R)-1-phenylethyl (4-bromo-1-methyl-1H-pyrazol-5-yl)carbamate

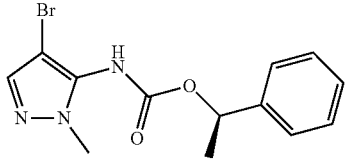 [SMILES: C[C@@H](OC(=O)Nc1c(Br)cnn1C)c1ccccc1]

A mixture of 4-bromo-1-methyl-1H-pyrazole-5-carboxylic acid (200 mg, 0.97 mmol), (PhO)$_2$PON$_3$ (254 μL, 1.17 mmol) and (R)-1-phenylethanol (125 mg, 1.02 mmol), TEA (272 μL, 1.95 mmol) in toluene (3 mL) was stirred at 80° C. for 1 h, then was cooled to RT and concentrated in vacuo. The crude product was chromatographed (SiO$_2$; continuous gradient from 0% to 100% EtOAc in hexanes over 20 min) to give the title compound (200 mg, 0.617 mmol, 63.2% yield). LCMS [M+H]$^+$=325.8; $^1$H NMR (400 MHz, CDCl$_3$) δ 7.75 (d, J=8.4 Hz, 2H), 7.37 (d, J=8.8 Hz, 2H), 5.94 (br. s., 1H), 4.02 (s, 2H), 4.01-3.95 (m, 2H), 3.70 (s, 3H), 2.49 (s, 2H), 2.29 (s, 3H), 2.11 (d, J=9.2 Hz, 4H), 2.01-1.85 (m, 4H), 0.93-0.74 (m, 1H), 0.67-0.21 (m, 4H).

Intermediate 11. (R)-1-(2-chlorophenyl)ethyl (4-bromo-1-methyl-1H-pyrazol-5-yl)carbamate

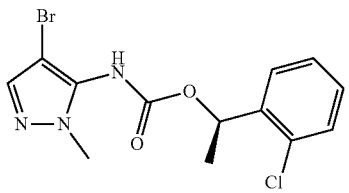 [SMILES: C[C@@H](OC(=O)Nc1c(Br)cnn1C)c1ccccc1Cl]

Intermediate 11 was prepared by the same procedure that was used to synthesize Intermediate 10, by using (R)-1-(2-chlorophenyl)ethanol as starting material instead of (R)-1-phenylethanol. $^1$H NMR (400 MHz, CDCl$_3$) δ 7.44 (s, 1H), 7.41-7.27 (m, 3H), 7.24 (s, 1H), 6.22 (q, J=6.5 Hz, 1H), 6.16-6.04 (m, 1H), 3.76 (s, 3H), 1.59 (d, J=5.3 Hz, 3H).

Intermediate 12. (±)-1-(4-chlorophenyl)ethyl (4-bromo-1-methyl-1H-pyrazol-5-yl)carbamate

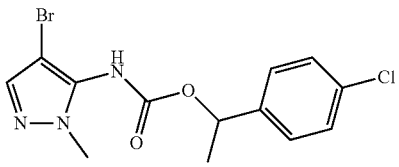 [SMILES: CC(OC(=O)Nc1c(Br)cnn1C)c1ccc(Cl)cc1]

Intermediate 12 was prepared by the same procedure that was used to synthesize Intermediate 10, by using (±)-1-(4-chlorophenyl)ethan-1-ol as starting material instead of (R)-

1-phenylethanol. $^1$H NMR (400 MHz, CDCl$_3$) δ: 7.47 (s, 1H), 7.30-7.42 (m, 4H), 6.01-6.36 (m, 1H), 5.86 (q, J=6.6 Hz, 1H), 3.76 (s, 3H), 1.61 (s, 3H).

Intermediate 13. methyl 2-(4-(4-(3-methyl-4-((((4-nitrophenoxy)carbonyl)oxy) methyl)isoxazol-5-yl)phenyl)-2-oxabicyclo[2.2.2]octan-1-yl)acetate

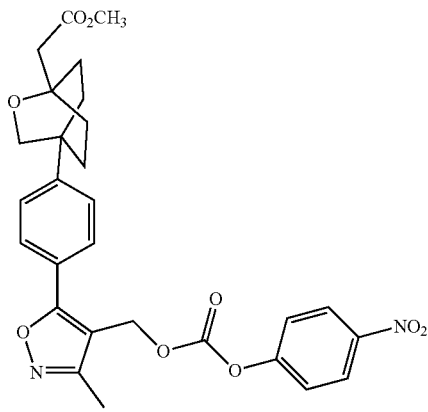 [SMILES: COC(=O)CC12CCC(c3ccc(-c4onc(C)c4COC(=O)Oc4ccc([N+](=O)[O-])cc4)cc3)(CC1)CO2]

Intermediate 13A.
(5-bromo-3-methylisoxazol-4-yl)methanol

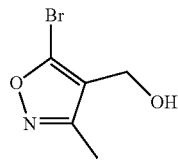

To a solution of ethyl 5-bromo-3-methylisoxazole-4-carboxylate (480 mg, 2.05 mmol)) in THF added DIBALH (6.5 mL of a 1M solution in DCM; 6.50 mmol) dropwise over 5 min at RT. The reaction was stirred at RT for 1 h, then was quenched with aq. sodium potassium tartrate (10 mL of a 1M solution) & stirred at RT for 1 h. The resultant mixture was filtered through a plug of Celite®; the plug was washed with EtOAc (2×5 mL) and concentrated in vacuo to give the title compound as a white solid (334 mg, 1.74 mmol, 85% yield). LCMS [M+H]$^+$=193.9; $^1$H NMR (CDCl$_3$) δ: 4.51 (s, 2H), 2.40 (s, 3H).

Intermediate 13B. methyl 2-(4-(4-(4-(hydroxymethyl)-3-methylisoxazol-5-yl)phenyl)-2-oxabicyclo[2.2.2]octan-1-yl)acetate

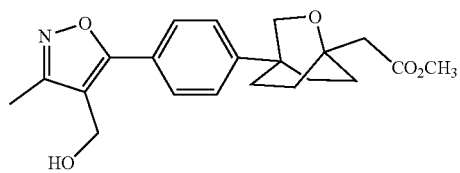 [SMILES: COC(=O)CC12CCC(c3ccc(-c4onc(C)c4CO)cc3)(CC1)CO2]

To a solution of Intermediate 1 (40.2 mg, 0.10 mmol) and Intermediate 13A (20 mg, 0.104 mmol) in THF/water was added K$_2$CO$_3$ (43.2 mg, 0.31 mmol). The solution was degassed under N$_2$, after which PdCl$_2$(dppf) (7.6 mg, 10.4 μmol) was added. The reaction mixture was heated in a sealed tube at 80° C. for 18 h, then was cooled to RT and filtered through a plug of Celite. The Celite plug was washed with EtOAc (2×2 mL). The combined filtrates were partitioned between water and EtOAc (5 mL each). The aqueous layer was extracted with EtOAc (3×2 mL). The combined organic extracts were washed with brine, dried (MgSO$_4$), and concentrated in vacuo. The residue was chromatographed (SiO$_2$; continuous gradient from 0% to 100% EtOAc in hexanes over 20 min) to give the title compound as a light yellow oil (18 mg, 0.068 mmol, 46.5% yield). LCMS [M+H]$^+$=373.1; $^1$H NMR (400 MHz, CDCl$_3$) δ 7.77 (d, J=8.6 Hz, 2H), 7.42 (d, J=8.6 Hz, 2H), 4.66 (s, 2H), 4.06 (s, 2H), 3.73 (s, 3H), 2.51 (s, 2H), 2.40 (s, 3H), 2.14 (d, J=8.6 Hz, 4H), 1.95 (d, J=7.5 Hz, 4H).

Intermediate 13

To a solution of Intermediate 13B (18 mg, 0.048 mmol) in DCE (1 mL) was added pyridine (0.020 mL, 0.24 mmol), followed by 4-nitrophenyl chloroformate (19.5 mg, 0.097 mmol). The reaction mixture was stirred at RT for 18 h, then was filtered and concentrated in vacuo. The residue was chromatographed (SiO$_2$; continuous gradient from 0% to 100% EtOAc in hexanes over 20 min) to give the title compound as a light yellow solid (16 mg, 0.030 mmol, 60.5% yield). LCMS [M+H]$^+$=537.2; $^1$H NMR (400 MHz, CDCl$_3$) δ 8.31 (d, J=9.2 Hz, 2H), 7.77 (d, J=8.6 Hz, 2H), 7.44 (dd, J=18.0, 9.0 Hz, 4H), 5.29 (s, 2H), 4.07 (s, 2H), 3.73 (s, 3H), 2.52 (s, 2H), 2.46 (s, 3H), 2.15 (d, J=8.6 Hz, 4H), 2.05-1.87 (m, 4H).

Intermediate 14. methyl 2-(4-(4-(1-methyl-5-((((4-nitrophenoxy)carbonyl)oxy)methyl)-1H-pyrazol-4-yl)phenyl)-2-oxabicyclo[2.2.2]octan-1-yl)acetate

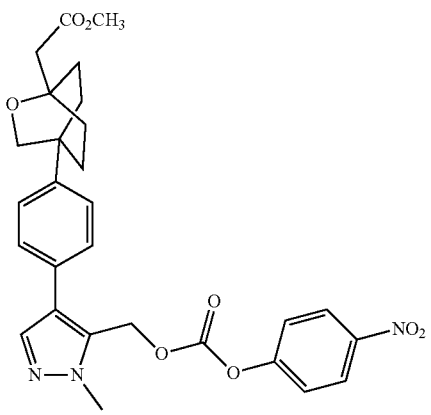 [SMILES: COC(=O)CC12CCC(c3ccc(-c4cnn(C)c4COC(=O)Oc4ccc([N+](=O)[O-])cc4)cc3)(CC1)CO2]

Intermediate 14A.
(4-bromo-1-methyl-1H-pyrazol-5-yl)methanol

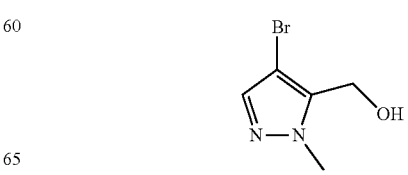

To a solution of ethyl 5-bromo-3-methylisoxazole-4-carboxylate (480 mg, 2.05 mmol)) in THF added DIBALH (6.5 mL of a 1M solution in DCM; 6.50 mmol) dropwise over 5 min at RT. The reaction was stirred at RT for 1 h, then was quenched with aq. sodium potassium tartrate (10 mL of a 1M solution) & stirred at RT for 1 h. The resultant mixture was filtered through a plug of Celite; the plug was washed with EtOAc (2×5 mL) and concentrated in vacuo to give the title compound as a white solid (334 mg, 1.74 mmol, 85% yield). LCMS [M+H]$^+$=193.9; $^1$H NMR (CDCl$_3$) δ: 4.51 (s, 2H), 2.40 (s, 3H).

Intermediate 14B. methyl 2-(4-(4-(5-(hydroxymethyl)-1-methyl-1H-pyrazol-4-yl)phenyl)-2-oxabicyclo[2.2.2] octan-1-yl)acetate

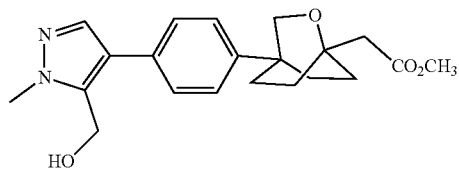 [SMILES: COC(=O)CC12CCC(c3ccc(-c4cnn(C)c4CO)cc3)(CC1)CO2]

To a solution of Intermediate 1 (101 mg, 0.26 mmol) and Intermediate 14A (50 mg, 0.26 mmol) in THF/water was added K$_2$CO$_3$ (109 mg, 0.79 mmol). The solution was degassed under N$_2$, after which PdCl$_2$(dppf) (19.2 mg, 0.026 mmol) was added. The reaction was heated in a sealed tube at 80° C. for 18 h, then was cooled to RT and filtered through a plug of Celite. The Celite plug was washed with EtOAc (2×2 mL). The combined filtrates were partitioned between water and EtOAc (5 mL each). The aqueous layer was extracted with EtOAc (3×5 mL). The combined organic extracts were washed with brine, dried (MgSO$_4$), and concentrated in vacuo. The residue was chromatographed (SiO$_2$ ISCO column; continuous gradient from 0% to 100% EtOAc in hexanes over 20 min) to give the title compound as a light yellow oil (75 mg, 0.20 mmol, 77% yield). LCMS [M+H]$^+$=372.1; $^1$H NMR (400 MHz, CDCl$_3$) δ 7.45 (s, 1H), 7.32-7.15 (m, 5H), 4.67 (d, J=5.1 Hz, 2H), 3.99-3.87 (m, 5H), 3.63 (s, 3H), 2.41 (s, 2H), 2.04 (d, J=7.0 Hz, 4H), 1.91-1.80 (m, 4H).

Intermediate 14

To a solution of Intermediate 14B (75 mg, 0.20 mmol) in DCE (2 mL) were successively added pyridine (0.082 mL, 1.01 mmol) and 4-nitrophenyl chloroformate (73.5 mg, 0.36 mmol). The reaction mixture was stirred at RT for 18 h, then was filtered and concentrated in vacuo. The residue was chromatographed (SiO$_2$ ISCO column; continuous gradient from 0% to 100% EtOAc in hexanes over 20 min) to give the title compound as a light yellow solid (76 mg, 0.14 mmol, 70% yield). LCMS [M+H]$^+$=536.1; $^1$H NMR (400 MHz, CDCl$_3$) δ 8.33 (d, J=9.2 Hz, 1H), 7.64 (s, 1H), 7.47-7.33 (m, 7H), 5.41 (s, 2H), 4.06 (s, 5H), 3.73 (s, 3H), 2.52 (s, 2H), 2.15 (d, J=7.0 Hz, 4H), 2.04-1.89 (m, 4H).

Intermediate 15. methyl 3-(4-(4-(5-(hydroxymethyl)-1-methyl-1H-1,2,3-triazol-4-yl)phenyl)-2-oxabicyclo[2.2.2]octan-1-yl)propanoate

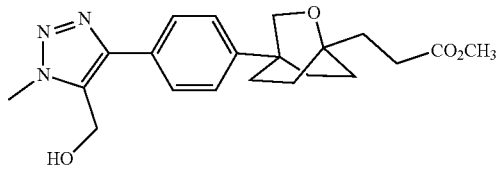 [SMILES: COC(=O)CCC12CCC(c3ccc(-c4nnn(C)c4CO)cc3)(CC1)CO2]

Intermediate 15A. 2-(4-(4-bromophenyl)-2-oxabicyclo[2.2.2]octan-1-yl)ethan-1-ol

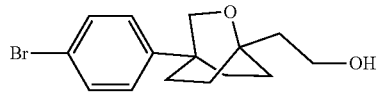

To a 0° C. solution of methyl 2-(4-(4-bromophenyl)-2-oxabicyclo[2.2.2]octan-1-yl)acetate (1.01 g, 2.98 mmol, prepared according to the procedures described in U.S. Pat. No. 8,993,619) in THF (59.5 mL) was added DIBALH (14.9 mL of a 1M solution in THF, 14.9 mmol). After stirring at 30 min at 0° C., the reaction was quenched with aq. sodium potassium tartrate (60 mL). The aqueous layer was extracted with EtOAc (3×60 mL); the combined organic extracts were dried (Na$_2$SO$_4$) and concentrated in vacuo to give the title compound (0.97 g, 3.12 mmol, 105% yield) as an oil. $^1$H NMR (400 MHz, CDCl$_3$) 7.44 (d, J=8.6 Hz, 2H), 7.14 (d, J=8.6 Hz, 2H), 3.96 (s, 2H), 3.81 (br. s., 2H), 3.32-3.07 (m, 1H), 2.21-1.84 (m, 6H), 1.82-1.63 (m, 4H).

Intermediate 15B. 2-(4-(4-bromophenyl)-2-oxabicyclo[2.2.2]octan-1-yl)ethyl methanesulfonate

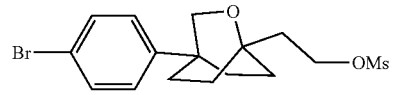

To a 0° C. solution of Intermediate 15A (1.0 g, 3.21 mmol) in THF (32.1 mL) was added Et$_3$N (2.24 mL, 16.1 mmol) and methanesulfonyl chloride (0.376 ml, 4.82 mmol) at 0° C. and the reaction was stirred at RT for 30 min. LCMS showed that the reaction was complete. Satd aq. NaHCO$_3$ (10 mL) was added slowly to the reaction mixture. The mixture was extracted with EtOAc (2×20 mL), and the combined organic extracts were dried (Na$_2$SO$_4$) and concentrated in vacuo to give Intermediate 15B (1.3 g, 3.34 mmol, 104% yield) as an oil, which was used in the. next step without further purification. $^1$H NMR (400 MHz, CDCl$_3$) δ 7.44 (d, J=8.8 Hz, 2H), 7.13 (d, J=8.6 Hz, 2H), 4.38 (t, J=7.0 Hz, 2H), 3.94 (s, 2H), 3.01 (s, 3H), 2.10-1.84 (m, 8H), 1.80-1.64 (m, 2H).

Intermediate 15 C. 3-(4-(4-bromophenyl)-2-oxabi-cyclo[2.2.2]octan-1-yl)propanenitrile

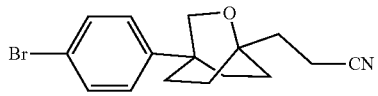

To a solution of Intermediate 15B (1.3 g, 3.34 mmol) in DMSO (33.4 mL) were added NaCN (0.491 g, 10.02 mmol) and Bu$_4$NI (0.123 g, 0.334 mmol) and the reaction was stirred at 90° C. for 16 h, after which LCMS showed presence of desired product. The reaction was cooled to RT and H$_2$O (10 mL) was added slowly to the reaction mixture. The mixture was then extracted with EtOAc (2×20 mL), and the combined organic extracts were dried (Na$_2$SO$_4$) and concentrated in vacuo. The crude product was chromatographed (SiO$_2$; continuous gradient from 0% to 100% EtOAc in hexanes over 20 min) to give the title compound (0.85 g, 2.65 mmol, 79% yield). $^1$H NMR (400 MHz, CDCl$_3$) δ 7.53-7.40 (m, 2H), 7.20-7.08 (m, 2H), 3.99-3.89 (m, 2H), 2.55-2.37 (m, 2H), 2.16-1.90 (m, 6H), 1.87-1.65 (m, 4H).

Intermediate 15 D. methyl 3-(4-(4-bromophenyl)-2-oxabicyclo[2.2.2]octan-1-yl)propanoate

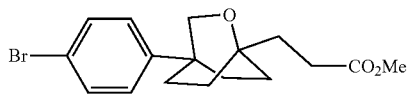 [SMILES: COC(=O)CCC12CCC(c3ccc(Br)cc3)(CC1)CO2]

Preparation of a 3.6 M HCl solution in MeOH/MeOAc: To a solution of MeOH (30 mL) at 0° C. was added dropwise acetyl chloride (10 mL, d=1.104 g/mL, MW=78.49). Upon completion of the addition, the resulting solution was warmed to RT for 30 min. This 3.6 M HCl solution in MeOH/MeOAc (36.9 mL, 133 mmol) was added to Intermediate 15C (850 mg, 2.65 mmol) and the reaction was stirred at RT for 72 h. The reaction mixture was diluted with MeCN (25 mL) and was concentrated in vacuo to remove MeOH and MeCN. The residue was dissolved in EtOAc (30 mL) and washed with satd aq NaHCO$_3$ (2×30 mL), water (30 mL), and brine (30 mL). The organic layer was dried (Na$_2$SO$_4$) and concentrated in vacuo. The crude product was chromatographed (SiO$_2$; continuous gradient from 0% to 100% EtOAc in hexanes over 20 min) to give the title compound (810 mg, 2.293 mmol, 86% yield) as an oil. $^1$H NMR (400 MHz, CDCl$_3$) δ 7.43 (d, J=8.6 Hz, 2H), 7.21-6.99 (m, 2H), 4.00-3.84 (m, 2H), 3.67 (s, 3H), 2.49-2.28 (m, 2H), 2.12-1.85 (m, 6H), 1.82-1.73 (m, 2H), 1.71-1.60 (m, 2H), 1.35-1.18 (m, 1H), 0.92-0.75 (m, 1H).

Intermediate 15E. methyl 3-(4-(4-(3-hydroxyprop-1-yn-1-yl)phenyl)-2-oxabicyclo[2.2.2]octan-1-yl)propanoate

To a degassed solution of Intermediate 15D (200 mg, 0.566 mmol) in THF (2.8 ml) were added successively: CuI (10.8 mg, 0.057 mmol), Pd(PPh$_3$)$_4$ (65.4 mg, 0.057 mmol), and DBU (0.25 mL, 1.70 mmol). The resulting mixture was degassed again and prop-2-yn-1-ol (0.1 mL, 1.70 mmol) was added over 10 min. The reaction mixture was slowly heated to 60° C. and then stirred at 60° C. overnight, then was cooled to RT and diluted with ether (50 mL). The mixture was washed with water (20 mL), 15% aq. HCl (2×20 mL) and satd aq. NaHCO$_3$ (25 mL). The organic layer was dried (MgSO$_4$) and concentrated in vacuo. The residue was chromatographed (SiO$_2$; continuous gradient from 0% to 100% EtOAc in hexanes over 20 min) to give the title compound (160 mg, 86%) as an oil. $^1$H NMR (400 MHz, CDCl$_3$) δ 7.46-7.35 (m, 2H), 7.25-7.11 (m, 2H), 4.57-4.46 (m, 2H), 4.03-3.91 (m, 2H), 3.77-3.61 (m, 2H), 2.49-2.35 (m, 4H), 2.04-1.85 (m, 4H), 1.84-1.75 (m, 2H), 1.72-1.66 (m, 2H).

Intermediate 15

A solution of Intermediate 15E (160 mg, 0.487 mmol) in toluene (0.5 ml) and TMSCH$_2$N$_3$ (315 mg, 2.44 mmol) was heated at reflux under Ar for 15 h, then was cooled to RT. Volatiles were removed in vacuo and the residue was dissolved in THF (0.5 mL). To the mixture was added Bu$_4$NF (0.5 mL of a 1 M solution in THF, 0.50 mmol) at 0° C. After stirring for 10 min at 0° C., the reaction mixture was concentrated in vacuo and the residue was chromatographed (SiO$_2$; continuous gradient from 0% to 100% EtOAc in hexanes over 20 min) to give the title compound (35 mg, 19%) as an oil. $^1$H NMR (400 MHz, CDCl$_3$) δ 7.65-7.55 (m, 2H), 7.35-7.30 (m, 2H), 4.87-4.81 (m, 2H), 4.11-4.08 (m, 3H), 3.98-3.95 (m, 2H), 3.71-3.67 (m, 3H), 2.45-2.38 (m, 2H), 2.13-2.06 (m, 2H), 2.00-1.89 (m, 4H), 1.84-1.76 (m, 2H), 1.73-1.61 (m, 2H).

Intermediate 16. 4-(4-(1-(3-methoxy-3-oxopropyl)-2-oxabicyclo[2.2.2]octan-4-yl)phenyl)-1-methyl-1H-1,2,3-triazole-5-carboxylic acid

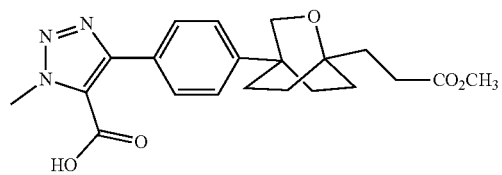 [SMILES: COC(=O)CCC12CCC(c3ccc(-c4nnn(C)c4C(=O)O)cc3)(CC1)CO2]

To a 0° C. solution of Intermediate 15 (16 mg, 0.043 mmol) in acetone (1.4 mL) was added Jones reagent (0.3 mL, 0.90 mmol). The reaction mixture was stirred at 0° C. for 1 h, after which iPrOH (1 mL) was added and volatiles were concentrated in vacuo. Water (10 mL) was added and the mixture was extracted with EtOAc (3×10 mL). The combined organic extracts were concentrated in vacuo to give the title compound (16 mg, 0.042 mmol, 96% yield). This material was used for the next step without further purification. LCMS [M+H]$^+$=386.1.

Intermediate 17. methyl 4-(4-bromophenyl)-2-oxabicyclo[2.2.2]octane-1-carboxylate

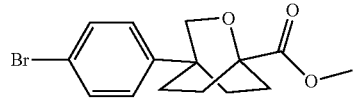

Intermediate 17A. 1-(2-bromoethyl)-4-(4-bromophenyl)-2-oxabicyclo[2.2.2]octane

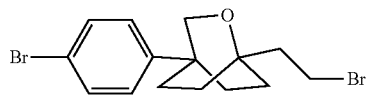

To a 0° C. solution of 2-(4-(4-bromophenyl)-2-oxabicyclo[2.2.2]octan-1-yl)ethanol (2.5 g, 8.03 mmol)) in DCM (2 mL) were successively added CBr$_4$ (4.00 g, 12.1 mmol) and Ph$_3$P (2.53 g, 9.64 mmol). The reaction mixture was stirred at 0° C. for 2 h, then was allowed to warm to RT and stirred at RT for 2 h, after which it was concentrated in vacuo. The residue was chromatographed (SiO$_2$; continuous gradient from 0% to 100% EtOAc in hexanes over 20 min) to give the title compound (2.8 g, 93%). $^1$H NMR (400 MHz, CDCl$_3$) 7.53-7.43 (m, 2H), 7.22-7.10 (m, 2H), 4.10-3.85 (m, 2H), 3.57-3.36 (m, 2H), 2.16-1.86 (m, 8H), 1.79-1.62 (m, 2H).

Intermediate 17B. 4-(4-bromophenyl)-1-vinyl-2-oxabicyclo[2.2.2]octane

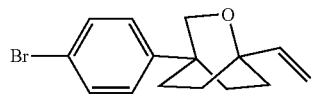

To a solution of Intermediate 17A (2.70 g, 7.22 mmol)) in DMSO (144 ml) was added KOtBu (1.22 g, 10.83 mmol). The reaction mixture was stirred at 80° C. for 1 h, then was cooled to RT, after which sat'd aq. NaHCO$_3$ (10 mL) was slowly added. The mixture was extracted with EtOAc (2×20 mL) and the combined organic extracts were dried (Na$_2$SO$_4$), and concentrated in vacuo to give the title compound (1.70 g, 80%). $^1$H NMR (400 MHz, CDCl$_3$) 7.58-7.40 (m, 2H), 7.22-7.11 (m, 2H), 5.98-5.83 (m, 1H), 5.27-5.17 (m, 1H), 5.12-4.98 (m, 1H), 4.14-3.99 (m, 2H), 2.19-2.02 (m, 4H), 2.00-1.93 (m, 2H), 1.89-1.79 (m, 2H).

Intermediate 17C. 4-(4-bromophenyl)-2-oxabicyclo[2.2.2]octane-1-carboxylic acid

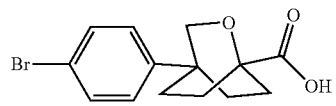

To a solution of Intermediate 17B (600 mg, 2.05 mmol) in MeCN (3 mL), CCl$_4$ (3 mL) and water (3 mL) was added NaIO$_4$ (1.7 g, 8.19 mmol) and Ru(III)Cl$_3$ (42.4 mg, 0.205 mmol). The reaction mixture was stirred at RT for 23 h, then was filtered. The filtrate was diluted with EtOAc (10 mL) and washed with 1N aq. HCl (10 mL), then was concentrated in vacuo. The crude material was triturated with EtOAc (3 mL) to give the title compound (600 mg, 1.928 mmol, 94% yield) as a solid. $^1$H NMR (400 MHz, CDCl$_3$). 42-7.34 (m, 2H), 7.11-6.99 (m, 2H), 4.10-3.98 (m, 2H), 2.24-1.76 (m, 8H).

Intermediate 17

To a 0° C. solution of Intermediate 17C (300 mg, 0.964 mmol) in THF (0.3 mL)/MeOH (0.6 mL) was added TMSCHN$_2$ (0.482 mL of a 2 M solution in Et$_2$O, 0.964 mmol) dropwise. The reaction mixture was slowly warmed to RT and stirred at RT for 1 h. Volatiles were removed in vacuo. The crude product was chromatographed (SiO$_2$; continuous gradient from 0% to 100% EtOAc in hexanes over 20 min) to give the title compound (300 mg, 96%). $^1$H NMR (400 MHz, CDCl$_3$) 7.34-7.25 (m, 2H), 7.01-6.89 (m, 2H), 3.93-3.86 (m, 2H), 3.84-3.70 (m, 3H), 2.03-1.33 (m, 8H).

Intermediate 18. (R)-1-phenylethyl (4-bromo-1-(cyclopropylmethyl)-1H-pyrazol-5-yl)carbamate

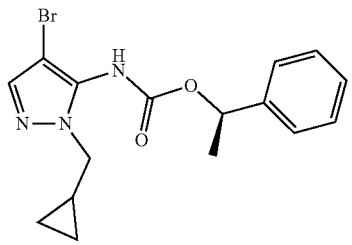 [SMILES: C[C@@H](OC(=O)Nc1c(Br)cnn1CC1CC1)c1ccccc1]

18A. methyl 1-(cyclopropylmethyl)-1H-pyrazole-5-carboxylate

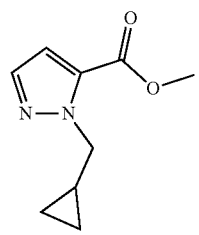

To a solution of methyl 1H-pyrazole-5-carboxylate (100 mg, 0.793 mmol), cyclopropyl-methanol (68 mg, 0.952 mmol), and Ph$_3$P (260 mg, 0.991 mmol) in DCM (1 mL) was added DEAD (176 μL, 1.11 mmol) at RT. The reaction mixture was stirred at RT for 16 h, then was concentrated in vacuo. The crude material was chromatographed (SiO$_2$; continuous gradient from 0% to 100% EtOAc in hexanes over 20 min) to afford the title compound (45 mg, 0.25 mmol, 31.5% yield) as a clear, colorless oil. $^1$H NMR (400 MHz, CDCl$_3$) 7.27 (d, J=2.0 Hz, 1H), 6.62 (d, J=2.0 Hz, 1H), 4.22 (d, J=7.3 Hz, 2H), 3.66 (s, 3H), 1.21-0.99 (m, 1H), 0.30 (s, 2H), 0.22-0.10 (m, 2H).

18B. methyl 4-bromo-1-(cyclopropylmethyl)-1H-pyrazole-5-carboxylate

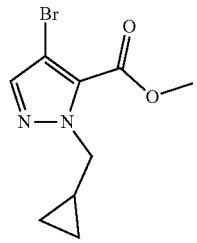

A mixture of Intermediate 18A (45 mg, 0.250 mmol) and NBS (49 mg, 0.275 mmol) in MeCN (1.25 mL) was stirred at RT for 16 h, then was concentrated in vacuo. The crude product was chromatographed (24 g SiO$_2$; continuous gradient from 0-50% EtOAc in hexanes over 15 min) to afford crude Intermediate 18B (30 mg, 0.116 mmol, 46.4% yield) as a pale yellow oil. $^1$H NMR (400 MHz, CDCl$_3$) δ 7.37-7.17 (m, 1H), 4.38-4.07 (m, 2H), 3.80-3.63 (m, 3H), 0.69-0.64 (m, 1H), 0.39-0.28 (m, 2H), 0.21-0.11 (m, 2H).

Intermediate 18C. 4-bromo-1-(cyclopropylmethyl)-1H-pyrazole-5-carboxylic acid

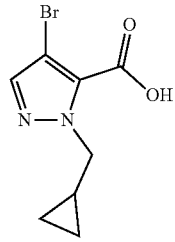 [SMILES: O=C(O)c1c(Br)cnn1CC1CC1]

To a stirred solution of crude Intermediate 18B (40 mg, 0.154 mmol) in THF (1.5 mL), MeOH (0.100 mL) and water (0.15 mL) at RT was added 2.0 M aq. LiOH (0.23 mL, 0.463 mmol). The reaction mixture was stirred at RT for 16 h, then was acidified by dropwise addition of 1M aq. HCl (0.5 mL). The aqueous layer was extracted with EtOAc (3×3 mL). The combined organic extracts were dried (Na$_2$SO$_4$) and concentrated in vacuo to give the title compound (40 mg, 0.163 mmol, 106% yield). LCMS [M+H]$^+$=246.9.

Intermediate 18

A mixture of Intermediate 18C (35 mg, 0.143 mmol), (PhO)$_2$PON$_3$ (0.040 mL, 0.186 mmol), (R)-1-phenylethanol (0.023 mL, 0.186 mmol), and TEA (0.10 mL, 0.714 mmol) in toluene (5 mL) was stirred at 80° C. for 1 h, then was cooled to RT and concentrated in vacuo. The crude oil was chromatographed (4 g SiO$_2$; continuous gradient from 0% to 50% EtOAc in hexane over 10 min) to give the title compound (36 mg, 0.099 mmol, 69.2% yield) as a clear oil. $^1$H NMR (400 MHz, CDCl$_3$) 7.14-6.82 (m, 5H), 6.14-5.81 (m, 1H), 5.73-5.56 (m, 1H), 3.74-3.53 (m, 1H), 1.47-1.24 (m, 4H), 1.03-0.83 (m, 1H), 0.33-0.22 (m, 2H), 0.10-0.01 (m, 2H).

Example 1. 2-(4-(4-(3-methyl-4-((((R)-1-phenylethoxy)carbonyl)amino)isoxazol-5-yl)phenyl)-2-oxabicyclo[2.2.2]octan-1-yl)acetic acid

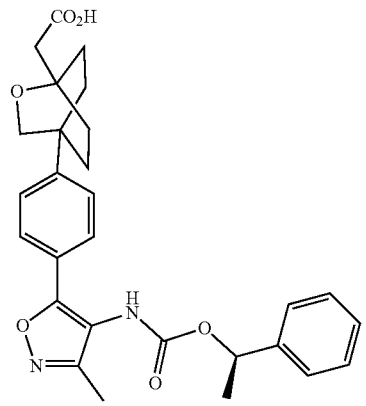 [SMILES: Cc1noc(-c2ccc(C34CCC(CC(=O)O)(CC3)OC4)cc2)c1NC(=O)O[C@H](C)c1ccccc1]

1A. methyl 2-(4-(4-(3-methyl-4-((((R)-1-phenylethoxy)carbonyl)amino)isoxazol-5-yl)phenyl)-2-oxabicyclo[2.2.2]octan-1-yl)acetate

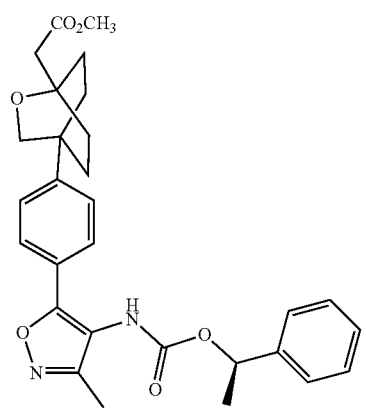 [SMILES: COC(=O)CC12CCC(c3ccc(-c4onc(C)c4NC(=O)O[C@H](C)c4ccccc4)cc3)(CC1)CO2]

A solution of Intermediate 1 (50 mg, 0.13 mmol), Intermediate 4 (42 mg, 0.13 mmol), K$_2$CO$_3$ (54 mg, 0.39 mmol) and PdCl$_2$(dppf) (10 mg, 0.013 mmol) in THF (5 mL) and water (1.25 mL) was purged with Ar for 5 min. The reaction mixture was then heated to 80° C. for 18 h under Ar, then was cooled to RT and filtered through Celite. The filtrate was partitioned between EtOAc (3 mL) and water (3 mL); the aqueous phase was extracted with EtOAc (2×3 mL). The combined organic extracts were washed with water (2 mL), brine (2 mL), dried (MgSO$_4$) and concentrated in vacuo. The crude product was chromatographed (SiO$_2$ ISCO column; continuous gradient from 0% to 100% EtOAc in hexanes over 20 min) to give title compound as a colorless oil. (23 mg, 0.045 mmol, 34.5% yield) LCMS [M+H]$^+$=505.0; $^1$H NMR (400 MHz, CDCl$_3$) δ 8.00-7.23 (m, 9H), 5.87 (d, J=6.4 Hz, 2H), 4.01 (s, 2H), 3.70 (s, 3H), 2.49 (s, 3H), 2.21 (s, 3H), 2.16-2.04 (m, 4H), 2.00-1.88 (m, 4H), 1.70-1.59 (m, 2H).

Example 1

To a solution of compound 1A (22 mg, 0.044 mmol) in THF (1 mL) was added 1M aq. LiOH (0.44 mL, 0.44 mmol).

The reaction was stirred at RT for 18 h, then was concentrated in vacuo. The residue was dissolved in H$_2$O (1 mL), and the pH was adjusted with 1N aq. HCl to ~3 and extracted with EtOAc (2×1 mL). The combined organic extracts were washed with brine (1 mL), dried (MgSO$_4$) and concentrated in vacuo. The crude product was purified by preparative LC/MS: Column: Waters XBridge C18, 19×200 mm, 5-μm particles; Guard Column: Waters XBridge C18, 19×10 mm, 5-μm particles; Mobile Phase A: 5:95 MeCN:H$_2$O with 0.1% TFA; Mobile Phase B: 95:5 MeCN:H$_2$O with 0.1% TFA; Gradient: 50-90% B over 20 min, then a 5-min hold at 100% B; Flow: 20 mL/min. Fractions containing the desired product were combined and concentrated in vacuo by centrifugal evaporation to give the title compound (11 mg, 0.023 mmol, 52.3% yield). LCMS [M+H]$^+$=491.2; $^1$H NMR (400 MHz, CDCl$_3$) δ 7.61 (br. s., 2H), 7.22 (d, J=6.6 Hz, 6H), 7.10-6.90 (m, 1H), 6.01-5.72 (m, 2H), 4.03 (s, 2H), 2.49 (s, 2H), 2.14 (s, 3H), 2.09-1.72 (m, 8H), 1.55 (br. s., 3H); hLPA$_1$ Antagonist IC$_{50}$=116 nM.

Example 2. 2-(4-(4-(1-methyl-5-((((R)-1-phenylethoxy)carbonyl)amino)-1H-pyrazol-4-yl)phenyl)-2-oxabicyclo[2.2.2]octan-1-yl)acetic acid

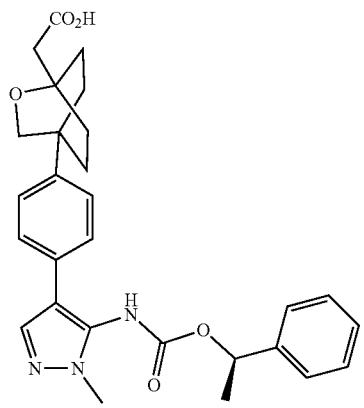 [SMILES: C[C@@H](OC(=O)Nc1c(-c2ccc(C34CCC(CC(=O)O)(CC3)OC4)cc2)cnn1C)c1ccccc1]

2A. methyl 2-(4-(4-(1-methyl-5-((((R)-1-phenylethoxy)carbonyl)amino)-1H-pyrazol-4-yl)phenyl)-2-oxabicyclo[2.2.2]octan-1-yl)acetate

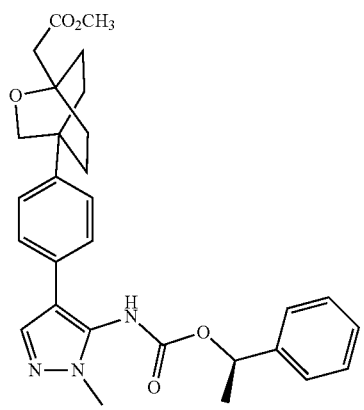 [SMILES: COC(=O)CC12CCC(c3ccc(-c4cnn(C)c4NC(=O)O[C@H](C)c4ccccc4)cc3)(CC1)CO2]

A solution of Intermediate 1 (20 mg, 0.052 mmol), Pd(OAc)$_2$ (2.3 mg, 10.4 μmol), K$_3$PO$_4$ (33 mg, 0.16 mmol) and Xphos (5 mg, 10.4 μmol) in toluene (1.5 mL) and water (0.2 mL) was purged with Ar for 5 min, then was heated to 100° C. for 4 h under Ar. After cooling to RT, the reaction mixture was filtered through Celite. The filtrate was partitioned between EtOAc (2 mL) and water (2 mL); the aqueous phase was extracted with EtOAc (2×1 mL). The combined organic extracts were washed with water (1 mL), brine (1 mL), dried (MgSO$_4$) and concentrated in vacuo. The crude product was chromatographed (SiO$_2$ ISCO column; continuous gradient from 0% to 100% EtOAc in hexanes over 20 min) to give the title compound. (13 mg, 0.026 mmol, 49.9% yield). LCMS [M+H]$^+$=504.0; $^1$H NMR (400 MHz, CDCl$_3$) δ: 7.55-7.73 (m, 1H), 7.28-7.47 (m, 6H), 7.17-7.23 (m, 2H), 6.07-6.20 (m, 1H), 5.89 (br d, 1H), 4.01 (s, 2H), 3.65-3.85 (m, 6H), 2.49 (s, 2H), 2.10 (br d, 3H), 1.86-1.96 (m, 3H), 1.60 (br d, 3H), 1.20-1.37 (m, 3H).

Example 2

To a stirred solution of compound 2A (13 mg, 0.026 mmol) in THF (1.0 mL) and water (0.5 mL) at RT was added 2.0 M aq LiOH (0.039 mL, 0.077 mmol). The reaction mixture was stirred at RT for 5 h, then was concentrated in vacuo. The residue was dissolved in H$_2$O (1 mL), and the pH was adjusted with 1N aq. HCl to ~3 and extracted with EtOAc (2×1 mL). The combined organic extracts were washed with brine (1 mL), dried (MgSO$_4$) and concentrated in vacuo. The crude product was purified by preparative LC/MS: Column: Waters XBridge C18, 19×200 mm, 5-μm particles; Guard Column: Waters XBridge C18, 19×10 mm, 5-μm particles; Mobile Phase A: 5:95 MeCN:H$_2$O with 0.1% TFA; Mobile Phase B: 95:5 MeCN:H$_2$O with 0.1% TFA; Gradient: 50-90% B over 20 min, then a 5-min hold at 100% B; Flow: 20 mL/min. Fractions containing the desired product were combined and concentrated in vacuo by centrifugal evaporation to give the title compound (8 mg, 0.016 mmol, 60.8% yield). LCMS [M+H]$^+$=490.1; $^1$H NMR (400 MHz, CD$_3$CN) δ 7.55 (s, 1H), 7.43-6.93 (m, 9H), 5.74-5.45 (m, 1H), 3.92 (s, 2H), 3.58 (s, 3H), 2.35 (s, 2H), 2.10-1.64 (m, 8H), 1.54-1.20 (m, 3H); hLPA$_1$ IC$_{50}$=88 nM.

Example 3. 2-(4-(4-(4-(((cyclopentyl(methyl)carbamoyl)oxy)methyl)-3-methylisoxazol-5-yl)phenyl)-2-oxabicyclo[2.2.2]octan-1-yl)acetic acid

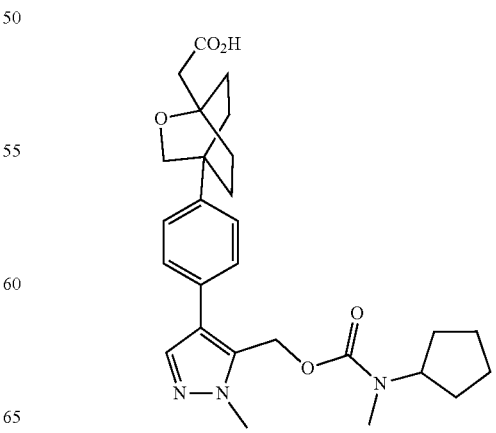

To a solution of Intermediate 13 (3.5 mg, 6.52 µmol) in THF (1 mL) was added iPr$_2$NEt (2.3 µL, 0.013 mmol) followed by N-methylcyclopentanamine (0.65 mg, 6.5 µmol). The reaction mixture was stirred at RT for 18 h, after which 2M aq. LiOH (33 µL, 0.065 mmol) was added. The reaction was stirred at RT for 18 h, then was concentrated in vacuo. The residue was dissolved in H$_2$O (1 mL), and the pH was adjusted with 1N aq. HCl to ~3 and extracted with EtOAc (2×1 mL). The combined organic extracts were washed with brine (1 mL), dried (MgSO$_4$) and concentrated in vacuo. The crude product was purified by preparative LC/MS: Column: Waters XBridge C18, 19×200 mm, 5 µm particles; Guard Column: Waters XBridge C18, 19×10 mm, 5-µm particles; Mobile Phase A: 5:95 MeCN:H$_2$O with 0.1% TFA; Mobile Phase B: 95:5 MeCN:H$_2$O with 0.1% TFA; Gradient: 50-90% B over 20 min, then a 5-min hold at 100% B; Flow: 20 mL/min. Fractions containing the desired product were combined and concentrated in vacuo by centrifugal evaporation to give the title compound (2.7 mg, 5.6 µmol, 86% yield). LCMS [M+H]$^+$=483.4; $^1$H NMR (400 MHz; DMSO-d$_6$) δ: 7.75 (d, J=8.2 Hz, 2H), 7.54 (d, J=8.2 Hz, 2H), 5.07 (s, 2H), 3.93 (s, 2H), 3.41 (s, 1H), 2.67 (s, 3H), 2.30-2.37 (m, 5H), 1.82-2.08 (m, 8H), 1.30-1.72 (m, 8H); hLPA$_1$ IC$_{50}$=317 nM.

Example 4. 2-(4-(4-(5-(((cyclopentyl(methyl)carbamoyl)oxy)methyl)-1-methyl-1H-pyrazol-4-yl)phenyl)-2-oxabicyclo[2.2.2]octan-1-yl)acetic acid

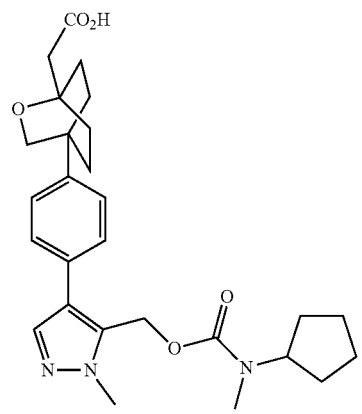 [SMILES: CN(C(=O)OCc1c(-c2ccc(C34CCC(CC(=O)O)(CC3)OC4)cc2)cnn1C)C1CCCC1]

To a solution of Intermediate 14 (5.0 mg, 9.3 µmol) in THF (1 mL) was added DIEA (9 µL, 0.012 mmol) followed by N-methylcyclopentanamine (1.5 mg, 7 µmol). The reaction mixture was stirred at RT for 18 h, after which aq. 2M LiOH (22 µL, 0.022 mmol) was added. The reaction was stirred at RT for 18 h, then was concentrated in vacuo. The residue was dissolved in H$_2$O (1 mL), and the pH was adjusted with 1N aq. HCl to ~3 and extracted with EtOAc (2×1 mL). The combined organic extracts were washed with brine (1 mL), dried (MgSO$_4$) and concentrated in vacuo. The crude product was purified by preparative LC/MS: Column: Waters XBridge C18, 19×200 mm, 5-µm particles; Guard Column: Waters XBridge C18, 19×10 mm, 5-µm particles; Mobile Phase A: 5:95 MeCN:H$_2$O with 0.1% TFA; Mobile Phase B: 95:5 MeCN:H$_2$O with 0.1% TFA; Gradient: 50-90% B over 20 min, then a 5-min hold at 100% B; Flow: 20 mL/min. Fractions containing the desired product were combined and concentrated in vacuo by centrifugal evaporation to give the title compound (1.5 mg, 3.1 µmol, 33% yield); [MS]$^+$=482.4. $^1$H NMR (400 MHz; DMSO-d$_6$) δ: 7.63 (s, 1H), 7.30-7.43 (m, 4H), 5.18 (s, 2H), 3.85-3.95 (m, 5H), 2.63-2.73 (m, 3H), 2.55 (s, 1H), 2.31 (s, 2H), 1.85-2.05 (m, 8H), 1.61 (br s, 4H), 1.47 (br s, 4H). hLPA$_1$ IC$_{50}$=1610 nM.

Example 5. (±)-3-(4-(4-(5-((((1-Cyclobutylethyl)(methyl)carbamoyl)oxy)methyl)-1-methyl-1H-1,2,3-triazol-4-yl)phenyl)-2-oxabicyclo[2.2.2]octan-1-yl)propanoic acid

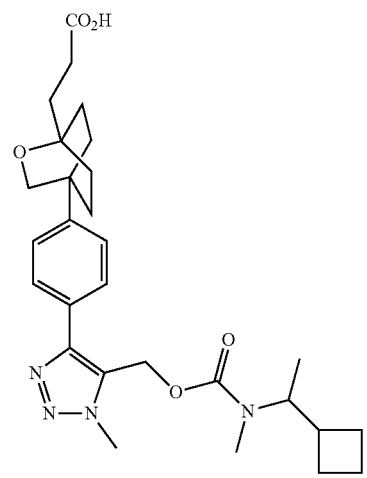 [SMILES: CC(C1CCC1)N(C)C(=O)OCc1c(-c2ccc(C34CCC(CCC(=O)O)(CC3)OC4)cc2)nnn1C]

To a solution of Intermediate 15 (12 mg, 0.031 mmol) and DIPEA (0.022 mL, 0.125 mmol) in THF (0.5 mL) was added 4-nitrophenyl chloroformate (12.0 mg, 0.062 mmol). The reaction mixture was stirred at RT for 16 h, after which 1-cyclobutyl-N-methylmethanamine (3.09 mg, 0.031 mmol) was added. The reaction mixture was stirred for 1 h at RT, after which MeOH (0.3 mL) and 2N aq. LiOH (0.5 mL) were added, and the mixture was heated at 50° C. for 30 min, then was cooled to RT. 3N aq. HCl (0.5 mL) was added to mixture, which was concentrated in vacuo. The residue was purified by preparative LC/MS: Column: Waters XBridge C18, 19×200 mm, 5-µm particles; Guard Column: Waters XBridge C18, 19×10 mm, 5-µm particles; Mobile Phase A: 5:95 MeCN:H$_2$O with 0.1% TFA; Mobile Phase B: 95:5 MeCN:H$_2$O with 0.1% TFA; Gradient: 50-90% B over 20 min, then a 5-min hold at 100% B; Flow: 20 mL/min. Fractions containing the desired product were combined and concentrated in vacuo by centrifugal evaporation to give the title compound (11 mg, 62.3% yield). LCMS [M+H]$^+$=511.2; $^1$H NMR (500 MHz, DMSO-d$_6$) δ 8.33-8.22 (m, 2H), 7.48-7.28 (m, 2H), 6.72-6.57 (m, 2H), 5.34-5.16 (m, 2H), 4.20-4.06 (m, 5H), 2.28-2.17 (m, 2H), 2.02-1.48 (m, 10H), 1.24-1.07 (m, 10H), 0.93-0.74 (m, 4H); hLPA$_1$ antagonist IC$_{50}$=440 nM.

Example 6. 2-(4-(4-(5-((((Cyclopentyl(methyl)carbamoyl)oxy)methyl)-1-methyl-1H-1,2,3-triazol-4-yl)-2-fluorophenyl)-2-oxabicyclo[2.2.2]octan-1-yl)acetic acid

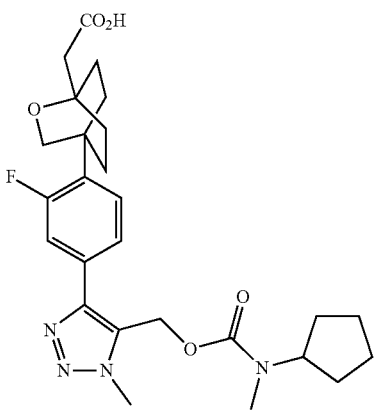 [SMILES: CN(C(=O)OCc1c(-c2ccc(C34CCC(CC(=O)O)(CC3)OC4)c(F)c2)nnn1C)C1CCCC1]

Example 6 was prepared according to the general procedures described in Scheme 7 and for the synthesis of Example 5 by using 2-(4-(4-bromo-2-fluorophenyl)-2-oxabicyclo[2.2.2] octan-1-yl)acetic acid as the intermediate and N-methylcyclopentanamine instead of 1-cyclo-butyl-N-methylmethanamine. LCMS [M+H]$^+$=501.2; $^1$H NMR (DMSO-d$_6$) δ: 8.53-8.55 (m, 1H), 7.55-7.61 (m, 1H), 7.52 (dd, J=14.0, 1.7 Hz, 1H), 7.35 (t, J=8.4 Hz, 1H), 5.34 (s, 2H), 4.13 (s, 3H), 4.02 (s, 2H), 2.67 (s, 3H), 2.29 (s, 2H), 1.87-2.15 (m, 9H), 1.35-1.71 (m, 8H); hLPA$_1$ antagonist IC$_{50}$=363 nM.

Example 7. 3-(4-(4-(1-methyl-5-((((R)-1-phenylethoxy)carbonyl)amino)-1H-1,2,3-triazol-4-yl)phenyl)-2-oxabicyclo[2.2.2]octan-1-yl)propanoic acid

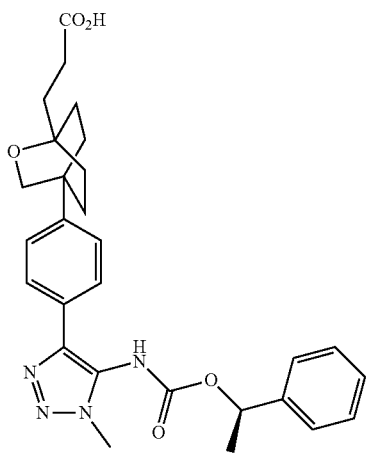 [SMILES: C[C@@H](OC(=O)Nc1c(-c2ccc(C34CCC(CCC(=O)O)(CC3)OC4)cc2)nnn1C)c1ccccc1]

A mixture of Intermediate 16 (6 mg, 0.015 mmol), (PhO)$_2$PON$_3$ (16 μL, 0.075 mmol), (R)-1-phenylethanol (2 mg, 0.016 mmol) and Et$_3$N (20 μL, 0.15 mmol) in toluene (1 mL) was stirred at 65° C. for 2 h, then was cooled to RT and concentrated in vacuo. The crude product was dissolved in THF (1 mL) and 2N aq. LiOH (0.5 mL) and stirred for 1 h at RT. 3M aq. HCl (0.5 mL) was added, and the mixture was concentrated in vacuo. The residue was purified by preparative LC/MS: Column: Waters XBridge C18, 19×200 mm, 5-~m particles; Guard Column: Waters XBridge C18, 19×10 mm, 5-~m particles; Mobile Phase A: 5:95 MeCN: H$_2$O with 0.1% TFA; Mobile Phase B: 95:5 MeCN:H$_2$O with 0.1% TFA; Gradient: 50-90% B over 20 min, then a 5-min hold at 100% B; Flow: 20 mL/min. Fractions containing the desired product were combined and concentrated in vacuo by centrifugal evaporation to give the title compound (1 mg, 13% yield). LCMS [M+H]$^+$=505.2; $^1$H NMR (500 MHz, DMSO-d$_6$) δ 7.69-7.52 (m, 2H), 7.49-7.35 (m, 2H), 7.33-7.13 (m, 5H), 5.27-4.96 (m, 2H), 3.73-3.41 (m, 4H), 2.03-1.84 (m, 5H), 1.86-1.64 (m, 2H), 1.51-1.33 (m, 2H), 1.38-1.18 (m, 2H), 1.06-0.78 (m, 6H); hLPA$_1$ IC$_{50}$=264 nM.

Example 8. 3-(4-(4-(5-((((R)-1-(2-chlorophenyl)ethoxy)carbonyl)amino)-1-methyl-1H-1,2,3-triazol-4-yl)phenyl)-2-oxabicyclo[2.2.2]octan-1-yl)propanoic acid

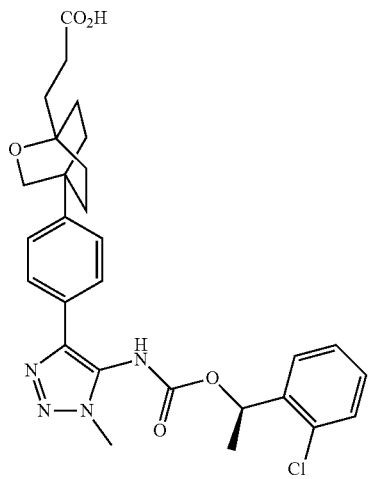 [SMILES: C[C@@H](OC(=O)Nc1c(-c2ccc(C34CCC(CCC(=O)O)(CC3)OC4)cc2)nnn1C)c1ccccc1Cl]

Example 8 was prepared according to the procedure used for the synthesis of Example 7 by using (R)-1-(2-chlorophenyl)ethan-1-ol as the alcohol in the Curtius rearrangement reaction instead of (R)-1-phenylethanol. LCMS [M+H]$^+$=539.2; $^1$H NMR (500 MHz, DMSO-d$_6$) δ 7.81-7.56 (m, 3H), 7.53-7.26 (m, 5H), 6.08-5.89 (m, 1H), 3.71-3.45 (m, 3H), 2.35-2.18 (m, 3H), 2.09-1.76 (m, 8H), 1.73-1.41 (m, 7H); hLPA$_1$ IC$_{50}$=418 nM.

Example 9. (R)-4-(4-(1-methyl-5-(((1-phenylethoxy)carbonyl)amino)-1H-pyrazol-4-yl)phenyl)-2-oxabicyclo[2.2.2]octane-1-carboxylic acid Example 10. (R)-2-(4-(4-(1-(cyclopropylmethyl)-5-(((1-phenylethoxy)carbonyl)amino)-1H-pyrazol-4-yl)phenyl)-2-oxabicyclo[2.2.2]octan-1-yl)acetic acid

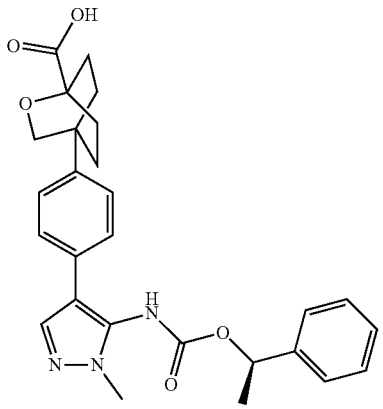 [SMILES: C[C@@H](OC(=O)Nc1c(-c2ccc(C34CCC(C(=O)O)(CC3)OC4)cc2)cnn1C)c1ccccc1]

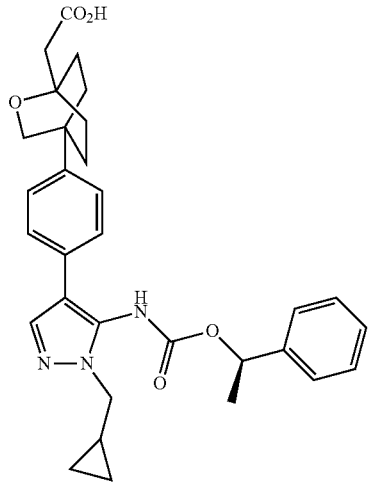 [SMILES: C[C@@H](OC(=O)Nc1c(-c2ccc(C34CCC(CC(=O)O)(CC3)OC4)cc2)cnn1CC1CC1)c1ccccc1]

Example 10 was prepared from the bromo-pyrazole N-carbamate intermediate 18 and Intermediate 1 according to the synthetic sequence described for the synthesis of Example 2 (as well as Scheme 2). LCMS [M+H]$^+$=530.2; $^1$H NMR (500 MHz, DMSO-d$_6$) δ 9.61-9.41 (m, 1H), 7.85-7.64 (m, 1H), 7.50-7.32 (m, 6H), 7.26-7.16 (m, 2H), 5.81-5.67 (m, 1H), 3.82-3.66 (m, 2H), 3.49-3.38 (m, 1H), 2.42-2.25 (m, 3H), 2.06-1.74 (m, 9H), 1.64-1.44 (m, 3H), 1.21-1.01 (m, 2H), 0.59-0.40 (m, 2H), 0.36-0.21 (m, 2H); hLPA$_1$ IC$_{50}$=422 nM.

Example 9 was synthesized according to the procedures/synthetic sequence described for the synthesis of Examples 1 and 2, but using Intermediate 17 instead of Intermediate 1. LCMS [M+H]$^+$=501.2; $^1$H NMR (DMSO-d$_6$) δ: 8.53-8.55 (m, 1H), 7.55-7.61 (m, 1H), 7.52 (dd, J=14.0, 1.7 Hz, 1H), 7.35 (t, J=8.4 Hz, 1H), 5.34 (s, 2H), 4.13 (s, 3H), 4.02 (s, 2H), 2.67 (s, 3H), 2.29 (s, 2H), 1.87-2.15 (m, 9H), 1.35-1.71 (m, 8H); hLPA$_1$ IC$_{50}$=278 nM.

The compounds listed in Table 1 were prepared using the same general synthetic methods as described for the synthesis of respective Example indicated using the appropriate intermediates as described above (Schemes 1 and 6).

TABLE 1

| Ex # | Structure & Name | Analytical & Biological Data | Method |
|------|------------------|------------------------------|--------|
| 11 | ![structure] 2-(4-(4-(4-((((R)-1-cyclopropylethoxy)carbonyl)amino)-3-methylisoxazol-5-yl)phenyl)-2-oxabicyclo[2.2.2]octan-1-yl)acetic acid | LCMS [M + H]$^+$ = 455.1; $^1$H NMR (DMSO-d$_6$) δ: 8.91-9.29 (m, 1H), 7.72 (br d, 2H), 7.50 (br d, 2H), 4.20 (br s, 1H), 3.90 (s, 2H), 3.60 (br d, 2H), 2.33 (s, 2H), 2.15 (br s, 3H), 1.80-2.06 (m, 8H), 1.30 (br s, 2H), 0.06-1.12 (m, 5H); hLPA$_1$ IC$_{50}$ = 194 nM. | Example 1 |

TABLE 1-continued

| Ex # | Structure & Name | Analytical & Biological Data | Method |
|---|---|---|---|
| 12 | 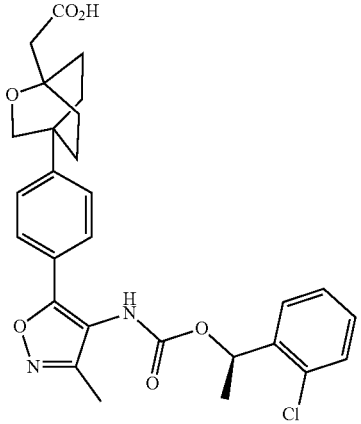 [SMILES: Cc1noc(-c2ccc(C34CCC(CC(=O)O)(CC3)OC4)cc2)c1NC(=O)O[C@H](C)c1ccccc1Cl]<br>2-(4-(4-(4-((((R)-1-(2-chlorophenyl)ethoxy)carbonyl)amino)-3-methyl isoxazol-5-yl)phenyl)-2-oxabicyclo[2.2.2]octan-1-yl)acetic acid | LCMS [M + H]$^+$ = 525.1;<br>$^1$H NMR (DMSO-d$_6$) δ: 9.27-9.44 (m, 1H), 7.56-7.76 (m, 3H), 7.33-7.53 (m, 5H), 5.83-6.09 (m, 1H), 3.90 (s, 2H), 3.42-3.68 (m, 2H), 2.34 (s, 2H), 2.11 (br s, 2H), 2.00 (br d, 4H), 1.81-1.94 (m, 4H), 1.20-1.64 (m, 3H);<br>hLPA$_1$ IC$_{50}$ = 72 nM. | Example 1 |
| 13 | 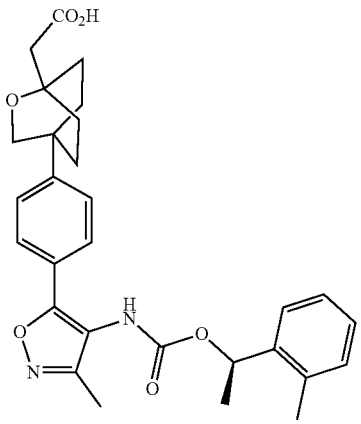 [SMILES: Cc1ccccc1[C@@H](C)OC(=O)Nc1c(C)noc1-c1ccc(C23CCC(CC(=O)O)(CC2)OC3)cc1]<br>2-(4-(4-(3-methyl-4-((((R)-1-(o-tolyl)ethoxy)carbonyl)amino)isoxazol-5-yl)phenyl)-2-oxabicyclo[2.2.2]octan-1-yl)acetic acid | LCMS [M + H]$^+$ = 505.2;<br>$^1$H NMR (DMSO-d$_6$) δ: 9.25 (br s, 1H), 7.64 (br d, 2H), 7.03-7.52 (m, 6H), 5.87 (br d, 1H), 3.89 (s, 2H), 3.33-3.62 (m, 1H), 2.33 (br d, 5H), 2.09 (br s, 3H), 1.81-2.04 (m, 8H), 1.51 (br d, 3H);<br>hLPA$_1$ IC$_{50}$ = 184 nM. | Example 1 |
| 14 | 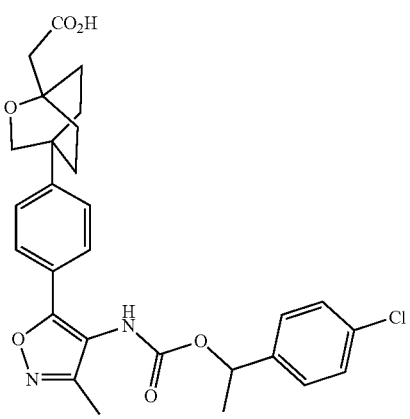 [SMILES: Cc1noc(-c2ccc(C34CCC(CC(=O)O)(CC3)OC4)cc2)c1NC(=O)OC(C)c1ccc(Cl)cc1]<br>(±)-2-(4-(2-fluoro-4-(3-methyl-4-((((R)-1-phenylethoxy)carbonyl)amino)isoxazol-5-yl)phenyl)-2-oxabicyclo[2.2.2]octan-1-yl)acetic acid | LCMS [M + H]$^+$ = 525.0;<br>$^1$H NMR (DMSO-d$_6$) δ: 9.16-9.39 (m, 1H), 7.58 (br d, J = 7.6 Hz, 2H), 7.31-7.53 (m, 6H), 5.69 (br d, J = 6.4 Hz, 1H), 3.88 (s, 2H), 2.33 (s, 2H), 2.10 (br s, 3H), 1.95-2.02 (m, 4H), 1.84-1.92 (m, 4H), 1.51 (br d, J = 5.5 Hz, 3H);<br>hLPA$_1$ IC$_{50}$ = 117 nM. | Example 1 |

TABLE 1-continued

| Ex # | Structure & Name | Analytical & Biological Data | Method |
|---|---|---|---|
| 15 | 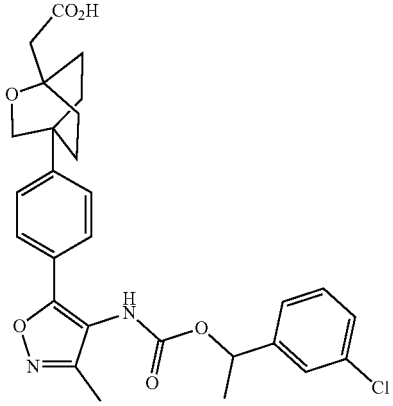 [SMILES: Cc1noc(-c2ccc(C34CCC(CC(=O)O)(CC3)OC4)cc2)c1NC(=O)OC(C)c1cccc(Cl)c1]<br>(±)-2-(4-(4-(4-(((1-(3-chlorophenyl)ethoxy)carbonyl)amino)-3-methyl-isoxazol-5-yl)phenyl)-2-oxabicyclo[2.2.2]octan-1-yl)acetic acid | LCMS [M + H]$^+$ = 525.3; $^1$H NMR (DMSO-d$_6$) δ: 9.31 (br s, 1H), 7.65 (br d, J = 7.3 Hz, 2H), 7.36-7.51 (m, 6H), 5.73 (br d, J = 5.5 Hz, 1H), 3.89 (s, 2H), 2.34 (s, 2H), 2.12 (br s, 3H), 1.99 (br d, J = 10.1 Hz, 4H), 1.85-1.93 (m, 4H), 1.53 (br d, J = 5.8 Hz, 3H); hLPA$_1$ IC$_{50}$ = 379 nM. | Example 1 |
| 16 | 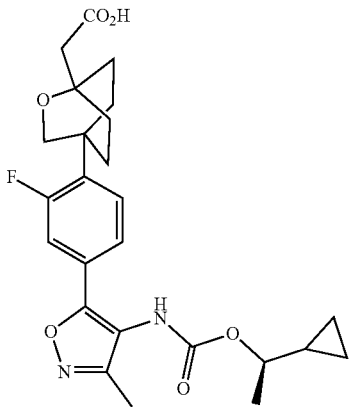 [SMILES: Cc1noc(-c2ccc(C34CCC(CC(=O)O)(CC3)OC4)c(F)c2)c1NC(=O)O[C@H](C)C1CC1]<br>2-(4-(4-(4-((((R)-1-cyclopropylethoxy)carbonyl)amino)-3-methylisoxazol-5-yl)-2-fluorophenyl)-2-oxabicyclo[2.2.2]octan-1-yl)acetic acid | LCMS [M + H]$^+$ = 473.1; $^1$H NMR (DMSO-d$_6$) δ: 9.05-9.34 (m, 1H), 7.64 (br d, 1H), 7.56 (br d, 1H), 7.49 (br m, 1H), 4.27 (br s, 1H), 4.08 (s, 2H), 3.65 (br s, 2H), 2.40 (s, 2H), 2.23 (br s, 3H), 2.01-2.18 (m, 5H), 1.90-2.00 (m, 2H), 1.12 (br s, 1H), 1.37 (br s, 3H), 0.27-0.71 (m, 3H); hLPA$_1$ IC$_{50}$ = 407 nM. | Example 1 |
| 17 | 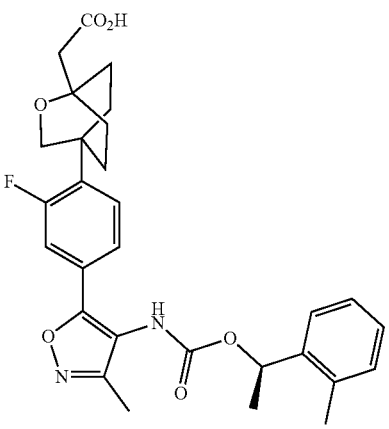 [SMILES: Cc1ccccc1[C@@H](C)OC(=O)Nc1c(C)noc1-c1ccc(C23CCC(CC(=O)O)(CC2)OC3)c(F)c1]<br>2-(4-(2-fluoro-4-(3-methyl-4-((((R)-1-(o-tolyl)ethoxy)carbonyl)amino)isoxazol-5-yl)phenyl)-2-oxabicyclo[2.2.2]octan-1-yl)acetic acid | LCMS [M + H]$^+$ = 523.1; $^1$H NMR (400 MHz, DMSO-d$_6$) δ: 9.34 (br s, 1H), 7.41-7.55 (m, 3H), 7.14-7.37 (m, 4H), 5.88 (br d, 1H), 4.00 (s, 2H), 2.27-2.39 (m, 5H), 2.11 (br s, 3H), 2.02 (br s, 6H), 1.85-1.93 (m, 2H), 1.52 (br d, 3H); hLPA$_1$ IC$_{50}$ = 119 nM. | Example 1 |

TABLE 1-continued

| Ex # | Structure & Name | Analytical & Biological Data | Method |
|---|---|---|---|
| 18 | 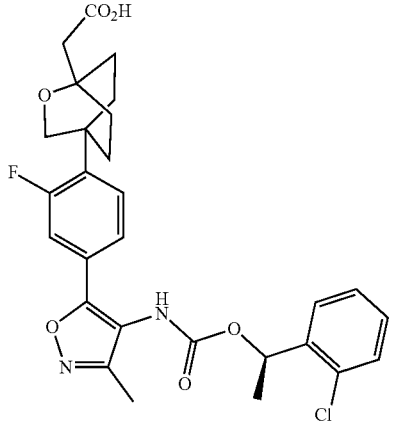 [SMILES: Cc1noc(-c2ccc(C34CCC(CC(=O)O)(CC3)OC4)c(F)c2)c1NC(=O)O[C@H](C)c1ccccc1Cl]<br>2-(4-(4-(4-((((R)-1-(2-chlorophenyl)ethoxy)carbonyl)amino)-3-methyl-isoxazol-5-yl)-2-fluorophenyl)-2-oxabicyclo[2.2.2]octan-1-yl)acetic acid | LCMS [M + H]$^+$ = 543.2;<br>$^1$H NMR (400 MHz, DMSO-d$_6$) δ: 9.24-9.78 (m, 1H), 7.26-7.67 (m, 7H), 5.97 (br d, J = 6.4 Hz, 1H), 4.00 (s, 2H), 2.34 (s, 2H), 2.12 (br s, 3H), 1.94-2.07 (m, 6H), 1.84-1.92 (m, 2H), 1.54 (br d, J = 5.2 Hz, 3H);<br>hLPA$_1$ IC$_{50}$ = 56 nM. | Example 1 |
| 19 | 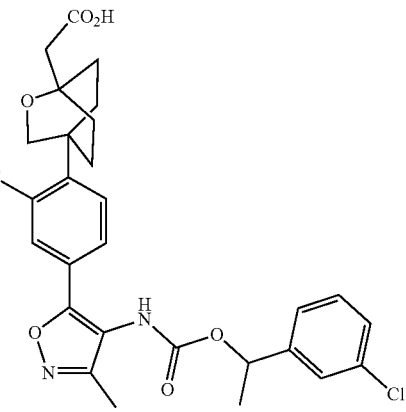<br>(±)-2-(4-(4-(4-(((1-(3-chlorophenyl)ethoxy)carbonyl)amino)-3-methyl-isoxazol-5-yl)-2-fluorophenyl)-2-oxabicyclo[2.2.2]octan-1-yl)acetic acid | LCMS [M + H]$^+$ = 543.3;<br>$^1$H NMR $^1$H NMR (DMSO-d$_6$) δ: 9.36-9.44 (m, 1H), 7.27-7.56 (m, 7H), 5.73 (br d, J = 5.8 Hz, 1H), 4.00 (s, 2H), 2.33 (s, 2H), 2.13 (br s, 3H), 1.96-2.05 (m, 6H), 1.84-1.94 (m, 2H), 1.53 (br s, 3H);<br>hLPA$_1$ IC$_{50}$ = 692 nM. | Example 1 |
| 20 | 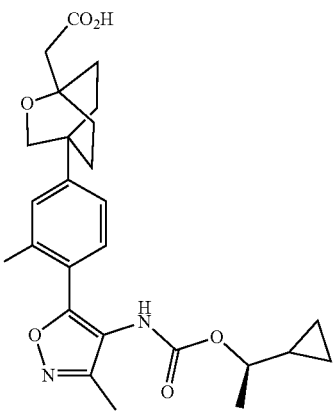<br>2-(4-(4-(4-((((R)-1-cyclopropylethoxy)carbonyl)amino)-3-methyl isoxazol-5-yl)-3-fluorophenyl)-2-oxabicyclo[2.2.2]octan-1-yl) acetic acid | LCMS [M + H]$^+$ = 473.1;<br>$^1$H NMR (DMSO-d$_6$) δ: 8.91-9.13 (m, 1H), 7.62 (m, 1H), 7.27-7.48 (m, 2H), 4.16 (br s, 1H), 3.91 (s, 2H), 2.34 (s, 2H), 2.20 (br s, 3H), 1.80-2.08 (m, 8H), 0.91-1.48 (m, 4H), −0.01-0.66 (m, 4H);<br>hLPA$_1$ IC$_{50}$ = 863 nM. | Example 1 |

TABLE 1-continued

| Ex # | Structure & Name | Analytical & Biological Data | Method |
|---|---|---|---|
| 21 | 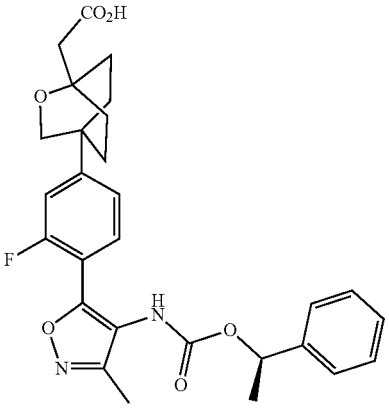 [SMILES: Cc1noc(-c2ccc(C34CCC(CC(=O)O)(CC3)OC4)cc2F)c1NC(=O)O[C@H](C)c1ccccc1]2-(4-(3-fluoro-4-(3-methyl-4-((((R)-1-phenylethoxy)carbonyl)amino)isoxazol-5-yl)phenyl)-2-oxabicyclo[2.2.2]octan-1-yl)acetic acid | LCMS [M + H]$^+$ = ;<br>$^1$H NMR (DMSO-d$_6$) δ: 8.96-9.44 (m, 1H), 7.53-7.64 (m, 1H), 7.20-7.46 (m, 7H), 5.70 (br d, 1H), 3.90 (s, 2H), 2.35 (s, 2H), 2.16 (s, 3H), 1.80-2.06 (m, 8H), 1.10-1.69 (m, 3H);<br>hLPA$_1$ IC$_{50}$ = 95 nM. | Example 1 |
| 22 | 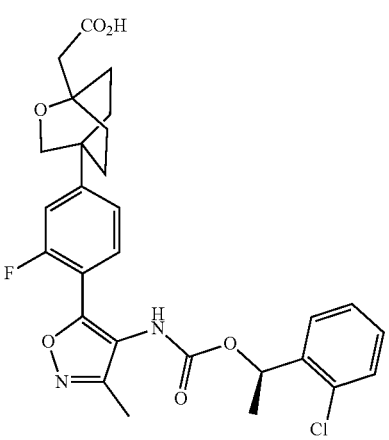 [SMILES: Cc1noc(-c2ccc(C34CCC(CC(=O)O)(CC3)OC4)cc2F)c1NC(=O)O[C@H](C)c1ccccc1Cl]2-(4-(4-(4-((((R)-1-(2-chlorophenyl)ethoxy)carbonyl)amino)-3-methylisoxazol-5-yl)-3-fluorophenyl)-2-oxabicyclo[2.2.2]octan-1-yl)acetic acid | LCMS [M + H]$^+$ = 543.3;<br>$^1$H NMR (DMSO-d$_6$) δ: 9.19- 9.46 (m, 1H), 7.23-7.73 (m, 7H), 5.93 (br d, 1H), 3.90 (s, 2H), 3.35 (br s, 1H), 2.35 (s, 2H), 2.16 (br s, 3H), 1.84-2.04 (m, 8H), 1.52 (br d, 2H);<br>hLPA$_1$ IC$_{50}$ = 64 nM. | Example 1 |
| 23 | 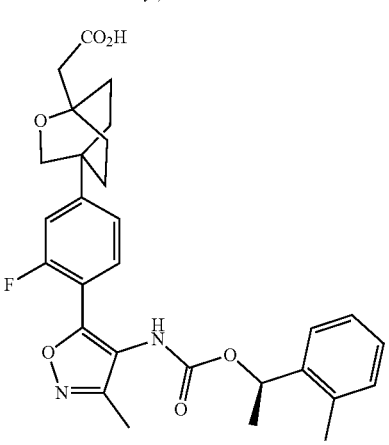2-(4-(3-fluoro-4-(3-methyl-4-((((R)-1-(o-tolyl)ethoxy)carbonyl)amino)isoxazol-5-yl)phenyl)-2-oxabicyclo[2.2.2]octan-1-yl)acetic acid | LCMS [M + H]$^+$ = 523.1;<br>$^1$H NMR (DMSO-d$_6$) δ: 9.17 (br s, 1H), 7.56 (br s, 1H), 7.12-7.48 (m, 6H), 5.84 (br s, 1H), 3.90 (s, 2H), 2.27-2.39 (m, 5H), 2.14 (br s, 3H), 1.87-2.05 (m, 8H), 1.49 (br d, 3H);<br>hLPA$_1$ IC$_{50}$ = 98 nM. | Example 1 |

TABLE 1-continued

| Ex # | Structure & Name | Analytical & Biological Data | Method |
|---|---|---|---|
| 24 | 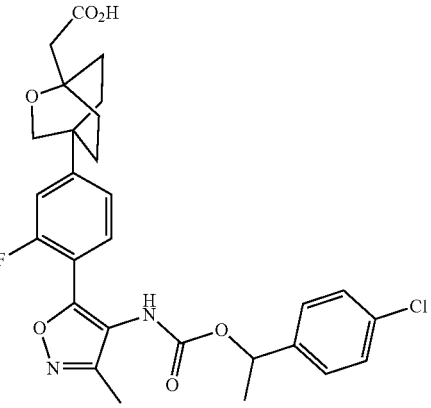<br>(±)-2-(4-(4-(4-(((1-(4-chlorophenyl)ethoxy)carbonyl)amino)-3-methyl-isoxazol-5-yl)-3-fluorophenyl)-2-oxabicyclo[2.2.2]octan-1-yl)acetic acid | LCMS [M + H]$^+$ = 542.9;<br>$^1$H NMR (DMSO-d$_6$) δ: 9.09-9.38 (m, 1H), 7.56 (br d, J = 7.3 Hz, 1H), 7.47 (br s, 2H), 7.40 (br d, J = 7.3 Hz, 2H), 7.20-7.34 (m, 2H), 5.68 (br d, J = 5.8 Hz, 1H), 3.91 (s, 2H), 2.35 (s, 2H), 2.17 (br s, 3H), 2.00 (br d, J = 8.5 Hz, 4H), 1.84-1.95 (m, 4H), 1.50 (br d, J = 5.2 Hz, 3H);<br>hLPA$_1$ IC$_{50}$ = 406 nM. | Example 1 |
| 25 | 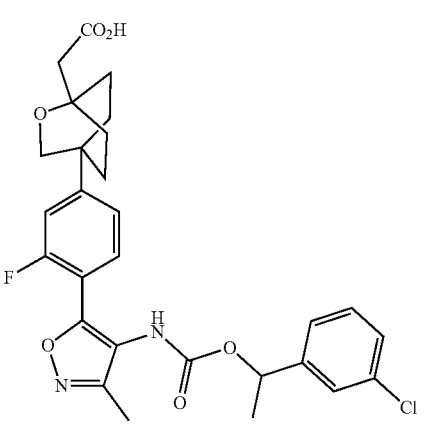 [SMILES: Cc1noc(-c2ccc(C34CCC(CC(=O)O)(CC3)OC4)cc2F)c1NC(=O)OC(C)c1cccc(Cl)c1]<br>(±)-2-(4-(4-(4-(((1-(3-chlorophenyl)ethoxy)carbonyl)amino)-3-methyl-isoxazol-5-yl)-3-fluorophenyl)-2-oxabicyclo[2.2.2]octan-1-yl)acetic acid | LCMS [M + H]$^+$ = 543.0;<br>$^1$H NMR (DMSO-d$_6$) δ: 9.11-9.49 (m, 1H), 7.58 (br d, J = 7.0 Hz, 1H), 7.24-7.49 (m, 6H), 5.70 (br d, J = 6.4 Hz, 1H), 3.90 (s, 2H), 2.35 (s, 2H), 2.17 (br s, 3H), 1.88-2.02 (m, 8H), 1.51 (br d, J = 5.2 Hz, 3H);<br>hLPA$_1$ IC$_{50}$ = 345 nM. | Example 1 |
| 26 | 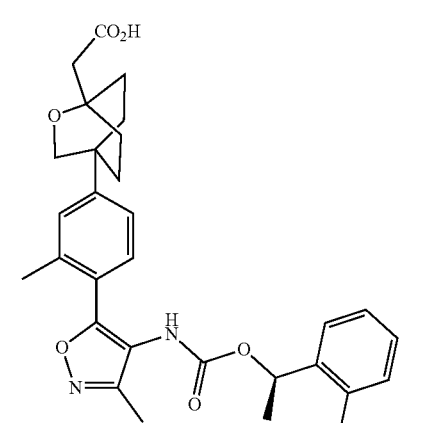<br>(±)-2-(4-(3-methyl-4-(3-methyl-4-((((R)-1-(o-tolyl)ethoxy)carbonyl)amino)isoxazol-5-yl)phenyl)-2-oxabicyclo[2.2.2]octan-1-yl)acetic acid | LCMS [M + H]$^+$ = 519.2;<br>$^1$H NMR (DMSO-d$_6$) δ: 9.02 (br s, 1H), 7.09-7.42 (m, 7H), 5.75-5.90 (m, 1H), 3.91 (s, 2H), 2.34 (s, 2H), 2.30 (br s, 2H), 2.24 (s, 4H), 2.12 (br s, 2H), 1.83-2.05 (m, 9H), 1.39-1.55 (m, 3H);<br>hLPA$_1$ IC$_{50}$ = 92 nM. | Example 1 |

TABLE 1-continued

| Ex # | Structure & Name | Analytical & Biological Data | Method |
|---|---|---|---|
| 27 | 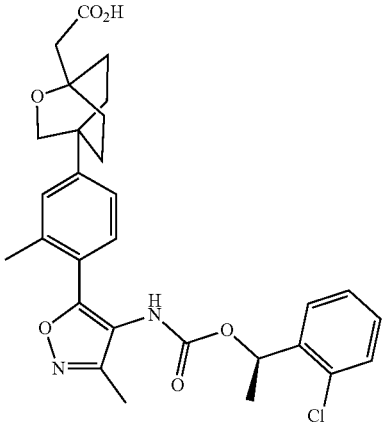 [SMILES: Cc1cc(C23CCC(CC(=O)O)(CC2)OC3)ccc1-c1onc(C)c1NC(=O)O[C@H](C)c1ccccc1Cl]<br>2-(4-(4-(4-((((R)-1-(2-chlorophenyl)ethoxy)carbonyl)amino)-3-methyl-isoxazol-5-yl)-3-methylphenyl)-2-oxabicyclo[2.2.2]octan-1-yl)acetic acid | LCMS [M + H]$^+$ = 539.1;<br>$^1$H NMR (DMSO-d$_6$) δ: 9.06-9.22 (m, 1H), 7.09-7.55 (m, 7H), 5.95 (br d, J = 6.1 Hz, 1H), 3.91 (s, 2H), 2.34 (s, 3H), 2.25 (s, 3H), 2.13 (br s, 2H), 2.01 (br d, J = 6.4 Hz, 4H), 1.85-1.96 (m, 4H), 1.50 (br d, J = 4.6 Hz, 3H);<br>hLPA$_1$ IC$_{50}$ = 185 nM. | Example 1 |
| 28 | 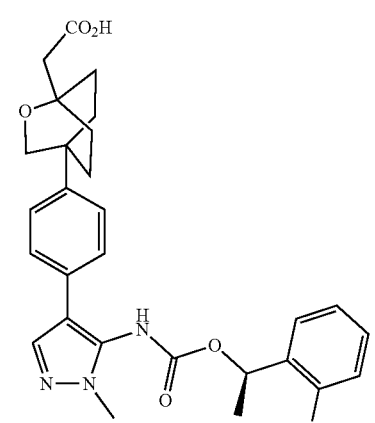<br>2-(4-(4-(5-((((R)-1-(2-chlorophenyl)ethoxy)carbonyl)amino)-1-methyl-1H-pyrazol-4-yl)phenyl)-2-oxa-bicyclo[2.2.2]octan-1-yl)acetic acid | LCMS [M + H]$^+$ = 524.0;<br>$^1$H NMR (DMSO-d$_6$) δ: 9.13-9.91 (m, 1H), 7.72 (br s, 1H), 7.19-7.66 (m, 8H), 5.77-6.17 (m, 1H), 3.87 (s, 2H), 3.38-3.73 (m, 2H), 2.52 (br s, 2H), 2.34 (s, 2H), 1.99 (br d, 4H), 1.88 (br d, 4H), 1.09-1.71 (m, 3H);<br>hLPA$_1$ IC$_{50}$ = 164 nM. | Example 2 |
| 29 | 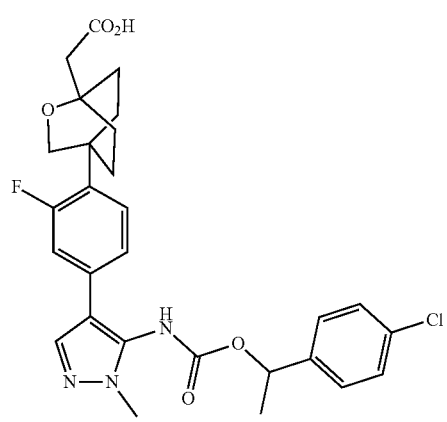 [SMILES: CC(OC(=O)Nc1c(-c2ccc(C34CCC(CC(=O)O)(CC3)OC4)c(F)c2)cnn1C)c1ccc(Cl)cc1]<br>(±)-2-(4-(4-(5-(((1-(4-chlorophenyl)ethoxy)carbonyl)amino)-1-methyl-1H-pyrazol-4-yl)-2-fluorophenyl)-2-oxabicyclo[2.2.2]octan-1-yl)acetic acid | LCMS [M + H]$^+$ = 542.1;<br>$^1$H NMR (DMSO-d$_6$) δ: 7.68-7.87 (m, 1H), 7.40 (br s, 4H), 7.02-7.25 (m, 4H), 5.49-5.86 (m, 1H), 2.17-2.28 (m, 3H), 1.87-2.03 (m, 11H), 1.50 (br s, 3H), 1.17-1.25 (m, 1H);<br>hLPA$_1$ IC$_{50}$ = 1140 nM. | Example 2 |

TABLE 1-continued

| Ex # | Structure & Name | Analytical & Biological Data | Method |
|---|---|---|---|
| 30 | 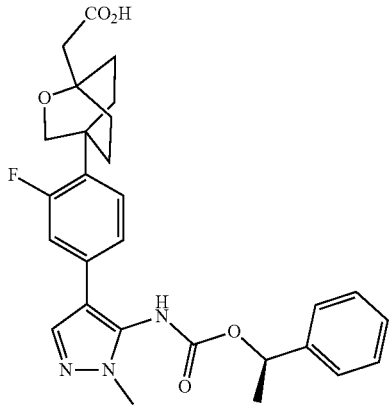 [SMILES: C[C@@H](OC(=O)Nc1c(-c2ccc(C34CCC(CC(=O)O)(CC3)OC4)c(F)c2)cnn1C)c1ccccc1]<br>2-(4-(2-fluoro-4-(1-methyl-5-((((R)-1-phenylethoxy)carbonyl)amino)-1H-pyrazol-4-yl)phenyl)-2-oxabicyclo[2.2.2]octan-1-yl)acetic acid | LCMS [M + H]$^+$ = 508.2;<br>$^1$H NMR (DMSO-d$_6$) δ: 7.74-7.93 (m, 1H), 6.91-7.56 (m, 7H), 5.76 (br s, 1H), 3.95 (s, 2H), 3.62 (s, 2H), 3.35-3.47 (m, 3H), 2.09-2.21 (m, 2H), 1.76-2.23 (m, 7H), 1.16-1.68 (m, 3H);<br>hLPA$_1$ IC$_{50}$ = 365 nM. | Example 2 |
| 31 | 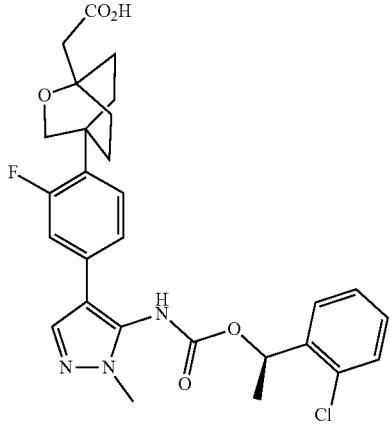 [SMILES: C[C@@H](OC(=O)Nc1c(-c2ccc(C34CCC(CC(=O)O)(CC3)OC4)c(F)c2)cnn1C)c1ccccc1Cl]<br>2-(4-(4-(5-((((R)-1-(2-chlorophenyl)ethoxy)carbonyl)amino)-1-methyl-1H-pyrazol-4-yl)-2-fluorophenyl)-2-oxabicyclo[2.2.2]octan-1-yl)acetic acid | LCMS [M + H]$^+$ = 542.1;<br>$^1$H NMR (500 MHz, DMSO-d$_6$) δ: 9.73 (br. s., 1H), 7.81 (br. s., 1H), 7.60 (br. s., 1H), 7.55-7.34 (m, 3H), 7.31-7.10 (m, 3H), 6.01 (br. s., 1H), 3.99 (s, 2H), 3.63 (br. s., 3H), 3.35 (br. s., 1H), 2.34 (s, 2H), 2.14-1.81 (m, 8H), 1.57 (br. s., 3H);<br>hLPA$_1$ IC$_{50}$ = 112 nM. | Example 2 |
| 32 | 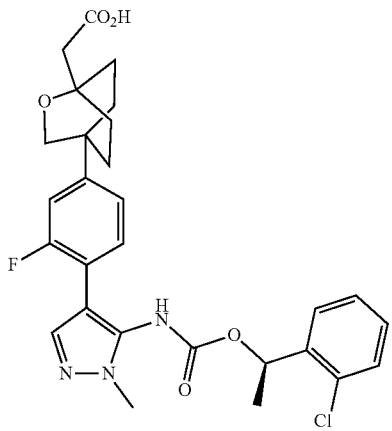 [SMILES: C[C@@H](OC(=O)Nc1c(-c2ccc(C34CCC(CC(=O)O)(CC3)OC4)cc2F)cnn1C)c1ccccc1Cl]<br>2-(4-(4-(5-((((R)-1-(2-chlorophenyl)ethoxy)carbonyl)amino)-1-methyl-1H-pyrazol-4-yl)-3-fluorophenyl)-2-oxabicyclo[2.2.2]octan-1-yl)acetic acid | LCMS [M + H]$^+$ = 542.1;<br>$^1$H NMR $^1$H NMR (DMSO-d$_6$) δ: 9.22-9.76 (m, 1H), 7.26-7.69 (m, 5H), 6.99-7.24 (m, 2H), 5.86-6.09 (m, 1H), 3.88 (s, 2H), 3.65 (br s, 1H), 3.20-3.76 (m, 3H), 2.34 (s, 2H), 1.72-2.13 (m, 8H), 1.02-1.66 (m, 3H);<br>hLPA$_1$ IC$_{50}$ = 115 nM. | Example 2 |

TABLE 1-continued

| Ex # | Structure & Name | Analytical & Biological Data | Method |
|---|---|---|---|
| 33 | 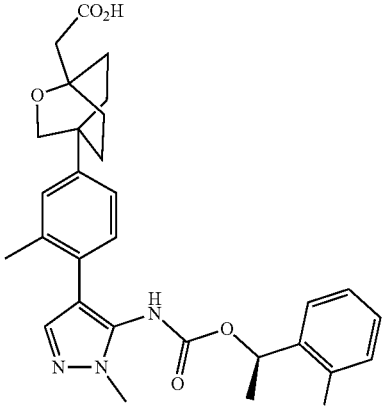<br>2-(4-(4-(5-((((R)-1-(2-chlorophenyl)ethoxy)carbonyl)amino)-1-methyl-1H-pyrazol-4-yl)-3-methylphenyl)-2-oxabicyclo[2.2.2]octan-1-yl)acetic acid | LCMS [M + H]$^+$ = 538.1;<br>$^1$H NMR (DMSO-d$_6$) δ: 9.33-9.76 (m, 1H), 7.48 (br s, 2H), 7.40 (br d, J = 10.1 Hz, 1H), 7.25 (br s, 1H), 7.20 (br s, 1H), 7.14 (br s, 1H), 7.00-7.10 (m, 2H), 5.74-6.11 (m, 1H), 3.88 (s, 2H), 3.63 (br s, 3H), 2.34 (s, 2H), 2.19 (br s, 3H), 1.79-2.04 (m, 8H), 1.09-1.65 (m, 3H);<br>hLPA$_1$ IC$_{50}$ = 537 nM. | Example 2 |
| 34 | 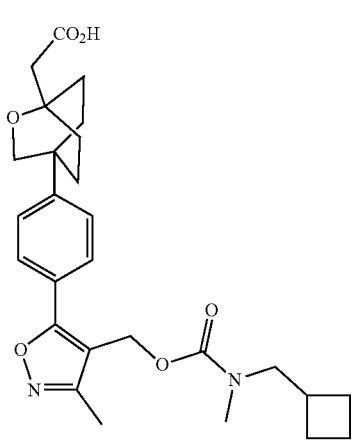<br>2-(4-(4-(4-((((cyclobutylmethyl)(methyl)carbamoyl)oxy)methyl)-3-methylisoxazol-5-yl)phenyl)-2-oxabicyclo[2.2.2]octan-1-yl)acetic acid | LCMS [M + H]$^+$ = 497.2;<br>$^1$H NMR (DMSO-d$_6$) δ: 7.80 (br d, J = 7.9 Hz, 1H), 7.73 (br d, J = 7.9 Hz, 1H), 7.55 (br t, J = 7.9 Hz, 2H), 5.01-5.14 (m, 2H), 4.04-3.8 (br d, J = 9.5 Hz, 1H), 3.92 (s, 2H), 2.58 (br s, 2H), 2.26-2.39 (m, 6H), 1.85-2.06 (m, 9H), 1.62-1.84 (m, 3H), 1.42-1.60 (m, 2H), 1.18-1.39 (m, 1H), 0.74-1.00 (m, 3H);<br>hLPA$_1$ IC$_{50}$ = 158 nM. | Example 3 |
| 35 | 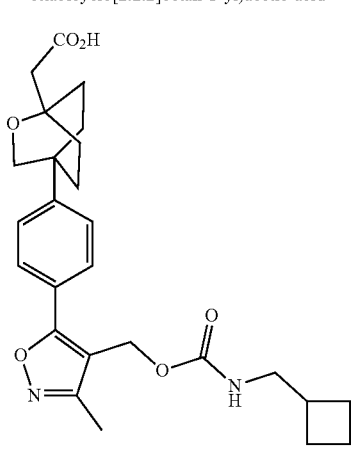<br>2-(4-(4-(4 2-(4-(4-((((cyclobutyl-methyl)carbamoyl)oxy)methyl)-3-methylisoxazol-5-yl)phenyl)-2-oxabicyclo[2.2.2]octan-1-yl)acetic acid | LCMS [M + H]$^+$ = 483.4;<br>$^1$H NMR (DMSO-d$_6$) δ: 7.76 (br s, 2H), 7.61 (s, 2H), 5.07 (br s, 2H), 3.93 (s, 2H), 3.11 (br d, J = 6.4 Hz, 2H), 2.77 (br s, 3H), 2.34 (br d, J = 5.5 Hz, 5H), 1.98-2.04 (m, 4H), 1.88-1.97 (m, 4H), 1.79-1.88 (m, 2H), 1.59-1.74 (m, 2H), 1.45-1.76 (m, 3H);<br>hLPA$_1$ IC$_{50}$ = 655.3 nM | Example 3 |

TABLE 1-continued

| Ex # | Structure & Name | Analytical & Biological Data | Method |
|---|---|---|---|
| 36 | 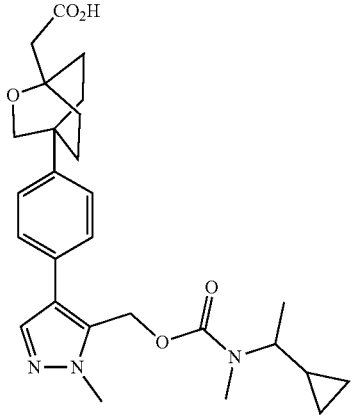 [SMILES: CC(C1CC1)N(C)C(=O)OCc1c(-c2ccc(C34CCC(CC(=O)O)(CC3)OC4)cc2)cnn1C]<br>(rac)-2-(4-(4-(5-((((1-cyclopropyl-ethyl)(methyl)carbamoyl)oxy)methyl)-1-methyl-1-pyrazol-4-yl)phenyl)-2-oxabicyclo[2.2.2]octan-1-yl)acetic acid | LCMS [M + H]$^+$ = 482.4;<br>$^1$H NMR (DMSO-d$_6$) δ: 7.51 (br s, 1H), 7.24 (br s, 4H), 5.05 (s, 2H), 3.11-3.27 (m, 1H), 2.63 (br s, 3H), 2.42 (s, 4H), 2.20 (br s, 2H), 1.61-2.00 (m, 8H), 0.71-1.17 (m, 5H), −0.33-0.46 (m, 4H);<br>hLPA$_1$ IC$_{50}$ = 1890 nM. | Example 4 |
| 37 | 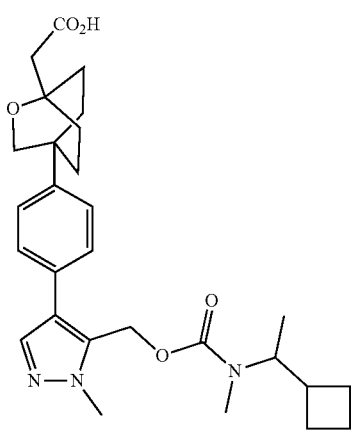 [SMILES: CC(C1CCC1)N(C)C(=O)OCc1c(-c2ccc(C34CCC(CC(=O)O)(CC3)OC4)cc2)cnn1C]<br>(rac)-2-(4-(4-(5-((((1-cyclobutyl-ethyl)(methyl)carbamoyl)oxy)methyl)-1-methyl-1H-pyrazol-4-yl)phenyl)-2-oxabicyclo[2.2.2]octan-1-yl)acetic acid | LCMS [M + H]$^+$ = 496.3;<br>$^1$H NMR (DMSO-d$_6$) δ: 7.65 (br d, J = 16.5 Hz, 1H), 7.40-7.47 (m, 1H), 7.37 (br s, 3H), 5.20 (br d, J = 8.9 Hz, 2H), 4.00-4.13 (m, 1H), 3.92 (br s, 1H), 2.54-2.67 (m, 6H), 2.33 (s, 3H), 1.35-1.79 (m, 1H), 1.34-2.10 (m, 14H), 0.80-1.00 (m, 3H);<br>hLPA$_1$ IC$_{50}$ = 166 nM. | Example 4 |
| 38 | 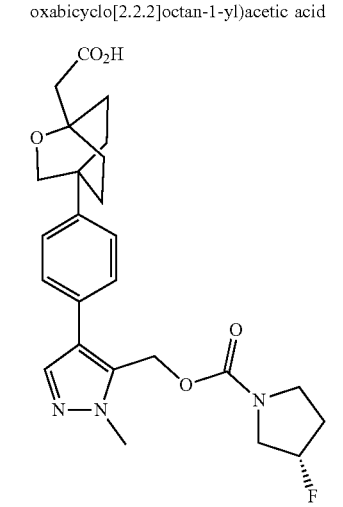<br>2-(4-(4-(5-(((((S)-3-fluoropyrrolidine-1-carbonyl)oxy)methyl)-1-methyl-1H-pyrazol-4-yl)phenyl)-2-oxabicyclo[2.2.2]octan-1-yl)acetic acid | LCMS [M + H]$^+$ = 494.3;<br>$^1$H NMR (DMSO-d$_6$) δ: 7.63 (br s, 1H), 7.39 (br s, 4H), 5.35 (br s, 1H), 5.10-5.28 (m, 3H), 3.92 (br s, 3H), 3.42-3.67 (m, 2H), 2.55 (br s, 2H), 2.33 (br s, 2H), 1.76-2.21 (m, 11H);<br>hLPA$_1$ IC$_{50}$ = 1900 nM. | Example 4 |

TABLE 1-continued

| Ex # | Structure & Name | Analytical & Biological Data | Method |
|---|---|---|---|
| 39 | 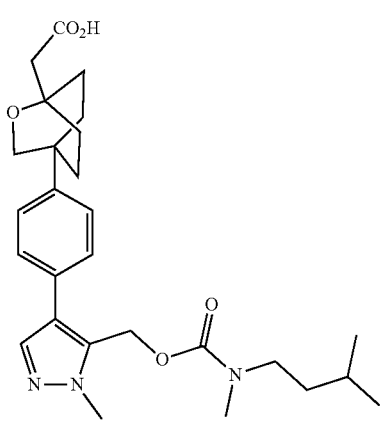 [SMILES: CC(C)CCN(C)C(=O)OCc1c(-c2ccc(C34CCC(CC(=O)O)(CC3)OC4)cc2)cnn1C]<br>2-(4-(4-(5-(((isopentyl(methyl)carbamoyl)oxy)methyl)-1-methyl-1H-pyrazol-4-yl)phenyl)-2-oxabicyclo[2.2.2]octan-1-yl)acetic acid | LCMS [M + H]$^+$ = 484.2;<br>$^1$H NMR (400 MHz, CDCl$_3$) δ 9.70-8.52 (m, 1H), 7.56 (s, 1H), 7.37-7.28 (m, 2H), 7.25-7.15 (m, 2H), 5.12 (s, 2H), 4.04 (s, 2H), 3.92 (s, 3H), 3.32-3.07 (m, 2H), 2.94-2.70 (m, 3H), 2.48 (s, 2H), 2.16-1.71 (m, 8H), 1.59-1.23 (m, 3H), 0.95-0.71 (m, 6H);<br>hLPA$_1$ IC$_{50}$ = 520 nM. | Example 4 |
| 40 | 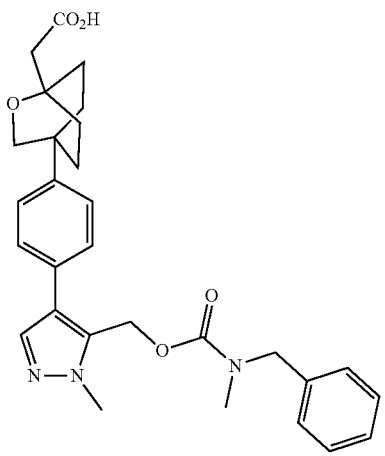 [SMILES: CN(Cc1ccccc1)C(=O)OCc1c(-c2ccc(C34CCC(CC(=O)O)(CC3)OC4)cc2)cnn1C]<br>2-(4-(4-(5-(((benzyl(methyl)carbamoyl)oxy)methyl)-1-methyl-1H-pyrazol-4-yl)phenyl)-2-oxabicyclo[2.2.2]octan-1-yl)acetic acid | LCMS [M + H]$^+$ = 504.2;<br>$^1$H NMR (DMSO-d$_6$) δ: 7.63 (br d, J = 8.5 Hz, 1H), 7.18-7.47 (m, 8H), 7.11 (br d, J = 5.9 Hz, 1H), 5.08-5.37 (m, 2H), 4.32-4.46 (m, 2H), 3.74-4.00 (m, 3H), 2.79-2.91 (m, 2H), 2.73 (s, 2H), 2.29 (s, 2H), 1.77-2.02 (m, 9H);<br>hLPA$_1$ IC$_{50}$ = 767 nM. | Example 4 |
| 41 | 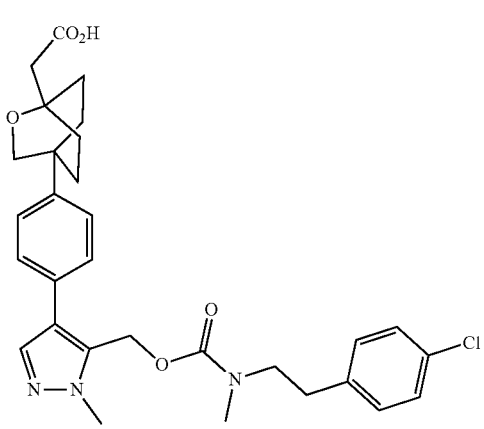<br>2-(4-(4-(5-((((4-chlorophenethyl)(methyl)carbamoyl)oxy)methyl)-1-methyl-1H-pyrazol-4-yl)phenyl)-2-oxabicyclo[2.2.2]octan-1-yl)acetic acid | LCMS [M + H]$^+$ = 538.2;<br>$^1$H NMR (DMSO-d$_6$) δ: 7.62 (s, 1H), 7.43 (br t, J = 5.3 Hz, 1H), 7.35 (s, 3H), 7.31 (br d, J = 8.2 Hz, 2H), 7.21 (br d, J = 8.0 Hz, 2H), 5.07 (s, 2H), 3.88 (s, 2H), 3.46-3.64 (m, 1H), 3.22 (br d, J = 6.3 Hz, 2H), 2.65-2.77 (m, 2H), 2.55 (s, 1H), 2.30 (s, 2H), 1.80-2.11 (m, 9H);<br>hLPA$_1$ IC$_{50}$ = 2790 nM. | Example 4 |

TABLE 1-continued

| Ex # | Structure & Name | Analytical & Biological Data | Method |
|---|---|---|---|
| 42 | 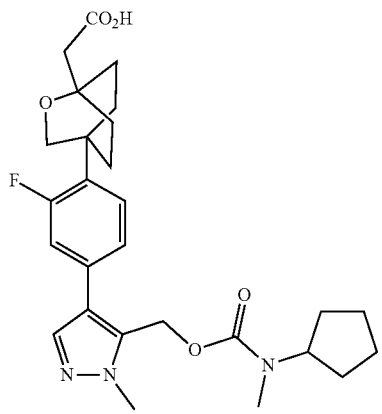 [SMILES: CN(C(=O)OCc1c(-c2ccc(C34CCC(CC(=O)O)(CC3)OC4)c(F)c2)cnn1C)C1CCCC1]<br>2-(4-(4-(5-(((cyclopentyl(methyl)carbamoyl)oxy)methyl)-1-methyl-1H-pyrazol-4-yl)-2-fluorophenyl)-2-oxabicyclo[2.2.2]octan-1-yl)acetic acid | LCMS [M + H]$^+$ = 500.4; $^1$H NMR (DMSO-d$_6$) δ: 7.71 (s, 1H), 7.23-7.31 (m, 3H), 5.22 (s, 2H), 3.92 (s, 3H), 2.69 (br s, 3H), 2.34 (s, 3H), 1.96-2.13 (m, 6H), 1.83-1.94 (m, 2H), 1.79 (br s, 1H), 1.56-1.73 (m, 4H), 1.47 (br s, 5H); hLPA$_1$ IC$_{50}$ = 232 nM. | Example 4 |
| 43 | 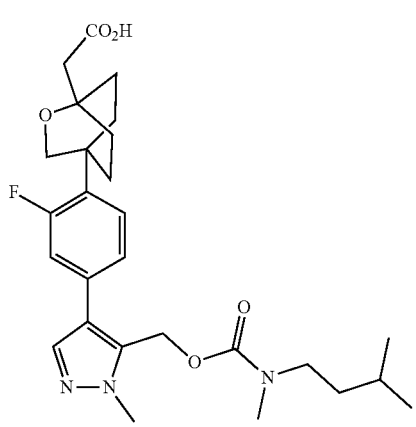 [SMILES: CC(C)CCN(C)C(=O)OCc1c(-c2ccc(C34CCC(CC(=O)O)(CC3)OC4)c(F)c2)cnn1C]<br>2-(4-(2-fluoro-4-(5-(((isopentyl(methyl)carbamoyl)oxy)methyl)-1-methyl-1H-pyrazol-4-yl)phenyl)-2-oxabicyclo[2.2.2]octan-1-yl)acetic acid | LCMS [M + H]$^+$ = 502.4; $^1$H NMR (DMSO-d$_6$) δ: 7.73 (br d, J = 10.7 Hz, 1H), 7.26 (br d, J = 5.8 Hz, 3H), 5.22 (br d, J = 6.7 Hz, 2H), 4.01 (br s, 2H), 3.92 (s, 3H), 3.04-3.42 (m, 2H), 2.75-2.89 (m, 3H), 2.34 (s, 2H), 1.95-2.12 (m, 6H), 1.81-1.94 (m, 2H), 1.21-1.54 (m, 3H), 0.70-0.98 (m, 6H); hLPA$_1$ IC$_{50}$ = 271 nM. | Example 4 |
| 44 | 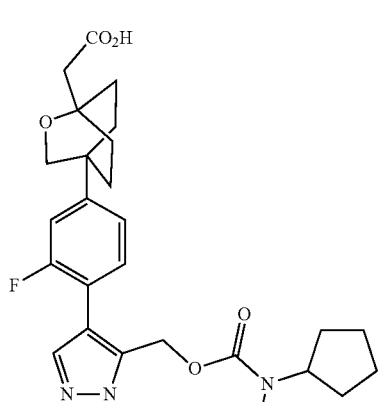<br>2-(4-(4-(5-(((cyclopentyl(methyl)carbamoyl)oxy)methyl)-1-methyl-1H-pyrazol-4-yl)-3-fluorophenyl)-2-oxabicyclo[2.2.2]octan-1-yl)acetic acid | LCMS [M + H]$^+$ = 500.0; $^1$H NMR (DMSO-d$_6$) δ: 7.56 (s, 1H), 7.36 (br t, J = 8.1 Hz, 1H), 7.17-7.29 (m, 2H), 6.29-6.33 (m, 1H), 5.12 (s, 2H), 4.10 (s, 1H), 3.91 (s, 3H), 2.61 (br s, 3H), 2.31-2.43 (m, 3H), 1.96-2.07 (m, 4H), 1.82-1.94 (m, 4H), 1.37-1.70 (m, 9H); hLPA$_1$ IC$_{50}$ = 1860 nM. | Example 4 |

TABLE 1-continued

| Ex # | Structure & Name | Analytical & Biological Data | Method |
|---|---|---|---|
| 45 | 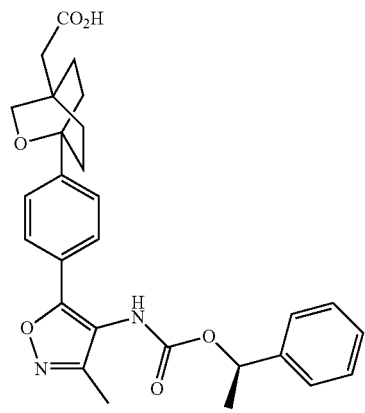<br>2-(4-(3-fluoro-4-(5-(((isopentyl(methyl)carbamoyl)oxy)methyl)-1-methyl-1H-pyrazol-4-yl)phenyl)-2-oxabicyclo[2.2.2]octan-1-yl)acetic acid | LCMS [M + H]$^+$ = 502.1;<br>$^1$H NMR (DMSO-d$_6$) δ: 7.52-7.61 (m, 1H), 7.36 (br d, J = 5.8 Hz, 1H), 7.16-7.28 (m, 2H), 5.12 (br s, 2H), 3.90 (br d, J = 8.2 Hz, 5H), 3.18 (br s, 1H), 3.07 (br s, 1H), 2.79 (br s, 1H), 2.67 (br s, 1H), 2.34 (s, 2H), 1.97-2.04 (m, 4H), 1.84-1.95 (m, 4H), 1.44-1.52 (m, 1H), 1.17-1.36 (m, 3H), 0.73-0.93 (m, 6H);<br>hLPA$_1$ IC$_{50}$ = 1120 nM. | Example 4 |

Example 46. 2-(1-(4-(3-Methyl-5-((((R)-1-phenylethoxy)carbonyl)amino)isoxazol-4-yl)phenyl)-2-oxabicyclo[2.2.2]octan-4-yl)acetic acid

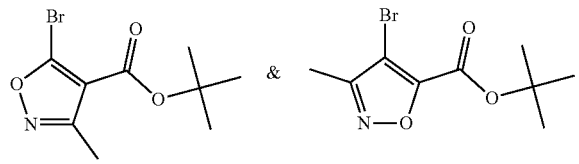

46A. tert-butyl 5-bromo-3-methylisoxazole-4-carboxylate and tert-butyl 4-bromo-3-methyl-isoxazole-5-carboxylate (mixture)

Aq. 6% NaOCl (70.2 mL, 68.3 mmol) was added to a solution of acetaldoxime (2.42 g, 41.0 mmol) and tert-butyl 3-bromopropiolate (5.60 g, 27.3 mmol) in DCM (100 mL) dropwise at RT over 2 h. The reaction was stirred at RT for 30 min, after which analytical HPLC showed starting material was still present. More acetaldoxime (2.42 g, 41.0 mmol) and 6% aq. NaOCl (70.2 mL, 68.3 mmol) were added and the reaction was stirred at RT until analytical HPLC showed that the reaction was complete. The organic phase was separated, washed with water and brine, dried (MgSO$_4$), and concentrated in vacuo. The crude product (an oil) was chromatographed (40 g SiO$_2$; continuous gradient from 0% to 30% EtOAc in hexane over 10 min) to give a mixture of the two isomeric title compounds (3.20 g, 12.2 mmol, 44.7% yield) as a clear oil.

46B. (1-(4-bromophenyl)-2-oxabicyclo[2.2.2]octan-4-yl)methyl 4-methylbenzenesulfonate

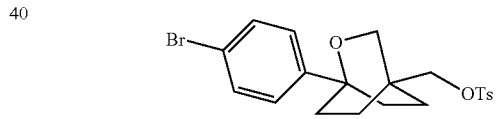

A solution of 1.6 M nBuLi in hexane (8.0 mL, 12.8 mmol) was added dropwise to a −78° C. solution of 1,4-dibromobenzene (5.47 g, 23.2 mmol) in THF (25 mL). The reaction was stirred at −78° C. for 2 h, after which a solution of (4-oxocyclohexane-1,1-diyl)bis(methylene) bis(4-methylbenzenesulfonate; synthesized according to Example 1E, page 55 in U.S. Pat. No. 8,962,660; 5.1 g, 10.9 mmol) in THF (20 mL) was added. The reaction mixture was allowed to slowly warm to RT over 1 h and stirred at RT for another 1 h, after which LC-MS showed formation of the desired product. Powdered NaOH (2.19 g, 54.7 mmol) was carefully added. The reaction mixture was heated at reflux under N$_2$ for 18 h, then was cooled to RT and partitioned between EtOAc and water (50 mL each). The organic layer was washed with water (50 mL×3), dried (MgSO$_4$), and partially concentrated in vacuo. The solid precipitate was collected by filtration to give the title compound (3.70 g, 8.20 mmol, 75% yield) as an off-white solid. LCMS [M+H]$^+$=450.9/452.9; $^1$H NMR (CDCl$_3$) δ: 7.81-7.75 (m, 2H), 7.44-7.39 (m, 2H), 7.36 (dt, J=8.2, 0.8 Hz, 2H), 7.25-7.20 (m, 2H), 3.81 (t, J=1.5 Hz, 2H), 3.75 (s, 2H), 2.46 (s, 3H), 1.98 (t, J=8.0 Hz, 4H), 1.81-1.57 (m, 4H).

46C. 2-(1-(4-bromophenyl)-2-oxabicyclo[2.2.2]octan-4-yl)acetonitrile

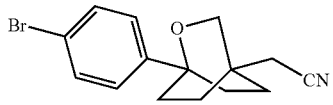 [SMILES: N#CCC12CCC(c3ccc(Br)cc3)(CC1)OC2]

A mixture of compound 46B (3.70 g, 8.20 mmol), NaCN (1.47 g, 30.0 mmol), and a catalytic amount of KI in DMSO (10 mL) was stirred at 80° C. for 18 h, then was cooled to RT. Analytical HPLC showed that the reaction was complete. The reaction mixture was partitioned between EtOAc and water (50 mL each). The organic layer was washed with 1N aq. NaOH (×1), water (×3), dried (MgSO$_4$), and concentrated in vacuo to give the title compound (2.50 g, 8.16 mmol, 100% yield) as an off-white solid. LCMS [M+Na]$^+$=360.9/362.9; 1H NMR (CDCl$_3$) δ: 7.46-7.41 (m, 2H), 7.28-7.23 (m, 2H), 3.93 (t, J=1.4 Hz, 2H), 2.23 (s, 2H), 2.11-1.99 (m, 4H), 1.91-1.78 (m, 4H).

46D. 2-(1-(4-bromophenyl)-2-oxabicyclo[2.2.2]octan-4-yl)acetic acid

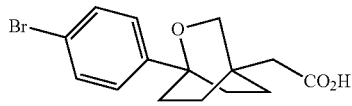 [SMILES: O=C(O)CC12CCC(c3ccc(Br)cc3)(CC1)OC2]

A mixture of compound 46C (2.50 g, 8.16 mmol) and 40% aq. KOH (5.75 mL, 40.8 mmol) in ethylene glycol (20 mL) was stirred at 120° C. for 18 h, then was cooled to RT. Analytical HPLC showed that the reaction was complete. The reaction mixture was partially concentrated in vacuo. The remaining solution was diluted with water (200 mL), then was acidified to pH=2 with conc. HCl at 0° C. The mixture was filtered, and the collected solids were washed with water until the filtrate was neutral. The solids were dried in vacuo to give the title compound (2.58 g, 7.93 mmol, 97% yield) as a white solid. LCMS [M−H]$^+$=323.1/325.1; 1H NMR (DMSO-d$_6$) δ: 12.13 (s, 1H), 7.51-7.45 (m, 2H), 7.35-7.30 (m, 2H), 3.84 (t, J=1.4 Hz, 2H), 2.11-2.00 (m, 4H), 1.85-1.65 (m, 6H).

46E. Methyl 2-(1-(4-bromophenyl)-2-oxabicyclo[2.2.2]octan-4-yl)acetate

A solution of 2.0 M TMSCHN$_2$ in hexane (7.69 mL, 15.38 mmol) was added to a solution of compound 46D (2.50 g, 7.69 mmol) in THF (10 mL)/MeOH (5 mL) at 0° C. The reaction mixture was allowed to warm to RT and stirred at RT for 2 h, then was concentrated in vacuo. The crude oil was chromatographed (40 g SiO$_2$; continuous gradient from 0% to 50% EtOAc in hexane over 10 min) to give the title compound (2.5 g, 7.37 mmol, 96% yield) as a white solid. [M+Na]$^+$=360.9/362.9; $^1$H NMR (CDCl$_3$) δ: 7.44-7.40 (m, 2H), 7.28-7.24 (m, 2H), 3.93 (t, J=1.3 Hz, 2H), 3.67 (s, 3H), 2.18 (s, 2H), 2.06-1.95 (m, 4H), 1.86-1.73 (m, 4H).

46F. Methyl 2-(1-(4-(5,5-dimethyl-1,3,2-dioxaborinan-2-yl)phenyl)-2-oxabicyclo[2.2.2]octan-4-yl)acetate

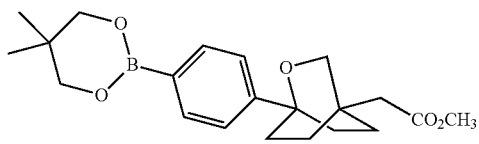 [SMILES: COC(=O)CC12CCC(c3ccc(B4OCC(C)(C)CO4)cc3)(CC1)OC2]

A mixture of PdCl$_2$(dppf) (101 mg, 0.139 mmol), bis(pinacolato)diboron (438 mg, 1.94 mmol), KOAc (218 mg, 2.22 mmol), and compound 46E (470 mg, 1.39 mmol) in anhydrous DMSO (10 mL) was degassed under Ar. The reaction mixture was stirred at 80° C. under Ar for 2 h, then was cooled to RT and poured into cold 1N aq. HCl (20 mL) and extracted with EtOAc (3×). The combined organic extracts were washed with brine (2×), dried (Na$_2$SO$_4$) and concentrated in vacuo. The crude oil was chromatographed (24 g SiO$_2$; continuous gradient from 0% to 30% EtOAc in hexane over 10 min) to give the title compound (418 mg, 1.12 mmol, 81% yield) as an off-white solid. $^1$H NMR (CDCl$_3$) δ: 7.74 (d, J=8.3 Hz, 2H), 7.37 (d, J=8.3 Hz, 2H), 3.94 (s, 2H), 3.75 (s, 4H), 3.67 (s, 3H), 2.18 (s, 2H), 2.10-1.99 (m, 4H), 1.85-1.73 (m, 4H), 1.01 (s, 6H)

46G. tert-butyl 5-(4-(4-(2-methoxy-2-oxoethyl)-2-oxabicyclo[2.2.2]octan-1-yl)phenyl)-3-methylisoxazole-4-carboxylate

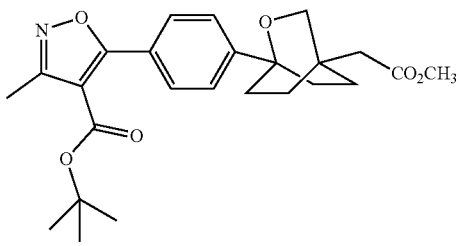 [SMILES: COC(=O)CC12CCC(c3ccc(-c4onc(C)c4C(=O)OC(C)(C)C)cc3)(CC1)OC2]

A mixture of compound 46A (93 mg, 0.355 mmol), compound 46F (110 mg, 0.295 mmol), (Ph$_3$P)$_2$Pd(II)Cl$_2$ (21 mg, 0.030 mmol), and K$_2$CO$_3$ (123 mg, 0.89 mmol) in DME (8 mL) was degassed under Ar, then was stirred at 80° C. for 4 h and cooled to RT. The reaction mixture was acidified with 1N aq. HCl and extracted with EtOAc. The organic layer was washed with water and concentrated in vacuo. The crude product (an oil) was purified by preparative HPLC (Phenomenex Axia 5u C18 30×100 mm column; detection at 220 nm; flow rate=40 mL/min; continuous gradient from 50% B to 100% B over 10 min+2 min hold time at 100% B, where A=90:10:0.1 H$_2$O:MeOH:TFA and B=90:10:0.1 MeOH:H$_2$O:TFA) to give the title compound (20 mg, 0.045 mmol, 15.3% yield) as a light brownish oil. LCMS [M+H]$^+$=442.1; 1H NMR (CDCl$_3$) δ: 7.82 (d, J=8.1 Hz, 2H), 7.50 (d, J=8.4 Hz, 2H), 3.97 (s, 2H), 3.68 (s, 3H), 2.48 (s, 3H), 2.20 (s, 2H), 2.14-1.95 (m, 4H), 1.92-1.75 (m, 4H), 1.51 (s, 9H).

46H. 5-(4-(4-(2-methoxy-2-oxoethyl)-2-oxabicyclo[2.2.2]octan-1-yl)phenyl)-3-methylisoxazole-4-carboxylic acid

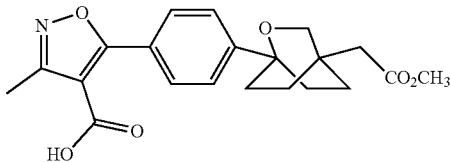 [SMILES: COC(=O)CC12CCC(c3ccc(-c4onc(C)c4C(=O)O)cc3)(CC1)OC2]

A mixture of compound 46G (20 mg, 0.045 mmol) and formic acid (174 µL, 4.53 mmol) was stirred at RT for 18 h, then was concentrated in vacuo. The residue was dissolved in EtOAc, washed with water, dried (MgSO$_4$) and concentrated in vacuo to give the title compound (17 mg, 0.044 mmol, 97% yield) as a light brownish solid. [M−H]$^+$=384.3; $^1$H NMR (CDCl$_3$) δ: 7.88 (d, J=8.5 Hz, 2H), 7.52 (d, J=8.5 Hz, 2H), 3.97 (s, 2H), 3.69 (s, 3H), 2.53 (s, 3H), 2.20 (s, 2H), 2.14-2.04 (m, 4H), 1.91-1.76 (m, 4H)

46I. Methyl 2-(1-(4-(3-methyl-4-((((R)-1-phenylethoxy)carbonyl)amino)isoxazol-5 yl) phenyl)-2-oxabicyclo[2.2.2]octan-4-yl)acetate

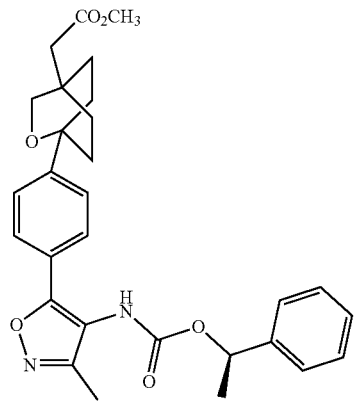 [SMILES: COC(=O)CC12CCC(c3ccc(-c4onc(C)c4NC(=O)O[C@H](C)c4ccccc4)cc3)(CC1)OC2]

A mixture of compound 46H (17 mg, 0.044 mmol), (PhO)$_2$PON$_3$ (0.011 mL, 0.053 mmol), (R)-(+)-1-phenylethanol (5.4 µL, 0.049 mmol), and TEA (8 µL, 0.057 mmol) in toluene (1 mL) was stirred at 80° C. for 1 h, then was cooled to RT and concentrated in vacuo. The crude oily product was purified by preparative HPLC (Phenomenex Axia 5u C18 30×100 mm column; detection at 220 nm; flow rate=40 mL/min; continuous gradient from 50% B to 100% B over 10 min+2 min hold time at 100% B, where A=90:10:0.1 H$_2$O:MeOH:TFA and B=90:10:0.1 MeOH:H$_2$O:TFA) to give the title compound (17 mg, 0.034 mmol, 76% yield) as off white solid. LCMS [M+H]$^+$=505.1; $^1$H NMR (CDCl$_3$) δ: 7.82-7.01 (m, 9H), 6.71-5.75 (m, 2H), 4.02-3.92 (m, 2H), 3.74-3.64 (m, 3H), 2.27-2.13 (m, 5H), 2.04 (t, J=8.0 Hz, 4H), 1.92-1.72 (m, 4H), 1.71-1.33 (m, 3H).

Example 46

A solution of compound 46I (17 mg, 0.034 mmol) and 1N aq. NaOH (0.34 mL, 0.34 mmol) in THF (0.5 mL)/MeOH (0.5 mL) was stirred at RT for 2 h, then was concentrated in vacuo. The residue was acidified to pH=2 with 1N aq. HCl and then purified by preparative HPLC (Phenomenex Axia 5u C18 30×100 mm column; detection at 220 nm; flow rate=40 mL/min; continuous gradient from 30% B to 100% B over 10 min+2 min hold time at 100% B, where A=90:10:0.1 H$_2$O:MeOH:TFA and B=90:10:0.1 MeOH:H$_2$O:TFA) to give the title compound (11 mg, 0.021 mmol, 63.2% yield) as a clear oil. LCMS [M−H]$^+$=489.2; $^1$H NMR (CDCl$_3$) δ: 7.83-7.05 (m, 9H), 6.20-5.79 (m, 1H), 3.98 (s, 2H), 2.28-2.14 (m, 5H), 2.06 (t, J=7.9 Hz, 4H), 1.86 (q, J=7.6, 7.0 Hz, 4H), 1.70-1.35 (m, 3H); hLPA$_1$ IC$_{50}$=190 nM.

The compounds listed in Table 2 were prepared by using same synthetic sequence and the same intermediates as described for the synthesis of Example 46 (and also as described in the synthetic sequence shown in Scheme 3).

TABLE 2

| Ex # | Structure & Name | Analytical & Biological Data |
|---|---|---|
| 47 | ![structure] 2-(1-(4-(4-((((R)-1-cyclopropylethoxy)carbonyl)amino)-3-methylisoxazol-5-yl)phenyl)-2-oxabicyclo[2.2.2]octan-4-yl)acetic acid | LCMS [M + H]$^+$ = 455.5; $^1$H NMR (500 MHz, CDCl$_3$) δ 7.58 (s, 2H), 7.31 (d, J = 8.3 Hz, 2H), 5.74 (s, 1H), 4.11 (s, 1H), 3.79 (s, 2H), 2.10 (s, 3H), 2.03 (s, 2H), 1.96-1.81 (m, 4H), 1.76-1.60 (m, 4H), 1.28-0.58 (m, 4H), 0.44-0.06 (m, 4H); hLPA$_1$ IC$_{50}$ = 583 nM. |

TABLE 2-continued

| Ex # | Structure & Name | Analytical & Biological Data |
|---|---|---|
| 48 | 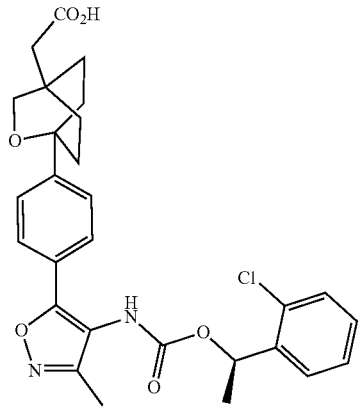 [SMILES: Cc1noc(-c2ccc(C34CCC(CC(=O)O)(CC3)CO4)cc2)c1NC(=O)O[C@H](C)c1ccccc1Cl]

2-(1-(4-(4-((((R)-1-(2-chlorophenyl)ethoxy) carbonyl)amino)-3-methyl-isoxazol-5-yl)phenyl)-2-oxabicyclo[2.2.2]octan-4-yl)acetic acid | LCMS [M + H]⁺ = 525.4; $^1$H NMR (500 MHz, CDCl$_3$) δ 7.87-7.62 (m, 2H), 7.57-6.96 (m, 7H), 6.21 (q, J = 6.5 Hz, 1H), 3.97 (br. s., 2H), 2.30-2.14 (m, 5H), 2.11-1.99 (m, 4H), 1.91-1.77 (m, 4H), 1.68-1.37 (m, 3H); hLPA$_1$ IC$_{50}$ = 354 nM. |
| 49 | 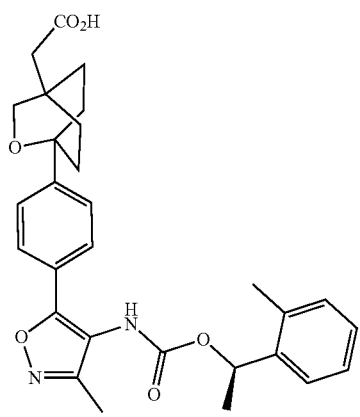 [SMILES: Cc1ccccc1[C@@H](C)OC(=O)Nc1c(C)noc1-c1ccc(C23CCC(CC(=O)O)(CC2)CO3)cc1]

2-(1-(4-(3-methyl-4-(((((R)-1-(o-tolyl)ethoxy) carbonyl)amino)isoxazol-5-yl)phenyl)-2-oxabicyclo[2.2.2]octan-4-yl)acetic acid | LCMS [M − H]⁺ = 503.4; $^1$H NMR (500 MHz, CDCl$_3$) δ 7.85-7.58 (m, 2H), 7.55-7.36 (m, 3H), 7.31-6.96 (m, 4H), 6.20-6.00 (m, 1H), 3.97 (br. s., 2H), 2.45-2.27 (m, 3H), 2.26-2.17 (m, 5H), 2.09-2.01 (m, 4H), 1.85 (d, J = 6.9 Hz, 4H), 1.65-1.35 (m, 3H); hLPA$_1$ IC$_{50}$ = 303 nM. |
| 50 | 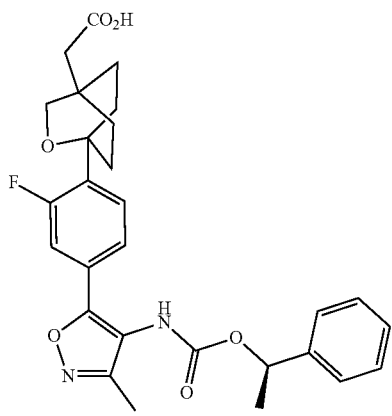 [SMILES: Cc1noc(-c2ccc(C34CCC(CC(=O)O)(CC3)CO4)c(F)c2)c1NC(=O)O[C@H](C)c1ccccc1]

2-(1-(2-fluoro-4-(3-methyl-4-((((R)-1-phenylethoxy)carbonyl)amino)isoxazol-5-yl)phenyl)-2-oxabicyclo[2.2.2]octan-4-yl)acetic acid | LCMS [M + H]⁺ = 507.1; $^1$H NMR (500 MHz, DMSO-d$_6$) δ 9.31 (br s, 1H), 7.74-6.97 (m, 8H), 5.73 (br s, 1H), 2.32-2.20 (m, 2H), 2.11 (br s, 5H), 1.91-1.66 (m, 6H), 1.53 (br s, 2H), 2 protons are in water suppression area; hLPA$_1$ IC$_{50}$ = 57 nM. |

TABLE 2-continued

| Ex # | Structure & Name | Analytical & Biological Data |
|---|---|---|
| 51 | 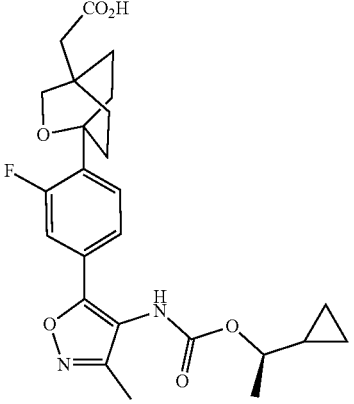 [SMILES: Cc1noc(-c2ccc(C34CCC(CC(=O)O)(CC3)CO4)c(F)c2)c1NC(=O)O[C@H](C)C1CC1]<br>2-(1-(4-(4-((((R)-1-cyclopropylethoxy)carbonyl)amino)-3-methylisoxazol-5-yl)-2-fluorophenyl)-2-oxabicyclo[2.2.2]octan-4-yl)acetic acid | LCMS $[M + H]^+$ = 473.1;<br>$^1$H NMR (500 MHz, DMSO-$d_6$) δ 9.13 (br s, 1H), 7.70 (br t, J = 7.9 Hz, 1H), 7.58 (br d, J = 7.9 Hz, 1H), 7.50 (br d, J = 12.8 Hz, 1H), 4.22 (br s, 1H), 2.55 (s, 2H), 2.27 (br t, J = 11.1 Hz, 2H), 2.22-2.08 (m, 5H), 1.92-1.68 (m, 6H), 1.31 (br s, 2H), 1.07 (br s, 1H), 0.62-0.23 (m, 4H), 2 protons are in water suppression area;<br>hLPA$_1$ IC$_{50}$ = 222 nM. |
| 52 | 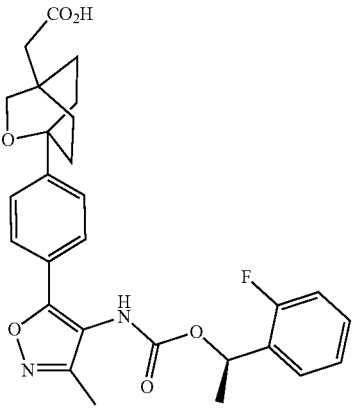 [SMILES: Cc1noc(-c2ccc(C34CCC(CC(=O)O)(CC3)CO4)cc2)c1NC(=O)O[C@H](C)c1ccccc1F]<br>2-(1-(4-(4-((((R)-1-(2-fluorophenyl)ethoxy)carbonyl)amino)-3-methyl-isoxazol-5-yl)phenyl)-2-oxabicyclo[2.2.2]octan-4-yl)acetic acid | LCMS $[M - H]^+$ = 507.4;<br>$^1$H NMR (500 MHz, CDCl$_3$) δ 8.36 (br. s., 2H), 7.81-7.36 (m, 5H), 7.35-6.90 (m, 3H), 6.12 (q, J = 6.6 Hz, 1H), 3.98 (br. s., 2H), 2.22 (d, J = 3.3 Hz, 5H), 2.11-1.99 (m, 4H), 1.92-1.77 (m, 4H), 1.71-1.36 (m, 3H); $^{19}$F NMR (471 MHz, CDCl$_3$) δ 118.05 (s), −118.49 (s);<br>hLPA$_1$ IC$_{50}$ = 134 nM. |

Example 53. 2-(1-(4-(4-((((cyclopentyl(methyl)carbamoyl)oxy)methyl)-3-methylisoxazol-5-yl)phenyl)-2-oxabicyclo[2.2.2]octan-4-yl)acetic acid

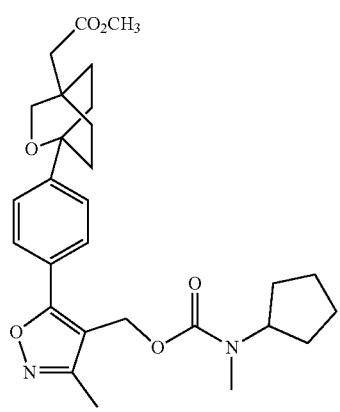 [SMILES: COC(=O)CC12CCC(c3ccc(-c4onc(C)c4COC(=O)N(C)C4CCCC4)cc3)(CC1)OC2]

53A. 5-bromo-3-methylisoxazole-4-carboxylic acid and 4-bromo-3-methylisoxazole-5-carboxylic acid (mixture)

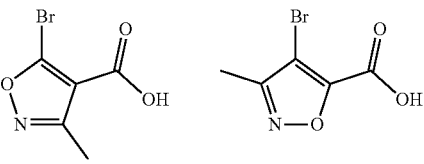

A solution of compound 46A (mixture of two isomers as described above; 1.00 g, 3.82 mmol) in TFA (0.88 mL, 11.5 mmol) and DCM was stirred at 50° C. for 2 h, then was cooled to RT and concentrated in vacuo to give a mixture of 5-bromo-3-methylisoxazole-4-carboxylic acid and 4-bromo-3-methylisoxazole-5-carboxylic acid (0.786 g, 3.82 mmol, 100% yield) as a clear oil.

53B. mixture of 5-bromo-3-methylisoxazol-4-yl)methanol and (4-bromo-3-methylisoxazol-5-yl)methanol

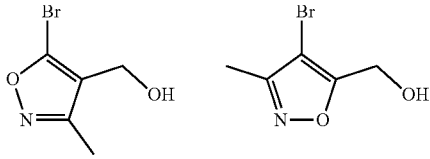

A solution of 1 M BH₃·THF in THF (2.77 mL, 2.77 mmol) was added to compound 53A (285 mg, 1.38 mmol) in THF (2 mL) at −20° C. The reaction was allowed to warm to RT and stirred at RT for 18 h, then was concentrated in vacuo. The residue was dissolved in EtOAc and washed with water. The organic layer was concentrated in vacuo. The crude product (oil) was purified by preparative HPLC (Phenomenex Axia 5u C18 30×100 mm column; detection at 220 nm; flow rate=40 mL/min; continuous gradient from 20% B to 100% B over 10 min+2 min hold time at 100% B, where A=90:10:0.1 H₂O:MeOH:TFA and B=90:10:0.1 MeOH:H₂O:TFA) to give the title compound (93 mg, 0.484 mmol, 35.0% yield).

53C. methyl 2-(1-(4-(4-(hydroxymethyl)-3-methyl-isoxazol-5-yl)phenyl)-2-oxabicyclo[2.2.2]octan-4-yl)acetate

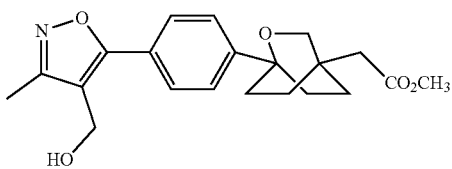 [SMILES: COC(=O)CC12CCC(c3ccc(-c4onc(C)c4CO)cc3)(CC1)OC2]

A mixture of Intermediate 1 (811 mg, 2.18 mmol), compound 53B (1.26 g, 4.79 mmol), Pd(Ph₃P)₄ (12 mg, 10.1 µmol), and K₂CO₃ (139 mg, 1.01 mmol) in DME (5 mL)/H₂O (0.2 mL) was degassed under Ar, then was stirred at 80° C. for 18 h and cooled to RT. The reaction mixture was filtered and the filtrate was concentrated in vacuo. The crude product (oil) was purified by preparative HPLC (Phenomenex Axia 5u C18 30×100 mm column; detection at 220 nm; flow rate=40 mL/min; continuous gradient from 30% B to 100% B over 10 min+2 min hold time at 100% B, where A=90:10:0.1 H₂O:MeOH:TFA and B=90:10:0.1 MeOH:H₂O:TFA) to give the title compound (22 mg, 0.059 mmol, 29.4% yield) as a light yellowish solid. LCMS [M+H]⁺=372.2; ¹H NMR (CDCl₃) δ 7.71 (d, J=8.6 Hz, 2H), 7.51 (d, J=8.6 Hz, 2H), 4.63 (s, 2H), 3.96 (s, 2H), 3.68 (s, 3H), 2.37 (s, 4H), 2.19 (s, 2H), 2.10-2.00 (m, 4H), 1.90-1.75 (m, 4H).

53D. methyl 2-(1-(4-(3-methyl-4-((((4-nitrophenoxy)carbonyl)oxy)methyl)isoxazol-5-yl)phenyl)-2-oxabicyclo[2.2.2]octan-4-yl)acetate

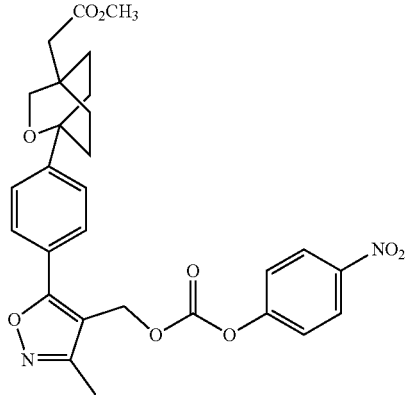 [SMILES: COC(=O)CC12CCC(c3ccc(-c4onc(C)c4COC(=O)Oc4ccc([N+](=O)[O-])cc4)cc3)(CC1)OC2]

A solution of 4-nitrophenyl chloroformate (24 mg, 0.12 mmol) in DCM (0.5 mL) was added to a solution of compound 53C (22 mg, 0.059 mmol) and iPr₂NEt (0.041 mL, 0.24 mmol) in DCM (1 mL). The reaction mixture was stirred at RT for 18 h, then was concentrated in vacuo. The crude oily product was chromatographed (4 g SiO₂; continuous gradient from 0% to 30% EtOAc in hexane over 10 min) to give the title compound (30 mg, 0.056 mmol, 94% yield) as a light yellowish oil. ¹H NMR (CDCl₃) δ: 8.29 (d, J=9.1 Hz, 2H), 7.66 (d, J=8.5 Hz, 2H), 7.49 (d, J=8.5 Hz, 2H), 7.32 (d, J=9.2 Hz, 2H), 5.20 (s, 2H), 3.90 (s, 2H), 3.62 (s, 3H), 2.37 (s, 3H), 2.14 (s, 2H), 2.09-1.94 (m 4H), 1.83-1.69 (m, 4H).

53E. methyl 2-(1-(4-(4-(((cyclopentyl(methyl)carbamoyl)oxy)methyl)-3-methylisoxazol-5-yl)phenyl)-2-oxabicyclo[2.2.2]octan-4-yl)acetate

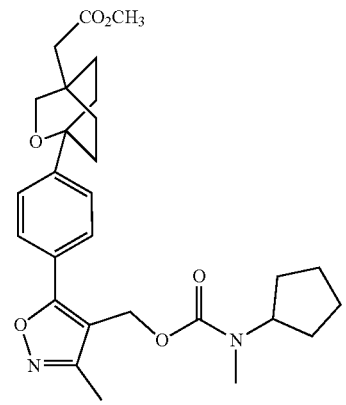 [SMILES: COC(=O)CC12CCC(c3ccc(-c4onc(C)c4COC(=O)N(C)C4CCCC4)cc3)(CC1)OC2]

A mixture of compound 53D (30 mg, 0.056 mmol), cycloheptylmethylamine (0.020 mL, 0.17 mmol), and iPr₂NEt (0.049 mL, 0.28 mmol) in THF (1 mL) was stirred at RT for 2 h and then concentrated in vacuo. The crude product was chromatographed (4 g SiO₂; continuous gradient from 0% to 50% EtOAc in hexane over 10 min) to give the title compound (27 mg, 0.054 mmol, 97% yield) as a clear oil. ¹H NMR (CDCl₃) δ 7.65 (d, J=8.3 Hz, 2H), 7.48-7.42 (m, 2H), 5.02 (s, 2H), 3.89 (s, 2H), 3.62 (s, 3H), 2.69 (br s, 3H), 2.32 (s, 3H), 2.13 (s, 2H), 2.06-1.94 (m, 4H), 1.83-1.35 (m, 13H).

Example 53

A mixture of compound 53E (27 mg, 0.054 mmol) and 2.0 M aq. LiOH (0.27 mL, 0.54 mmol) in THF (0.5 mL)/MeOH (0.2 mL) was stirred at RT for 5 h, then was partitioned between EtOAc and 1N aq. HCl. The organic layer was washed with water and concentrated in vacuo. The crude product (oil) was purified by preparative HPLC (Column: XBridge C18, 19×200 mm, 5-μm particles; Mobile Phase A: 5:95 MeCN:H$_2$O with 0.1% TFA; Mobile Phase B: 95:5 MeCN:H$_2$O with 0.1% TFA; Gradient: 30-70% B over 25 min, then a 5-min hold at 100% B; Flow: 20 mL/min) to give the title compound (18.3 mg, 0.036 mmol, 66.3% yield) as an oil. LCMS [M−H]$^+$=481.05; $^1$H NMR (DMSO-d$_6$) δ: 7.71 (d, J=8.1 Hz, 2H), 7.56 (d, J=8.2 Hz, 2H), 5.05 (s, 2H), 3.86 (s, 2H), 2.65 (s, 3H), 2.31 (s, 3H), 2.18-1.96 (m, 4H), 1.89-1.16 (m, 15H); hLPA$_1$ IC$_{50}$=2,552 nM.

Example 54. (R)-2-(4-(4-(3-methyl-4-(((1-phenylethoxy)carbonyl)amino)isoxazol-5-yl)-2-oxabicyclo[2.2.2]octan-1-yl)phenyl)acetic acid

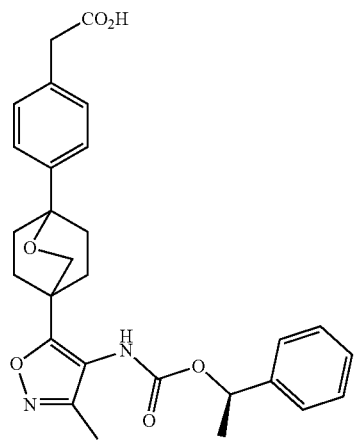 [SMILES: Cc1noc(C23CCC(c4ccc(CC(=O)O)cc4)(CC2)OC3)c1NC(=O)O[C@H](C)c1ccccc1]

54A. (1-(4-(((tetrahydro-2H-pyran-2-yl)oxy)methyl)phenyl)-2-oxabicyclo[2.2.2]octan-4-yl) methyl 4-methylbenzenesulfonate

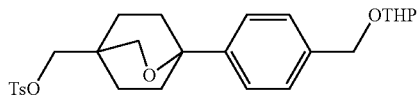

A solution of 1.6 M n-BuLi in hexane (8.0 mL, 12.8 mmol) was added dropwise to a solution of 2-((4-bromobenzyl)oxy)tetrahydro-2H-pyran (7.0 g, 25.8 mmol) in THF (25 mL) at −78° C. The reaction was stirred at −78° C. for 2 h, after which a solution of (4-oxocyclohexane-1,1-diyl)bis(methylene)bis(4-methylbenzenesulfonate) (synthesized according to compound 1E, page 55 in U.S. Pat. No. 8,962,660; 10.0 g, 21.4 mmol) in THF (50 mL) was added. The reaction mixture was allowed to slowly warm up to RT over 1 h and stirred at RT for 1 h. LC-MS showed the formation of the initial alcohol product from the ArLi addition. Powdered NaOH (4.29 g, 107 mmol) was added. The reaction mixture was heated at reflux under N$_2$ for 18 h, then was cooled to RT. The residue was partitioned between EtOAc (50 mL) and water. The organic layer was washed with water (50 mL×3), dried (MgSO$_4$) and concentrated in vacuo. The crude product (an oil) was chromatographed (80 g SiO$_2$; continuous gradient from 0% to 20% EtOAc in hexane over 20 min) to give the title compound (4.80 g, 9.86 mmol, 46.0% yield) as an off white solid. [M−OTHP]$^+$=385.1; $^1$H NMR (CDCl$_3$) δ: 7.80 (d, J=8.3 Hz, 2H), 7.41-7.29 (m, 6H), 4.76 (d, J=12.0 Hz, 1H), 4.69 (t, J=3.6 Hz, 1H), 4.48 (d, J=12.0 Hz, 1H), 3.92 (ddd, J=11.6, 8.5, 3.1 Hz, 1H), 3.83 (t, J=1.4 Hz, 2H), 3.76 (s, 2H), 3.58-3.50 (m, 1H), 2.47 (s, 3H), 2.02 (t, J=8.0 Hz, 4H), 1.93-1.48 (m, 10H).

54B. (1-(4-(((tetrahydro-2H-pyran-2-yl)oxy)methyl)phenyl)-2-oxabicyclo[2.2.2]octan-4-yl)methyl acetate

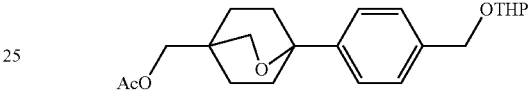

A mixture of compound 54A (2.72 g, 5.59 mmol) and NaOAc (2.29 g, 27.9 mmol) in DMSO (10 mL) was stirred at 80° C. for 8 days, then was cooled to RT and partitioned between EtOAc and water (50 mL each). The organic layer was washed with water, dried (MgSO$_4$), and concentrated in vacuo to give the crude title compound (2.0 g, 5.34 mmol, 96% yield) as a light brownish oil. This material was used in the next reaction without further purification. [M−THPO]$^+$=273.1.

54C. (1-(4-(hydroxymethyl)phenyl)-2-oxabicyclo[2.2.2]octan-4-yl)methyl acetate

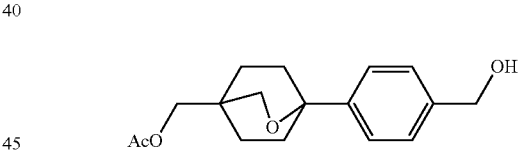

A mixture of compound 54B (2.0 g, 5.34 mmol) and PPTS (0.134 g, 0.534 mmol) in MeOH (10 mL) was stirred at 50° C. for 5 h, then was cooled to RT and concentrated in vacuo. The crude oil was chromatographed (24 g SiO$_2$; continuous gradient from 0% to 50% EtOAc/hexane over 10 min) to give the title compound (1.25 g, 4.31 mmol, 81% yield) as a light yellowish solid. $^1$H NMR (500 MHz, CDCl$_3$) δ 7.41-7.37 (m, 2H), 7.30 (d, J=8.3 Hz, 2H), 4.65 (s, 2H), 3.93 (s, 2H), 3.84 (s, 2H), 2.08-2.02 (m, 7H), 1.86-1.74 (m, 3H), 1.73-1.63 (m, 2H).

54D. (1-(4-(((methylsulfonyl)oxy)methyl)phenyl)-2-oxabicyclo[2.2.2]octan-4-yl)methyl acetate

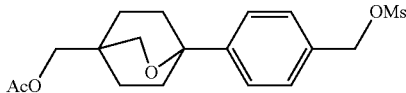

Methanesulfonyl chloride (0.403 mL, 5.17 mmol) was added dropwise to a solution of compound 54C (1.25 g, 4.31 mmol) and Et₃N (1.20 mL, 8.61 mmol) in DCM (10 mL) at 0° C. The reaction was allowed to warm to RT and stirred at RT for 2 h. HPLC showed the reaction was complete at this point. The reaction mixture was concentrated in vacuo. The residue was partitioned between EtOAc and water (25 mL each). The organic layer was washed with 1N aq. HCl and water, dried (MgSO₄) and concentrated in vacuo to give the title compound (1.58 g, 4.29 mmol, 100% yield) as a yellowish oil. [M−OAc]⁺=309.4.

54E. (1-(4-(cyanomethyl)phenyl)-2-oxabicyclo[2.2.2]octan-4-yl)methyl acetate

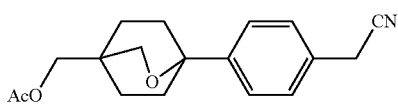

A mixture of compound 54D (1.58 g, 4.29 mmol) and NaCN (0.420 g, 8.58 mmol) in DMSO (10 mL) was stirred at 80° C. for 18 h, then was cooled to RT and partitioned between EtOAc and water (25 mL each). The organic layer was washed with water (2×) and concentrated in vacuo to give the crude title compound (1.284 g, 4.29 mmol, 100% yield) as a yellowish oil. This crude material was used in the next reaction without further purification. [M+H]⁺=300.4.

54F. 2-(4-(4-(hydroxymethyl)-2-oxabicyclo[2.2.2]octan-1-yl)phenyl)acetic acid

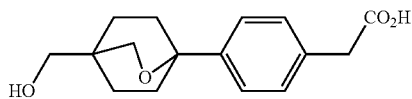

A mixture of compound 54E and aq. 30% NaOH (2.86 g, 21.5 mmol) in EtOH (10 mL) was stirred under reflux for 30 h, then was cooled to RT. The reaction mixture was acidified to pH=2 with conc. HCl, then was extracted with EtOAc (3×). The combined organic extracts were washed with brine, dried (MgSO₄), and concentrated in vacuo to give the title compound (0.41 g, 1.48 mmol, 34.6% yield) as a white solid. [M−H]⁺=275.4.

54G. methyl 2-(4-(4-(hydroxymethyl)-2-oxabicyclo[2.2.2]octan-1-yl)phenyl)acetate

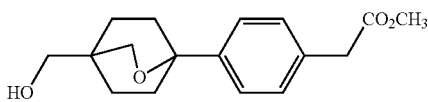 [SMILES: COC(=O)Cc1ccc(C23CCC(CO)(CC2)CO3)cc1]

A mixture of compound 54F (410 mg, 1.48 mmol) and TMSCHN₂ (1.48 mL of a 2.0 M solution in hexane; 2.97 mmol) in MeOH (10 mL)/THF (10 mL) was stirred at RT for 2 h, then was concentrated in vacuo. The crude product (oil) was chromatographed (4 g SiO₂; continuous gradient from 0% to 50% EtOAc/hexane over 10 min) to give the title compound (280 mg, 0.964 mmol, 65.0% yield) as a clear oil.

¹H NMR (500 MHz, CDCl₃) δ 7.37 (d, J=8.3 Hz, 2H), 7.23 (d, J=8.3 Hz, 2H), 3.94 (t, J=1.4 Hz, 2H), 3.68 (s, 3H), 3.60 (s, 2H), 3.39 (s, 2H), 2.08-2.02 (m, 4H), 1.82-1.59 (m, 5H).

54H. methyl 2-(4-(4-formyl-2-oxabicyclo[2.2.2]octan-1-yl)phenyl)acetate

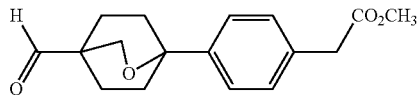 [SMILES: COC(=O)Cc1ccc(C23CCC(C=O)(CC2)CO3)cc1]

DMSO (0.205 mL, 2.89 mmol) was added dropwise to a solution of (COCl)₂ (0.127 mL, 1.45 mmol) in DCM (5 mL) at −78° C. After stirring at −78° C. for 15 min, a solution of compound 54G (280 mg, 0.964 mmol) in DCM (5 mL) was added dropwise and the reaction was stirred at −78° C. for 15 min. Et₃N (0.67 mL, 4.82 mmol) was added dropwise and the reaction was allowed to warm to RT over 2 h, then was concentrated in vacuo. The residue was dissolved in EtOAc (5 mL) and washed with 1N aq. HCl (1×5 mL), water (2×5 mL), satd aq. NaHCO₃, and brine. The organic layer was dried (Na₂SO₄) and concentrated in vacuo to give the crude title compound (278 mg, 0.964 mmol, 100% yield) as a clear yellowish oil, which was used in the next reaction without further purification. [M+H]⁺=289.3.

54I. 1-(4-(2-methoxy-2-oxoethyl)phenyl)-2-oxabicyclo[2.2.2]octane-4-carboxylic acid

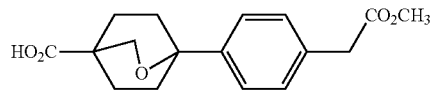 [SMILES: COC(=O)Cc1ccc(C23CCC(C(=O)O)(CC2)CO3)cc1]

To a mixture of compound 54H (278 mg, 0.964 mmol), 2-methyl-2-butene (7.23 mL of a 2.0M solution in THF; 14.5 mmol), NaH₂PO₄ (578 mg, 4.82 mmol), water (1 mL), and t-BuOH (4 mL) was added NaClO₂ (545 mg, 4.82 mmol) at 0° C. The reaction mixture was allowed to warm to RT and stirred at RT for 18 h, then was poured into brine and extracted with EtOAc (3×). The combined organic extracts were dried (Na₂SO₄) and concentrated in vacuo. The crude product was purified by preparative HPLC (Phenomenex Axia 5u C18 30×100 mm column; detection at 220 nm; flow rate=40 mL/min; continuous gradient from 30% B to 100% B over 10 min+2 min hold time at 100% B, where A=90:10:0.1 H₂O:MeOH:TFA and B=90:10:0.1 MeOH:H₂O:TFA) to give the title compound (293 mg, 0.963 mmol, 100% yield) as a white solid. [M−H]⁺=303.3; ¹H NMR (500 MHz, CDCl₃) δ 7.36 (d, J=8.3 Hz, 2H), 7.24 (d, J=8.3 Hz, 2H), 4.19 (s, 2H), 3.69 (s, 3H), 3.61 (s, 2H), 2.18-2.04 (m, 8H).

54J. Methyl 2-(4-(4-(chlorocarbonyl)-2-oxabicyclo[2.2.2]octan-1-yl)phenyl)acetate

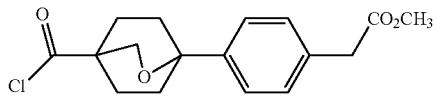

A solution of compound 54I (293 mg, 0.963 mmol) and 1-chloro-N,N,2-trimethyl-prop-1-en-1-amine (0.127 mL, 0.963 mmol) in DCM (5 mL) was stirred at RT for 1 h, then was concentrated in vacuo to give the crude title compound as an oil (311 mg, 0.96 mmol, 100% yield). This material was used directly in the next reaction without further purification.

54K. (E)-tert-butyl 2-(1-(4-(2-methoxy-2-oxoethyl)phenyl)-2-oxabicyclo[2.2.2]octane-4-carbonyl)-3-(methylimino)butanoate

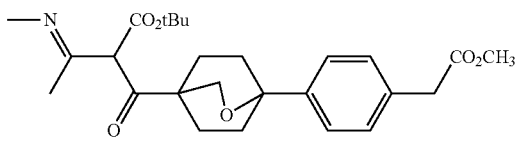 [SMILES: C/N=C(\C)C(C(=O)OC(C)(C)C)C(=O)C12CCC(c3ccc(CC(=O)OC)cc3)(CC1)OC2]

To a 0° C. solution of (E)-tert-butyl 3-(methylimino)butanoate (247 mg, 1.45 mmol) and pyridine (0.31 mL, 3.85 mmol) in THF (5 mL) was added dropwise a solution of compound 54J (311 mg, 0.96 mmol) in DCM over 10 min. The reaction was stirred at RT for 24 h, then was concentrated in vacuo. The residue was partitioned between EtOAc and water (10 mL each). The aqueous phase was extracted with EtOAc, and the combined organic extracts were dried (MgSO$_4$) and concentrated in vacuo. The crude product (oil) was chromatographed (4 g SiO$_2$; continuous gradient from 0% to 50% EtOAc/hexane over 10 min) to give the title compound (240 mg, 0.53 mmol, 54.4% yield) as an orange oil. [M+H]$^+$=458.3.

54L. tert-butyl 5-(1-(4-(2-methoxy-2-oxoethyl)phenyl)-2-oxabicyclo[2.2.2]octan-4-yl)-3-methylisoxazole-4-carboxylate

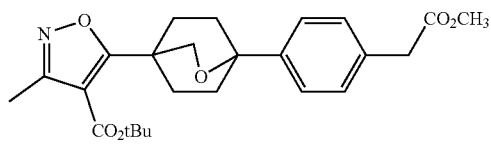 [SMILES: COC(=O)Cc1ccc(C23CCC(c4onc(C)c4C(=O)OC(C)(C)C)(CC2)CO3)cc1]

A mixture of compound 54K (240 mg, 0.53 mmol) and NH$_2$OH·HCl (109 mg, 1.57 mmol) in MeOH (2 mL)/H$_2$O (0.2 mL) was stirred at 60° C. for 18 h, then was cooled to RT and concentrated in vacuo. The crude product was purified by preparative HPLC (Phenomenex Axia 5u C18 30×100 mm column; detection at 220 nm; flow rate=40 mL/min; continuous gradient from 50% B to 100% B over 10 min+2 min hold time at 100% B, where A=90:10:0.1 H$_2$O:MeOH:TFA and B=90:10:0.1 MeOH:H$_2$O:TFA) to give the title compound (70 mg, 0.16 mmol, 30.2% yield) as a white solid. $^1$H NMR (500 MHz, CDCl$_3$) δ 7.39 (d, J=8.5 Hz, 2H), 7.25 (d, J=8.3 Hz, 2H), 4.41 (s, 2H), 3.69 (s, 3H), 3.62 (s, 2H), 2.43-2.31 (m, 7H), 2.21-2.12 (m, 4H), 1.60 (s, 9H); $^{13}$C NMR (126 MHz, CDCl$_3$) δ 177.9, 172.0, 161.4, 160.6, 144.7, 132.4, 128.9, 124.9, 110.6, 82.3, 72.1, 69.5, 51.9, 40.7, 35.8, 32.7, 28.2, 27.4, 12.3

54M. 5-(1-(4-(2-methoxy-2-oxoethyl)phenyl)-2-oxabicyclo[2.2.2]octan-4-yl)-3-methylisoxazole-4-carboxylic acid

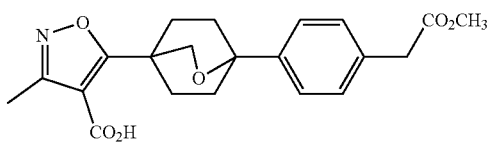

A mixture of compound 54L (70 mg, 0.159 mmol) and formic acid (608 µL; 15.9 mmol) was stirred at RT for 6 h, then was concentrated in vacuo. The residue was dissolved in EtOAc (2 mL), washed with water, dried (MgSO$_4$) and concentrated in vacuo to give the title compound (60 mg, 0.156 mmol, 98% yield) as a white solid. [M+H]$^+$=386.2

54N. (R)-methyl 2-(4-(4-(3-methyl-4-(((1-phenylethoxy)carbonyl)amino)isoxazol-5-yl)-2-oxabicyclo[2.2.2]octan-1-yl)phenyl)acetate

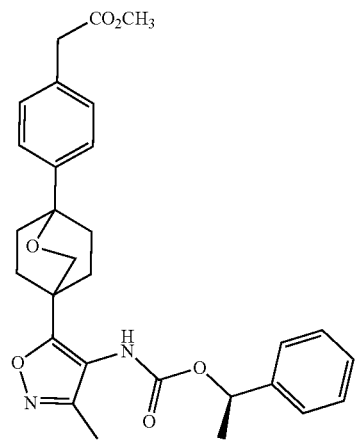 [SMILES: COC(=O)Cc1ccc(C23CCC(c4onc(C)c4NC(=O)O[C@H](C)c4ccccc4)(CC2)CO3)cc1]

A mixture of compound 54M (18 mg, 0.047 mmol), (PhO$_2$)PON$_3$ (0.012 mL, 0.056 mmol), (R)-(+)-1-phenylethanol (10.4 µL, 0.093 mmol), and Et$_3$N (0.020 mL, 0.140 mmol) in toluene (1 mL) was stirred at 80° C. for 1 h, then was cooled to RT and concentrated in vacuo. The crude oil was purified by preparative HPLC (Phenomenex Axia 5u C18 30×100 mm column; detection at 220 nm; flow rate=40 mL/min; continuous gradient from 30% B to 100% B over 10 min+2 min hold time at 100% B, where A=90:10:0.1 H$_2$O:MeOH:TFA and B=90:10:0.1 MeOH:H$_2$O:TFA) to give the title compound (11 mg, 0.022 mmol, 46.7% yield) as a clear oil.

Example 54

A mixture of compound 54N (11 mg, 0.022 mmol) and 2.0 M aq. LiOH (0.109 mL, 0.218 mmol) in THF (1 mL)/MeOH (0.1 mL) was stirred at RT for 2 h, then was acidified to pH=2 with 1N aq. HCl. The mixture was extracted with EtOAc (2×2 mL). The combined organic extracts were washed with water (2 mL) and concentrated in vacuo. The crude product (oil) was purified by preparative HPLC (Phenomenex Axia 5u C18 30×100 mm column; detection at 220 nm; flow rate=40 mL/min; continuous gradient from 50% B to 100% B over 10 min+2 min hold time at 100% B, where A=90:10:0.1 H₂O:MeOH:TFA and B=90:10:0.1 MeOH:H₂O:TFA) to give the title compound (4.2 mg, 8.39 µmol, 38.5% yield) as a white solid. [M−H]+=489.2; ¹H NMR (500 MHz, CDCl₃) δ 7.45-7.07 (m, 9H), 5.99-5.82 (m, 1H), 4.22 (br. s., 2H), 3.66 (s, 2H), 2.27-1.94 (m, 11H), 1.69-1.48 (m, 3H); hLPA₁ IC₅₀=88 nM.

The following compounds were prepared by the same synthetic sequence as described for the synthesis of Example 54.

| Ex # | Structure & Name | Analytical & Biological Data |
|---|---|---|
| 55 | (R)-2-(4-(4-(((1-cyclopropylethoxy)carbonyl)amino)-3-methyl-isoxazol-5-yl)-2-oxabicyclo[2.2.2]octan-1-yl)phenyl)acetic acid | [M − H]+ = 453.3; ¹H NMR (400 MHz, CDCl₃) δ 7.50 (br. s., 1H), 7.35 (d, J = 7.5 Hz, 2H), 7.30-7.24 (m, 2H), 4.34-4.21 (m, 3H), 3.63 (s, 2H), 2.33-1.93 (m, 11H), 1.40-1.24 (m, 3H), 1.08-0.83 (m, 1H), 0.62-0.18 (m, 4H); hLPA₁ Binding Ki = 724 nM. |
| 56 | (R)-2-(4-(4-(((1-(2-chlorophenyl)ethoxy)carbonyl)amino)-3-methyl-isoxazol-5-yl)-2-oxabicyclo[2.2.2]octan-1-yl)phenyl)acetic acid | [M + H]+ = 525.3; ¹H NMR (500 MHz, CDCl₃) δ 7.55-7.08 (m, 8H), 6.33-6.13 (m, 1H), 5.79 (br. s., 1H), 4.23 (s, 2H), 3.63 (s, 2H), 2.31-1.93 (m, 11H), 1.69-1.47 (m, 3H); hLPA₁ IC₅₀ = 93 nM. |

Example 57. 2-(4-(2-fluoro-4-(3-methyl-4-((((R)-1-phenylethoxy)carbonyl)amino) isoxazol-5-yl)phenyl)-2-oxabicyclo[2.2.2]octan-1-yl)acetic acid

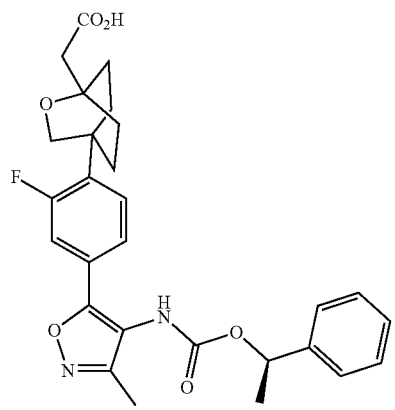 [SMILES: Cc1noc(-c2ccc(C34CCC(CC(=O)O)(CC3)OC4)c(F)c2)c1NC(=O)O[C@H](C)c1ccccc1]

Example 57 was prepared according to the general procedures described for the synthesis of Example 1 by using Intermediate 2 instead of Intermediate 1. LCMS [M+H]+=509.0; ¹H NMR (400 MHz, CDCl₃) δ 7.53-7.27 (m, 6H), 7.17 (t, J=8.0 Hz, 2H), 6.09-5.93 (m, 1H), 5.87 (q, J=6.6 Hz, 1H), 4.25 (s, 2H), 2.56 (s, 3H), 2.27-2.21 (m, 2H), 2.20-1.80 (m, 8H), 1.62 (br. s., 3H); hLPA₁ IC₅₀=41 nM.

Example 58. 3-(1-(4-(3-methyl-4-((((R)-1-phenylethoxy)carbonyl)amino)isoxazol-5-yl)phenyl)-2-oxabicyclo[2.2.2]octan-4-yl)propanoic acid

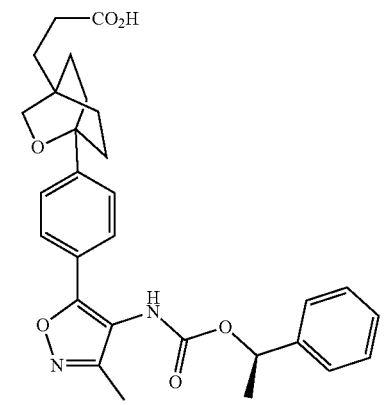 [SMILES: Cc1noc(-c2ccc(C34CCC(CCC(=O)O)(CC3)CO4)cc2)c1NC(=O)O[C@H](C)c1ccccc1]

58A. 2-(1-(4-(((tetrahydro-2H-pyran-2-yl)oxy)methyl)phenyl)-2-oxabicyclo[2.2.2]octan-4-yl)acetonitrile

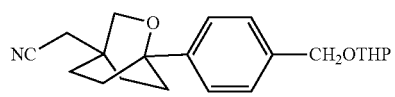

A mixture of compound 54A (1 g, 2.055 mmol) and NaCN (0.302 g, 6.16 mmol) in DMSO (5 mL) was stirred at 80° C.

for 3 days, then was cooled to RT and partitioned between EtOAc and water (20 mL each). The organic layer was washed with water, dried (MgSO$_4$), and concentrated in vacuo. The crude oil was chromatographed (12 g SiO$_2$; continuous gradient from 0% to 50% EtOAc in hexane over 10 min) to give the title compound (0.65 g, 1.904 mmol, 93% yield) as clear oil. [M−OTHP]=240.1; $^1$H NMR (400 MHz, CDCl$_3$) δ: 7.37 (d, J=8.3 Hz, 2H), 7.33 (d, J=8.4 Hz, 2H), 4.77 (d, J=12.0 Hz, 1H), 4.71-4.68 (m, 1H), 4.49 (d, J=12.0 Hz, 1H), 3.99-3.88 (m, 3H), 3.59-3.51 (m, 1H), 2.23 (s, 2H), 2.10 (t, J=8.2 Hz, 4H), 1.93-1.49 (m, 10H).

58B. 2-(1-(4-(((tetrahydro-2H-pyran-2-yl)oxy) methyl)phenyl)-2-oxabicyclo[2.2.2]octan-4-yl) acet-aldehyde

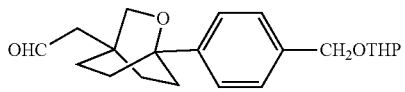

A solution of 1M DIBALH in CH$_2$Cl$_2$ (2.28 mL, 2.28 mmol) was added dropwise to a solution of compound 58A (0.65 g, 1.90 mmol) in CH$_2$Cl$_2$ (10 ml) at −78° C. under N$_2$. The reaction mixture was stirred at −78° C. for 2 h, then Celite (1 g) was added and the reaction was quenched with satd aq. NH$_4$Cl (2 mL). The mixture was stirred at RT for 30 min, then MgSO$_4$ (1 g) was added and the mixture was stirred at RT for 30 min, then was filtered. The solids were washed with CH$_2$Cl$_2$ (3×). The combined filtrates were concentrated in vacuo. The crude oil was chromatographed (12 g SiO$_2$; continuous gradient from 0% to 50% EtOAc in hexane over 10 min) to give the title compound (0.58 g, 1.684 mmol, 88% yield) as a clear oil. $^1$H NMR (CDCl$_3$) δ 9.85 (t, J=2.7 Hz, 1H), 7.37 (d, J=8.3 Hz, 2H), 7.35-7.30 (m, 2H), 4.77 (dd, J=12.0, 2.1 Hz, 1H), 4.69 (t, J=3.5 Hz, 1H), 4.49 (d, J=12.0 Hz, 1H), 4.01-3.88 (m, 3H), 3.60-3.49 (m, 1H), 2.28 (d, J=2.8 Hz, 2H), 2.12-2.03 (m, 4H), 1.96-1.47 (m, 10H).

58C. 2-(1-(4-(((tetrahydro-2H-pyran-2-yl)oxy) methyl)phenyl)-2-oxabicyclo[2.2.2]octan-4-yl) etha-nol

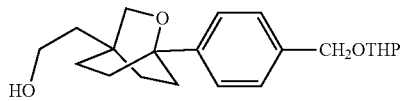

A solution of 1.0 M DIBALH in CH$_2$Cl$_2$ (2.02 mL, 2.021 mmol) was added dropwise to a solution of compound 58B (0.58 g, 1.684 mmol) in CH$_2$Cl$_2$ (10 ml) at −78° C. under N$_2$. The reaction mixture was stirred at −78° C. for 2 h, after which Celite (1 g) was added and the reaction was quenched with satd aq. NH$_4$Cl (2 mL). The reaction was stirred at RT for 30 min, MgSO$_4$ (1 g) was added and the mixture was stirred at RT for 30 min, then was filtered. The solids were washed with CH$_2$Cl$_2$ (3×). The combined filtrates were concentrated in vacuo. The crude oil was chromatographed (12 g SiO$_2$; continuous gradient from 0% to 50% EtOAc in hexane over 10 min) to give the title compound (0.49 g, 1.414 mmol, 84% yield) as a clear oil. $^1$H NMR (CDCl$_3$) δ 7.38 (d, J=8.3 Hz, 2H), 7.31 (d, J=8.2 Hz, 2H), 4.77 (d, J=11.9 Hz, 1H), 4.69 (t, J=3.6 Hz, 1H), 4.48 (d, J=11.9 Hz, 1H), 3.98-3.84 (m, 3H), 3.72 (t, J=7.3 Hz, 2H), 3.60-3.50 (m, 1H), 2.09-1.98 (m, 4H), 1.93-1.80 (m, 1H), 1.79-1.44 (m, 12H).

58D. 2-(1-(4-(((tetrahydro-2H-pyran-2-yl)oxy) methyl)phenyl)-2-oxabicyclo[2.2.2]octan-4-yl) ethyl methanesulfonate

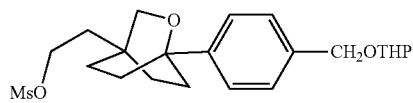

MsCl (0.132 mL, 1.70 mmol) was added dropwise at RT to a solution of compound 58C (0.49 g, 1.41 mmol) and TEA (0.30 mL, 2.12 mmol) in CH$_2$Cl$_2$ (5 mL). The reaction was stirred at RT for 2 h, then was concentrated in vacuo. The residue was partitioned between EtOAc and water. The organic layer was washed with 1N aq. HCl and water, dried (MgSO$_4$), and concentrated in vacuo to give the title compound (0.6 g, 1.413 mmol, 100% yield) as a light yellowish oil which was used directly in the next reaction without further purification. $^1$H NMR (500 MHz, CDCl$_3$) δ 7.39-7.35 (m, 2H), 7.34-7.29 (m, 2H), 4.76 (d, J=11.8 Hz, 1H), 4.69 (t, J=3.6 Hz, 1H), 4.48 (d, J=11.8 Hz, 1H), 4.29 (t, J=7.0 Hz, 2H), 3.92 (ddd, J=11.3, 8.5, 3.0 Hz, 1H), 3.88 (s, 2H), 3.57-3.51 (m, 1H), 3.02 (s, 3H), 2.08-2.02 (m, 4H), 1.92-1.82 (m, 1H), 1.80-1.49 (m, 11H).

58E. 3-(1-(4-(((tetrahydro-2H-pyran-2-yl)oxy) methyl)phenyl)-2-oxabicyclo[2.2.2]octan-4-yl) pro-panenitrile

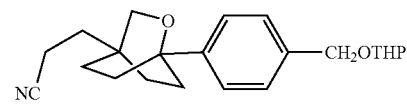

A mixture of compound 58D (0.60 g, 1.41 mmol) and NaCN (0.14 g, 2.83 mmol) in DMSO (5 mL) was stirred at 50° C. for 18 h, then was cooled to RT and partitioned between EtOAc and water. The organic layer was washed with water, dried (MgSO$_4$), and concentrated in vacuo. The crude oil was chromatographed (24 g SiO$_2$; continuous gradient from 0% to 50% EtOAc in hexane over 10 min) to give the title compound (0.4 g, 1.125 mmol, 80% yield) as a white solid. $^1$H NMR (500 MHz, CDCl$_3$) δ 7.40-7.36 (m, 2H), 7.35-7.31 (m, 2H), 4.78 (d, J=12.1 Hz, 1H), 4.70 (t, J=3.6 Hz, 1H), 4.49 (d, J=11.8 Hz, 1H), 3.93 (ddd, J=11.3, 8.4, 3.2 Hz, 1H), 3.84 (s, 2H), 3.58-3.52 (m, 1H), 2.34-2.28 (m, 2H), 2.06 (t, J=8.0 Hz, 4H), 1.91-1.83 (m, 1H), 1.78-1.50 (m, 11H).

58F. 3-(1-(4-(((tetrahydro-2H-pyran-2-yl)oxy) methyl)phenyl)-2-oxabicyclo[2.2.2]octan-4-yl) pro-panoic acid

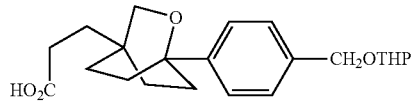

A mixture of compound 58E (200 mg, 0.563 mmol) and 40% aq. KOH (1.13 mL, 11.3 mmol) in ethylene glycol (5 mL) was stirred at 160° C. for 18 h, then was cooled to RT and concentrated in vacuo. The residue was partitioned between EtOAc and 1N aq. HCl. The organic layer was washed with water, dried (MgSO$_4$), and concentrated in vacuo to give the title compound (200 mg, 0.534 mmol, 95% yield) as a white solid. [M–H]$^+$=373.3; $^1$H NMR (500 MHz, CDCl$_3$) δ 7.31-7.27 (m, 2H), 7.25-7.21 (m, 2H), 4.68 (d, J=12.1 Hz, 1H), 4.62 (t, J=3.6 Hz, 1H), 4.40 (d, J=12.1 Hz, 1H), 3.85 (ddd, J=11.3, 8.5, 3.0 Hz, 1H), 3.76 (s, 2H), 3.51-3.44 (m, 1H), 2.28-2.22 (m, 2H), 1.96 (t, J=7.8 Hz, 4H), 1.84-1.73 (m, 1H), 1.70-1.41 (m, 11H).

58G. Methyl 3-(1-(4-(((tetrahydro-2H-pyran-2-yl)oxy)methyl)phenyl)-2-oxabicyclo[2.2.2] octan-4-yl)propanoate

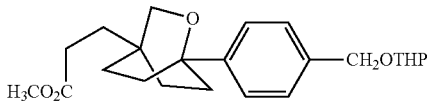

A solution of 2 M TMSCHN$_2$ in hexane (0.80 mL, 1.602 mmol) was added to a solution of compound 58F (200 mg, 0.534 mmol) in THF (5 mL) and MeOH (1 mL). The reaction was stirred at RT for 2 h, then was concentrated in vacuo to give the title compound (200 mg, 0.515 mmol, 96% yield) as a white solid. $^1$H NMR (500 MHz, CDCl$_3$) δ 7.40-7.35 (m, 2H), 7.34-7.29 (m, 2H), 4.77 (d, J=11.8 Hz, 1H), 4.69 (t, J=3.6 Hz, 1H), 4.48 (d, J=12.1 Hz, 1H), 3.93 (ddd, J=11.3, 8.5, 3.0 Hz, 1H), 3.83 (s, 2H), 3.69 (s, 3H), 3.58-3.51 (m, 1H), 2.33-2.26 (m, 2H), 2.03 (t, J=8.0 Hz, 4H), 1.87 (d, J=9.4 Hz, 1H), 1.78-1.50 (m, 11H).

58H. Methyl 3-(1-(4-(hydroxymethyl)phenyl)-2-oxabicyclo[2.2.2]octan-4-yl)propanoate

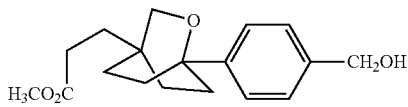

A mixture of compound 58G (200 mg, 0.515 mmol) and PPTS (13 mg, 0.051 mmol) in MeOH (10 mL) was stirred at 50° C. for 3 h, then was cooled to RT and concentrated in vacuo. The crude oil was chromatographed (12 g SiO$_2$; continuous gradient from 0% to 50% EtOAc in hexane over 10 min) to give the title compound (156 mg, 0.513 mmol, 100% yield) as a white solid. $^1$H NMR (500 MHz, CDCl$_3$) δ 7.42-7.36 (m, 2H), 7.34-7.28 (m, 2H), 4.66 (s, 2H), 3.83 (s, 2H), 3.69 (s, 3H), 2.33-2.26 (m, 2H), 2.03 (t, J=8.1 Hz, 4H), 1.76-1.60 (m, 5H), 1.58-1.50 (m, 2H).

58I. methyl 3-(1-(4-formylphenyl)-2-oxabicyclo[2.2.2]octan-4-yl)propanoate

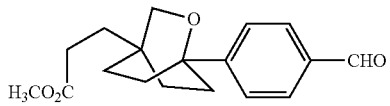

A mixture of compound 58H (128 mg, 0.421 mmol), Dess-Martin periodinane (268 mg, 0.631 mmol), and Na$_2$CO$_3$ (446 mg, 4.21 mmol) in CH$_2$Cl$_2$ (5 mL) was stirred at RT for 3 h, then was filtered. The filtrate was concentrated in vacuo. The residue was dissolved in EtOAc and washed with 1N aq. NaOH and water, dried (MgSO$_4$), and concentrated in vacuo to give the title compound (126 mg, 0.417 mmol, 99% yield) as a white solid, which was used in the next reaction without further purification. [M+H]$^+$=303.2.

58J. 4-(4-(3-methoxy-3-oxopropyl)-2-oxabicyclo[2.2.2]octan-1-yl)benzoic acid

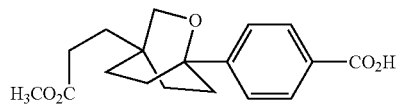

To a 0° C. mixture of compound 58I (127 mg, 0.420 mmol), a 2M solution of 2-methyl-2-butene in THF (3.15 mL, 6.30 mmol) and NaH$_2$PO$_4$ (252 mg, 2.100 mmol) in water (1 mL) and t-BuOH (4 mL) was added NaClO$_2$ (190 mg, 2.100 mmol). The reaction mixture was allowed to warm to RT and stirred at RT for 18 h, then was poured into brine and extracted with EtOAc (5 mL×3). The combined organic extracts were dried (Na$_2$SO$_4$) and concentrated in vacuo. The crude oil was purified by preparative HPLC (Phenomenex Axia 5u C18 30×100 mm column; detection at 220 nm; flow rate=40 mL/min; continuous gradient from 30% B to 100% B over 10 min+2 min hold time at 100% B, where A=90:10:0.1 H$_2$O:MeOH:TFA and B=90:10:0.1 MeOH:H$_2$O:TFA) to give the title compound (110 mg, 0.346 mmol, 82% yield) as a white solid. $^1$H NMR (500 MHz, CDCl$_3$) δ 8.07 (d, J=8.5 Hz, 2H), 7.51 (d, J=8.5 Hz, 2H), 3.86 (s, 2H), 3.71 (s, 3H), 2.36-2.28 (m, 2H), 2.14-1.99 (m, 4H), 1.78-1.63 (m, 4H), 1.58 (t, J=8.4 Hz, 2H).

58K. methyl 3-(1-(4-(chlorocarbonyl)phenyl)-2-oxabicyclo[2.2.2]octan-4-yl)propanoate

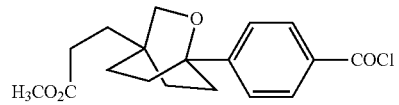

A mixture of compound 58J (110 mg, 0.346 mmol) and 1-chloro-N,N,2-trimethyl prop-1-en-1-amine (0.055 mL, 0.415 mmol) in CH$_2$Cl$_2$ (1 mL) was stirred at RT for 1 h. Analytical HPLC showed that the reaction was complete. This crude product was used in the next reaction directly.

58L. (E)-tert-butyl 2-(4-(4-(3-methoxy-3-oxopropyl)-2-oxabicyclo[2.2.2]octan-1-yl)benzoyl)-3-(methylimino)butanoate

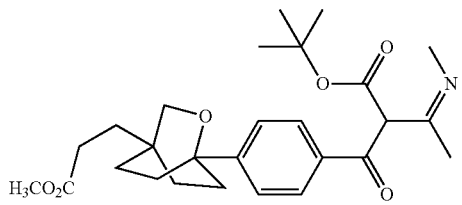 [SMILES: C/N=C(/C)C(C(=O)OC(C)(C)C)C(=O)c1ccc(C23CCC(CCC(=O)OC)(CC2)CO3)cc1]

A solution of compound 58K (116 mg, 0.344 mmol) in CH$_2$Cl$_2$ (2 mL) was added dropwise to a solution of (E)-tert-butyl 3-(methylimino)butanoate (88 mg, 0.517 mmol) and pyridine (0.111 mL, 1.38 mmol) in THF (1 mL) at 0° C. over 5 min. The reaction was allowed to warm to RT and stirred at RT for 24 h, then was concentrated in vacuo and the residue was partitioned between EtOAc and water. The aqueous phase was extracted with EtOAc, and the combined organic layers were dried (MgSO$_4$) and concentrated in vacuo to give the crude title compound (162 mg, 0.344 mmol, 100% yield) as an orange oil. This crude compound was used in the next reaction without further purification. [M+H]$^+$=472.2.

58M. tert-butyl 5-(4-(4-(3-methoxy-3-oxopropyl)-2-oxabicyclo[2.2.2]octan-1-yl)phenyl)-3-methylisoxazole-4-carboxylate

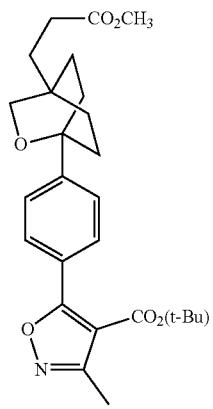

A mixture of crude compound 58L (162 mg, 0.344 mmol) and NH$_2$OH·HCl (71.6 mg, 1.031 mmol) in MeOH (3 mL)/H$_2$O (0.3 mL) was stirred at 60° C. for 18 h. LC-MS showed that the reaction was complete. The mixture was concentrated in vacuo, and the residue was purified by preparative HPLC (Phenomenex Axia 5u C18 30×100 mm column; detection at 220 nm; flow rate=40 mL/min; continuous gradient from 50% B to 100% B over 10 min+3 min hold time at 100% B, where A=90:10:0.1 H$_2$O:MeOH:TFA and B=90:10:0.1 MeOH:H$_2$O:TFA) to give the title compound (87 mg, 0.191 mmol, 55.6% yield) as white solid. [M+H]$^+$=456.5; $^1$H NMR (500 MHz, CDCl$_3$) δ 7.86-7.81 (m, 2H), 7.53-7.48 (m, 2H), 3.85 (s, 2H), 3.70 (s, 3H), 2.48 (s, 3H), 2.33-2.26 (m, 2H), 2.11-1.99 (m, 4H), 1.75-1.62 (m, 4H), 1.59-1.53 (m, 2H), 1.52 (s, 9H).

58N. 5-(4-(4-(3-methoxy-3-oxopropyl)-2-oxabicyclo[2.2.2]octan-1-yl)phenyl)-3-methyl-isoxazole-4-carboxylic acid

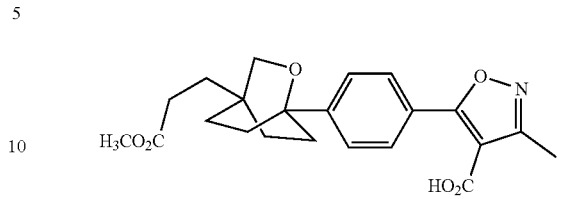

A mixture of compound 58M (87 mg, 0.191 mmol) and HCO$_2$H (146 µL, 3.82 mmol) was stirred at RT for 2 h, then was concentrated in vacuo to give the title compound (75 mg, 0.188 mmol, 98% yield) as a white solid. [M−H]$^+$=398.3.

58O. (R)-methyl-3-(1-(4-(3-methyl-4-(((1-phenylethoxy)carbonyl)amino)isoxazol-5-yl)phenyl)-2-oxabicyclo[2.2.2]octan-4-yl)propanoate

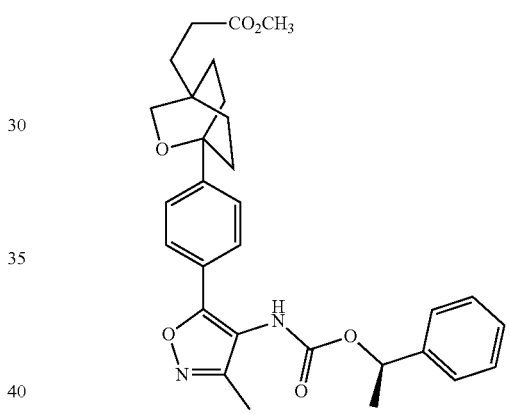

A mixture of compound 58N (21.7 mg, 0.054 mmol), (R)-(+)-1-phenylethanol (13.3 mg, 0.109 mmol), (PhO)$_2$PON$_3$ (18 mg, 0.065 mmol), and TEA (0.030 mL, 0.217 mmol) in toluene (1 mL) was stirred at 80° C. for 1 h, then was cooled to RT and concentrated in vacuo. The residue was purified by preparative HPLC (Phenomenex Axia 5u C18 30×100 mm column; detection at 220 nm; flow rate=40 mL/min; continuous gradient from 50% B to 100% B over 10 min+2 min hold time at 100% B, where A=90:10:0.1 H$_2$O:MeOH:TFA and B=90:10:0.1 MeOH:H$_2$O:TFA) to give the title compound (27 mg, 0.052 mmol, 96% yield) as a clear oil. [M+H]$^+$=519.4; $^1$H NMR (400 MHz, CDCl$_3$) δ 7.48-7.21 (m, 7H), 7.19-7.09 (m, 2H), 6.29-5.77 (m, 1H), 3.85 (s, 2H), 3.70 (s, 3H), 2.40-2.13 (m, 4H), 2.09-1.92 (m, 4H), 1.75-1.33 (m, 9H).

Example 58

A mixture of compound 58O (27 mg, 0.052 mmol) and 2.0 M aq. LiOH (0.2 mL, 0.40 mmol) in THF (1 mL)/MeOH (0.1 mL) was stirred at RT for 2 h, then was acidified to pH=2 with 1N aq. HCl. The mixture was extracted with EtOAc (2×). The combined organic extracts were washed with water and concentrated in vacuo. The crude oil was purified by preparative HPLC (Phenomenex Axia 5u C18

30×100 mm column; detection at 220 nm; flow rate=40 mL/min; continuous gradient from 50% B to 100% B over 10 min+2 min hold time at 100% B, where A=90:10:0.1 H$_2$O:MeOH:TFA and B=90:10:0.1 MeOH:H$_2$O:TFA) to give the title compound (12.5 mg, 0.024 mmol, 46.6% yield) as a white solid. [M−H]$^+$=503.2; $^1$H NMR (500 MHz, CDCl$_3$) δ 8.64 (br. s., 1H), 7.84-6.70 (m, 9H), 6.27-5.78 (m, 1H), 3.86 (s, 2H), 2.42-2.30 (m, 2H), 2.21 (br. s., 3H), 2.04 (t, J=8.0 Hz, 4H), 1.78-1.33 (m, 9H); hLPA$_1$ IC$_{50}$=157 nM.

Example 59. 2-(4-(3-(4-((((R)-1-(2-chlorophenyl)ethoxy)carbonyl)amino)-3-methylisoxazol-5-yl)phenyl)-2-oxabicyclo[2.2.2]octan-1-yl)acetic acid

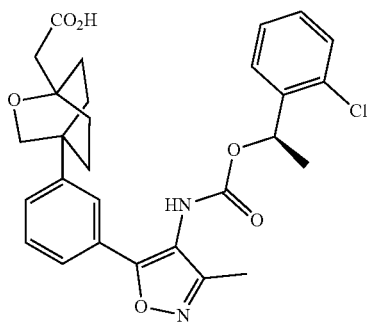 [SMILES: Cc1noc(-c2cccc(C34CCC(CC(=O)O)(CC3)OC4)c2)c1NC(=O)O[C@H](C)c1ccccc1Cl]

59A. methyl 2-(4-(3-(4-((((R)-1-(2-chlorophenyl)ethoxy)carbonyl)amino)-3-methylisoxazol-5-yl)phenyl)-2-oxabicyclo[2.2.2]octan-1-yl)acetate

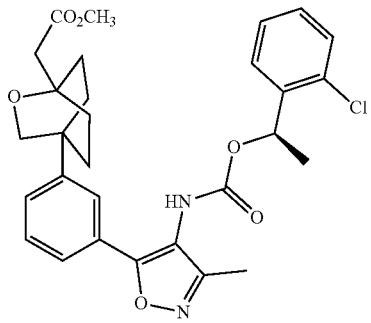 [SMILES: COC(=O)CC12CCC(c3cccc(-c4onc(C)c4NC(=O)O[C@H](C)c4ccccc4Cl)c3)(CC1)CO2]

A solution of Intermediate 19 (17 mg, 0.044 mmol), intermediate 6 (15.8 mg, 0.044 mmol), K$_2$CO$_3$ (18.2 mg, 0.13 mmol) and PdCl$_2$(dppf) (3.2 mg, 0.0044 mmol) in THF (4 mL) and water (1 mL) was purged with Ar for 5 min. The reaction mixture was then heated to 80° C. for 18 h under Ar, then was cooled to RT and filtered through Celite. The filtrate was partitioned between EtOAc (3 mL) and water (3 mL); the aqueous phase was extracted with EtOAc (2×3 mL). The combined organic extracts were washed with water (2 mL), brine (2 mL), dried (MgSO$_4$) and concentrated in vacuo. The crude product was chromatographed (SiO$_2$ ISCO column; continuous gradient from 0% to 100% EtOAc in hexanes over 20 min) to give the title compound as a colorless oil. (4.5 mg, 0.0084 mmol, 19% yield) LCMS [M+H]$^+$=539.2; $^1$H NMR (CDCl$_3$) δ: 7.70-7.76 (m, 1H), 7.58-7.68 (m, 1H), 7.48-7.55 (m, 1H), 7.33-7.45 (m, 4H), 6.26 (br d, J=6.6 Hz, 1H), 4.00-4.06 (m, 2H), 3.73 (s, 3H), 2.51 (s, 2H), 2.29 (s, 3H), 2.08-2.16 (m, 4H), 1.88-1.95 (m, 4H), 1.62-1.70 (m, 2H), 1.27-1.32 (m, 2H).

Example 59

To a solution of compound 59A (4.5 mg, 8.35 μmol) in THF (1 mL) was added 2M aq. LiOH (0.04 mL, 0.08 mmol). The reaction was stirred at RT for 18 h, then was concentrated in vacuo. The residue was dissolved in H$_2$O (1 mL), and the pH was adjusted with 1N aq. HCl to ~3 and extracted with EtOAc (2×1 mL). The combined organic extracts were washed with brine (1 mL), dried (MgSO$_4$) and concentrated in vacuo. The crude product was purified by preparative LC/MS: Column: Waters XBridge C18, 19×200 mm, 5-μm particles; Guard Column: Waters XBridge C18, 19×10 mm, 5-μm particles; Mobile Phase A: 5:95 MeCN:H$_2$O with 0.1% TFA; Mobile Phase B: 95:5 MeCN:H$_2$O with 0.1% TFA; Gradient: 50-90% B over 20 min, then a 5-min hold at 100% B; Flow: 20 mL/min. Fractions containing the desired product were combined and concentrated in vacuo by centrifugal evaporation to give the title compound (2.2 mg, 0.004 mmol, 47.7% yield). LCMS [M+H]$^+$=525.3; $^1$H NMR (DMSO-d$_6$) δ: 9.41 (br s, 1H), 7.72 (br s, 1H), 7.55-7.65 (m, 2H), 7.42-7.52 (m, 4H), 7.38 (br d, J=7.6 Hz, 1H), 5.77-6.20 (m, 1H), 3.90 (br s, 2H), 3.46 (br s, 2H), 2.34 (s, 2H), 2.14 (br s, 3H), 2.00 (br s, 4H), 1.87 (br s, 4H), 1.55 (br d, J=5.8 Hz, 2H); hLPA$_1$ Antagonist IC$_{50}$=95 nM.

What is claimed is:

1. A compound of Formula (Ia):

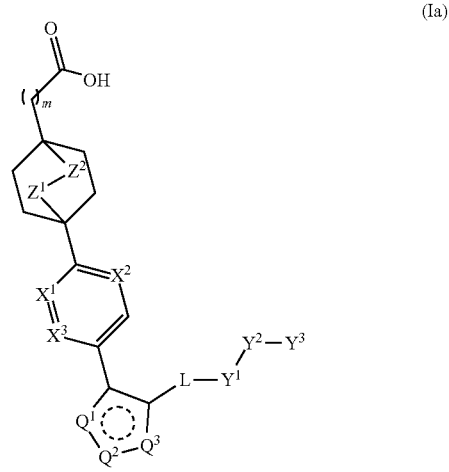

(Ia)

or a stereoisomer, tautomer, or pharmaceutically acceptable salt or solvate thereof, wherein:

one of $Z^1$ and $Z^2$ is O, and the other one is CH$_2$;

$X^1$, $X^2$, and $X^3$ are each independently CR$^6$ or N; provided that no more than two of $X^1$, $X^2$, or $X^3$ are N;

$Q^1$, $Q^2$, and $Q^3$ are independently N, O, NR$^{5a}$, or CR$^{5b}$, and the dashed circle denotes bonds forming an aromatic ring; provided that at least one of $Q^1$, $Q^2$, and $Q^3$ is not CR$^{5b}$;

L is independently a covalent bond or $C_{1-4}$ alkylene substituted with 0 to 4 $R^9$;

$Y^1$ is independently O or $NR^7$;

$Y^2$ is independently

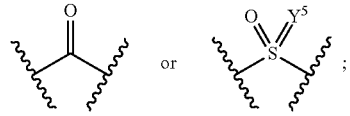

$Y^3$ is independently $OR^4$ or $NR^8R^4$, with the proviso that when $Y^1$ is O, then $Y^3$ is not $OR^4$;

$Y^5$ independently is O or NH;

$R^4$ is $-L-R^{4a}$, $L_1$ is independently a covalent bond or $C_{1-4}$ alkylene substituted with 0 to 4 $R^9$;

$R^{4a}$ is independently $C_{1-10}$ alkyl, $C_{1-10}$ haloalkyl, $C_{1-10}$ alkenyl, $C_{3-8}$ cycloalkyl, $C_{6-10}$ aryl, 3 to 8-membered heterocyclyl, 5 to 6-membered heteroaryl; wherein each of the alkyl, alkenyl, alkylene, cycloalkyl, aryl, heterocyclyl, and heteroaryl, by itself or as part of other moiety, is independently substituted with 0 to 3 $R^{10}$;

$R^{5a}$ is independently hydrogen, $C_{1-4}$ haloalkyl, $-(CH_2)_{0-1}-(C_{3-6}$ cycloalkyl), $(CH_2)_{0-1}$-phneyl, or $C_{1-6}$ alkyl substituted with 0 to 3 $R^a$;

$R^{5b}$ is independently hydrogen, halo, cyano, hydroxyl, amino, $C_{1-4}$ alkoxy, $C_{1-4}$ haloalkyl, $C_{1-4}$ haloalkoxy, $C_{1-4}$ alkylamino, $-(CH_2)_{0-1}-(C_{3-6}$ cycloalkyl), $-(CH_2)_{0-1}$-phneyl, or $C_{1-6}$ alkyl substituted with 0 to 3 $R^b$;

$R^6$ is each independently hydrogen, halo, cyano, hydroxyl, amino, $C_{1-4}$ alkylamino, $C_{1-4}$ haloalkyl, $C_{1-4}$ alkoxy, $C_{1-4}$ haloalkoxy or $C_{1-6}$ alkyl substituted with 0 to 1 $R^b$;

$R^7$ and $R^8$ are each independently hydrogen, $C_{1-6}$ alkyl, $C_{1-4}$ haloalkyl, $C_{3-6}$ cycloalkyl or $C_{1-6}$ alkyl substituted with 0 to 1 $R^c$;

$R^9$ is each independently halo, oxo, cyano, hydroxyl, amino, $C_{1-4}$ haloalkyl, $C_{1-4}$ alkoxy, $C_{1-4}$ haloalkoxy, $C_{3-6}$ cycloalkyl, or $C_{1-6}$ alkyl substituted with 0 to 3 $R^a$;

$R^{10}$ is each independently halo, hydroxyl, amino, cyano, $C_{2-6}$ alkenyl, $C_{2-6}$ alkynyl, $C_{1-4}$ alkylamino, $C_{1-4}$ haloalkyl, $C_{1-4}$ alkoxy, $C_{1-4}$ haloalkoxy, phenyl, or 5 to 6 membered heteroaryl, $C_{1-6}$ alkyl substituted with 0 to 3 $R^b$;

$R^a$ is independently halo, cyano, hydroxyl, $C_{1-4}$ alkoxy, $C_{1-4}$ haloalkyl, or $C_{1-4}$ haloalkoxy;

$R^b$ is independently halo, cyano, hydroxyl, amino, $C_{1-4}$ alkoxy, $C_{1-4}$ haloalkyl, or $C_{1-4}$ haloalkoxy;

$R^c$ is independently $C_{1-4}$ haloalkyl, $C_{3-6}$ cycloalkyl, or $C_{1-6}$ alkyl substituted with 0 to 3 $R^a$; and m is an integer of 0, 1, or 2.

2. The compound according to claim 1, wherein:

the

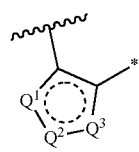

moiety is independently

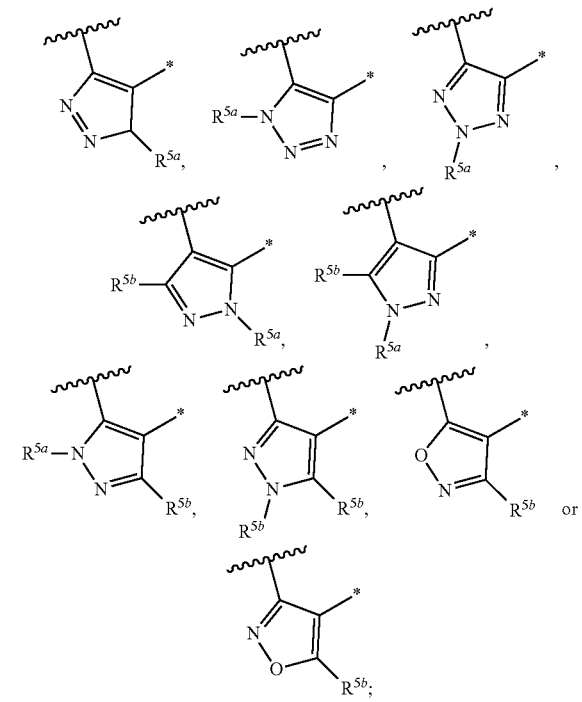

* denotes the attachment point to L; and $R^{5a}$ and $R^{5b}$ are the same as defined in claim 1.

3. The compound according to claim 2, wherein:

the

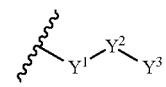

moiety is independently

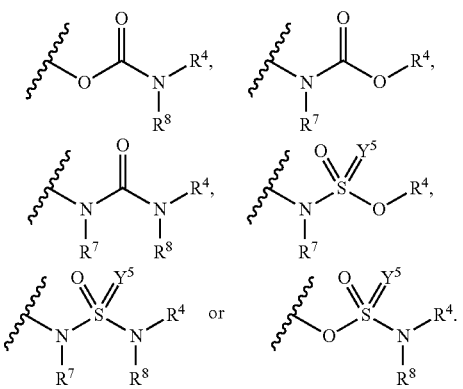

4. The compound according to claim 3, wherein L is a covalent bond or $C_{1-2}$ alkylene.

5. The compound according to claim 4, wherein:

$X^1$, $X^2$, and $X^3$ are independently CH or $CR^{6a}$; or one of $X^1$, $X^2$, and $X^3$ is N, and the remaining ones are CH or $CR^{6a}$; and $R^{6a}$ is independently halo, hydroxyl, $C_{1-6}$ alkyl, $C_{1-4}$ haloalkyl, or $C_{1-4}$ alkoxy.

6. The compound according to claim 5, wherein:
the

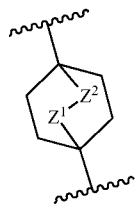

the moiety is independently

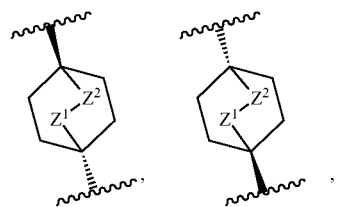

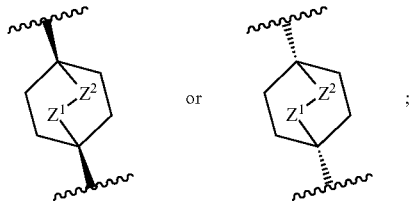

and
—Z¹-Z²— is —O—CH₂— or —CH₂—O—.

7. A compound of Formula (IIa):

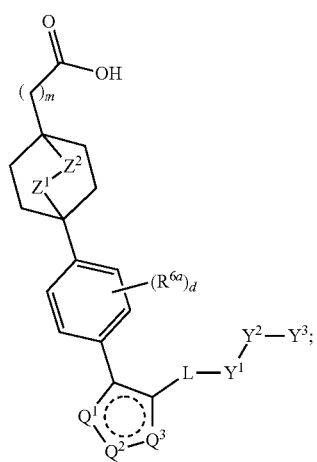

(IIa)

or a stereoisomer, tautomer, or pharmaceutically acceptable salt or solvate thereof, wherein:
—Z¹-Z²— is —O—CH₂— or —CH₂—O—;
the

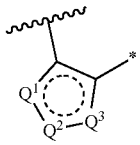

moiety is independently

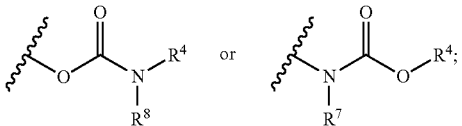

m is an integer of 1 or 2;
* denotes the attachment point to L;
L is independently a covalent bond or —CH₂—;
the

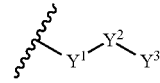

moiety is independently

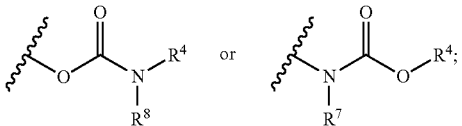

$R^4$ is independently $C_{3-6}$ cycloalkyl, —(CH₂)—$C_{3-6}$ cycloalkyl, —(CH($C_{1-2}$ alkyl))-$C_{3-6}$ cycloalkyl, —(CH₂)-phenyl or —(CH($C_{1-2}$ alkyl))-phenyl, wherein each of said cycloalkyl and phenyl is independently substituted with 0 to 3 $R^{10}$;

$R^{5a}$ is independently $C_{1-6}$ alkyl, or —CH₂—($C_{3-6}$ cycloalkyl);

$R^{5b}$ is independently hydrogen, halo, cyano, hydroxyl, $C_{1-4}$ alkyl, $C_{1-4}$ alkoxy, $C_{1-4}$ haloalkyl, or $C_{1-4}$ haloalkoxy;

$R^{6a}$ is each independently halo, hydroxyl, $C_{1-6}$ alkyl, $C_{1-4}$ haloalkyl, or $C_{1-4}$ alkoxy;

$R^7$ and $R^8$ are each independently hydrogen or $C_{1-2}$ alkyl;

$R^{10}$ is each independently halo, cyano, hydroxyl, $C_{1-6}$ alkyl, $C_{1-6}$ haloalkyl, $C_{1-6}$ alkoxy, or $C_{1-6}$ haloalkoxy; and d is independently 0, 1 or 2.

8. The compound according to claim 7, wherein:

the

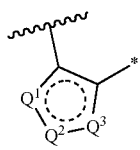

moiety is independently

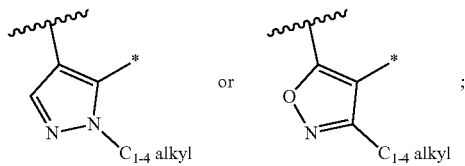

m is an integer of 1; and

R⁴ is independently —(CH₂)—C₃₋₆ cycloalkyl, —(CH(C₁₋₂ alkyl))—C₃₋₆ cycloalkyl, —(CH₂)-phenyl or —(CH(C₁₋₂ alkyl))-phenyl, wherein each of said cycloalkyl and phenyl is independently substituted with 0 to 2 R¹⁰.

9. A compound of Formula (IIIa):

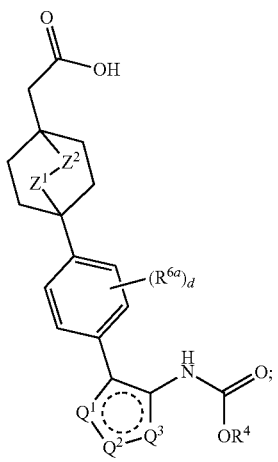

(IIIa)

wherein: —Z¹-Z²— is —O—CH₂— or —CH₂—O—;

the

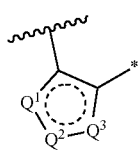

moiety is independently

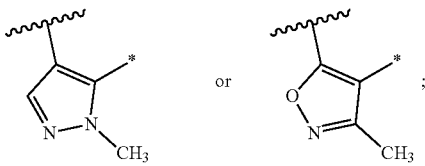

* denotes the attachment point to the nitrogen atom of —NH—C(O)—OR⁴;

R⁴ is independently —(CH₂)-phenyl, or —(CH(CH₃))-phenyl, wherein said phenyl is independently substituted with 0 to 2 R¹⁰, R⁶ᵃ is each independently halo or C₁₋₄ alkyl;

R¹⁰ is each independently halo, cyano, hydroxyl, C₁₋₄ alkyl, C₁₋₄ haloalkyl, or C₁₋₄ alkoxy; and d is independently 0 or 1.

10. A compound selected from;

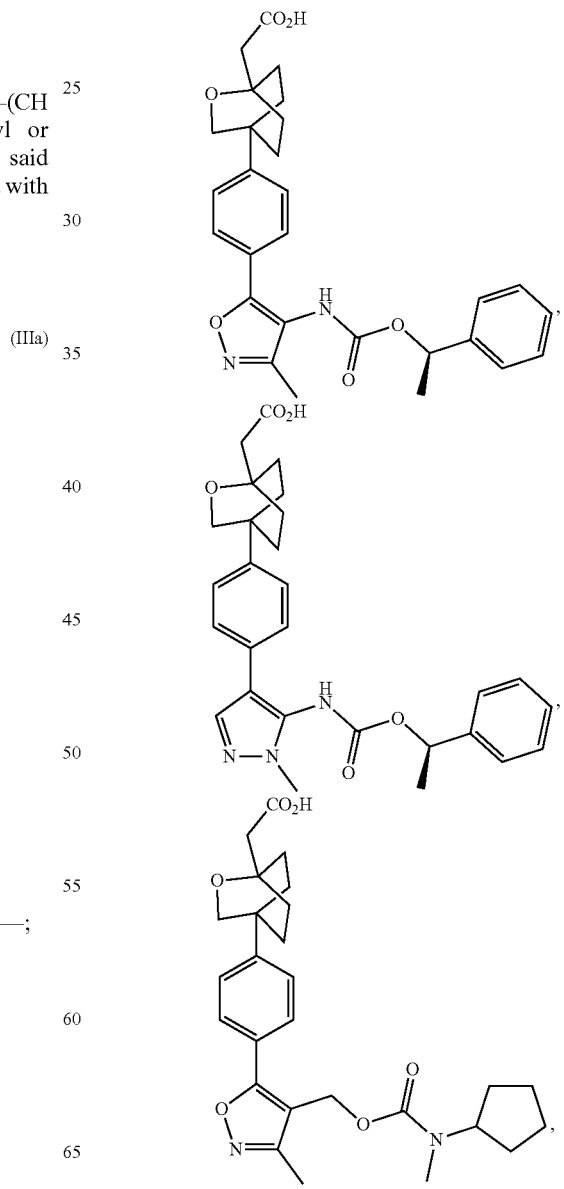

153
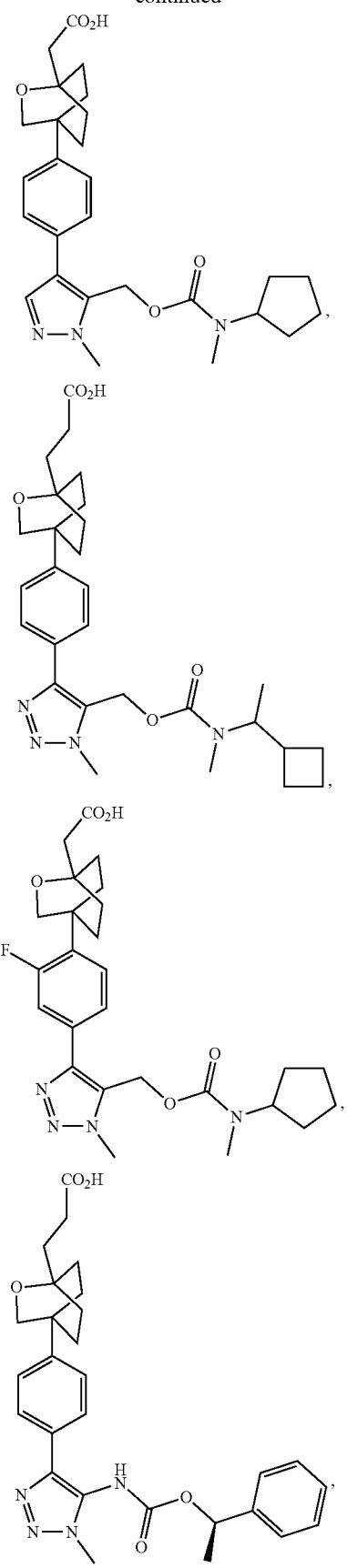
154
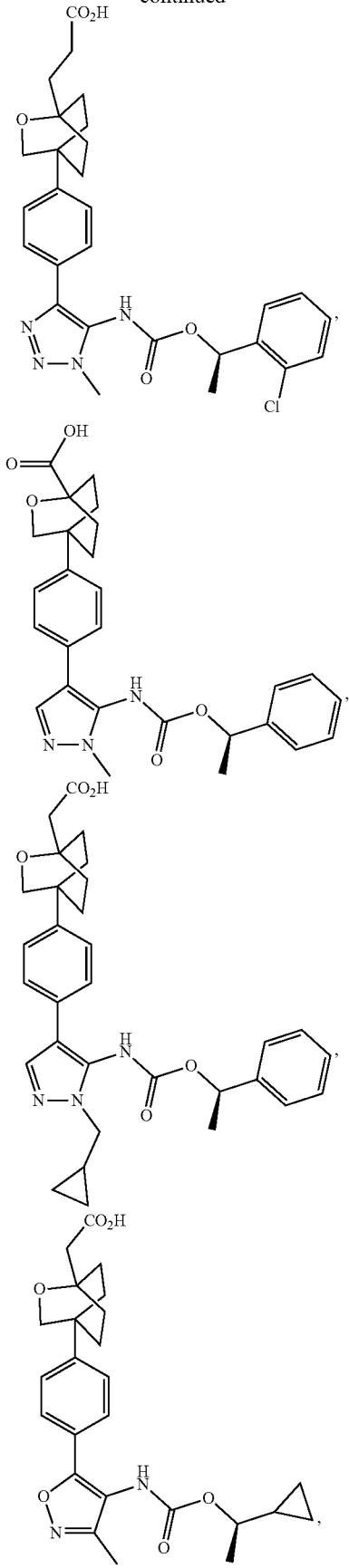

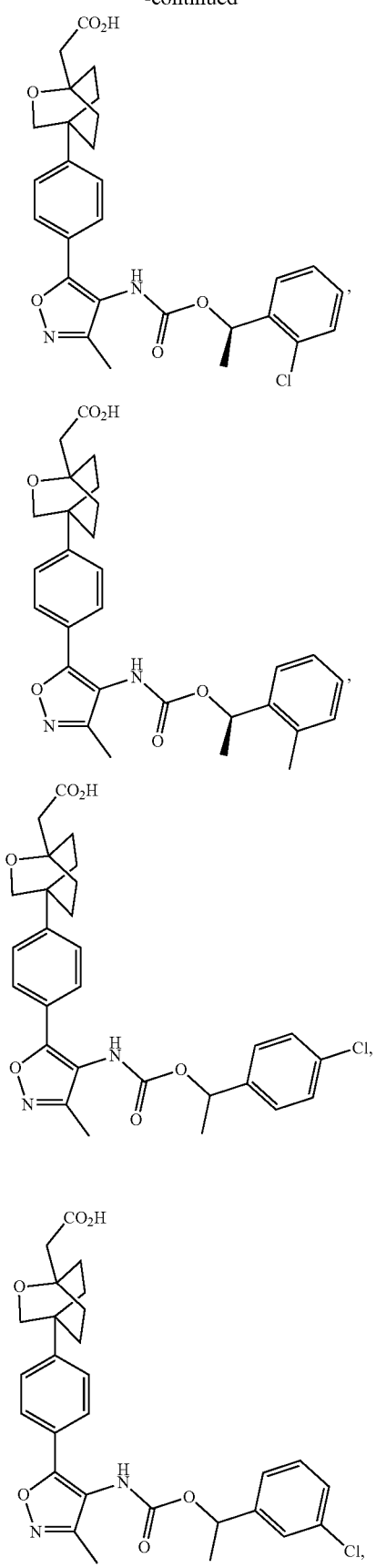

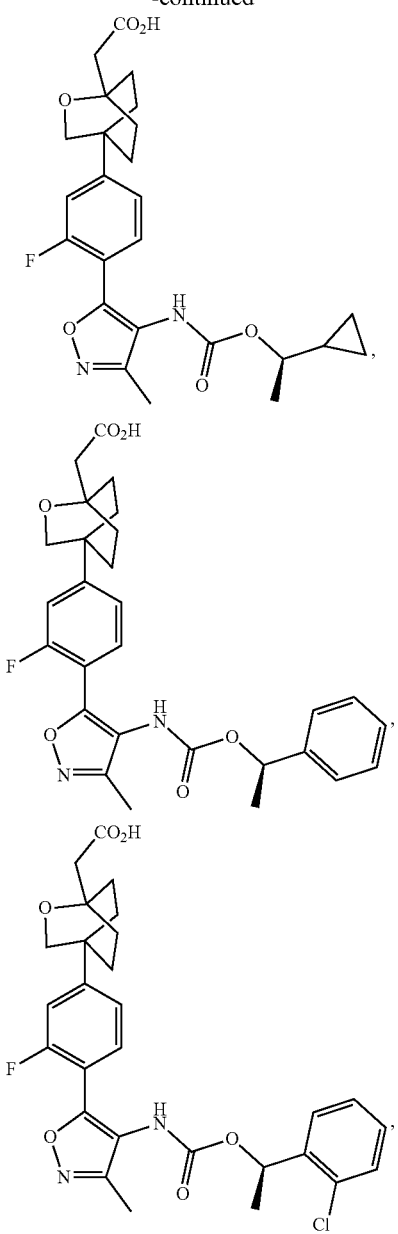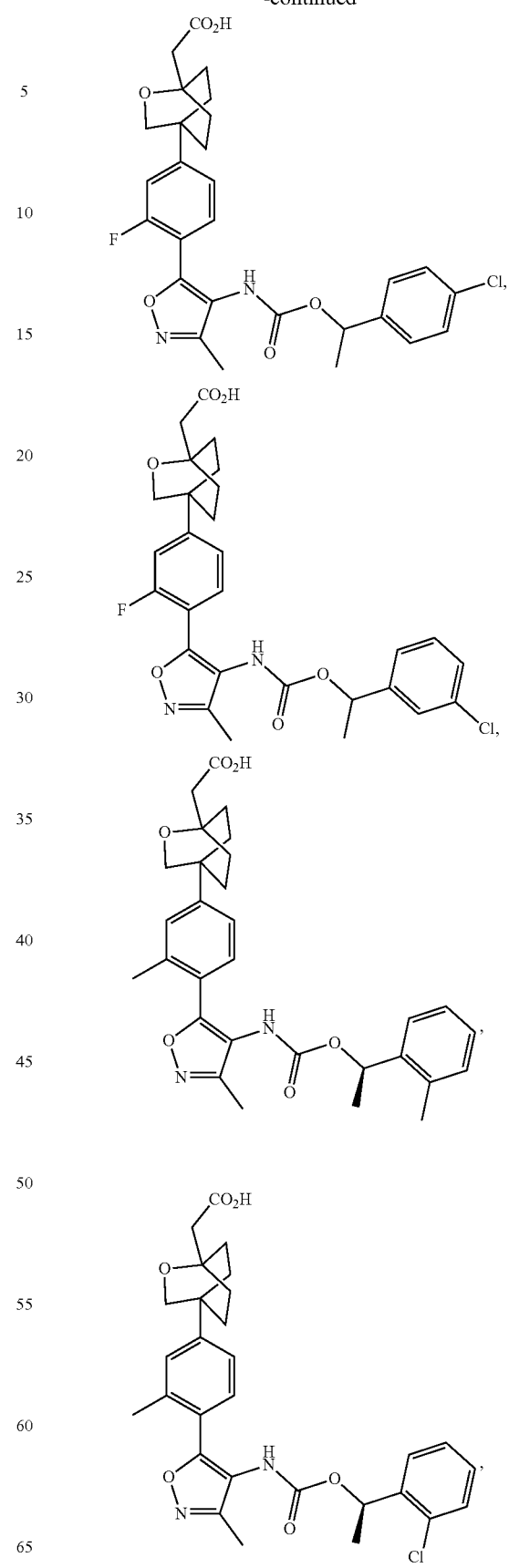

159
-continued
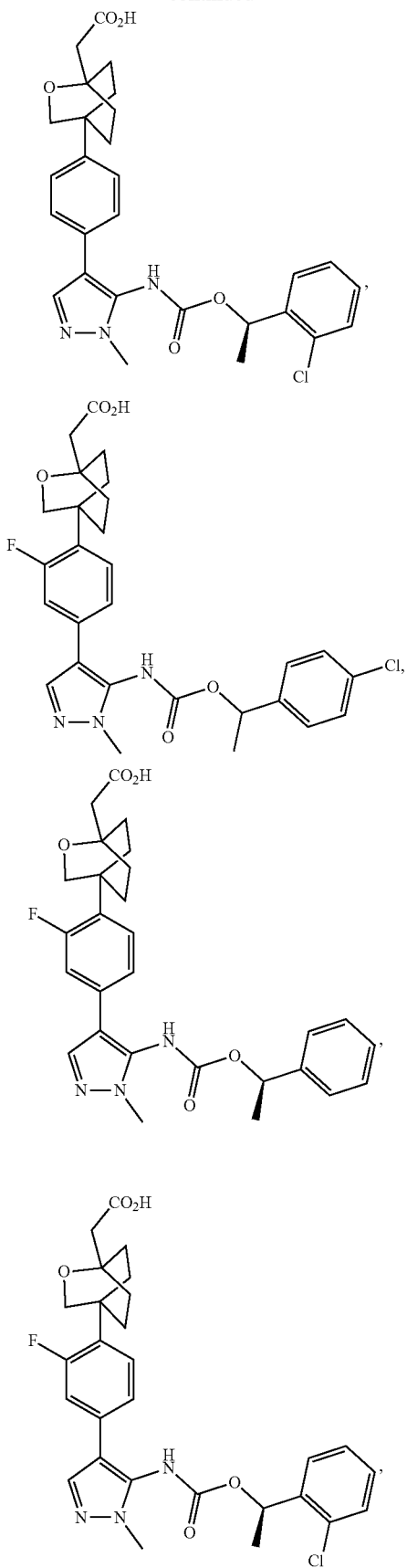
160
-continued
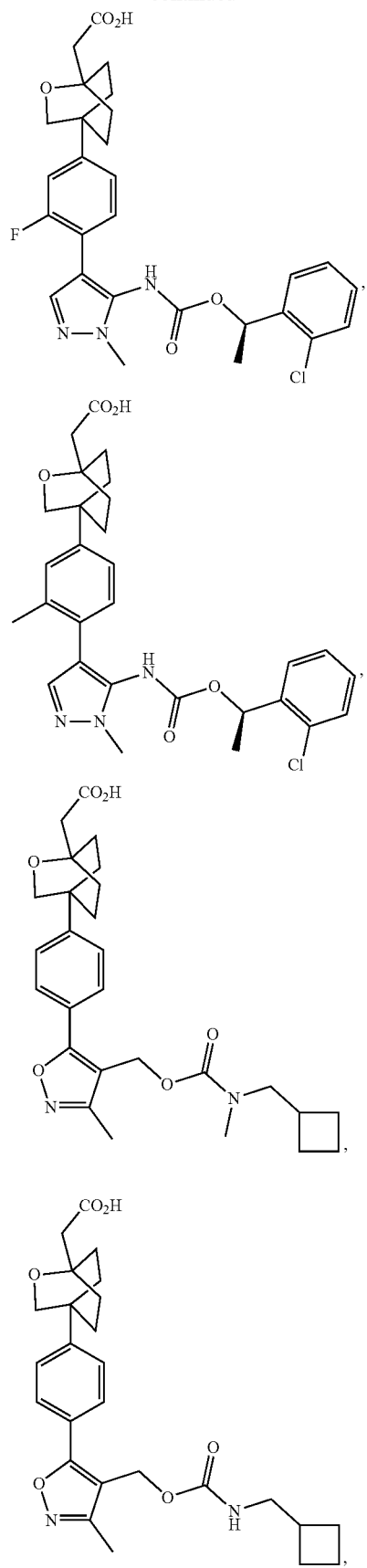

161
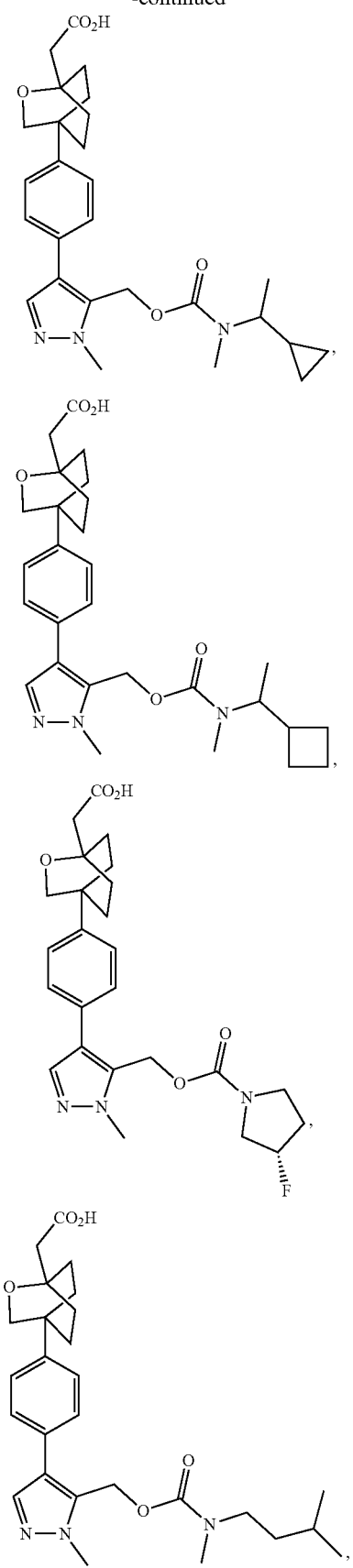
162
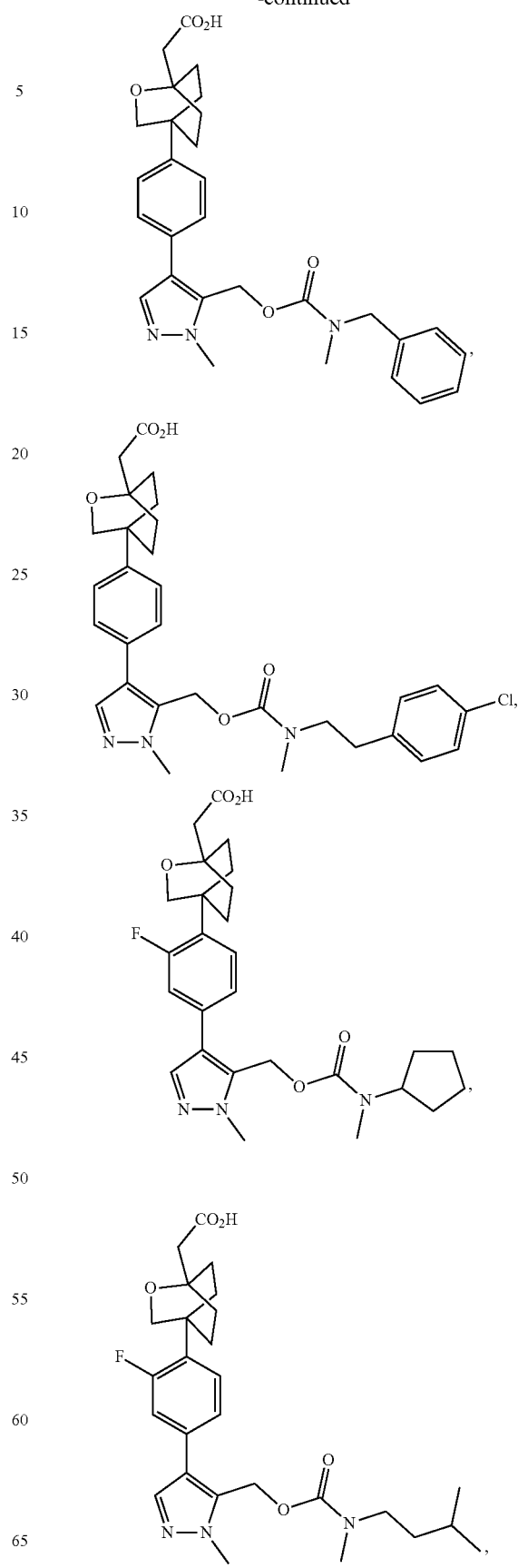

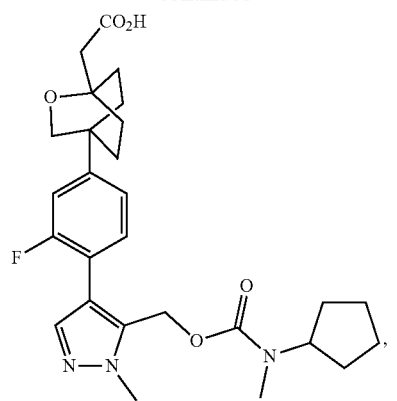
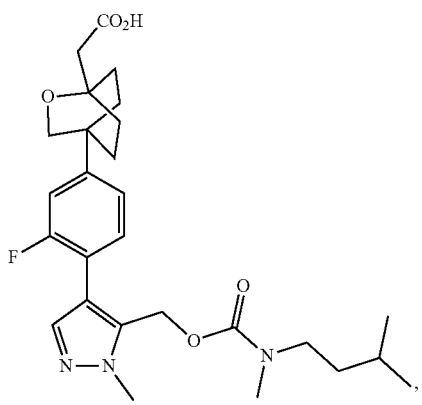
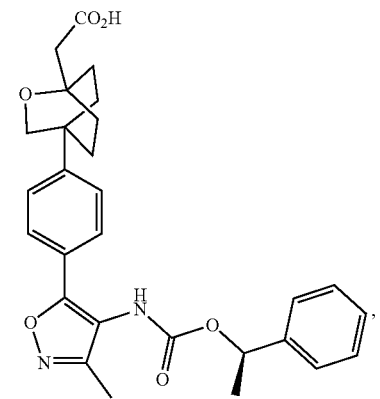
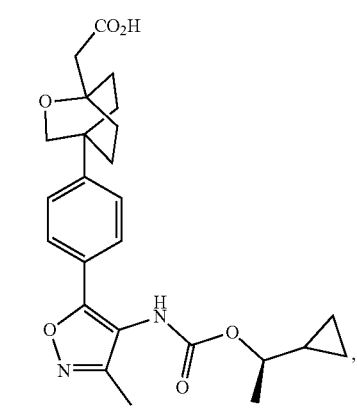
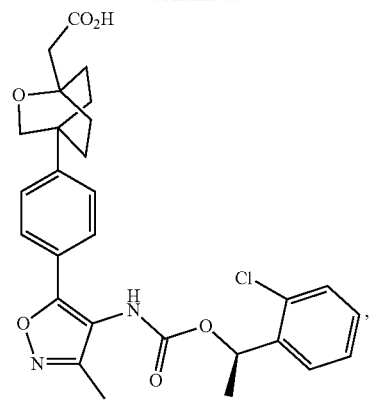
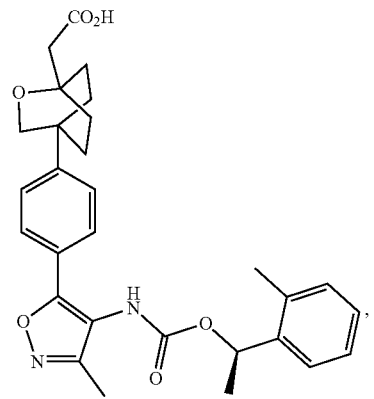
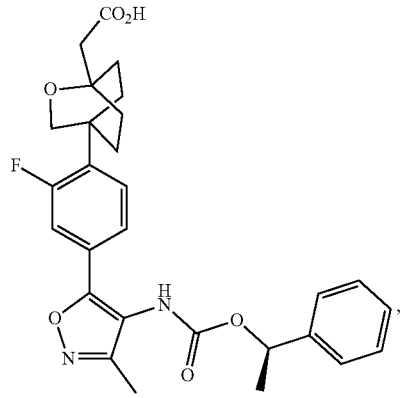
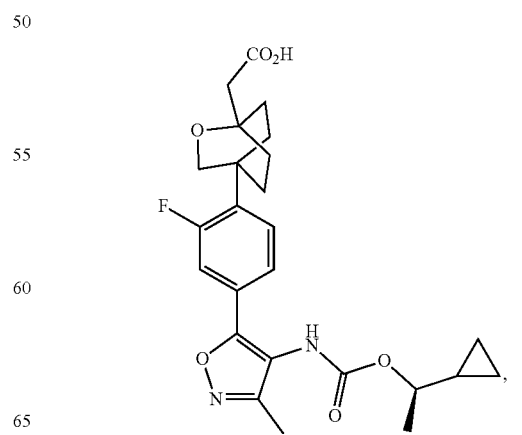

-continued

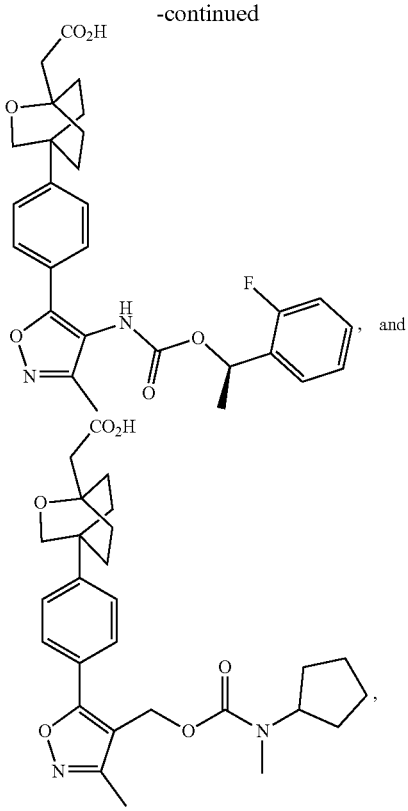

or a stereoisomer, a tautomer, or a pharmaceutically acceptable salt or solvate thereof.

11. A pharmaceutical composition comprising one or more compounds according to claim 1, or a stereoisomer, tautomer, or pharmaceutically acceptable salt or solvate thereof; and a pharmaceutically acceptable carrier or diluent.

12. A method of treating a disease, disorder, or condition associated with dysregulation of lysophosphatidic acid receptor 1 (LPA$_1$) in a patient having the disease, disorder, or condition, comprising administering a therapeutically effective amount of a compound or a stereoisomer, tautomer, or pharmaceutically acceptable salt or solvate thereof according to claim 1.

13. The method according to claim 12, wherein the disease, disorder, or condition is related to pathological fibrosis, transplant rejection, cancer, osteoporosis, or inflammatory disorders.

14. The method according to claim 13, wherein the pathological fibrosis is pulmonary, liver, renal, cardiac, dermal, ocular, or pancreatic fibrosis.

15. The method according to claim 12, wherein the disease, disorder, or condition is idiopathic pulmonary fibrosis (IPF), non-alcoholic steatohepatitis (NASH), non-alcoholic fatty liver disease (NAFLD), chronic kidney disease, diabetic kidney disease, or systemic sclerosis.

16. The method according to claim 13, wherein the cancer is of the bladder, blood, bone, brain, breast, central nervous system, cervix, colon, endometrium, esophagus, gall bladder, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid.

17. A method of treating fibrosis in a mammal having fibrosis, comprising administering a therapeutically effective amount of a compound or a stereoisomer, tautomer, or pharmaceutically acceptable salt or solvate thereof according to claim 1.

18. The method according to claim 17, wherein the fibrosis is idiopathic pulmonary fibrosis (IPF), nonalcoholic steatohepatitis (NASH), chronic kidney disease, diabetic kidney disease, or systemic sclerosis.

19. A method of treating a disease, disorder, or condition selected from: lung fibrosis, asthma, chronic obstructive pulmonary disease (COPD), renal fibrosis, acute kidney injury, chronic kidney disease, liver fibrosis, skin fibrosis, fibrosis of the gut, breast cancer, pancreatic cancer, ovarian cancer, prostate cancer, glioblastoma, bone cancer, colon cancer, bowel cancer, head and neck cancer, melanoma, multiple myeloma, chronic lymphocytic leukemia, cancer pain, tumor metastasis, transplant organ rejection, scleroderma, ocular fibrosis, age related macular degeneration (AMD), diabetic retinopathy, collagen vascular disease, atherosclerosis, Raynaud's phenomenon, or neuropathic pain in a mammal having the disease, disorder, or condition, comprising administering a therapeutically effective amount of a compound or a stereoisomer, a tautomer, or a pharmaceutically acceptable salt or solvate thereof according to claim 1, to the mammal.

20. A pharmaceutical composition comprising one or more compounds according to claim 7, or a stereoisomer, tautomer, or pharmaceutically acceptable salt or solvate thereof, and a pharmaceutically acceptable carrier or diluent.

21. A pharmaceutical composition comprising one or more compounds according to claim 8, or a stereoisomer, tautomer, or pharmaceutically acceptable salt or solvate thereof; and a pharmaceutically acceptable carrier or diluent.

22. A pharmaceutical composition comprising one or more compounds according to claim 9, or a stereoisomer, tautomer, or pharmaceutically acceptable salt or solvate thereof; and a pharmaceutically acceptable carrier or diluent.

23. A pharmaceutical composition comprising one or more compounds according to claim 10, or a stereoisomer, tautomer, or pharmaceutically acceptable salt or solvate thereof; and a pharmaceutically acceptable carrier or diluent.

* * * * *